(12) United States Patent
Picking et al.

(10) Patent No.: US 11,439,700 B2
(45) Date of Patent: Sep. 13, 2022

(54) METHODS AND COMPOSITIONS RELATED TO THE NEXT GENERATION VACCINE

(71) Applicant: UNIVERSITY OF KANSAS, Lawrence, KS (US)

(72) Inventors: Wendy L. Picking, Lawrence, KS (US); William D. Picking, Lawrence, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 0 days.

(21) Appl. No.: 17/053,544

(22) PCT Filed: May 3, 2019

(86) PCT No.: PCT/US2019/030694
§ 371 (c)(1),
(2) Date: Nov. 6, 2020

(87) PCT Pub. No.: WO2019/217243
PCT Pub. Date: Nov. 14, 2019

(65) Prior Publication Data
US 2021/0252127 A1      Aug. 19, 2021

Related U.S. Application Data

(60) Provisional application No. 62/667,599, filed on May 6, 2018.

(51) Int. Cl.
*A61K 39/104* (2006.01)
*A61K 39/118* (2006.01)
*A61K 39/02* (2006.01)

(52) U.S. Cl.
CPC ........ *A61K 39/118* (2013.01); *A61K 39/0291* (2013.01); *A61K 39/099* (2013.01); *A61K 39/104* (2013.01); *A61K 39/107* (2013.01); *C07K 2319/00* (2013.01)

(58) Field of Classification Search
None
See application file for complete search history.

(56) References Cited

U.S. PATENT DOCUMENTS

| | | |
|---|---|---|
| 9,492,523 B2 | 11/2016 | Picking et al. |
| 2008/0044438 A1 | 2/2008 | Ostroff et al. |
| 2009/0324638 A1 | 12/2009 | Dattwyler et al. |
| 2013/0149329 A1* | 6/2013 | Picking .......... C07K 14/25 424/192.1 |
| 2016/0220655 A1 | 8/2016 | Picking et al. |

FOREIGN PATENT DOCUMENTS

WO    2016193161 A1    12/2016

OTHER PUBLICATIONS

Romano et al. J. Biol. Chem. 291: 6304-6315, 2016.*
Ruan et al. Infect. Immun. 82: 1823-1832, 2014.*
Greenspan et al. Nature Biotechnology 17: 936-937, 1999.*
Rudinger J. In: Peptide Hormones. (Ed) JA Parsons, University Park Press, pp. 1-7, 1976.*
Skolnick et al. Trends in Biotechnology, 18: 34-39, 2000.*
Huang, "Characterization of the A Subunit Epitopes in Immunogenicity and Enterotoxicity of Enterotoxigenic *Escherichia coli* (ETEC) Heat-Labile Toxin," Thesis, Huazhong Agricultural University,College of Veterinary Medicine, Aug. 1, 2017, pp. 1-52.
Heine et al. "AA Combined YopB and LcrV Subunit Vaccine Elicits Protective Immunity against Yersinia Infection in Adult and Infant Mice," The Journal of Immunology, Feb. 20, 2019, vol. 203, Iss. 3, pp. 2005-2016.
Huang et al. "Significance of Enterotoxigenic *Escherichia coli* (ETEC) HeatLabile Toxin (LT) Enzymatic Subunit Epitopes in LT Enterotoxicity and Immunogenicity," Appl Environ Microbiol, May 25, 2018, vol. 84, Iss. 15, pp. 1-13.
International Search Report and Written Opinion for International Application No. PCT/US2019/030694 dated Aug. 20, 2019.
Communication Pursuant to Rule 164(1) EPC, issued for European Application No. 19800219.8, dated Jan. 20, 2022.
Martinez-Becerra, Francisco J., et al. "Characterization and protective efficacy of type III secretion proteins as a broadly protective subunit vaccine against Salmonella enterica serotypes." Infection and immunity 86.3 (2018) e00473-17.
Martinez-Becerra, Francisco J., et al. "Characterization of a novel fusion protein from IpaB and IpaD of Shigella spp. and its potential as a pan-Shigella vaccine." Infection and immunity 81.12 (2013): 4470-4477.
Nandre, Rahul M., et al. "Passive antibodies derived from intramuscularly immunized toxoid fusion 3xSTaN12S-dmLT protect against STa+ enterotoxigenic *Escherichia coli* (ETEC) diarrhea in a pig model." Vaccine 35.4 (2017): 552-556.
Müller, Simone, Mario F. Feldman, and Guy R. Cornelis. "The Type III secretion system of Gram-negative bacteria: a potential therapeutic target?. " Expert opinion on therapeutic targets 5.3 (2001): 327-339.

* cited by examiner

*Primary Examiner* — Sarvamangala Devi
(74) *Attorney, Agent, or Firm* — Meunier Carlin & Curfman LLC

(57) ABSTRACT

Disclosed are methods and compositions related to polypeptides comprising a fusion of the needle tip protein and translocator protein of a type III secretion apparatus (T3SA) from a type III secretion system (T3SS) of (a)
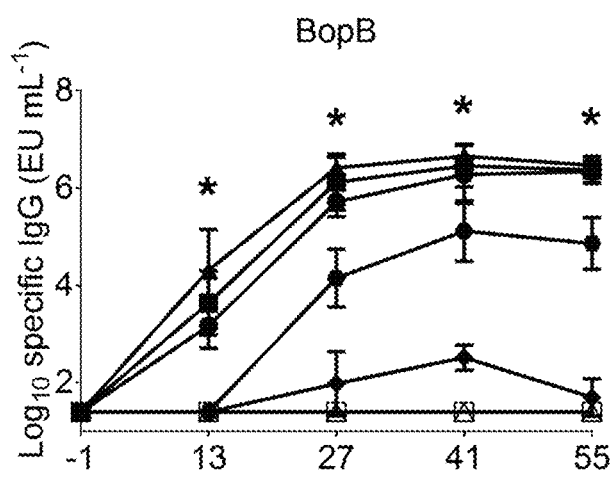
(b)
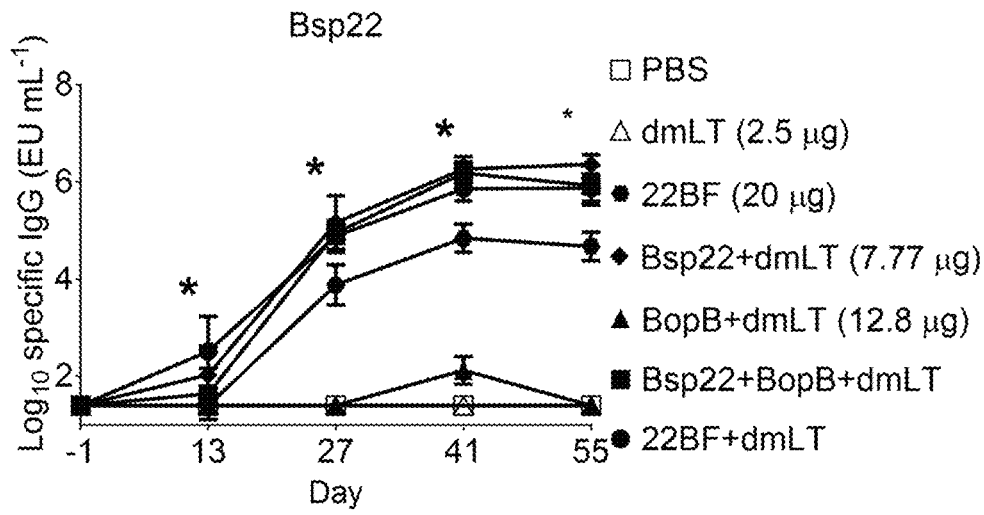
(c)
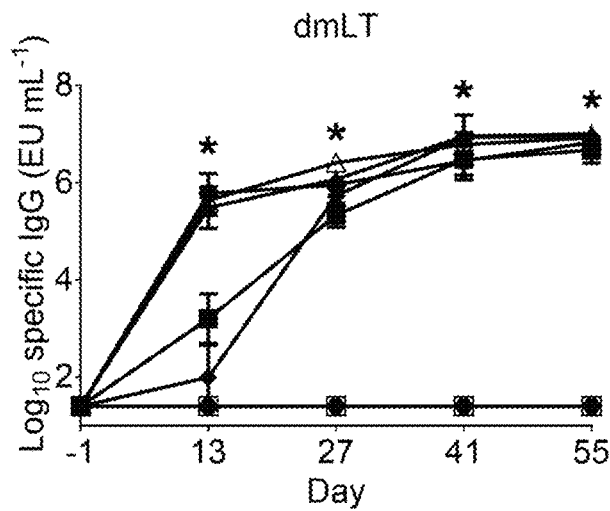
FIG. 4A, FIG. 4B, and FIG. 4C

Figure 1:
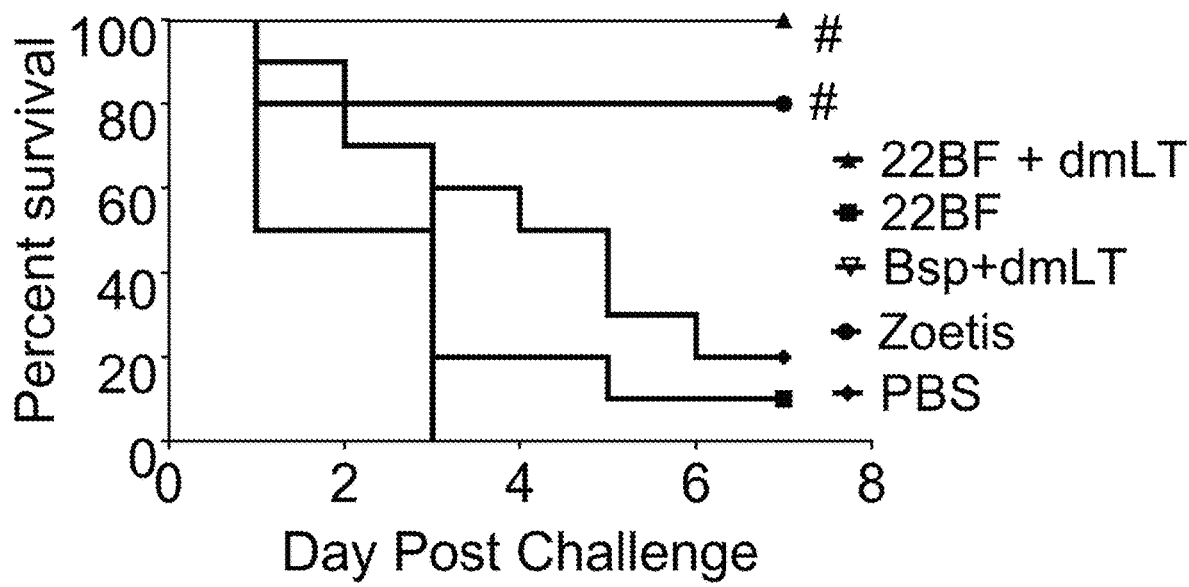

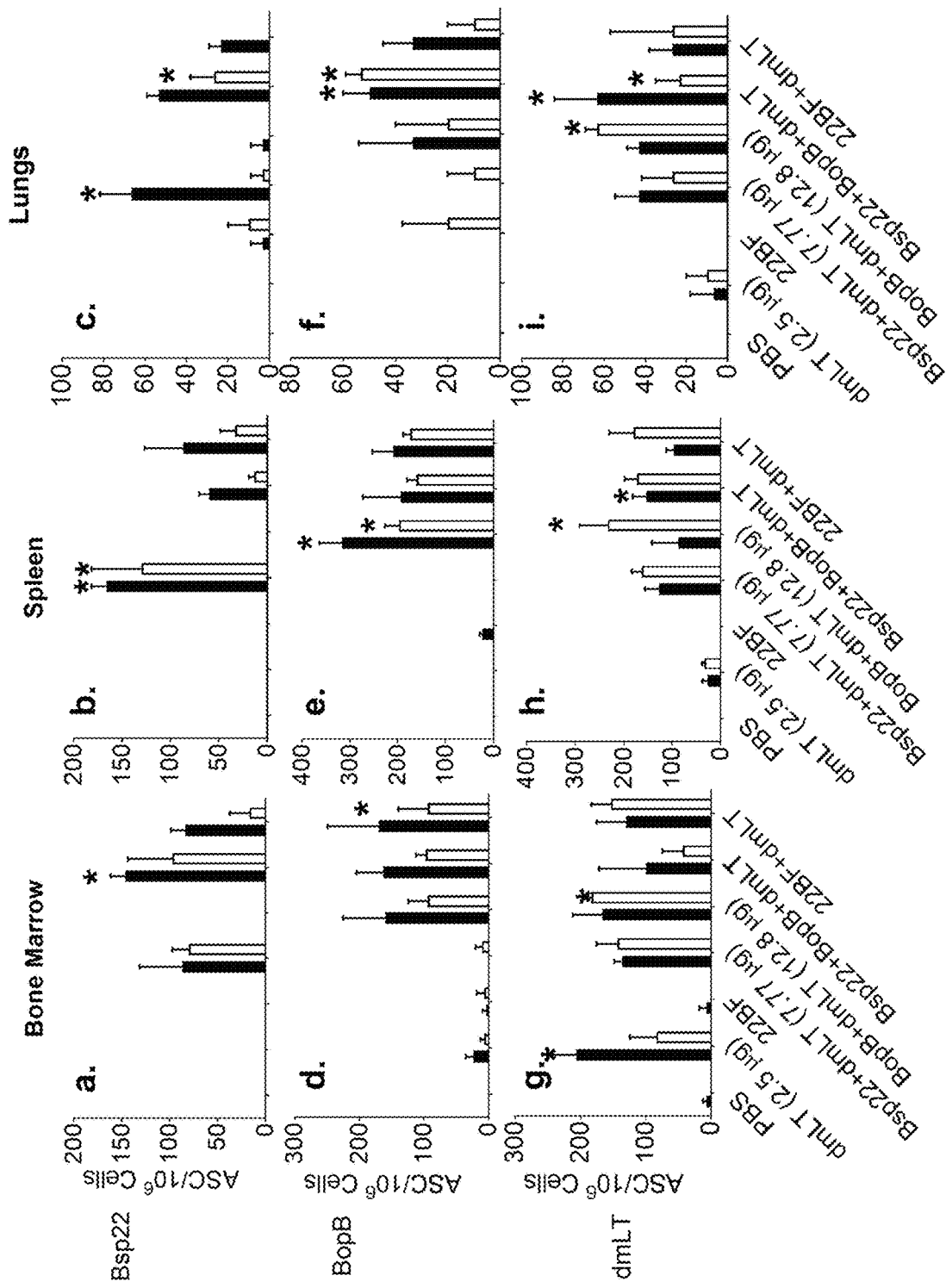
FIG. 5A, FIG. 5B, FIG. 5C, FIG. 5D, FIG. 5E, FIG. 5F, FIG. 5G, FIG. 5H, and FIG. 5I

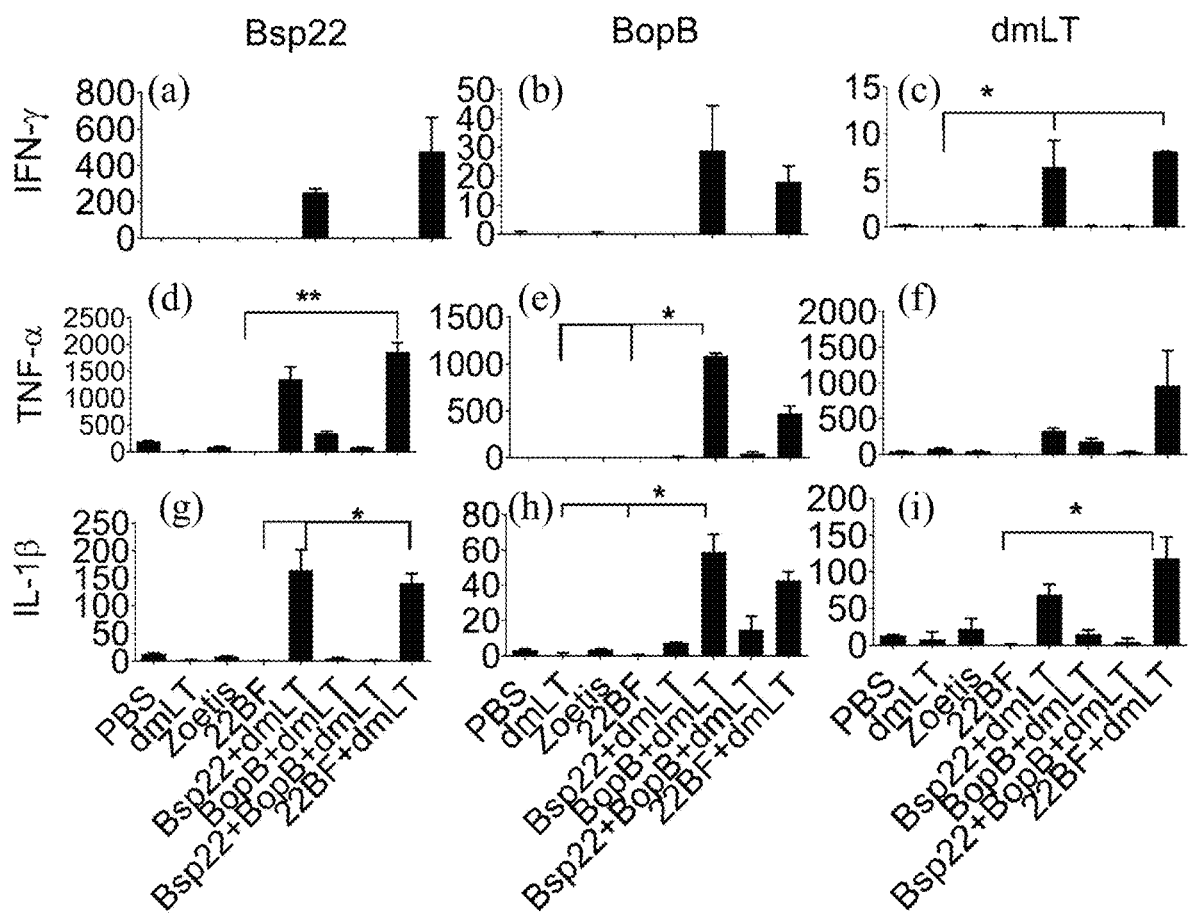
FIG. 6A, FIG. 6B, FIG. 6C, FIG. 6D, FIG. 6E, FIG. 6F, FIG. 6G, FIG. 6H, and FIG. 6I

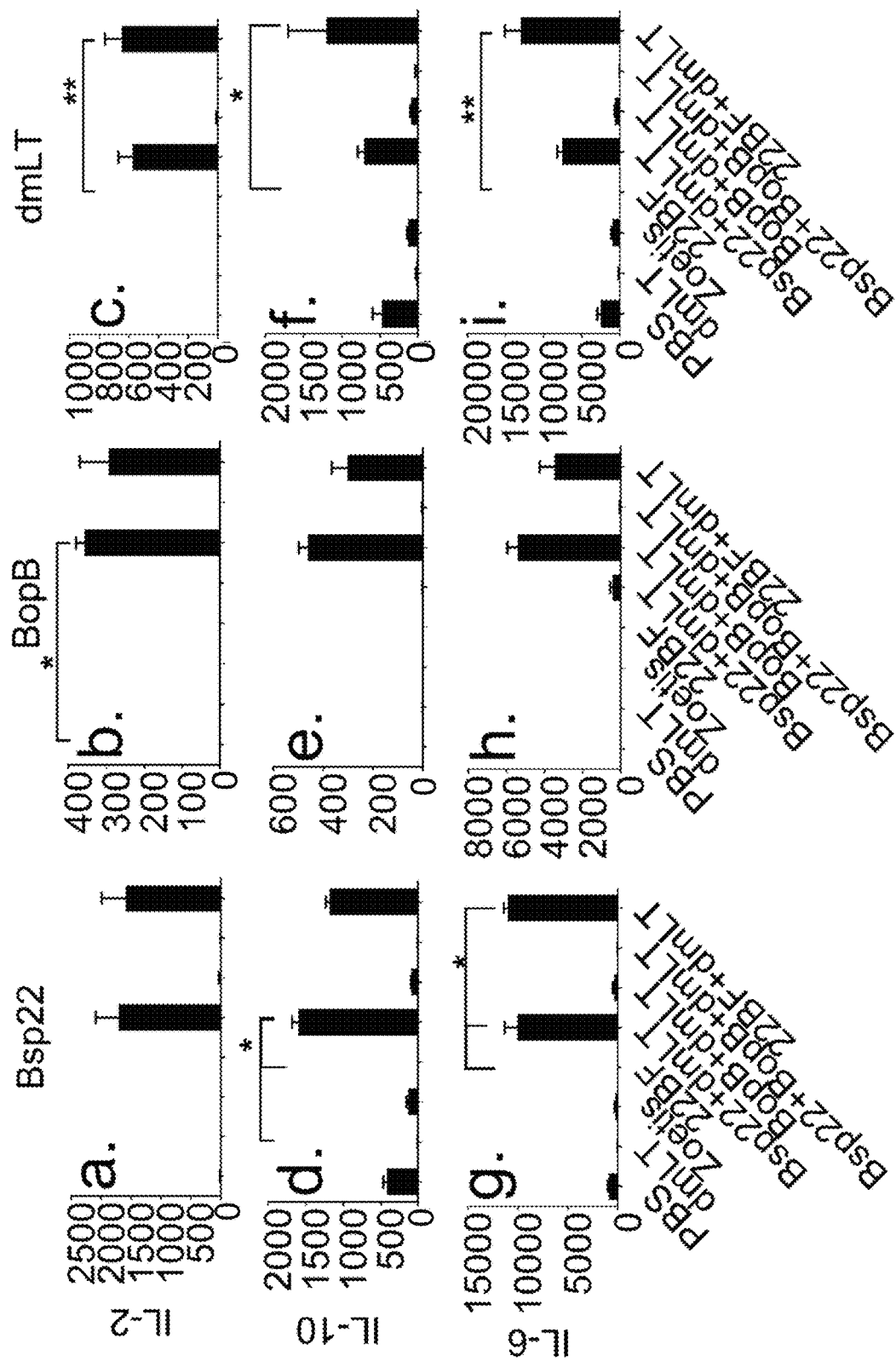
FIG. 7A, FIG, 7B, FIG. 7C, FIG. 7D, FIG 7E, FIG. 7F, FIG. 7G, FIG. 7H, and FIG. 7I

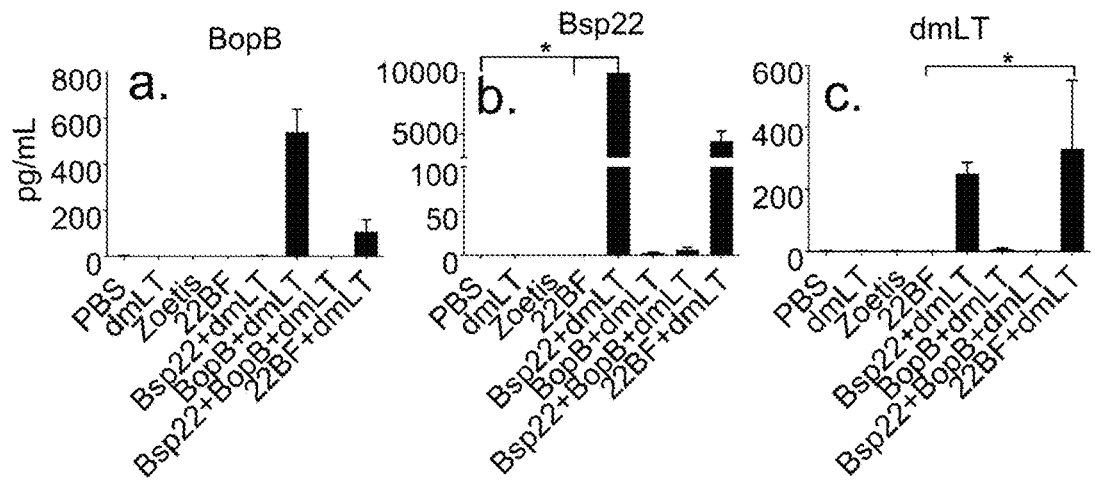
FIG. 8A, FIG. 8B, and FIG. 8C
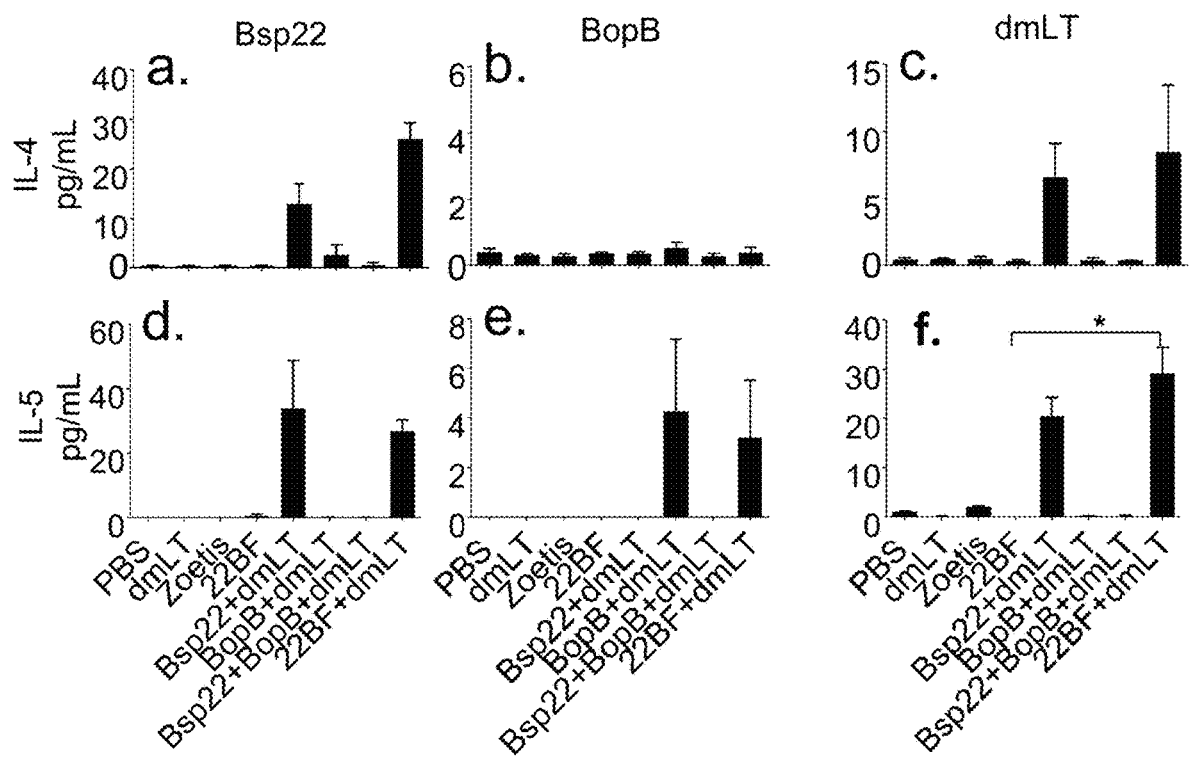
FIG. 9A, FIG. 9B, FIG. 9C, FIG. 9D, FIG. 9E, and FIG. 9F FIG. 11A, FIG. 11B, FIG. 11C, and FIG. 11D

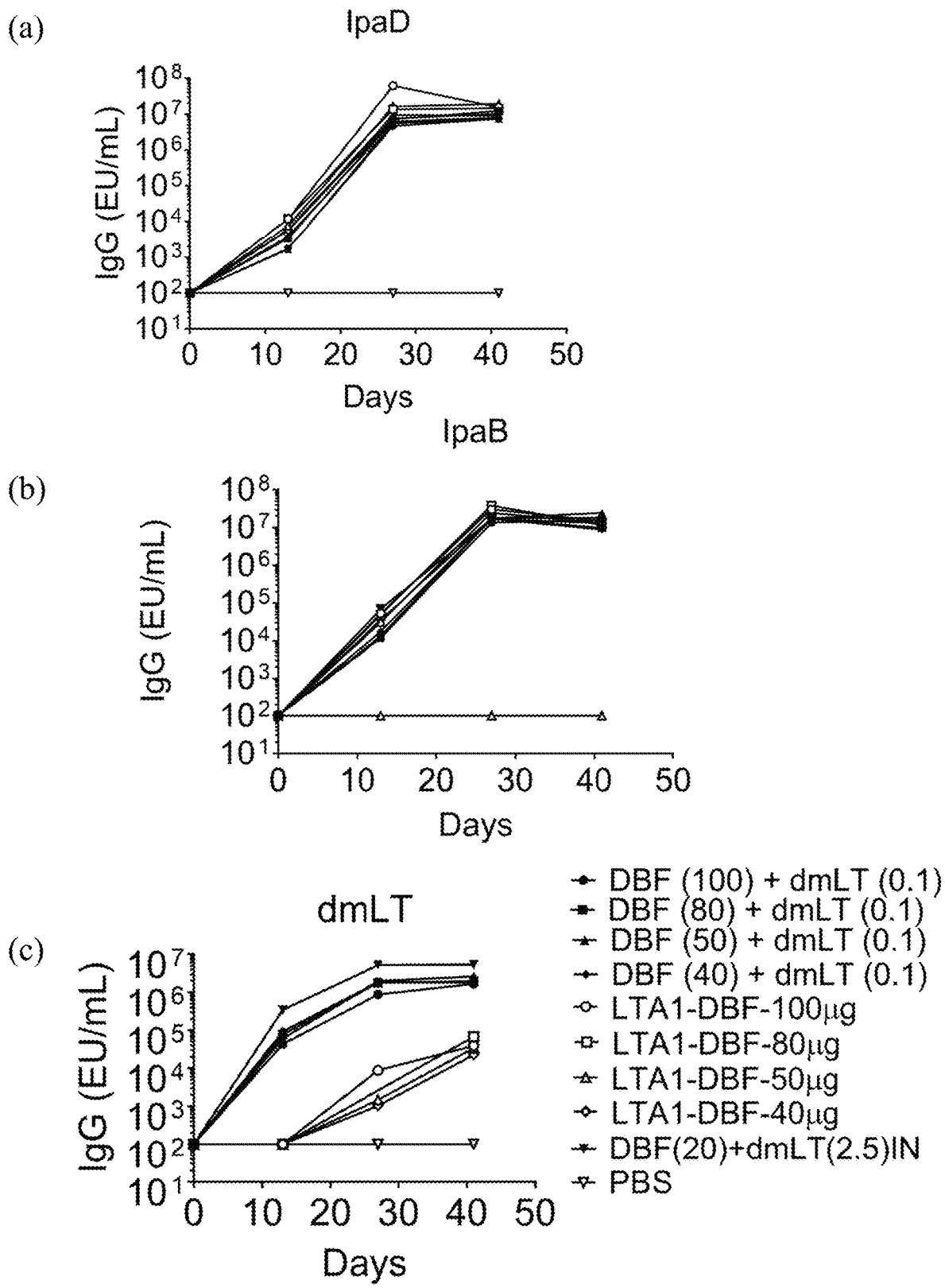
FIG. 15A, FIG. 15B, and FIG. 15C

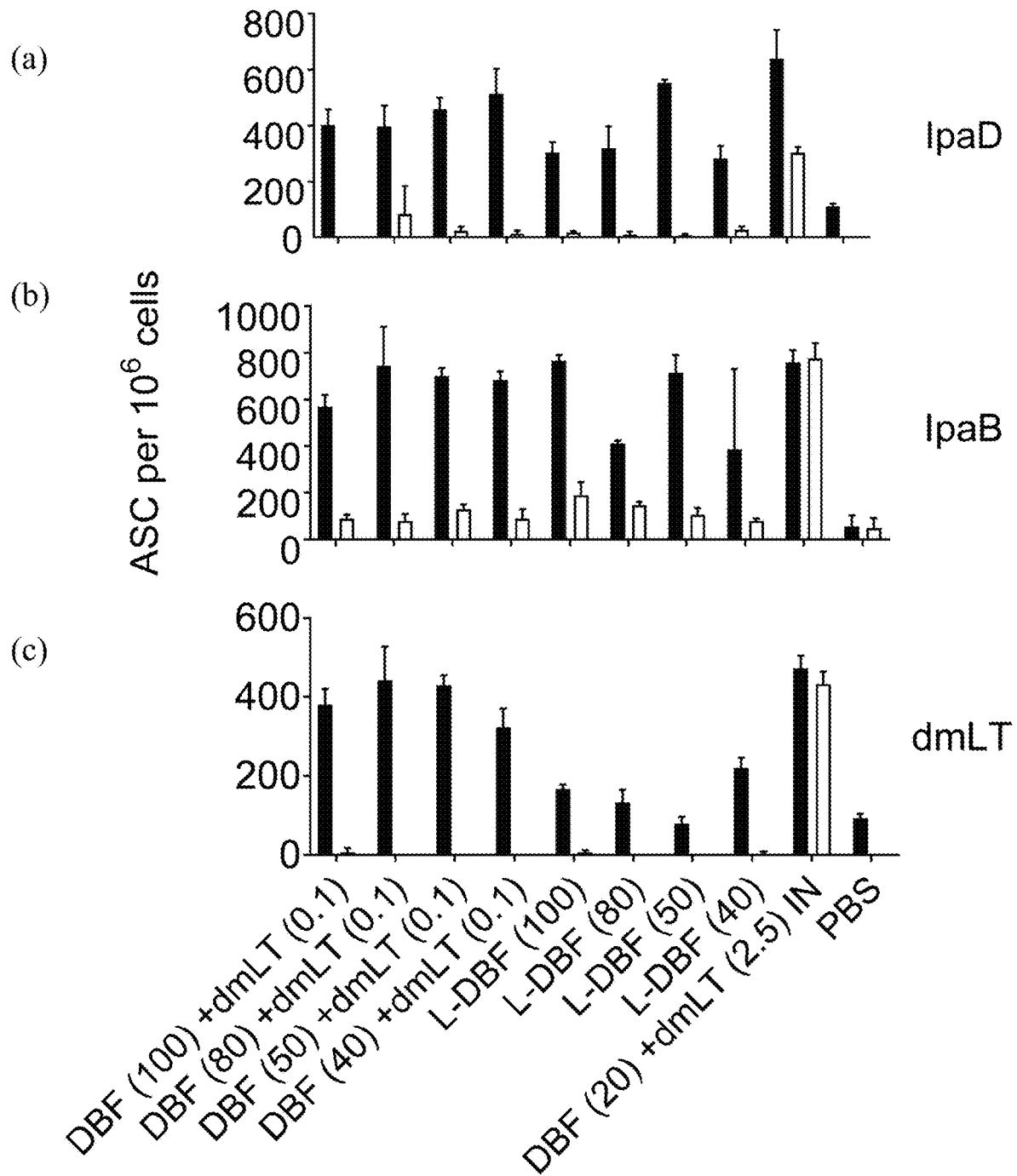
FIG. 16A, FIG. 16B, and FIG. 16C

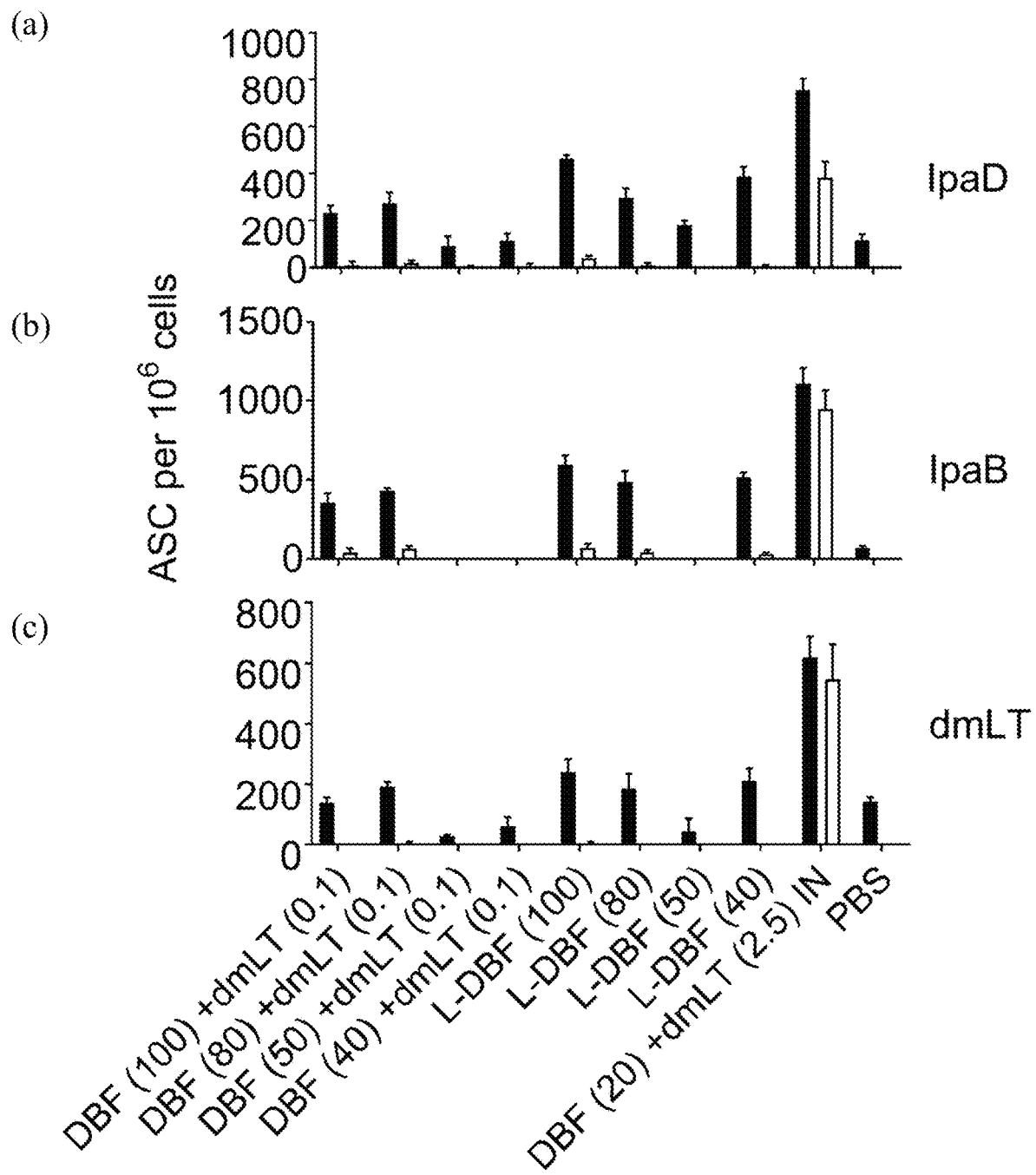
FIG. 17A, FIG. 17B, and FIG. 17C

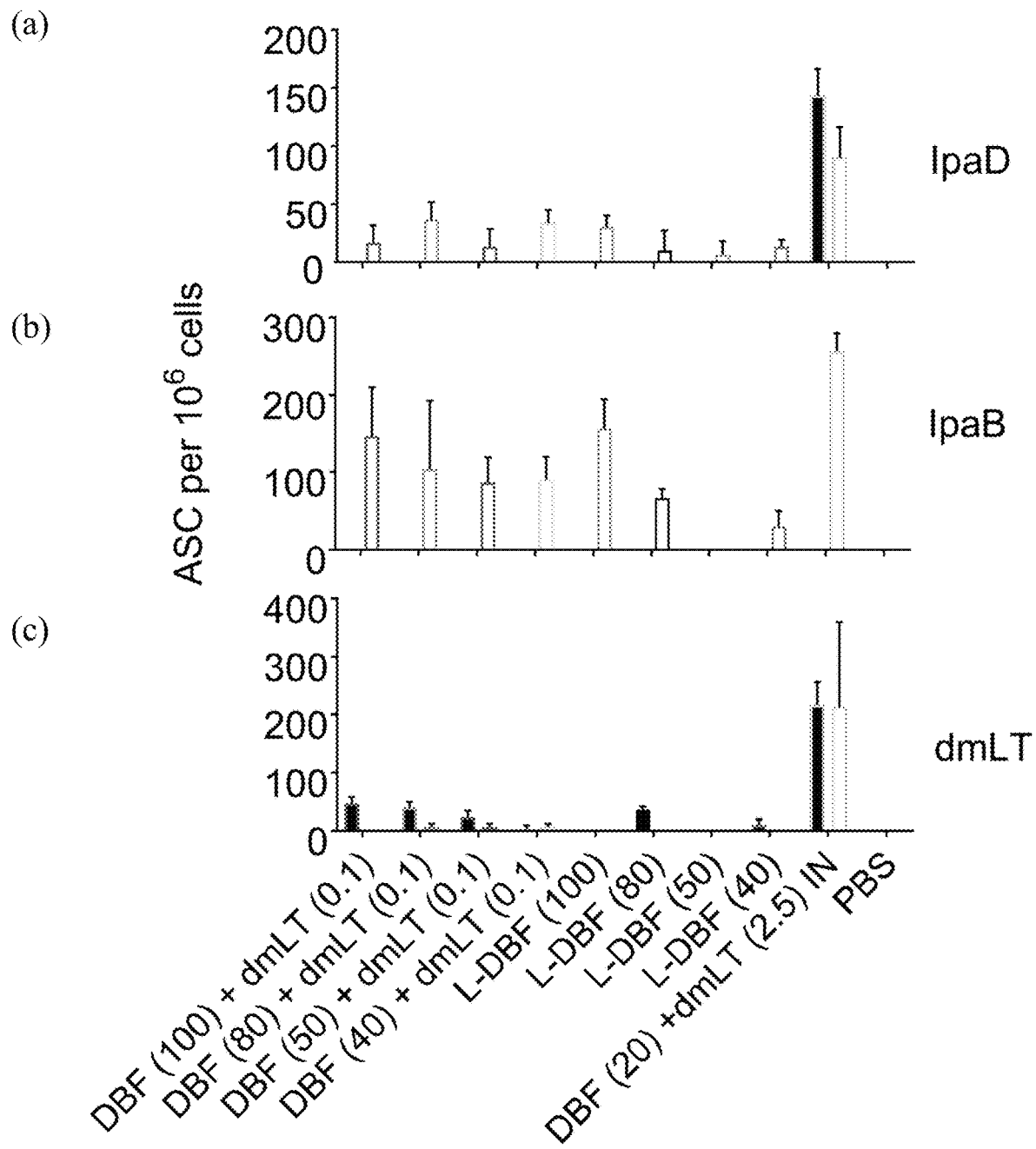
FIG. 18A, FIG. 18B, and FIG. 18C

METHODS AND COMPOSITIONS RELATED TO THE NEXT GENERATION VACCINE

I. CROSS-REFERENCE TO RELATED APPLICATIONS

This application is a national stage application filed under 35 U.S.C. § 371 of PCT/US2019/030694 filed on May 3, 2019, which claims the benefit of U.S. Provisional Patent Application Ser. No. 62/667,599, filed May 6, 2018, applications which are incorporated by reference in their entireties herein.

II. BACKGROUND

*Bordetella pertussis* is a Gram-negative bacterial pathogen that causes pertussis, or whooping cough, a highly contagious, severe respiratory disease that is life threatening for infants and young children. This pathogen colonizes the trachea and secretes toxins that paralyze the cilia, which prevents clearance of mucous. Severe (paroxysmal), non-productive coughing fits are a result and attempts to acquire oxygen are manifested by the characteristic "whoop" upon gasps for air. The majority of deaths associated with pertussis are actually caused by secondary respiratory infections resulting from the inability to clear pulmonary secretions. In the 1940s a whole-cell pertussis (wP) vaccine was introduced that dramatically reduced the mortality caused by pertussis. Due to side effects attributed to the wP vaccine, a new acellular pertussis (aP) vaccine was developed and introduced in the US and other parts of the world in the 1990s. Although the aP vaccine has few side effects, its protective efficacy is lower than that of the wP vaccine. In 2012, which is considered the most recent major epidemic, 48,277 cases of pertussis were reported and, in 2015, 20,762 cases were reported. During the last 15 years, in addition to a greater overall incidence of pertussis, there is growing concern over the increase in the peak number of reported cases for each ensuing epidemic. In 2015, 45% of the 0.5 to 6-year-old children that contracted pertussis had been vaccinated with DTaP at least three times (with five vaccinations being optimal: 2, 4, 6, 15 months and one at 4-6 years). Additionally, there is evidence that selective pressure is causing *B. pertussis* to eliminate virulence factors that are components of the aP vaccine, further compromising the vaccine's efficacy. Taken together, a better vaccine is needed.

III. SUMMARY

Disclosed are methods and compositions related to polypeptides comprising a fusion of the needle tip protein and translocator protein of a type III secretion apparatus (T3SA) from a type III secretion system (T3SS) of a Gram negative bacteria.

Disclosed herein are fusion polypeptides comprising a fusion of a needle tip protein (such as, for example, Bsp22, LcrV, BipD, PcrV, CT053, or CT668) or an antigenic fragment thereof and a translocator protein (such as, for example, BopB, YopB, BipB, PopB, CopB, or CopB2) or an antigenic fragment thereof from a Type III secretion system (T3SS) of a Gram negative bacteria (such as, for example, *Bordetella* spp., *Burkholderia* spp., *Chlamydia* spp., *Pseudomonas* spp., *Vibrio* spp. or *Yersinia* spp.); wherein the gram negative bacteria is not a *Salmonella enterica* or *Shigella* spp.

In one aspect, disclosed herein are fusion polypeptides, wherein the fusion polypeptide is arranged such that the needle tip protein is 5' of the translocator protein.

Also disclosed herein are fusion polypeptides of any preceding aspect, wherein the fusion further comprises an adjuvant such as, for example, Cholera Toxin or antigenic fragment thereof (such as, for example, CTA1) or double mutant labile toxin (dmLT) or an antigenic fragment thereof labile toxin (such as, for example, LTA1) from Enterotoxigenic *Escherichia coli*. In some aspect, the dmLT or fragment thereof can also be fused to the needle tip protein-translocator protein fusion at the 5' end.

In one aspect, disclosed herein are fusion polypeptides of any preceding aspect, wherein the fusion polypeptide further comprises pertussis toxoid (PTd).

Also disclosed herein are compositions comprising a T3SA needle tip protein (such as, for example, Bsp22, LcrV, BipD, PcrV, or CdsF) or an antigenic fragment thereof from a Gram negative bacteria (such as, for example, *Bordetella* spp., *Burkholderia* spp. *Chlamydia* spp., *Pseudomonas* spp., *Vibrio* spp., or *Yersinia* spp.) and a T3SA first translocator protein (such as, for example, BopB, YopB, BipB, PopB, or CopB/CopB2) or an antigenic fragment thereof from a Gram negative bacteria; wherein the gram negative bacteria is not a *Salmonella enterica* or *Shigella* spp. In one aspect, the composition can comprise the needle tip protein or fragment thereof and the translocator protein or fragment thereof as separate components or as a fusion polypeptide. Also disclosed herein are compositions of any preceding aspect, wherein the composition comprises an adjuvant (such as, for example, dmLT, LTA1, cholera toxin, or CTA1) and/or bacterial toxin protein such as a pertussis toxoid (PTd).

In one aspect, disclosed herein are vaccines comprising the fusion polypeptides or compositions of any preceding aspect. In some embodiments, the vaccine can further comprise an acellular gram negative vaccine or active components thereof. In one aspect, the vaccine can comprise pertussis toxoid (PTd).

Also disclosed herein are methods of treating, inhibiting, or preventing an infection of a Gram negative bacteria (such as, for example, *Bordetella* spp., *Burkholderia* spp., *Chlamydia* spp., *Pseudomonas* spp., *Vibrio* spp., or *Yersinia* spp.) in a subject comprising administering to the subject the fusion polypeptide, composition, or vaccine of any preceding aspect.

In one aspect, disclosed herein are methods of treating, inhibiting, or preventing an infection of a Gram negative bacteria of any preceding aspect, wherein the method further inhibits or prevents colony formation of the bacteria and/or transmission of the bacteria to another subject.

Also disclosed herein are methods of eliciting an immune response in a subject to a Gram negative bacteria (such as, for example, *Bordetella* spp., *Burkholderia* spp., *Chlamydia* spp., *Pseudomonas* spp., *Vibrio* spp., or *Yersinia* spp.) comprising administering to the subject the fusion polypeptide, composition, or vaccine of any preceding aspect. For example, disclosed herein are methods of eliciting an immune response against at least one Gram negative bacteria serovar in a subject in need thereof, comprising administering to the subject a composition comprising at least one needle tip protein or an antigenic fragment thereof and/or at least one translocator protein or an antigenic fragment thereof; wherein said composition is administered in an amount sufficient to elicit an immune response to said at least one Gram negative bacteria serovar in said subject; and wherein the Gram negative bacteria is not a *Shigella* spp. or *Salmonella enterica*.

In one aspect, disclosed herein are methods of eliciting an immune response in a subject to a Gram negative bacteria of any preceding aspect, wherein the immune response provides sterilizing immunity.

IV. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows the protective efficacy of intranasally administered 22BF against *B. bronchiseptica* challenge. Mice (n=10) were vaccinated intranasally biweekly three times with the indicated formulation which contained 10 μg protein±dmLT. Zoetis vaccine was delivered subcutaneously on day 1 and 21 as per manufacturer's directions. Mice were challenged with $1.3 \times 10^7$ *B. bronchiseptica* on day 56. BopB was not available at day 0. #P<0.05 compared to survival of mice vaccinated with PBS.

Figure 2:
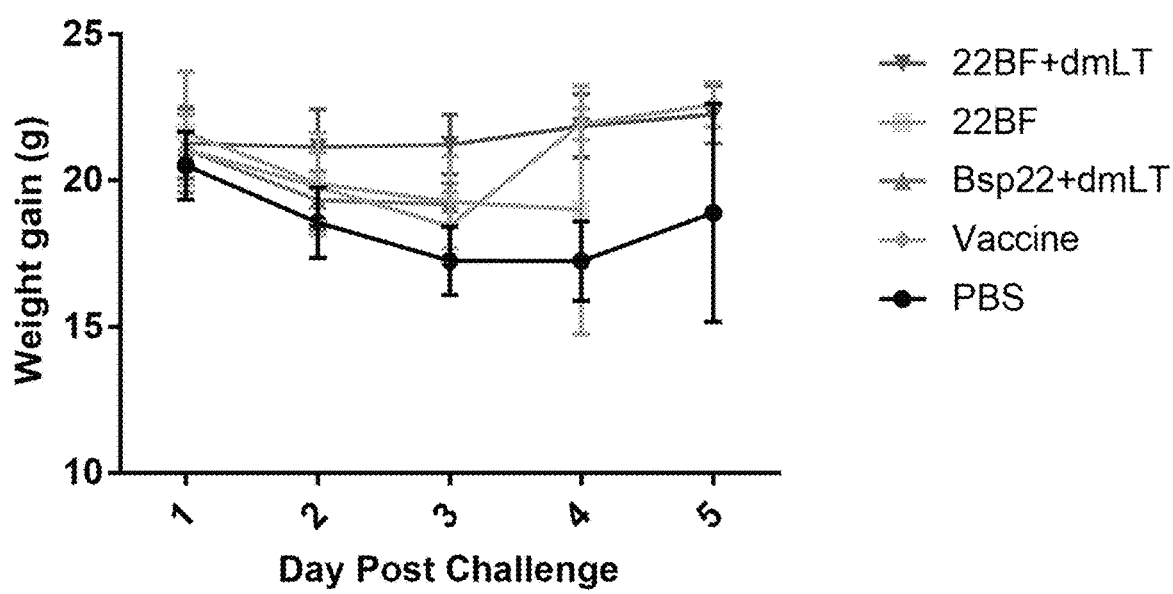

FIG. 2 shows the weight gain/loss of vaccinated mice during *B. brontchiseptica* challenge. Mice (same as above) were weighed daily in p.m. Note that the 22BF+dmLT mice gain weight and have small error bars.

Figures 3A, 3B:
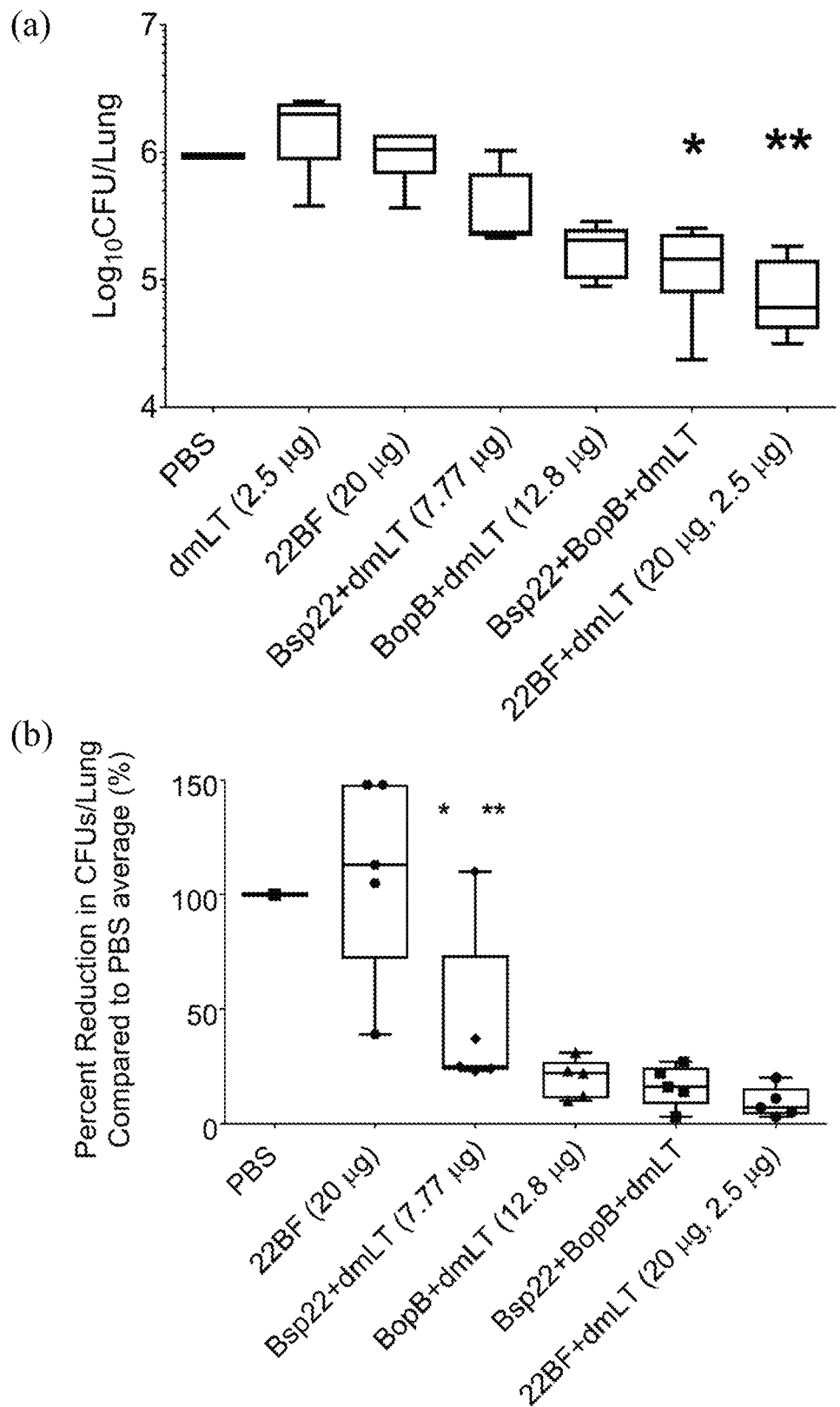

FIG. 3A and FIG. 3B show the protective efficacy of 22BF+dmLT. Mice were vaccinated on days 0, 14, 28 and challenged on day 56 with a sublethal dose of *B. bronchiseptica*. FIG. 3A shows that on day 7 of the challenge, the CFU/lung were determined. *=P<0.05, **=P<0.01 when compared to dmLT. FIG. 3B shows the decrease in CFU compared to the 22BF average. *=P<0.05, **=P<0.01 when compared to 22BF.

FIGS. 4A, 4B, and 4C show the kinetics of IgG response. Blood was collected on days −1, 13, 27, 41, and 55. The kinetics of anti-Bsp22, -BopB and -dmLT IgG were assessed in all sera and shown in (4A) BopB, (4B) Bsp22, and (4C) dmLT. Typical logarithmic increases were seen. *=P value of <0.05 when comparing to PBS controls.

FIGS. 5A, 5B, 5C, 5D, 5E, 5F, 5G, 5H, and 5I show stimulation of antibody secreting cells from bone marrow, spleen and lungs. Bone marrow, spleens and lungs were collected on day 56. Single cell suspensions from 5 mice per group were stimulated in vitro Bsp22, BopB or dmLT. IgG (black) and IgA (white) ASC were measured by ELISpot. Bars represent mean ASC per $10^6$ cells +SD from replicate wells. Data for bone marrow is shown in (4A), (5D), and (5G) for Bsp22, BopB, and dmLT, respectively. Data for spleen is shown in (5B), (5E), and (5H) for Bsp22, BopB, and dmLT, respectively. Data for lungs is shown in (5C), (5F), and (5I) for Bsp22, BopB, and dmLT, respectively.

FIGS. 6A, 6B, 6C, 6D, 6E, 6F, 6G, 6H, and 6I show Th1 cytokine secretion. Splenocytes were extracted from 5 mice of each group and incubated with Bsp22, BopB or dmLT. After 48 h, supernatants were collected and levels of cytokine secretion in response to specified antigen were then measured (in pg/ml) using an MSD cytokine detection plate. Each bar represents mean of triplicate wells±S.D. Asterisk specified a P<0.05 when comparing specified groups. Data for IFN-γ is shown in (6A), (6B), and (6C) for Bsp22, BopB, and dmLT, respectively. Data for TNF-α is shown in (6D), (6E), and (6F) for Bsp22, BopB, and dmLT, respectively. Data for IL-1β is shown in (6G), (6H), and (6I) for Bsp22, BopB, and dmLT, respectively.

FIGS. 7A, 7B, 7C, 7D, 7E, 7F, 7G, 7H, and 7I show Th1 cytokine secretion. Splenocytes were extracted from 5 mice of each group and incubated with Bsp22, BopB or dmLT. After 48 h, supernatants were collected and levels of cytokine secretion in response to specified antigen were then measured (in pg/ml) using an MSD cytokine detection plate. Each bar represents mean of triplicate wells±S.D. Asterisk specified a P<0.05 when comparing specified groups. Data for IL-2 is shown in (7A), (7B), and (7C) for Bsp22, BopB, and dmLT, respectively. Data for IL-10 is shown in (7D), (7E), and (7F) for Bsp22, BopB, and dmLT, respectively. Data for IL-6 is shown in (7G), (7H), and (7I) for Bsp22, BopB, and dmLT, respectively.

FIGS. 8A, 8B, and 8C shows IL-17 secretion. Splenocytes were extracted from 5 mice of each group and incubated with Bsp22, BopB or dmLT. After 48 h, supernatants were collected and levels of IL-17 secretion in response to labeled antigen were then measured by the MSD® U-Plex Platform Multiplex Assay and the data is shown in (8A) BopB, (8B) Bsp22, and (8C) dmLT. Each bar represents the mean of triplicate wells±S.D. Significance (Asterisk=P<0.05) was calculated for the comparison between labeled groups.

FIGS. 9A, 9B, 9C, 9D, 9E, and 9F show Th2 cytokine secretion. Splenocytes were extracted from 5 mice of each group and incubated with Bsp22, BopB or dmLT. After 48 h, supernatants were collected and levels of cytokine secretion in response to specified antigen were then measured (in pg/ml) using an MSD cytokine detection plate. Each bar represents mean of triplicate wells±S.D. Asterisk specified a P<0.05 when comparing specified groups. Data for IL-4 is shown in (9A), (9B), and (9C) for Bsp22, BopB, and dmLT, respectively. Data for IL-5 is shown in (9D), (9E), and (9F) for Bsp22, BopB, and dmLT, respectively.

Figure 10:
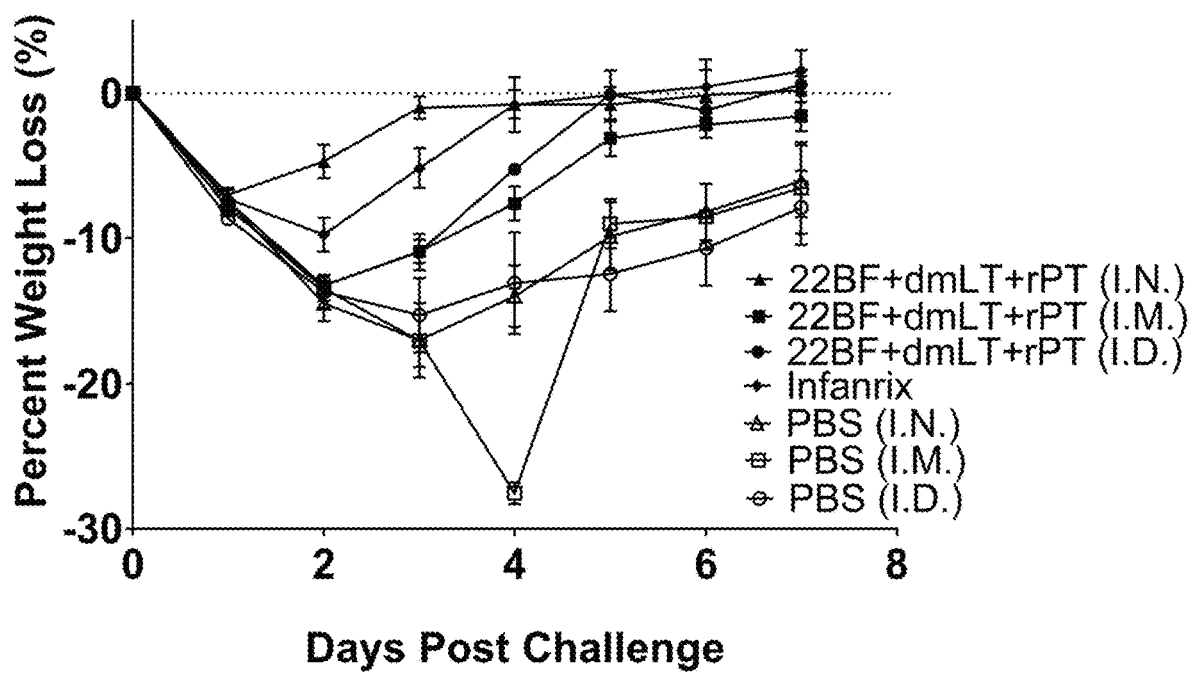
Figure 11:
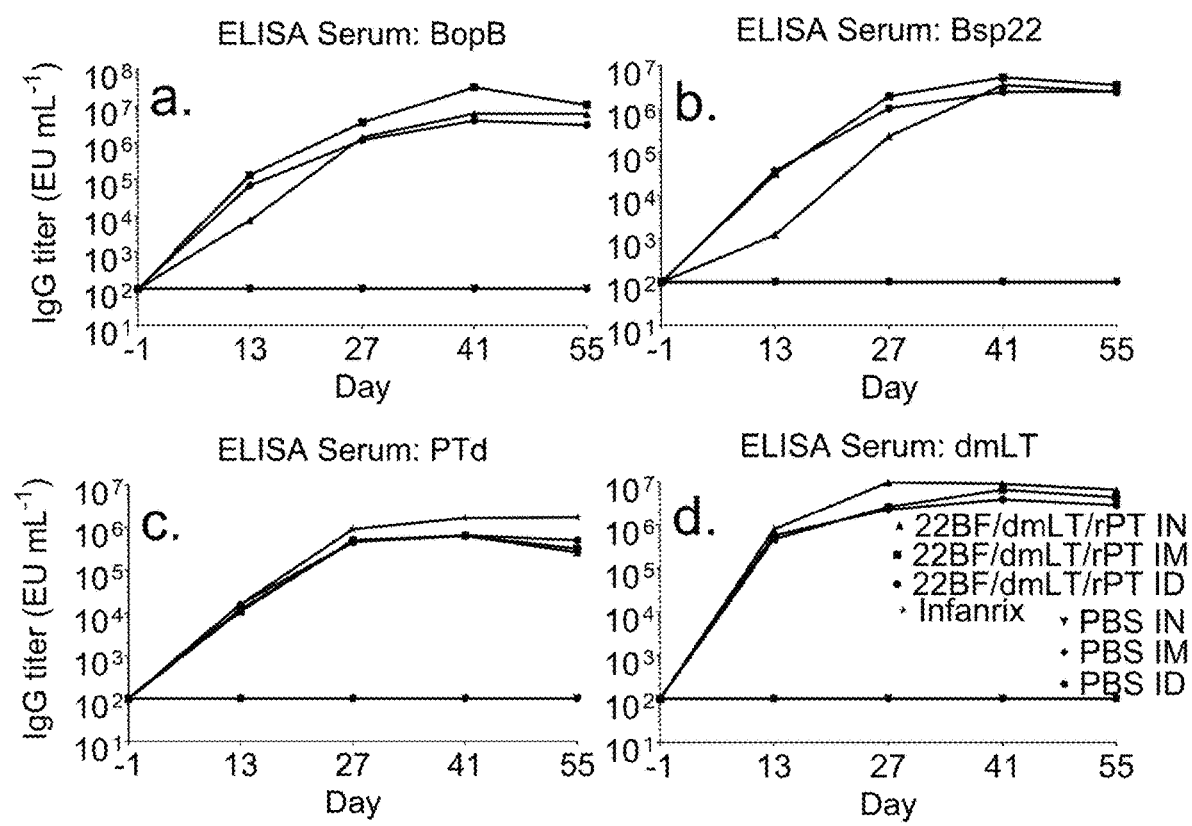

FIG. 10 shows the change in weight in percentage after infection with sublethal dosage of *B. pertussis* intranasally. There was an observable difference in weight loss between mice vaccinated with the 22BF+dmLT+PTd formulation and those that only received PBS. By Day 7 all mice aside from PBS treated mice had recovered to within 3% of pre-infection weight.

FIGS. 11A, 11B, 11C, and 11D show serum antibody responses to BopB, Bsp22, Pertussis Toxin Mutant, and dmLT. Mice were immunized on days 0, 14, and 28 with 22BF+PTd admixed with dmLT. Serum IgG antibodies specific for BopB, Bsp22, PTd, and dmLT were measured by ELISA and the data is shown in (11A) BopB, (11B) Bsp22, (11C) PTd, and (11D) dmLT. Data are the mean titers (EU ml^-1) from group pools of animal samples. An asterisk indicates a P value of 0.05 when comparing vaccinated mice and the PBS controls. No responses were seen in the control mice that received PBS. Mice vaccinated with Infanrix only displayed a response against pertussis toxin mutant, which is part of its formulation.

Figure 12:
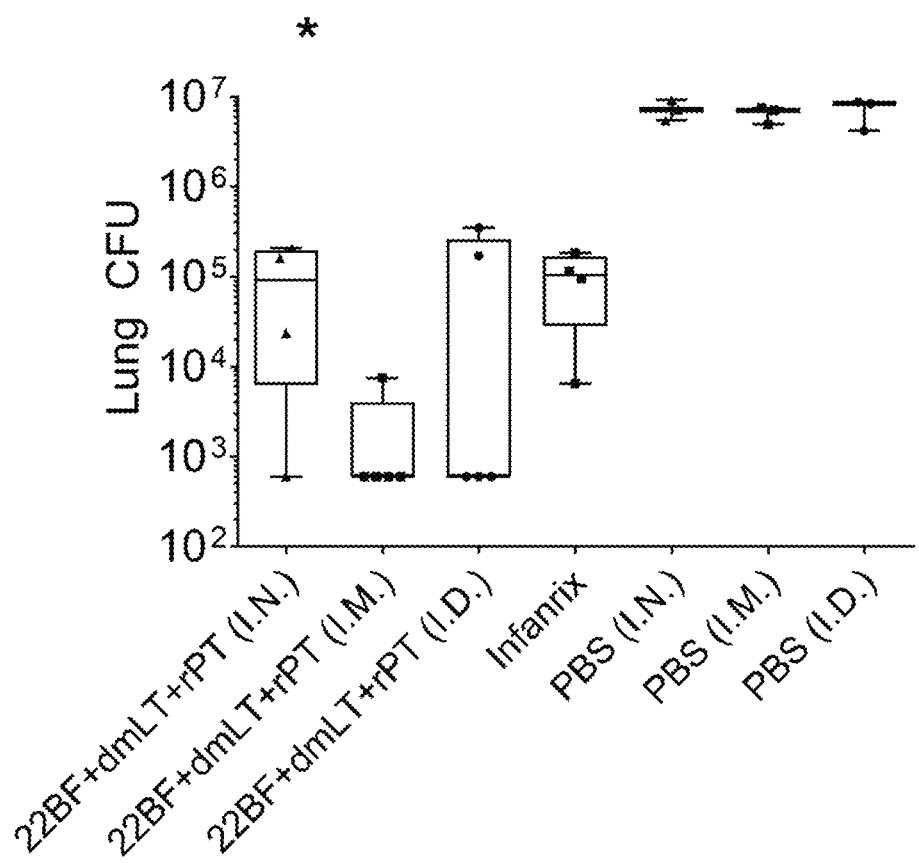

FIG. 12 shows the Lung Colony forming units (CFU) from mice 3 days post intranasal infection. Mice vaccinated intranasally with 22BF+PTd and dmLT showed statistical (P<0.05) decreases in lung CFUs when compared to PBS treated mice. The mice vaccinated intradermally and mice vaccinated intramuscularly with 22BF+PTd and dmLT either showed sterilizing immunity, or no statistical decrease in lung CFUs. Infanrix appeared to show a decrease in lung CFU, but this was not statistically significant (P>0.05). (*=P<0.05, KW p-value=0.0003).

Figure 13:
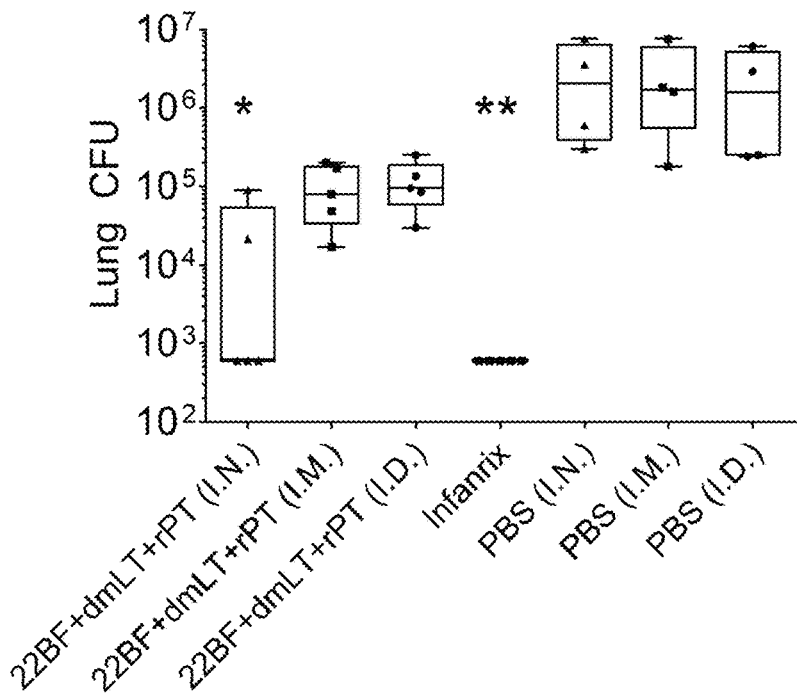

FIG. 13 shows the Lung Colony forming units (CFU) from mice 7 days post intranasal infection. Mice vaccinated intranasally with 22BF+PTd and dmLT showed statistical (P<0.05) decreases in lung CFUs when compared to PBS treated mice, with 60% of the mice showing sterilizing immunity. The mice vaccinated intramuscularly or intradermally with 22BF+PTd and dmLT showed no statistical decrease in lung CFUs. Infanrix appeared to display sterilizing immunity with CFU measuring below the limit of detection. (*=P<0.05, ** P<0.01, KW p-value=0.0001).

Figure 14:
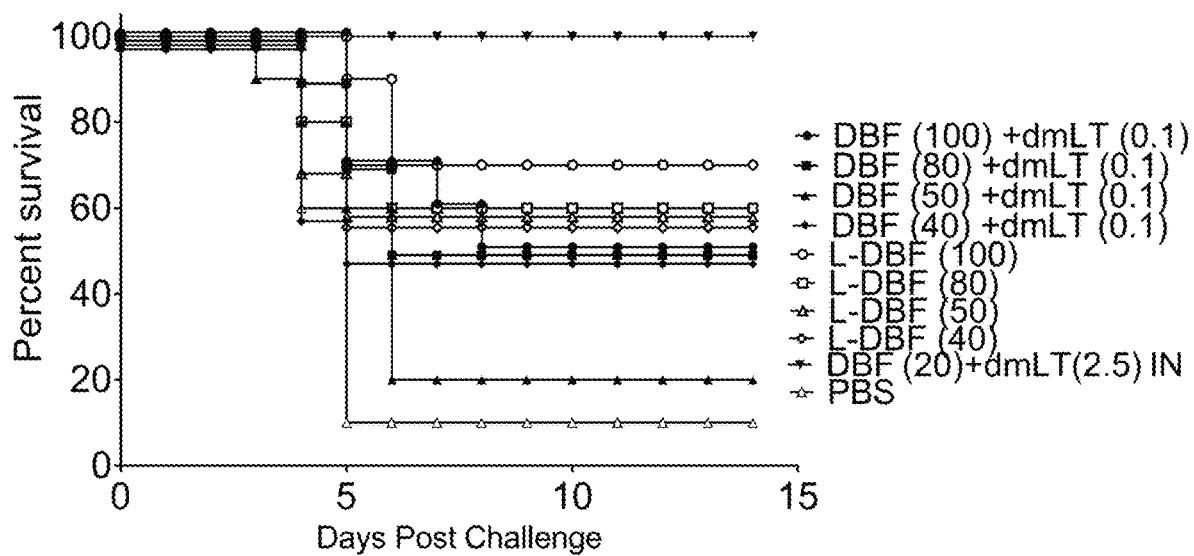

FIG. 14 shows the protective efficacy of LTA1–DBF vs DBF+dmLT. Mice were vaccinated intramuscularly on days 0, 14 and 28 with the indicated µg of DBF+0.1 µg dmLT or DBF equivalent of LTA1–DBF. The positive control was DBF+dmLT delivered intranasally. On day 56 the mice were challenged with *Shigella flexneri*. FIG. 14 indicates the percent survival of mice post infection with *Shigella flexneri*.

FIGS. 15A, 15B, and 15C show the kinetics of IgG response. Mice from FIG. 14 were bled prior to vaccination and on day 42. Sera were assessed for anti-IpaD, -IpaB and -dmLT IgG, and the data is shown in (15A) IpaD, (15Bb) IpaB, and (15C) dmLT. Differences in the IgG levels in mice vaccinated with dmLT vs. LTA1 are attributed to the recognition of the entire dmLT on the well.

FIGS. 16A, 16B, and 16C show the stimulation of antibody secreting cells from bone marrow. Bone marrow was collected on day 56. Single cell suspensions from 5 mice per group were stimulated in vitro IpaD, IpaB or dmLT. IgG (black) and IgA (white) ASC were measured by ELISpot, and the data is shown in (16A) IpaD, (16B) IpaB, and (16C) dmLT. Bars represent mean ASC per $10^6$ cells+SD from replicate wells.

FIGS. 17A, 17B, and 17C show the stimulation of antibody secreting cells from spleen. Spleens were collected on day 56. Single cell suspensions from 5 mice per group were stimulated in vitro IpaD, IpaB or dmLT. IgG (black) and IgA (white) ASC were measured by ELISpot. Bars represent mean ASC per $10^6$ cells+SD from replicate wells.

FIGS. 18A, 18B, and 18C show the stimulation of antibody secreting cells from lungs. Lungs were collected on day 56. Single cell suspensions from 5 mice per group were stimulated in vitro IpaD, IpaB or dmLT. IgG (black) and IgA (white) ASC were measured by ELISpot, and the data is shown in (18A) IpaD, (18B) IpaB, and (18C) dmLT. Bars represent mean ASC per $10^6$ cells +SD from replicate wells.

Figures 19A, 19B, 19C, 19D:
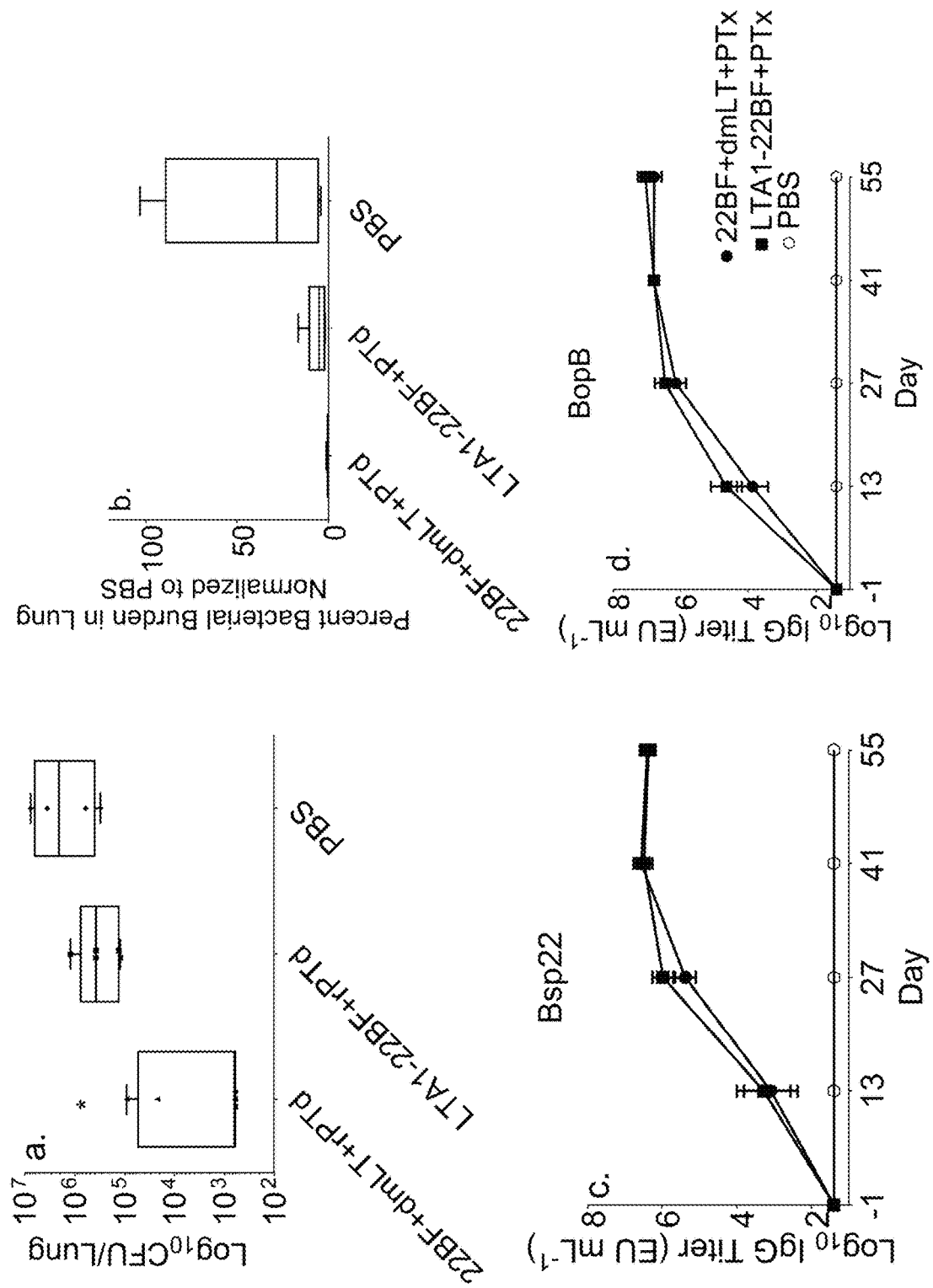

FIGS. 19A, 19B, 19C, and 19D show the protective efficacy and IgG response kinetics of LTA1-22BF. Mice were vaccinated on days 0, 14, 28 and challenged on day 56 with a sublethal dose of *B. pertussis*. On day 7 of the challenge, the CFU/lung were determined. FIG. 19A shows the CFU/lung while FIG. 19B shows the decrease in CFU compared to the PBS average. *=P<0.05 when compared to PBS. FIGS. 19C and 19D how the kinetics of the response of the anti-Bsp22 and anti-BopB IgG, respectively. No difference is seen between the mice vaccinated with 22BF+ dmLT and LTA1-22BF.

Figure 20:
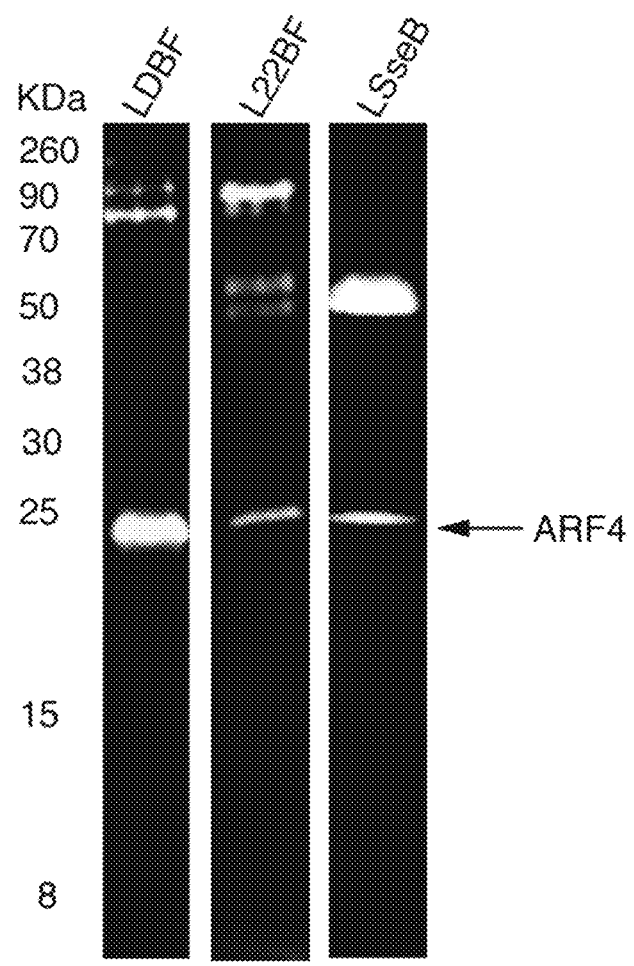

FIG. 20 shows the ADPr activity of L-antigens. LTA1 was fused to DBF, 22BF or SseB. LTA1, however, must retain its ADP-ribosylation activity to maintain adjuvant activity. The ADPr of NAD+ was biotin conjugated and LTA1 transferred the biotin-ADPr moiety to ARF4. The biotin was then detected with Streptavidin-IR800. Lane 1: LTA1-DBF; 2: LTA1-22BF; 3: LTA1-SseB.

V. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The needle tip protein and/or translocator proteins or antigenic portions thereof disclosed herein are used to elicit an immune response in subjects to whom they are administered. By "elicit an immune response", "induces or enhances an immune response", or "stimulates an immune response" which are used interchangeably herein, is meant that the subject mounts one or both of an innate and/or an adaptive immune reaction against antigenic determinants of the proteins or antigenic portions thereof that are administered. Preferably a statistically measurable induction or increase in an immune response over a control sample to which the needle tip protein and/or translocator proteins or antigenic portions thereof disclosed herein has not been administered. Preferably the induction or enhancement of the immune response results in a prophylactic or therapeutic response in a subject. In particular, the adaptive immune reaction entails production of e.g. B and T cell lymphocytes and antibodies specific for binding and forming complexes with the antigenic determinants. In some embodiments, the proteins and/or antigenic fragments thereof elicit a protective immune response in the subject, i.e. administration of one or more of the proteins and/or antigenic portions thereof results in an immune response that is protective against later challenge by the disease causing organism itself, either preventing infection altogether, or lessening the impact of infection by decreasing disease symptoms that would otherwise occur, had the subject not been vaccinated as described herein.

"Vaccine" as used herein is a preparation that stimulates an immune response that produces immunity against particular antigens, e.g. Gram negative bacteria. Vaccines may be administered prophylactically (for example, to prevent or inhibit the establishment of an infection) or therapeutically to inhibit, reduce, or treat an established infection, or to ameliorate the effects or symptoms of an infection. Vaccines may contain, but are not limited to, live, attenuated infectious material such as viruses or bacteria, and dead or inactivated organisms or purified products derived therefrom. A vaccine can be administered by injection, orally, or by inhalation. Injections may be, but are not limited to, subcutaneous (sc), intramuscular (im), intraperitoneal (ip), intradermal (id) or intravenous (iv).

"Optional" or "optionally" means that the subsequently described event or circumstance may or may not occur, and that the description includes instances where said event or circumstance occurs and instances where it does not.

The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient. The term "patient" refers to a subject under the treatment of a clinician, e.g., physician or veterinarian.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. COMPOSITIONS

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a particular needle tip protein (such as, for example, IpaD, SipD, SseB, Bsp22, LcrV, BipD, PcrV, CT053, or CT668), translocator protein (such as, for example, IpaB, SipB, SseC, BopB, YopB, BipB, PopB, CopB, or CopB2), or fusion polypeptide thereof (such as, for example, 22BF, BurkF, PaF, YerF, CT053-CopB, CT053-CopB2, CT668-CopB, or CT668-CopB2) is disclosed and discussed and a number of modifications that can be made to a number of molecules including the needle tip protein (such as, for example, IpaD, SipD, SseB, Bsp22, LcrV, BipD, PcrV, CT053, or CT668), translocator protein (such as, for example, IpaB, SipB, SseC, BopB, YopB, BipB, PopB, CopB, or CopB2), or fusion polypeptide thereof (such as, for example, 22BF, BurkF, PaF, YerF, CT053-CopB, CT053-CopB2, CT668-CopB, or CT668-CopB2) are discussed, specifically contemplated is each and every combination and permutation of needle tip protein such as, for example, IpaD, SipD, SseB, Bsp22, LcrV, BipD, PcrV, CT053, or CT668), translocator protein (such as, for example, IpaB, SipB, SseC, BopB, YopB, BipB, PopB, CopB, or CopB2), or fusion polypeptide thereof (such as, for example, DBF, S1, S2, 22BF, BurkF, PaF, YerF, CT053-CopB, CT053-CopB2, CT668-CopB, or CT668-CopB2) and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

To infect a host, B. pertussis uses an arsenal of well-characterized virulence factors. These factors include pertussis toxin (PT), adenylate cyclase toxin (ACT), the type III secretion system (T3SS), tracheal cytotoxin (TCT), dermonecrotic toxin (DNT), filamentous hemagglutinin (FHA), pertactin (PRN), and lipooligosaccharide (LOS). Current aP vaccines are comprised of PT, FHA, PRN, and the fimbrial proteins in varying proportions, but not necessarily all four proteins. Though the aP vaccine causes fewer adverse reactions than the wP vaccine, it is not as efficacious. This same situation exists for other pathogenic Gram negative bacteria. Accordingly, disclosed herein are fusion polypeptides from a Type III secretion system (T3SS) of a Gram negative bacteria (such as, for example, *Shigella* spp., *Salmonella enterica*, *Bordetella* spp. (such as, for example *B. pertussis* and/or *B. bronchiseptica*), *Burkholderia* spp. (such as, for example, *B. cepacian*, *B. mallei*, and/or *B. pseudomallei*), *Chlamydia* spp. (such as, for example, *C. trachomatis*), *Pseudomonas* spp., *Vibrio* spp. or *Yersinia* spp.) comprising a polypeptide of needle tip protein (such as, for example, IpaD, SipD, SseB, Bsp22, LcrV, BipD, PcrV, CT053, or CT668) or an antigenic fragment thereof and polypeptides of a translocator protein (such as, for example, IpaB, SipB, SseC, BopB, YopB, BipB, PopB, CopB, or CopB2) or an antigenic fragment thereof. In some aspect, the fusion polypeptide does not comprise a needle tip protein polypeptide or translocator polypeptide from a *Shigella* spp. (IpaD and IpaB) or a *Salmonella* spp. (such as, for example, *S. enterica*) (SipD, SseB, SipB, and SseC). It is recognized and herein contemplated that the disclosed polypeptides can be separate components of a composition or more preferably a fusion construct. By a "fusion polypeptide" is meant a peptide, polypeptide, or protein that is translated from a single, contiguous nucleic acid molecule, and which comprises sequences from at least two different proteins or antigenic regions thereof. Typically, the individual sequences are joined via a linker or spacer sequence of e.g. from about 2 to about 20 amino acids, usually from about 2 to about 10 amino acids. The amino acids in linking sequences are typically uncharged and the linker sequence usually does not exhibit secondary or tertiary structure, but does allow the fused protein/peptide segments to adopt functional secondary, tertiary, etc. conformations. One such exemplary fusion polypeptide includes Bsp22 (as set forth in SEQ ID NO: 4 and encoded by the nucleic acid sequence as set forth in SEQ ID NO: 3) and BopB (as set forth in SEQ ID NO: 6 and encoded by the nucleic acid sequence as set forth in SEQ ID NO: 5). The amino acid sequence of this chimera (i.e., 22BF) is set forth in SEQ ID NO: 2. The chimera may be encoded by any suitable nucleic acid sequence, e.g. the exemplary nucleic acid sequence depicted in SEQ ID NO: 1.

Thus, in one aspect, disclosed herein are fusion polypeptides comprising a fusion of a needle tip protein (such as, for example, IpaD, SipD, SseB, Bsp22, LcrV, BipD, PcrV, CT053, or CT668) or an antigenic fragment thereof and a translocator protein (such as, for example, IpaB, SipB, SseC, BopB, YopB, BipB, PopB, CopB, or CopB2) or an antigenic fragment thereof from a Type III secretion system (T3SS) of a Gram negative bacteria (such as, for example, *Bordetella* spp., *Burkholderia* spp., *Chlamydia* spp., *Pseudomonas* spp., *Vibrio* spp. or *Yersinia* spp. For example, the fusion polypeptide can comprise a fusion of the *Shigella* spp. needle tip protein (IpaD) and first translocator protein (IpaB) or fragments thereof (the fusion referred to as DBF), *Salmonella* spp. (such as, for example, *S. enterica*) SPI-1 needle tip protein (SipD) (as set forth in SEQ ID NO: 52 and encoded by the nucleic acid sequence as set forth in SEQ ID NO: 51) and translocator protein (SipB) (as set forth in SEQ ID NO: 54 and encoded by the nucleic acid sequence as set forth in SEQ ID NO: 53) or fragments thereof (the fusion referred to as S1) (as set forth in SEQ ID NO: 56 and encoded by the nucleic acid sequence as set forth in SEQ ID NO: 55), *Salmonella* spp. (such as, for example, *S. enterica*) SPI-2 needle tip protein (SseB) (as set forth in SEQ ID NO: 62 and encoded by the nucleic acid sequence as set forth in SEQ ID NO: 61) and translocator protein (SseC) (as set forth in SEQ ID NO: 64 and encoded by the nucleic acid sequence as set forth in SEQ ID NO: 63) or fragments thereof (the fusion referred to as S2) (as set forth in SEQ ID NO: 66 and encoded by the nucleic acid sequence as set forth in SEQ ID NO: 65), *Bordetella* spp. needle-tip protein (Bsp22) and translocator protein (BopB), or fragments thereof (the fusion referred to as 22BF); a fusion of the *Yersinia* spp. needle-tip protein (LcrV) (as set forth in SEQ ID NO: 42 and encoded by the nucleic acid sequence as set forth in SEQ ID NO: 41) and translocator protein (YopB) (as set forth in SEQ ID NO: 44 and encoded by the nucleic acid sequence as set forth in SEQ ID NO: 43), or fragments thereof (the fusion referred to as YerF) (as set forth in SEQ ID NO: 46 and encoded by the nucleic acid sequence as set forth in SEQ ID NO: 45); a fusion of the *Burkholderia* spp. needle-tip protein (BipD) (as set forth in SEQ ID NO: 22 and encoded by the nucleic acid sequence as set forth in SEQ ID NO: 21) and translocator protein (BipB) (as set forth in SEQ ID NO: 24 and encoded by the nucleic acid sequence as set forth in SEQ ID NO: 23), or fragments thereof (the fusion referred to as BurkF) (as set forth in SEQ ID NO: 26 and encoded by the nucleic acid sequence as set forth in SEQ ID NO: 25); a fusion of the *Pseudomonas* spp. needle-tip protein (PcrV) (as set forth in SEQ ID NO: 32 and encoded by the nucleic acid sequence as set forth in SEQ ID NO: 31) and translocator protein (PopB) (as set forth in SEQ ID NO: 34 and encoded by the nucleic acid sequence as set forth in SEQ ID NO: 33), or fragments thereof (the fusion referred to as PaF) (as set forth in SEQ ID NO: 36 and encoded by the nucleic acid sequence as set forth in SEQ ID NO: 35); and/or a fusion of the *Chlamydia* spp. needle-tip protein CT053 (as set forth in SEQ ID NO: 74 and encoded by the nucleic acid sequence as set forth in SEQ ID NO: 73) or CT668 (as set forth in SEQ ID NO: 84 and encoded by the nucleic acid sequence as set forth in SEQ ID NO: 83) and translocator protein (CopB (as set forth in SEQ ID NO: 76 and encoded by the nucleic acid sequence as set forth in SEQ ID NO: 75) or CopB2 (as set forth in SEQ ID NO: 92 and encoded by the nucleic acid sequence as set forth in SEQ ID NO: 91)), or fragments thereof such fusions including but not limited to CT053-CopB (the CT053-CopB fusion as set forth in SEQ ID NO: 78 and encoded by the nucleic acid sequence as set forth in SEQ ID NO: 77), CT668-CopB (the CT668-CopB fusion as set forth in SEQ ID NO: 86 and encoded by the nucleic acid sequence as set forth in SEQ ID NO: 85), CT053-CopB2 (the CT053-CopB2 fusion as set forth in SEQ ID NO: 94 and encoded by the nucleic acid sequence as set forth in SEQ ID NO: 93), and CT053-CopB2 (the CT668-CopB2 fusion as set forth in SEQ ID NO: 100 and encoded by the nucleic acid sequence as set forth in SEQ ID NO: 99) and collectively each fusion being referred to as ChlamF. In one aspect, the fusion polypeptide does not comprise any needle tip protein or translocator protein or fragment thereof from a *Salmonella* spp. or a *Shigella* spp. Accordingly, disclosed herein are fusion polypeptides comprising a fusion of a needle tip protein (such as, for example, Bsp22, LcrV, BipD, PcrV, CT053, or CT668) or an antigenic fragment thereof and a translocator protein (such as, for example, BopB, YopB, BipB, PopB, CopB, or CopB2) or an antigenic fragment thereof from a Type III secretion system (T3SS) of a Gram negative bacteria (such as, for example, *Bordetella* spp., *Burkholderia* spp., *Chlamydia* spp., *Pseudomonas* spp., *Vibrio* spp. or *Yersinia* spp. wherein the gram negative bacteria is not a *Salmonella enterica* or *Shigella* spp.

It is understood and herein contemplated that the arrangement of the polypeptides in a fusion construct can have significant impact on the antigenicity of the fusion construct. Accordingly, in one aspect, disclosed herein are fusion polypeptides, wherein the fusion polypeptide is arranged such that the needle tip protein is 5' of the translocator protein.

The present invention provides compositions for use in eliciting an immune response and/or vaccinating an individual against Gram negative bacterial infection, and/or against disease symptoms caused by Gram negative bacterial infection. The compositions include one or more substantially purified proteins, polypeptides or antigenic regions thereof as described herein, or substantially purified nucleic acid sequences (e.g. DNA cDNA, RNA, etc.) encoding such proteins, polypeptides or antigenic regions thereof, and a pharmacologically suitable/compatible carrier. By "substantially purified" is meant that the molecule is largely free of other organic molecules, cellular debris, solvents, etc. when tested using standard techniques known to those of skill in the art (e.g. gel electrophoresis, column chromatography, sequencing, mass spectroscopy, etc.). For example, the molecule is generally at least about 50, 55, 60, 65, 70, or 75% pure by wt %, and preferably is at least about 80, 85, 90, 95% or more preferably pure (e.g. 96, 97, 98, 99 or even 100% pure). The preparation of proteins, polypeptides, and peptides as described herein is well-known to those in the art, and includes, for example, recombinant preparation; isolation from a natural source; chemical synthesis; etc. The purification of proteinaceous materials is also known. However, specific exemplary methods for preparing the vaccinating agents utilized in the practice of the invention are described in detail in the Examples section below.

In addition, the composition may contain adjuvants, many of which are known in the art. For example, adjuvants suitable for use in the invention include but are not limited to: bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof. Non-toxic derivatives of LPS include monophosphoryl lipid A (MPL) and 3-O-deacylated MPL (3dMPL). 3dMPL is a mixture of three de-O-acylated monophosphoryl lipid A with 4, 5 or 6 acylated chains. A preferred non-toxic derivative of LPS is 3 De-O-acylated monophosphoryl lipid A. Other non-toxic LPS derivatives include monophosphoryl lipid A mimics, such as aminoalkyl glucosaminide phosphate derivatives, e.g. RC-529.

Lipid A derivatives include derivatives of lipid A from *Escherichia coli* such as OM-174. Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory. The CpG's can include nucleotide modifications/analogs such as phosphorothioate modifications and can be double-stranded or single-stranded, e.g. replacement of guanosine with 2'-deoxy-7-deazaguanosine. The CpG sequence may include, for example, the motif GTCGTT or TTCGTT. The CpG sequence may be specific for inducing a Th1 immune response, such as a CpG-A ODN, or it may be more specific for inducing a B cell response, such a CpG-B ODN, CpG-A and CpG-B ODNs. Preferably, the CpG is a CpG-A ODN. Preferably, the CpG oligonucleotide is constructed so that the 5' end is accessible for receptor recognition. Optionally, two CpG oligonucleotide sequences may be attached at their 3' ends to form "immunomers".

Bacterial ADP-ribosylating toxins and detoxified derivatives thereof may be used as adjuvants in the invention. Preferably, the protein is derived from *E. coli* (e.g. *E. coli* heat labile enterotoxin "LT"), cholera ("CT") Table 1), or pertussis ("PT").

The toxin or toxoid is preferably in the form of aholotoxin, comprising both A and B subunits. Preferably, the A subunit contains adetoxifying mutation; preferably the B subunit is not mutated. More preferably, the adjuvant is adetoxified LT mutant such as LT-K63, LT-R72, and LT-G192. The use of ADP-ribosylating toxins and detoxified derivatives thereof, particularly LT-K63 and LT-R72, is known. Such adjuvants are described, for example, in issued U.S. Pat. No. 8,039,007 (the complete contents of which is hereby incorporated by reference in entirety). Various interleukins may also be used as adjuvants to increase the immune response in a subject. In preferred embodiments, the adjuvant is a mucosal adjuvant such as, for example, the double mutant heat-labile toxin (dmLT) as set forth in SEQ ID NOs: 113 and 114) from enterotoxigenic *E. coli* or the active moiety thereof known as LTA1 (as set forth in SEQ ID NO: 13 and encoded by the nucleic acid sequence as set forth in SEQ ID NO: 12) and encoded by nor cholera toxin or the active moiety thereof known as CTA1. Accordingly, disclosed herein are fusion polypeptides of any preceding aspect, wherein the fusion further comprises an adjuvant such as, for example, double mutant labile toxin (dmLT) or an antigenic fragment thereof (such as, for example, LTA1 or CTA1) from Enterotoxigenic *Escherichia coli*. In some aspect, the dmLT or fragment thereof can also be fused to the needle tip protein-translocator protein fusion at the 5' end.

TABLE 1

| Cholera Toxin (CTA1) subunits and sequences | | |
|---|---|---|
| Subunit | DNA sequence | AA sequence |
| Subunit A | ATGGTAAAGATAATATTTGTGTTTTTTATTTTCTT<br>ATCATCATTTTCATATGCAAATGATGATAAGTTAT<br>ATCGGGCAGATTCTAGACCTCCTGATGAAATAAA<br>GCAGTCAGGTGGTCTTATGCCAAGAGGACAGAGT<br>GAGTACTTTGACCGAGGTACTCAAATGAATATCA<br>ACCTTTATGATCATGCAAGAGGAACTCAGACGGG<br>ATTTGTTAGGCACGATGATGGATATGTTTCCACCT<br>CAATTAGTTTGAGAAGTGCCCACTTAGTGGGTCA<br>AACTATATTGTCTGGTCATTCTACTTATTATATAT<br>ATGTTATAGCCACTGCACCCAACATGTTTAACGTT<br>AATGATGTATTAGGGGCATACAGTCCTCATCCAG<br>ATGAACAAGAAGTTTCTGCTTTAGGTGGGATTCC<br>ATACTCCCAAATATATGGATGGTATCGAGTTCAT<br>TTTGGGGTGCTTGATGAACAATTACATCGTAATA<br>GGGGCTACAGAGATAGATATTACAGTAACTTAGA<br>TATTGCTCCAGCAGCAGATGGTTATGGATTGGCA<br>GGTTTCCCTCCGGAGCATAGAGCTTGGAGGGAAG<br>AGCCGTGGATTCATCATGCACCGCCGGGTTGTGG<br>GAATGCTCCAAGATCATCGATCAGTAATACTTGC<br>GATGAAAAAACCCAAAGTCTAGGTGTAAAATTCC<br>TTGACGAATACCAATCTAAAGTTAAAAGACAAAT<br>ATTTTCAGGCTATCAATCTGATATTGATACACATA<br>ATAGAATTAAGGATGAATTATGA<br>(SEQ ID NO: 115) | MVKIIFVFFIFLSSFSYAND<br>DKLYRADSRPPDEIKQSGG<br>LMPRGQSEYFDRGTQMNI<br>NLYDHARGTQTGFVRHDD<br>GYVSTSISLRSAHLVGQTIL<br>SGHSTYYIYVIATAPNMFN<br>VNDVLGAYSPHPDEQEVS<br>ALGGIPYSQIYGWYRVHFG<br>VLDEQLHRNRGYRDRYYS<br>NLDIAPAADGYGLAGFPPE<br>HRAWREEPWIHHAPPGCG<br>NAPRSSMSNTCDEKTQSLG<br>VKFLDEYQSKVKRQIFSGY<br>QSDIDTHNRIKDEL<br>(SEQ ID NO: 116) |
| Subunit B | ATGATTAAATTAAAATTTGGTGTTTTTTTTACAGT<br>TTTACTATCTTCAGCATATGCACATGGAACACCTC<br>AAAATATTACTGATTTGTGTGCAGAATACCACAA<br>CACACAAATATATACGCTAAATGATAAGATATTT<br>TCGTATACAGAATCTCTAGCTGGAAAAAGAGAGA<br>TGGCTATCATTACTTTTAAGAATGGTGCAATTTTT<br>CAAGTAGAAGTACCAGGTAGTCAACATATAGATT<br>CACAAAAAAAGCGATTGAAAGGATGAAGGATA<br>CCCTGAGGATTGCATATCTTACTGAAGCTAAAGT<br>CGAAAAGTTATGTGTATGGAATAATAAAACGCCT<br>CATGCGATTGCCGCAATTAGTATGGCAAATTAA<br>(SEQ ID NO: 117) | MIKLKFGVFFTVLLSSAYA<br>HGTPQNITDLCAEYHNTQI<br>YTLNDKIFSYTESLAGKRE<br>MAIITFKNGAIFQVEVPGS<br>QHIDSQKKAIERMKDTLRI<br>AYLTEAKVEKLCVWNNKT<br>PHAIAAISMAN<br>(SEQ ID NO: 118) |

For example, specifically disclosed herein are LTA1-DBF, LTA1-S1 (as set forth in SEQ ID NO: 57 and encoded by the nucleic acid sequence as set forth in SEQ ID NO: 58), LTA1-S2 (as set forth in SEQ ID NO: 68 and encoded by the nucleic acid sequence as set forth in SEQ ID NO: 67), LTA1-SseB (as set forth in SEQ ID NO: 70 and encoded by the nucleic acid sequence as set forth in SEQ ID NO: 69), LTA1-22BF (as set forth in SEQ ID NO: 18 and encoded by the nucleic acid sequence as set forth in SEQ ID NO: 17), LTA1-BurkF (as set forth in SEQ ID NO: 28 and encoded by the nucleic acid sequence as set forth in SEQ ID NO: 27), LTA1-CT668-CopB (as set forth in SEQ ID NO: 88 and encoded by the nucleic acid sequence as set forth in SEQ ID NO: 87), LTA1-CT668-CopB2 (as set forth in SEQ ID NO: 102 and encoded by the nucleic acid sequence as set forth in SEQ ID NO: 101), LTA1-CT053-CopB (as set forth in SEQ ID NO: 80 and encoded by the nucleic acid sequence as set forth in SEQ ID NO: 79), LTA1-CT053-CopB2 (as set forth in SEQ ID NO: 96 and encoded by the nucleic acid sequence as set forth in SEQ ID NO: 95), LTA1-PaF (as set forth in SEQ ID NO: 38 and encoded by the nucleic acid sequence as set forth in SEQ ID NO: 37), and LTA1-YerF (as set forth in SEQ ID NO: 48 and encoded by the nucleic acid sequence as set forth in SEQ ID NO: 47).

Whooping cough still causes significant mortality and morbidity in children all over the world. It also continues to be a problem in adults whose immunity has waned. Herein is disclosed a strong candidate for a new protective vaccine based on research on the T3SS proteins and resulting subunit vaccines, including the vaccine against shigellosis. It is demonstrated herein that the vaccine has 100% protective efficacy against *B. bronchiseptica* using 22BF+dmLT. While this is a remarkable step forward, examined herein is the immune response and the protective efficacy of 22BF+dmLT±PTd against *B. pertussis*. The vaccine can also be taken a step further by eliciting sterilizing immunity so that the *B. pertussis* transmission chain can be broken.

Originally, the mechanism of protection against *B. pertussis*, an extracellular organism, was thought to be the humoral immune response, however, cell-mediated immunity has been found to also be important for protection with bacterial clearance mediated by Th1 and Th17 cells. By measuring cytokines corresponding to specific immune pathways, Ross et al. concluded that the wP vaccine promotes Th1 and Th17 responses while the aP vaccine elicits a mix of Th1 and Th2 responses. These differences likely account for the increased protection seen for the wP vaccine. A study in a baboon model compared wP vaccines with an aP vaccine and confirmed that the wP elicits a Th1/Th17 response while the aP vaccine elicits a Th1/Th2 response. Moreover, these studies found that aP does not prevent colonization or transmission of *B. pertussis*, even in asymptomatic subjects. Thus, the current pertussis resurgence could be due, in part, to the ability of the aP vaccine to protect the host against the overt symptoms of the disease while not preventing colonization and the resulting transmission of *B. pertussis* to susceptible children. Furthermore, protection of newborns against pertussis via aP or wP is problematic due not only to possible side effects but also because newborns lack the ability to mount a vaccine-induced Th1 response elicited through the requisite antigen presentation and T-cell activation. Although it has been shown, in some cases, that neonatal immunization can prime the immune system for subsequent booster vaccinations, the development of a protective pertussis vaccine for infants remains a need.

As noted above, the current aP vaccine does not provide sterilizing immunity. That is, the aP vaccine protects the immunized host, but does not stop colonization and transmission of the *Bordetella* spp. In one aspect, disclosed herein are fusion polypeptides of any preceding aspect, wherein the composition or fusion polypeptide further comprises an acellular Gram negative vaccine component (such as, for example, the acellular pertussis vaccine (aP) component pertussis toxoid (PTd)).

Pertussis toxin (PTX) is produced by *Bordetella pertussis*, the bacterium responsible for whooping cough. Pertussis toxin is a multi-component protein composed of six non-covalently bound subunits ranging in molecular weight from approximately about 9 kDa to about 28 kDa. These subunits are designated as S1, S2, S3, S4 and S5 and occur in native pertussis toxin in a ratio of 1:1:1:2:1, where the subunit S4 is present in two copies The largest subunit S1, also called the A protomer, is responsible for the ADP-ribosyltransferase activity. List Labs produces Pertussis Toxin Mutant R9K, E129A (both in the S1 subunit), a genetically inactivated mutant of pertussis toxin, which has a modified sequence encoding the enzyme subunit (Table 2). Virulence of this pertussis mutant is reduced relative to that found with the wild type.

TABLE 2

Pertussis Toxic Mutant R9K, E129A

| Subunit | DNA sequence | AA sequence |
| --- | --- | --- |
| Subunit 1 | ATGCGTTGCACTCGGGCAATTCGCCAAACCGC | MRCTRAIRQTARTGWLTWL |
|  | AAGAACAGGCTGGCTGACGTGGCTGGCGATT | AILAVTAPVTSPAWADDPPA |
|  | CTTGCCGTCACGGCGCCCGTGACTTCGCCGGC | TVYRYDSRPPEDVFQNGFTA |
|  | ATGGGCCGACGATCCTCCCGCCACCGTATACC | WGNNDNVLDHLTGRSCQV |
|  | GCTATGACTCCCGCCCGCCGGAGGACGTTTTC | GSSNSAFVSTSSSRRYTEVYL |
|  | CAGAACGGATTCACGGCGTGGGGAAACAACG | EHRMQEAVEAERAGRGTGH |
|  | ACAATGTGCTCGACCATCTGACCGGACGTTCC | FIGYIYEVRADNNFYGNASS |
|  | TGCCAGGTCGGCAGCAGCAACAGCGCTTTCGT | YPEYVDTYGDNAGRILAGA |
|  | CTCCACCAGCAGCAGCCGGCGCTATACCGAG | LATYQSEYLAHRRIPPENIRR |
|  | GTCTATCTCGAACATCGCATGCAGGAAGCGGT | VTRVYHNGITGETTTTEYSN |
|  | CGAGGCCGAACGCGCCGGCAGGGGCACCGGC | ARYVSQQTRANPNPYTSRRS |
|  | CACTTCATCGGCTACATCTACGAAGTCCGCGC | VASIVGTLVRMAPVIGACM |

TABLE 2-continued

| Pertussis Toxic Mutant R9K, E129A | | |
|---|---|---|
| Subunit | DNA sequence | AA sequence |
| | CGACAACAATTTCTACGGCGCCGCCAGCTCGT<br>ACTTCGAATACGTCGACACTTATGGCGACAAT<br>GCCGGCCGTATCCTCGCCGGCGCGCTGGCCAC<br>CTACCAGAGCGAATATCTGGCACACCGGCGC<br>ATTCCGCCCGAAAACATCCGCAGGGTAACGC<br>GGGTCTATCACAACGGCATCACCGGCGAGAC<br>CACGACCACGGAGTATTCCAACGCTCGCTACG<br>TCAGCCAGCAGACTCGCGCCAATCCCAACCCC<br>TACACATCGCGAAGGTCCGTAGCGTCGATCGT<br>CGGCACATTGGTGCGCATGGCGCCGGTGATA<br>GGCGCTTGCATGGCGCGGCAGGCCGAAAGCT<br>CCGAGGCCATGGCAGCCTGGTCCGAACGCGC<br>CGGCGAGGCGATGGTTCTCGTGTACTACGAA<br>AGCATCGCGTATTCGTTCTAG<br>(SEQ ID NO: 103) | ARQAESSEAMAAWSERAGE<br>AMVLVYYESIAYSF<br>(SEQ ID NO: 104) |
| Subunit 2 | ATGCCGATCGACCGCAAGACGCTCTGCCATCT<br>CCTGTCCGTTCTGCCGTTGGCCCTCCTCGGAT<br>CTCACGTGGCGCGGGCCTCCACGCCAGGCATC<br>GTCATTCCGCCGCAGGAACAGATTACCCAGC<br>ATGGCAGCCCCTATGGACGCTGCGCGAACAA<br>GACCCGTGCCCTGACCGTGGCGGAATTGCGC<br>GGCAGCGGCGATCTGCAGGAGTACCTGCGTC<br>ATGTGACGCGCGGCTGGTCAATATTTGCGCTC<br>TACGATGGCACCTATCTCGGCGGCGAATATGG<br>CGGCGTGATCAAGGACGGAACACCCGGCGGC<br>GCATTCGACCTGAAAACGACGTTCTGCATCAT<br>GACCACGCGCAATACGGGTCAACCCGCAACG<br>GATCACTACTACAGCAACGTCACCGCCACTCG<br>CCTGCTCTCCAGCACCAACAGCAGGCTATGCG<br>CGGTCTTCGTCAGAAGCGGGCAACCGGTCATT<br>GGCGCCTGCACCAGCCCGTATGACGGCAAGT<br>ACTGGAGCATGTACAGCCGGCTGCGGAAAAT<br>GCTTTACCTGATCTACGTGGCCGGCATCTCCG<br>TACGCGTCCATGTCAGCAAGGAAGAACAGTA<br>TTACGACTATGAGGACGCAACGTTCGAGACTT<br>ACGCCCTTACCGGCATCTCCATCTGCAATCCT<br>GGATCATCCTTATGCTGA<br>(SEQ ID NO: 105) | MPIDRKTLCHLLSVLPLALL<br>GSHVARASTPGIVIPPQEQIT<br>QHGGPYGRCANKTRALTVA<br>ELRGSGDLQEYLRHVTRGW<br>SIFALYDGTYLGGEYGGVIK<br>DGTPGGAFDLKTTFCIMTTR<br>NTGQPATDHYYSNVTATRL<br>LSSTNSRLCAVFVRSGQPVIG<br>ACTSPYDGKYWSMYSRLRK<br>MLYLIYVAGISVRVHVSKEE<br>QYYDYEDATFETYALTGISI<br>CNPGSSLC<br>(SEQ ID NO: 106) |
| Subunit 3 | ATGCTGATCAACAACAAGAAGCTGCTTCATCA<br>CATTCTGCCCATCCTGGTGCTCGCCCTGCTGG<br>GCATGCGCACGGCCCAGGCCGTTGCGCCAGG<br>CATCGTCATCCCGCCGAAGGCACTGTTCACCC<br>AACAGGGCGGCGCCTATGGACGCTGCCCGAA<br>CGGAACCCGCGCCTTGACCGTGGCCGAACTG<br>CGCGGCAACGCCGAATTGCAGACGTATTTGC<br>GCCAGATAACGCCCGGCTGGTCCATATACGGT<br>CTCTATGACGGTACGTACCTGGGCCAGGCGTA<br>CGGCGGCATCATCAAGGACGCGCCGCCAGGC<br>GCGGGGTTCATTTATCGCGAAACTTTCTGCAT<br>CACGACCATATACAAGACCGGGCAACCGGCT<br>GCGGATCACTACTACAGCAAGGTCACGGCCA<br>CGCGCCTGCTCGCCAGCACCAACAGCAGGCT<br>GTGCGCGGTATTCGTCAGGGACGGGCAATCG<br>GTCATCGGAGCCTGCGCCAGCCCGTATGAAG<br>GCAGGTACAGAGACATGTACGACGCGCTGCG<br>GCGCCTGCTGTACATGATCTATATGTCCGGCC<br>TTGCCGTACGCGTCCACGTCAGCAAGGAAGA<br>GCAGTATTACGACTACGAGGACGCCACATTCC<br>AGACCTATGCCCTCACCGGCATTTCCCTCTGC<br>AACCCGGCAGCGTCGATATGCTGA<br>(SEQ ID NO: 107) | MLINNKKLLHHILPILVLALL<br>GMRTAQAVAPGIVIPPKALF<br>TQQGGAYGRCPNGTRALTV<br>AELRGNAELQTYLRQITPGW<br>SIYGLYDGTYLGQAYGGIIK<br>DAPPGAGFIYRETFCITTIYK<br>TGQPAADHYYSKVTATRLL<br>ASTNSRLCAVFVRDGQSVIG<br>ACASPYEGRYRDMYDALRR<br>LLYMIYMSGLAVRVHVSKE<br>EQYYDYEDATFQTYALTGIS<br>LCNPAASIC<br>(SEQ ID NO: 108) |
| Subunit 4 | ATGCTGAGACGCTTCCCCACTCGAACCACCGC<br>CCCGGGACAGGGCGGCGCCCGGCGGTCGCGC<br>GTGCGCGCCCTGGCGTGGTTGCTGGCATCCGG<br>CGCGATGACGCATCTTTCCCCCGCCCTGGCCG<br>ACGTTCCTTATGTGCTGGTGAAGACCAATATG<br>GTGGTCACCAGCGTAGCCATGAAGCCGTATG<br>AAGTCACCCCGACGCGCATGCTGGTCTGCGGC<br>ATCGCCGCCAAACTGGGCGCCGCGGCCAGCA<br>GCCCGGACGCGCACGTGCCGTTCTGCTTCGGC<br>AAGGATCTCAAGCGTCCCGGCAGCAGTCCCA<br>TGGAAGTCATGTTGCGCGCCGTCTTCATGCAA<br>CAACGGCCGCTGCGCATGTTTCTGGGTCCCAA | MLRRFPTRTTAPGQGGARRS<br>RVRALAWLLASGAMTHLSP<br>ALADVPYVLVKTNMVVTSV<br>AMKPYEVTPTRMLVCGIAA<br>KLGAAASSPDAHVPFCFGKD<br>LKRPGSSPMEVMLRAVFMQ<br>QRPLRMFLGPKQLTFEGKPA<br>LELIRMVECSGKQDCP<br>(SEQ ID NO: 110) |

TABLE 2-continued

Pertussis Toxic Mutant R9K, E129A

| Subunit | DNA sequence | AA sequence |
|---|---|---|
| | GCAACTCACTTTCGAAGGCAAGCCCGCGCTCG AACTGATCCGGATGGTCGAATGCAGCGGCAA GCAGGATTGCCCCTGA (SEQ ID NO: 109) | |
| Subunit 5 | ATGCAGCGGCAAGCAGGATTGCCCCTGAAGG CGAACCCCATGCATACCATCGCATCCATCCTG TTGTCCGTGCTCGGCATATACAGCCCGGCTGA CGTCGCCGGCTTGCCGACCCATCTGTACAAGA ACTTCACTGTCCAGGAGCTGGCCTTGAAACTG AAGGGCAAGAATCAGGAGTTCTGCCTGACCG CCTTCATGTCGGGCAGAAGCCTGGTCCGGGCG TGCCTGTCCGACGCGGGACACGAGCACGACA CGTGGTTCGACACCATGCTTGGCTTTGCCATA TCCGCGTATGCGCTCAAGAGCCGGATCGCGCT GACGGTGGAAGACTCGCCGTATCCGGGCACT CCCGGCGATCTGCTCGAACTGCAGATCTGCCC GCTCAACGGATATTGCGAATGA (SEQ ID NO: 111) | MQRQAGLPLKANPMHTIASI LLSVLGIYSPADVAGLPTHL YKNFTVQELALKLKGKNQE FCLTAFMSGRSLVRACLSDA GHEHDTWFDTMLGFAISAY ALKSRIALTVEDSPYPGTPG DLLELQICPLNGYCE (SEQ ID NO: 112) |

It is understood and herein contemplated that the disclosed polypeptides, adjuvants, and acellular vaccine components for use in eliciting an immune response or for treating, inhibiting, or preventing a Gram negative bacterial infection can be administered in compositions such as vaccines as individual polypeptides or as a fusion construct or a combination thereof. Thus, in one aspect, disclosed herein are compositions comprising a T3SA needle tip protein (such as, for example, Bsp22, LcrV, BipD, PcrV, CT053, or CT668) or an antigenic fragment thereof from a Gram negative bacteria (such as, for example, *Bordetella* spp., *Burkholderia* spp., *Chlamydia* spp., *Pseudomonas* spp., *Vibrio* spp. or *Yersinia* spp.) and a T3SA translocator protein (such as, for example, BopB, YopB, BipB, PopB, CopB, or CopB2) or an antigenic fragment thereof from a Gram negative bacteria; wherein the gram negative bacteria is not a *Salmonella enterica* or *Shigella* spp. In one aspect, the composition can comprise the needle tip protein or fragment thereof and the translocator protein or fragment thereof as separate components or as a fusion polypeptide. Also disclosed herein are compositions of any preceding aspect, wherein the composition comprises an adjuvant (such as, for example, cholera toxin, CTA1, dmLT, or LTA1) and/or bacterial toxin protein, such as a pertussis toxoid (PTd). Thus, in one aspect, disclosed herein are vaccines comprising any of the peptides, polypeptides, proteins, fusion peptides, fusion polypeptides, fusion proteins, or compositions disclosed herein. In some embodiments, the vaccine can further comprise an acellular gram negative vaccine or active components thereof.

1. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed (such as, for example, Bsp22, LcrV, BipD, PcrV, CT053, CT668, BopB, YopB, BipB, PopB, CopB, CopB2, 22BF, BurkF, PaF, YerF, CT053-CopB, CT053-CopB2, CT668-CopB, or CT668-CopB2) typically have at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. MoL Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

2. Nucleic Acids

There are a variety of molecules disclosed herein that are nucleic acid based, including for example the nucleic acids that encode, for example Bsp22, LcrV, BipD, PcrV, CT053, CT668, BopB, YopB, BipB, PopB, CopB, CopB2, 22BF, BurkF, PaF, YerF, CT053-CopB, CT053-CopB2, CT668-CopB, or CT668-CopB2 or antigenic fragments thereof, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxynbose. The phosphate moiety of a nucleotide is pentavalent phosphate. An non-limiting example of a nucleotide would be 3'-AMP (3'-adenosine monophosphate) or 5'-GMP (5'-guanosine monophosphate). There are many varieties of these types of molecules available in the art and available herein.

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine, as well as modifications at the sugar or phosphate moieties. There are many varieties of these types of molecules available in the art and available herein.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid. There are many varieties of these types of molecules available in the art and available herein.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., *Proc. Natl. Acad. Sci. USA,* 1989, 86, 6553-6556). There are many varieties of these types of molecules available in the art and available herein.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

b) Sequences

There are a variety of sequences related to the protein molecules involved in the signaling pathways disclosed herein, for example Bsp22, LcrV, BipD, PcrV, CT053, CT668, BopB, YopB, BipB, PopB, CopB, CopB2, 22BF, BurkF, PaF, YerF, CT053-CopB, CT053-CopB2, CT668-CopB, or CT668-CopB2, or any of the nucleic acids disclosed herein for making Bsp22, LcrV, BipD, PcrV, CT053, CT668, BopB, YopB, BipB, PopB, CopB, CopB2, 22BF, BurkF, PaF, YerF, CT053-CopB, CT053-CopB2, CT668-CopB, or CT668-CopB2, all of which are encoded by nucleic acids or are nucleic acids. The sequences for the human analogs of these genes, as well as other analogs, and alleles of these genes, and splice variants and other types of variants, are available in a variety of protein and gene databases, including GENBANK®. Those of skill in the art understand how to resolve sequence discrepancies and differences and to adjust the compositions and methods relating to a particular sequence to other related sequences. Primers and/or probes can be designed for any given sequence given the information disclosed herein and known in the art.

3. Nucleic Acid Delivery

In the methods described above which include the administration and uptake of exogenous DNA into the cells of a subject (i.e., gene transduction or transfection), the disclosed nucleic acids can be in the form of naked DNA or RNA, or the nucleic acids can be in a vector for delivering the nucleic acids to the cells, whereby the antibody-encoding DNA fragment is under the transcriptional regulation of a promoter, as would be well understood by one of ordinary skill in the art. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., Pastan et al., *Proc. Natl. Acad. Sci. USA*. 85:4486, 1988; Miller et al., *Mol. Cell. Biol.* 6:2895, 1986). The recombinant retrovirus can then be used to infect and thereby deliver to the infected cells nucleic acid encoding a broadly neutralizing antibody (or active fragment thereof). The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), pseudotyped retroviral vectors (Agrawal et al., *Exper. Hematol.* 24:738-747, 1996). Physical transduction techniques can also be used, such as liposome delivery and receptor-mediated and other endocytosis mechanisms (see, for example, Schwartzenberger et al., *Blood* 87:472-478, 1996). This disclosed compositions and methods can be used in conjunction with any of these or other commonly used gene transfer methods.

As one example, if the antibody-encoding nucleic acid is delivered to the cells of a subject in an adenovirus vector, the dosage for administration of adenovirus to humans can range from about $10^7$ to about $10^9$ plaque forming units (pfu) per injection but can be as high as about $10^{12}$ pfu per injection (Crystal, *Hum. Gene Ther.* 8:985-1001, 1997; Alvarez and Curiel, *Hum. Gene Ther.* 8:597-613, 1997). A subject can receive a single injection, or, if additional injections are necessary, they can be repeated at six month intervals (or other appropriate time intervals, as determined by the skilled practitioner) for an indefinite period and/or until the efficacy of the treatment has been established.

Parenteral administration of the nucleic acid or vector, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. For additional discussion of suitable formulations and various routes of administration of therapeutic compounds, see, e.g., *Remington: The Science and Practice of Pharmacy* (19th ed.) ed. A. R. Gennaro, Mack Publishing Company, Easton, Pa. 1995.

4. Delivery of the Compositions to Cells

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., *Science,* 247, 1465-1468, (1990); and Wolff, J. A. *Nature,* 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

a) Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as 22BF into the cell without degradation and include a promoter yielding expression of the gene in the cells into which it is delivered. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

(1) Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

(2) Adenoviral Vectors

The construction of replication-defective adenoviruses has been described (Berkner et al., *J. Virology* 61:1213-1220 (1987); Massie et al., *Mol. Cell. Biol.* 6:2872-2883 (1986); Haj-Ahmad et al., *J. Virology* 57:267-274 (1986); Davidson et al., *J. Virology* 61:1226-1239 (1987); Zhang "Generation and identification of recombinant adenovirus by liposome-mediated transfection and PCR analysis" *BioTechniques* 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, *J. Clin. Invest.* 92:1580-1586 (1993); Kirshenbaum, *J. Clin. Invest.* 92:381-387 (1993); Roessler, *J. Clin. Invest.* 92:1085-1092 (1993); Moullier, *Nature Genetics* 4:154-159 (1993); La Salle, *Science* 259:988-990 (1993); Gomez-Foix, *J. Biol. Chem.* 267:25129-25134 (1992): Rich, *Human Gene Therapy* 4:461-476 (1993); Zabner, *Nature Genetics* 6:75-83 (1994); Guzman, *Circulation Research* 73:1201-1207 (1993); Bout, *Human Gene Therapy* 5:3-10 (1994); Zabner, *Cell* 75:207-216 (1993); Caillaud, *Eur. J. Neuroscience* 5:1287-1291 (1993); and Ragot, *J. Gen. Virology* 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, *Virology* 40:462-477 (1970); Brown and Burlingham, *J. Virology* 12:386-396 (1973); Svensson and Persson, *J. Virolog* 55:442-449 (1985); Seth, et al., *J. Virol.* 51:650-655 (1984); Seth, et al., *Mol. Cell. Biol.* 4:1528-1533 (1984); Varga et al., *J. Virology* 65:6061-6070 (1991): Wickham et al., *Cell* 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

5. Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Large Payload Viral Vectors

Molecular genetic experiments with large human herpesviruses have provided a means whereby large heterologous DNA fragments can be cloned, propagated and established in cells permissive for infection with herpesviruses (Sun et al., *Nature genetics* 8: 33-41, 1994; Cotter and Robertson. *Curr Opin Mol Ther* 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

b) Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed needle tip protein-translocator protein fusion (such as, for example, 22BF) or vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews,* 129:57-80, (1992); and Roffler, et al., *Biochem. Pharmacol,* 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration.

Molecular and cellular mechanisms of receptor-mediated endocytosis has been reviewed (Brown and Greene, *DNA and Cell Biology* 10:6, 399-409 (1991)).

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can become integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

c) In Vivo/Ex Vivo

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell Bio.* 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the *E. coli* lacZ gene, which encodes ß-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR—cells and mouse LTK—cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puromycin.

7. Peptides a) Protein Variants

As discussed herein there are numerous variants of the needle tip protein-translocator protein fusion (such as, for example, Bsp22, LcrV, BipD, PcrV, CT053, CT668, BopB, YopB, BipB, PopB, CopB, CopB2, 22BF, BurkF, PaF, YerF, CT053-CopB, CT053-CopB2, CT668-CopB, or CT668-CopB2) that are known and herein contemplated. In addition, to the known functional strain variants there are derivatives of the needle tip protein and translocator protein which also function in the disclosed methods and compositions. Protein variants and derivatives are well understood to those of skill in the art and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than from about 2 to about 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of from about 1 to about 10 amino acid residues; and deletions will range from about 1 to about 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 3 and 4 and are referred to as conservative substitutions.

TABLE 3

Amino Acid Abbreviations

| Amino Add | Abbreviations | |
|---|---|---|
| Alanine | Ala | A |
| Allosoleucine | AIle | |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isolelucine | Ile | I |
| Leucine | Leu | L |
| Lysine | Lys | K |
| Phenylalanine | Phe | F |
| Proline | Pro | P |
| Pyroglutamic acid | pGlu | |
| Serine | Ser | S |
| Threonine | Thr | T |
| Tyrosine | Tyr | Y |
| Tryptophan | Trp | W |
| Valine | Val | V |

TABLE 4

Amino Acid Substitutions
Original Residue Exemplary Conservative
Substitutions, others are known in the art.

| | |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 4, i.e., selecting residues that differ more significantly in their effect on maintaining (a) the structure of the polypeptide backbone in the area of the substitution, for example as a sheet or helical conformation, (b) the charge or hydrophobicity of the molecule at the target site, or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; (d) a residue having a bulky side chain, e.g., phenylalanine, is substituted for (or by) one not having a side chain, e.g., glycine, in this case, or (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO: 1 sets forth a particular sequence of *Bordetella* needle tip protein-translocator protein fusion (22BF) and SEQ ID NO: 2 sets forth a particular sequence of a 22BF fusion protein. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. MoL Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. For example, one of the many nucleic acid sequences that can encode the protein sequence set forth in SEQ ID NO: 2 is set forth in SEQ ID NO: 1. It is understood that for this mutation all of the nucleic acid sequences that encode this particular derivative of the 22BF are also disclosed. It is also understood that while no amino acid sequence indicates what particular DNA sequence encodes that protein within an organism, where particular variants of a disclosed protein are disclosed herein, the known nucleic acid sequence that encodes that protein in the particular needle tip protein-translocator protein fusion (such as, for example, 22BF) from which that protein arises is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 3 and Table 4. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way.

Molecules can be produced that resemble peptides, but which are not connected via a natural peptide linkage. For example, linkages for amino acids or amino acid analogs can include $—CH_2NH—$, $—CH_2S—$, $—CH_2—CH_2—$, $—CH{=}CH—$ (cis and trans), $—COCH_2—$, $—CH(OH)CH_2—$, and $—CHH_2SO—$ (These and others can be found in Spatola, A. F. in *Chemistry and Biochemistry of Amino Acids, Peptides, and Proteins*, B. Weinstein, eds., Marcel Dekker, New York, p. 267 (1983); Spatola, A. F., *Vega Data* (March 1983), Vol. 1, Issue 3, Peptide Backbone Modifications (general review); Morley, *Trends Pharm Sci* (1980) pp. 463-468; Hudson, D. et al., Int J Pept Prot Res 14:177-185 (1979) ($—CH_2NH—$, $—CH_2CH_2—$); Spatola et al. *Life Sci* 38:1243-1249 (1986) ($—CH_2—S$); Hann *J. Chem. Soc Perkin Trans*. I 307-314 (1982) ($—CH{=}CH—$, cis and trans); Almquist et al. *J. Med. Chem.* 23:1392-1398 (1980) ($—COCH_2—$); Jennings-White et al. *Tetrahedron Lett* 23:2533 (1982) ($—COCH_2—$); Szelke et al. European Appln, EP 45665 CA (1982): 97:39405 (1982) ($—CH(OH)CH_2—$); Holladay et al. *Tetrahedron*. Lett 24:4401-4404 (1983) ($—C(OH)CH_2—$); and Hruby *Life Sci* 31:189-199 (1982) ($—CH_2—S—$); each of which is incorporated herein by reference. A particularly preferred non-peptide linkage is $—CH_2NH—$. It is understood that peptide analogs can have more than one atom between the bond atoms, such as β-alanine, γ-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations.

8. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, more preferably from about 7 to about 7.6, and most preferably about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-tri-alkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 μg/kg to up to 100 mg/kg of body weight or more per day, depending on the factors mentioned above.

In a preferred embodiment, the amount of protein that is administered per dose of vaccine is in the range of from about 0.0001 to about 1000 μg/kg. In one embodiment, the amount is in the range of from about 0.001 to about 1000 μg/kg of body weight of the recipient. In one embodiment, the amount is in the range of from about 0.01 to about 1000 μg/kg of body weight of the recipient. In one embodiment, the amount is in the range of from about 0.01 to about 100 μg/kg of body weight of the recipient. Those of skill in the art will recognize that the precise dosage may vary from situation to situation and from patient to patient, depending on e.g. age, gender, overall health, various genetic factors, and other variables known to those of skill in the art. Dosages are typically determined e.g. in the course of animal and/or human clinical trials as conducted by skilled medical personnel, e.g. physicians or veterinarians.

C. METHODS OF USING THE COMPOSITIONS

Herein, the protective efficacy of the *Bordetella* spp. tip/translocator fusion, 22BF, is examined against lethal lung challenge and with complete (sterilizing) clearance of colonizing bacteria. Unlike some components of the current aP vaccine, Bsp22 and BopB are required for infection and are not mutable since they must be retained structurally and functionally within the context of a large nanomachine residing within the *Bordetella* cell envelope. Furthermore, targeting the *Bordetella* T3SA renders the pathogen less able to fight off the host innate and adaptive immune responses. Regardless of whether 22BF is protective alone or when used with components of the current aP vaccine, the innovation of this high risk, high reward investigation lies in whether this subunit vaccine can elicit sterilizing immunity and thereby prevent the colonization that results in host to host transmission. It has been reported that Bsp22 (a component of the 22BF fusion vaccine) does not elicit a serum antibody response in humans during the course of natural infection and is not a protective antigen in mice. Nevertheless, as shown herein, protective and sterilizing immunity can be obtained with the compositions disclosed herein.

Thus, in one aspect, disclosed herein are methods of eliciting an immune response in a subject to a Gram negative bacteria (such as, for example, *Bordetella* spp., *Burkholderia* spp., *Chlamydia* spp., *Pseudomonas* spp., *Vibrio* spp. Enteropathogenic or Enterohemorrhagic *E. coli* or *Yersinia* spp.) comprising administering to the subject the fusion polypeptides, compositions, or vaccines disclosed herein. Accordingly, in one aspect, disclosed herein are methods of eliciting an immune response against at least one Gram negative bacteria serovar in a subject in need thereof, comprising administering to the subject a composition comprising at least one needle tip protein or a fragment thereof and/or at least one translocator protein or a fragment thereof; wherein said composition is administered in an amount sufficient to elicit an immune response to said at least one Gram negative bacteria serovar in said subject; and wherein the Gram negative bacteria is not a *Shigella* spp. or *Salmonella* spp. In one aspect, the immune response elicited provides sterilizing immunity to the infectious bacterium.

As can be appreciated by the skilled artisan, the methods of eliciting an immune response can be used for the purpose of treating, inhibiting, or preventing an infection of a Gram negative bacteria (such as, for example, *Bordetella* spp., *Burkholderia* spp., *Chlamydia* spp., *Pseudomonas* spp., *Vibrio* spp. Enteropathogenic or Enterohemorrhagic *E. coli* or *Yersinia* spp.). Thus, in one aspect, disclosed herein are methods of treating, inhibiting, or preventing an infection of a Gram negative bacteria in a subject comprising administering to the subject a therapeutic amount of any of the fusion polypeptides, compositions, or vaccines disclosed herein. As one goal of any vaccine is not only to prevent infection or reducing the severity of disease in the individual receiving the vaccine, but also to prevent further transmission of the infectious agent (sterilizing immunity), it is understood and herein contemplated that the disclosed methods of treatment, inhibition, or preventing an infection can further comprise inhibiting and/or preventing colony formation of the bacteria and/or transmission of the bacteria to another subject.

The term "therapeutically effective" refers to the amount of the composition used that is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "inhibit" refers to a decrease in an activity, response, condition, disease, or other biological parameter. This can include, but is not limited to, the complete ablation of the activity, response, condition, or disease. This can also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

D. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1 a) Use of a T3SS Needle Tip/Translocator Protein Fusion as a Protective Antigen Against *B. pertussis:*

The dominant antigen eliciting protection against Gram-negative pathogens is LPS, which confers O-antigen serotype specificity. The initial project focused on *Shigella*, however, there are at least 58 distinct *Shigella* serotypes. This reduces broad-spectrum efficacy for live, attenuated and whole, killed vaccines, which tend to be somatic antigen driven. IpaD and IpaB are the surface-localized needle tip and first translocator proteins of the T3SA, respectively. They are essential for virulence in all *Shigella*, are >98% conserved across all *Shigella* species, and provide serotype-independent protection. When IpaD+IpaB+dmLT was given IN to mice, the formulation was about 80-90% protective against lethal challenge by homologous and heterologous *Shigella* spp. (Table 5). To reduce the production cost, IpaD and IpaB were genetically fused to make DBF. Not only did the DBF provide protection against lethal challenge, it also unexpectedly increased the cell-mediated immunity, most notably the IL-17 and IFN-γ responses. When the *Salmonella enterica* tip and first translocator proteins of the T3SSs of SPI-1 and SPI-2 (*Salmonella* Pathogenicity Islands 1 and 2) were fused, about 70% protection against lethal challenge by two *S. enterica* serovars was observed when both fusion proteins were administered simultaneously (Table 5).

TABLE 5

Protective efficacy of tip/translocator fusions against challenge by appropriate pathogen.

| Vaccine | Protection (%) | Pathogen |
| --- | --- | --- |
| DBF + dmLT | 80-90 | *S. flexneri*, *S. sonnei* |
| S1S2 + MPL (IM) | 70 | *S. Typhimurium*, *S. Enteritidis* |
| 22BF + dmLT | 100 | *B. bronchiseptica* |

Mice (n = 10) were vaccinated 3 times biweekly with the vaccine and then challenged with indicated pathogen at day 56. Protection is indicated as percent survival after 21 days.

*B. bronchiseptica* and *B. pertussis* infections have been shown to also require a T3SS for virulence. To determine if a subunit of the T3SS could be used to confer protection, *B. pertussis* Bsp22 and BopB, the T3SS needle tip and first translocator proteins, which are 98% conserved with those of *B. bronchiseptica* were genetically fused. Mice were vaccinated biweekly, three times with 22BF, 22BF+dmLT, Bsp22+dmLT, or PBS. One group was also vaccinated twice with the Zoetis canine vaccine that is a killed cellular extract of *B. bronchiseptica*. The 22BF+dmLT exhibited 100% protection against *B. bronchiseptica* in a mouse lethal pulmonary model, while the commercial vaccine provided 80% protection (FIG. 1). Moreover, the mice vaccinated with 22BF+dmLT did not show signs of illness and they actually gained weight throughout the challenge (FIG. 2). In contrast, the mice vaccinated with the Zoetis vaccine lost weight and then regained it, however, they continued to display lower health scores than the mice vaccinated with 22BF+dmLT for the remainder of the experiment (FIG. 2).

Next, the protective efficacy of the 22BF fusion with and without dmLT and in comparison to the needle tip protein Bsp22 and translocator protein BopB and the effect of fusion of dmLT relative to concurrent administration was examined. Mice were vaccinated IN on days 0, 14, 28 and challenged with *Bordetella bronchiseptica* on day 56. On day 7 mice were sacrificed and the colony forming units (CFU)/lung were determined (FIG. 3). 22BF+dmLT reduced the *B. bronchiseptica* CFU lung burden by 96.5%. Blood and fecal samples were collected on days −1, 13, 27, 41, and 55. The kinetics of IgG were assessed. Typical logarithmic increases were seen (FIG. 4) regardless of the antigen on the well. No IgA was detected in fecal samples of any of the mice. Antibody secreting cells in the bone marrow, spleen, and lungs (FIG. 5) were stimulated with Bsp22, BopB and dmLT. All organs from mice that had been vaccinated with the single proteins or double proteins or fusion, as long as the dmLT was present, exhibited some level of IgG or IgA ASCs While protection is important, the key to a next generation subunit vaccine against *Bordetella* spp. must be that it exhibits sterilizing immunity (to prevent carriage). The lungs of the mice that survived the challenge of FIG. 2 were examined to look for sterilizing immunity. All of the remaining 22BF and PBS vaccinated mice exhibited CFU/lung. In contrast, the 22BF+dmLT vaccinated mice demonstrated 38% sterilizing immunity while only 12% of the mice vaccinated with the Zoetis vaccine demonstrated sterilizing immunity. Thus, the 22BF represents an innovative new antigen to protect against *B. bronchiseptica* and *B. pertussis* due to the conservation of these antigens.

It is shown herein that the use of a broad, serotype-independent subunit vaccine against *Shigella* spp. and *S. enterica* serotypes. These vaccines are based on the fusion of the T3SA tip and first translocator proteins, which are highly conserved within a given bacterial genus. The DBF has also been shown to protect monkeys from severe diarrhea and *S. enterica* S1S2 fusions are protective in a bovine calf model. A genetic fusion of the *B. pertussis* T3SA tip/translocator system, 22BF, was generated which protects 100% of the mice challenged with a lethal dose of the heterologous *B. bronchiseptica*. Furthermore, 22BF elicited 38% sterilizing immunity while the commercial vaccine provided 12%. Herein, not only was the *B. bronchiseptica* experiment repeated, but also it demonstrated that the 22BF+dmLT protects against *B. pertussis*. *B. bronchiseptica* was chosen as the first challenge pathogen since it lacks pertussis toxin (PT), which could conceivably compromise adequate assessment of the 22BF. PT is an especially important toxin secreted by *B. pertussis* that can significantly affect the health of the host. Shiga toxin was also considered when DBF vaccinated mice were challenged with *S. dysenteriae*, however, DBF protected 40% of those vaccinated mice while the individual proteins did not. Furthermore, due to the disease progression of *S. dysenteriae*, mice killed by the Shiga toxin versus those succumbing to the bacterial infection (based on health score immediately preceding death) were distinguished. 22BF provides some level of protection against *B. pertussis*, which can be boosted by the addition of pertussis toxoid (PTd). At the end of this study, it was demonstrated that 22BF protects against both *B. bronchiseptica* and *B. pertussis*. Results for two vaccination routes and doses are obtained. PTd is required in the protection against *B. pertussis* was shown herein. Finally, it is demonstrated that 22BF+dmLT elicits >90, if not 100%, sterilizing immunity.

b) Cytokine Assay

Cytokines were collected from splenocytes collected on Day 55. 100 μL of homogenized splenocytes were seeded at a concentration of $5\times10^6$ cells/mL onto a flat-bottom 96-well plate. 100 μL of BopB, Bsp22, or dmLT at a concentration of 20 μg/mL was added onto cells (bringing final protein concentration to 10 μg/mL). Plates were incubated at 37° C. and 5% $CO_2$ for 48 hours. After incubation, plates were centrifuged at 1600 rpm at 4° C. for seven minutes. Supernatants were collected and stored at −20° C. until analysis. Cytokines were analyzed using the MSD® U-Plex Platform Multiplex Assay for the following cytokines for the following immune responses: Th1: IFN-γ, TNF-α, IL-1β, IL-2, IL-6, IL-10; (FIGS. 6 and 7) Th17: IL-17A; (FIG. 8) Th2: IL-4, IL-5 (FIG. 9).

2. Example 2: Assess the Respective Humoral and Cell-Mediated Immune Responses Elicited by 22BF+dmLT Delivered IN and IM IN delivery of 20 μg 22BF+2.5 μg dmLT protects 100% of vaccinated mice from death and provide 38% sterilizing immunity in the lungs following *B. bronchiseptica* challenge. 50 μg or 15 μg 22BF IN is delivered and then in parallel deliver 100 μg or 20 μg 22BF IM or ID to assess the humoral and cell mediated responses in each case. Based on previous work, it is known that some of these dose/route combinations do not protect mice while others offer protection.

First the effect of the route of administration of 22BF following challenge was assessed. Group 1 is a 22BF+2.5 μg dmLT IN, group 2 is 22BF+2.5 μg dmLT IM, and group 3 is a 22BF+2.5 μg dmLT IN. For each administrative route, PBS vaccinated controls were included (Groups 4, 5, and 6). Group 7 (n=10) is vaccinated subcutaneously on day 1 and 21 with the Zoetis vaccine. After day 56 following initial vaccination, mice were challenged with a sublethal dosage of *B. pertussis* intranasally. There was an observable difference in weight loss between mice vaccinated with the 22BF+dmLT+PTd formulation and those that only received PBS. By Day 7 all mice aside from PBS treated mice had recovered to within 3% of pre infection weight.

The immune responses can be compared with the protective efficacy and potentially define a protective correlate in the mouse model. The correlate is useful in the development of the 22BF vaccine, making the necessary adjustments when it is translated to humans. The systemic immune response can be assessed by measuring serum IgG against BopB, Bsp22, and dmLT, as well as the mucosal immune response by assessing IgA in fecal pellets. Cytokine secretion is assessed in splenocytes from vaccinated mice.

This experiment can be performed in two parts. The IN route can use a high dose of 50 μg and low dose of 15 μg. The IM route uses a high dose of 100 μg and a low dose of 40 μg. For each route, three groups of female C57BL/6 mice (10/group) are vaccinated on days 0, 14 and 28. Group 1 is a 22BF+2.5 μg dmLT IN, group 2 is 22BF+2.5 μg dmLT IM, and group 3 is a 22BF+2.5 μg dmLT IN. For each administrative route, PBS vaccinated controls were included (Groups 4, 5, and 6). Group 7 (n=10) is vaccinated subcutaneously on day 1 and 21 with the Zoetis vaccine. Blood and fecal pellets are collected on days −1, 13, 27, 41 and 55 to assess mucosal and systemic humoral responses. Individual samples are tested for the presence of anti-Bsp22, -BopB, -dmLT, -PTd IgG and IgA antibodies by ELISA. Mice were immunized on days 0, 14, and 28 with 22BF+PTd admixed with dmLT. Serum IgG antibodies specific for BopB, Bsp22, PTd, and dmLT were measured by ELISA. and IFN-γ/IL-17A secreting cells by ELISpot and cytokine secretion using Multi array assays. BAL is collected to measure IgG and IgA responses. GraphPad Prism 5.04 can be used for graphics and statistical comparisons. Differences were analyzed using t test or ANOVA where appropriate. A P value of less than 0.05 is considered significant for all comparisons.

For these experiments, serum IgG levels are $>10^5$ EU/ml, antibody secreting cells at >50 IgG ASC/$10^6$ cells or >20 IgA ASC/$10^6$ cells, and cytokine secreting cells at >50 IFN-γ/$10^6$ cells and IL-17/$10^6$ cells. There can also be unique systemic and mucosal humoral immune responses from mice immunized via the IN and IM routes. 50 μg IN was chosen to facilitate an increase in sterilizing immunity. The 100 μg IM dose was based on prior findings. Antibody secreting cells specific for both proteins are detected in both mucosal and memory compartments. Finally, the full profile of cytokine secretion elicited by the vaccine can demonstrate a dose and administration route dependence. Thus, these two routes (each with a high and low dose) are expected to give rise to unique immune response profiles.

Example 3: Determine the Protective Efficacy of 22BF+dmLT Against *B. bronchiseptica* and *B. pertussis* Challenge.

As discussed above, it is demonstrated herein that initial protective efficacy of 22BF+dmLT against *B. bronchiseptica* challenge. Insight is gained into the immune responses elicited by two doses of 22BF delivered IN and IM. Here, mice can be vaccinated and challenged with *B. bronchiseptica* and *B. pertussis*. In addition to assessing protective efficacy and sterilizing immunity of the 22BF+dmLT as well as the requirement for PTd, a protective correlate can be established for use. This method was used to identify a protective correlate associated with DBF protection of mice against *Shigella*. This, however, prior to the present disclosure has never been determined for such a vaccine type against an extracellular pathogen.

a) Assess Protective Efficacy of the 22BF+dmLT Delivered IN and IM Against *B. bronshiseptica* Challenge Using the Mouse Lung Model with Two Challenge Doses—a Lethal Dose to Assess Survival and a Sublethal Dose to Assess Sterilizing Immunity.

Protective efficacy of 22BF+dmLT delivered IN, IM, and ID against a *B. bronchiseptica* challenge can be assessed in the mouse lung model. A high dose of *B. bronchiseptica* can be administered initially to assess protection via the lethal dose. In a second trial, a lower dose can be used to assess sterilizing immunity.

Experimental Details: Mice (20/group) are vaccinated IN on days 0, 14 and 28. Serum, and stool samples are collected as described above to measure specific antibody responses to confirm that immune responses are comparable to those obtained above. For bacterial challenges, 10 mice are challenged on day 56 with $1 \times 10^7$ *B. bronchiseptica* (lethal dose) and 10 animals are challenged with $1 \times 10^6$ *B. bronchiseptica* (sub-lethal dose). The mouse experiment can be repeated with vaccination occurring by the IM route and ID. Survival can be plotted and a Log-rank test used to evaluate the differences. A P value of less than 0.05 is considered significant for all comparisons. Association of protective efficacy and markers of humoral and cellular immunity can be assessed with logistic regression models (see FIG. 1).

With respect to the IN vaccinated mice, at both doses, some level of protection is shown in the lethal lung model. The mice vaccinated with 50 µg are protected with complete sterilizing immunity. The 15 µg dose gives >90% protection with a moderate level of sterilizing immunity. Similarly, 100 µg 22BF+dmLT delivered IM has a high level of protection as well as sterilizing immunity, but perhaps not 100%, but greater than 70% protection. The 40 µg dose shows minimal protection. With these results, a protective correlate for *B. bronchiseptica* can be predicted, as long as the immune responses were above the levels anticipated.

b) Assess Protective Efficacy of the 22BF+dmLT±PTd Delivered IN, IM, and ID Against *B. pertussis* Challenge Using the Mouse Lung Model with Two Challenge Doses—a Lethal Dose to Assess Survival and a Sublethal Dose to Assess Sterilizing Immunity.

The ultimate test of the 22BF formulation is the protective efficacy against *B. pertussis*. Here, the protective efficacy of 22BF+dmLT is tested with a focus on a *B. pertussis* challenge using the mouse lung model. Vaccinations occur IN with PTd. Furthermore, a high dose of *B. pertussis* is used initially to assess protection via the lethal lung model.

Mice (10/group) are vaccinated IN on days 0, 14 and 28. Serum, and stool samples are collected. as described above to measure specific antibody responses to confirm a comparable immune response. For bacterial challenges, all mice can be challenged on day 56 with $1 \times 10^7$ *B. pertussis* (lethal dose). The experiment can be repeated using IM route and ID route again with the most protective vaccine and challenge with a lethal dose and a sub-lethal dose to assess protection and sterilizing immunity. Survival can be plotted and a Log-rank test used to evaluate the differences. A P value of less than 0.05 is considered significant for all comparisons.

PTd can additionally be administered for protection against *B. pertussis* and to prevent the cellular damage associated with PT as well as increase sterilizing immunity. Mice can be vaccinated IN, IM, or ID with 22BF+PTd and dmLT and challenged with *B. pertussis*. Lung CFU were measured at day 3 (FIG. 12) and day 7 (FIG. 13) post challenge. As with the predicted *B. bronchiseptica* results, 100% protection and sterilizing immunity is obtained with 50 µg 22BF+dmLT+PTd delivered IN with reduced protection for the 15 µg dose delivered IN. Similarly, the 100 µg 22BF+dmLT+PTd delivered IM and ID achieves some significant level of protection, but sterilizing immunity is limited though could be greater at higher dosage by day 7 post challenge. Antibodies are important, but the impact of cytokines cannot be ignored.

4. Example 4: LTA-1 Fusion

LTA1 is the active moiety of lethal toxin from Enterotoxigenic *E. coli* (ETEC). The activity of the LTA1 is required for the adjuvant activity of dmLT. The double mutants are in the region usually targeted by a protease to allow A1 to traffic to the cytoplasm of intestinal cells to cause the secretory diarrhea. Without the protease the LT still has some activation of cAMP. Likewise, LTA1 remains active.

a) LTA-Fusions:

The LTA1-fusions were expressed in a manner similar to the fusion alone. The LTA1 sequence was inserted 5' to the start of the each fusion. Some of the LTA1-fusions required a small linker between the LTA1 and fusion in order for protein production to occur. LTA1-DBF, LTA1-S1, LTA1-S2, LTA1-SseB, LTA1-22BF, LTA1-BurkF, and LTA1-PaF were produced. One of the assays that appear to be required for adjuvant activity is the ability to ADP ribosylate ARF4. The ADP ribosylation assay was performed with the LTA1-fusions. In the assay, ADPr was biotin conjugated and when mixed with LTA1 and rARF4, the LTA1 transferred the biot-ADPr to rARF4. The biotin was then detected with Streptavidin-IR800 (FIG. 20).

b) LTA1-Fusion Protective Efficacy:

Mice were vaccinated parenterally with LTA1-DBF or DBF+dmLT (FIG. 14). Although the DBF+dmLT delivered IN elicited complete protection, this formulation cannot be given to humans since the dmLT can travel the olfactory nerve to the brain causing Bell's palsy. Thus, parenteral routes or other mucosal routes are required. DBF (100 µg)+dmLT (0.1 µg) delivered IM was only 50% protective while LTA1-DBF at a concentration of 100 µg DBF equivalent was 70% protective. The lower dilutions, regardless of formulation, exhibited less protective efficacy. Similarly, LTA1-22BF+PTd elicited significant protective efficacy at a concentration of 80 µg of 22BF equivalents (FIG. 19A-D)

c) LTA1-DBF Immune Response:

When the kinetics of the IgG titer was examined, responses against IpaD and IpaB were essentially the same. Mice from FIG. 14 were bled prior to vaccination and on day 42. Sera were assessed for anti-IpaD, -IpaB and -dmLT IgG. The lower IgG titers of the LTA1 samples can be attributed to the lower recognition of the dmLT on the well for the LTA1 samples vs the samples from mice vaccinated with dmLT (FIG. 15). No IgA was detected in the fecal samples of the mice vaccinated IM, but was detectable in mice vaccinated IN with DBF+dmLT. Antibody-secreting cells (ASCs) present in the bone marrow (FIG. 16), spleen (FIG. 17), and lungs (FIG. 18) were also stimulated with IpaD, IpaB and dmLT. In each compartment, anti-IpaD, anti-IpaB, and anti-dmLT IgG ASCs could be detected. Interestingly, IgA ASCs could also be detected in the bone marrow against all dilutions of LTA1-DBF and resemble a curve similar to the dose escalation. A similar phenomenon was seen in the IgA ASCs from the lungs, but less pronounced.

d) LTA-DBF Purification.

The yield of LTA1-DBF was very low. Therefore, a linker was inserted in the DNA sequence between LTA1 and DBF to encode GSAAS (Seq. ID No. 14). The mother plasmid was Novagen's pACYCDuet-1. The translocator for each fusion cannot be made without its cognate chaperone. Therefore, the complex of LTA1-DBF/Histag-IpgC (IPG chaperone comprises the nucleic acid sequence as set forth in SEQ ID NO: 10 which encodes the amino acid sequence as set forth in SEQ ID NO: 11) was produced from the plasmid pACYC-His-IpgC-LTA1-GSAAS-DBF where the ipgC gene was inserted into the BamHI/HindIII sites allowing for expression of His-tag IpgC and LTA1-GSAAS-DBF (nucleic acid sequence as set forth in SEQ ID NO: 15 and amino acid sequence as set forth in SEQ ID NO: 16)) was inserted at the NdeI-XhoI site. The DBF sequence had a 3' stop codon prior to the XhoI restriction site.

pACYC-His-IpgC-LTA1-GSAAS-DBF was transformed into Tuner cells. A small overnight culture of LB+ Chloramphenicol (Cm) that had been inoculated with the freezer stock of the cells was transferred to 8 L TB, and grown at 37° C. until OD=1-1.5, add 0.5 mM IPTG with 20 ug/liter AEBSF, 16 C overnight, harvested at 4000 rpm for 15 min at 4° C., and resuspended in IMAC binding buffer. The cells were frozen at −80° C. until ready for purification. After thawing the suspension was sonicated at 70% amplitude for 3-4 min, 15 s on, 30 s off, clarified by centrifugation at 13000 rpm for 30 min at 4° C. and decanted to obtain supernatant.

IMAC purification with 5 ml NiNTA FF crude column on AKTA was as follows: (1) equilibrate column with 5CV binding buffer (20 mM Tris, 500 mM NaCl, 5 mM Imidazole pH 7.9), (2) load supernatant on column, collect FT in outlet1, (3) wash with binding buffer for 30CV, (4) elute with linear 0-60% elution buffer (20 mM Tris, 500 mM NaCl, 500 mM Imidazole pH 7.9) for 10CV, (5) elute with 60% elution buffer for 2CV, (6) wash column with 100% elution buffer for 3CV, (7) re-equilibrate column with 5CV binding buffer for 5CV.

HIC purification of the protein was as follows: Dilute pooled fraction into equal volume of 2×HIC binding buffer (50 mM Sodium Phosphate (dibasic), 1M Ammonium Sulfate, pH 7.0). Purify with 5 ml HIC Phenyl HP column: (1) equilibrate column with 5CV binding buffer, (2) load diluted sample on column, collect FT in outlet1, (3) wash with binding buffer for 5CV, (4) elute with linear 0-100% elution buffer (5 mM Sodium Phosphate (dibasic), pH 7.0) for 40CV, (6) elute with 100% elution buffer for 6CV, (7) wash column with 100% elution buffer for 3CV, (8) reequilibrate column with binding buffer for 5CV.

Pooled fractions were dialyzed in 4 L Q binding buffer for 2 hrs, exchanged buffer, and then dialyzed overnight.

Purification using a 5 mL Q FF columns on AKTA was as follows: (1) equilibrate column with 5CV binding buffer (50 mM Tris, pH 8.0), (2) load dialyzed sample on column, collect FT in outlet1, (3) wash with binding buffer for 5CV, (4) elute with linear 0-30% elution buffer (50 mM Tris, 1M NaCl, pH 8.0) for 20CV, (6) elute with 100% elution buffer for 5CV, (7) wash column with 100% elution buffer for 3CV, (8) re-equilibrate column with binding buffer for 5CV.

To facilitate final IMAC purification 8×IMAC binding buffer (NO Imidazole) was added to pooled fractions to obtain 1× and then LDAO to 0.05% was added Purification by LDAO IMAC using 5 ml NiNTA FF was as follows: (1) equilibrate column with 5CV LDAO (20 mM Tris, 500 mM NaCl, 0.05% LDAO pH 7.9) binding buffer, (2) load supernatant on column, fractionate FT, (3) wash with binding buffer for 5CV, fractionate, (4) wash with 3% LDAO elution buffer (20 mM Tris, 500 mM NaCl, 500 mM Imidazole, 0.005% LDAO pH 7.9) for 5CV, fractionate (5) elute with 6% LDAO elution buffer for 6.65CV, fractionate (6) elute with 100% LDAO elution buffer for 5CV, (8) re-equilibrate with 5CV binding buffer for 5CV.

Pooled samples were dialyzed in 4 L PBS+0.005% LDAO, exchanged buffer after 2 hrs, and then dialyzed overnight.

e) Protective Efficacy of LTA1-22BF

The initial assessment of the protective efficacy of the LTA1-22BF is presented here and demonstrated that LTA1-22BF+rPT reduced the CFU lung burden by 99.8% while the 22BF+dmLT+rPT reduced it to 99.98% (FIG. 19 (*a*)). Non-toxic pertussis toxin was added to the groups that prior to challenge by *B. pertussis* to offset the damage that pertussis toxin would cause and negatively impact the challenge. The kinetics of the IgG response is also shown where no differences are seen between the two groups (FIG. 19 (*b*))

f) LTA1-22BF Purification

The mother plasmid was Novagen's pACYCduet-1. The translocator for each fusion cannot be made without its cognate chaperone. Therefore, the complex of LTA1-22BF/Histag-BcrHI is produced from the plasmid pACYC-His-BcrH1-LTA1-22BF where the brcHI gene (as set forth in SEQ ID NO: 7 with a histidine tag and encodes the amino acid sequence as set forth in SEQ ID NO: 8, the sequence minus the his-tag set forth in SEQ ID NO: 9) is inserted into the BamHI/HindIII sites allowing for expression of His-tag BcrHI and 22BF is inserted at the NdeI-XhoI site. The 22BF sequence has a 3' stop codon prior to the XhoI restriction site.

pACYC-His-BcrHI-22BF was transformed into Tuner cells. A small overnight culture of LB+ Chloramphenicol (Cm) that had been inoculated with the freezer stock of the cells was transferred to 8 L TB, grown at 37° C. until OD=1-1.5, added 0.5 mM IPTG with 20 ug/liter AEBSF, 16° C. overnight, harvested at 4000 rpm for 15 min at 4 C, and resuspended in IMAC binding buffer. The cells were frozen at −80 until ready for purification. After thawing, the suspension was sonicated at 70% amplitude for 3-4 min, 15 s on, 30 s off, clarified by centrifugation at 13000 rpm for 30 min at 4° C., and decanted to obtain supernatant.

IMAC purification with 5 ml NiNTA FF crude column on AKTA was as follows: (1) equilibrate column with 5CV binding buffer (IMAC elution buffer: 20 mM Tris, 500 mM NaCl, 500 mM Imidazole pH 7.9), (2) load supernatant on column, collect FT in outlet1, (3) wash with binding buffer for 30CV, (4) elute with linear 0-60% elution buffer for 10CV, (5) elute with 60% elution buffer for 2CV, (6) wash column with 100% elution buffer for 3CV, (7) re-equilibrate column with 5CV binding buffer (IMAC binding buffer: 20 mM Tris, 500 mM NaCl, 5 mM Imidazole pH 7.9) for 5CV.

Diluted pooled fractions 20× into Q binding buffer Q binding buffer: 50 mM Tris, pH 8.0). Purification with 3×5 mL Q FF columns on AKTA was as follows: (1) equilibrate column with 6CV binding buffer, (2) load dialyzed sample on column, collect FT in outlet, (3) wash with binding buffer for 12CV, (4) elute with 15% elution buffer (Q elution buffer: 50 mM Tris, 1M NaCl, pH 8.0) for 6CV, (5) elute with linear 15-40% elution buffer for 34CV, (6) elute with 100% elution buffer for 6CV, (7) wash column with 100% elution buffer for 3CV, (8) re-equilibrate column with binding buffer for 6CV.

To facilitate final IMAC purification 8×IMAC binding buffer (NO Imidazole) was added to pooled fractions to obtain 1× and then LDAO to 0.05% was added. Purification by LDAO IMAC using 5 ml NiNTA FF was as follows: (1) equilibrate column with 5CV LDAO binding buffer (LDAO IMAC binding buffer: 20 mM Tris, 500 mM NaCl, 0.05% LDAO pH 7.9), (2) load supernatant on column, fractionate FT, (3) wash with binding buffer for 5CV, fractionate, (4) wash with 3% LDAO elution buffer (LDAO IMAC elution buffer: 20 mM Tris, 500 mM NaCl, 500 mM Imidazole, 0.005% LDAO pH 7.9) for 5CV, fractionate (5) elute with 6% LDAO elution buffer for 6.65CV, fractionate (6) elute with 100% LDAO elution buffer for 5CV, (8) re-equilibrate column with 5CV binding buffer for 5CV.

Pooled samples were dialyzed in 4 L PBS+0.005% LDAO, exchanged buffer after 2 hrs, and then dialyzed overnight.

g) LTA1-BurkF Purification

The mother plasmid was Novagen's pACYCDuet-1. The translocator for each fusion cannot be made without its cognate chaperone. Therefore, the complex of LTA1-BurkF/Histag-BicA (SEQ ID NOs: 28 and 20) was produced from the plasmid pACYC-His-BicA-LTA1-BurkF (as set forth in SEQ ID NO: 20 and encoded by the nucleic acid sequence as set forth in SEQ ID NO: 19) wherein the bicA gene was inserted into the BamHI/HindIII sites allowing for expression of His-tag BicA and LTA1-BurkF was inserted at the NdeI-XhoI site. The BurkF sequence had a 3' stop codon prior to the XhoI restriction site.

pACYC-His-BicA-LTA-BurkF was transformed into Tuner cells. A small overnight culture of LB+ Chloramphenicol (Cm) that had been inoculated with the freezer stock of the cells was transferred to 8 L TB, grown at 37° C. until OD=1-1.5, added 0.5 mM IPTG with 20 ug/liter AEBSF, 16° C. overnight, harvested at 4000 rpm for 15 min at 4 C, and resuspended in IMAC binding buffer. The cells were frozen at −80 until ready for purification. After thawing the suspension was sonicated at 70% amplitude for 3-4 min, 15 s on, 30 s off, Clarified by centrifugation at 13000 rpm for 30 min at 4° C., and decanted to obtain supernatant.

IMAC purification with 5 ml NiNTA FF crude column on AKTA was as follows: (1) equilibrate column with 5CV binding buffer (20 mM Tris, 500 mM NaCl, 5 mM Imidazole pH 7.9), (2) load supernatant on column, collect FT in outlet1, (3) wash with binding buffer for 30CV, (4) elute with linear 0-60% elution buffer (20 mM Tris, 500 mM NaCl, 500 mM Imidazole pH 7.9) for 10CV, (5) elute with 60% elution buffer for 2CV, (6) wash column with 100% elution buffer for 3CV, (7) re-equilibrate column with 5CV binding buffer for 5CV.

The pooled fractions were diluted 20× into Q binding buffer (50 mM Tris, pH 8.0). Purification using 3×5 mL Q FF columns on AKTA was as follows: (1) equilibrate column with 6CV binding buffer, (2) load dialyzed sample on column, collect FT in outlet, (3) wash with binding buffer for 12CV, (4) elute with 15% elution buffer (50 mM Tris, 1M NaCl, pH 8.0) for 6CV, (5) elute with linear 15-40% elution buffer for 34CV, (6) elute with 100% elution buffer for 6CV, (7) wash column with 100% elution buffer for 3CV, (8) re-equilibrate column with binding buffer for 6CV.

To facilitate final IMAC purification add 8×IMAC binding buffer (NO Imidazole) to pooled fractions to obtain 1× and then LDAO to 0.05% was added:

Purification by LDAO IMAC using 5 ml NiNTA FF was as follows: (1) equilibrate column with 5CV LDAO binding buffer (20 mM Tris, 500 mM NaCl, 0.05% LDAO pH 7.9), (2) load supernatant on column, fractionate FT, (3) wash with binding buffer for 5CV, fractionate, (4) wash with 3% LDAO elution buffer (20 mM Tris, 500 mM NaCl, 500 mM Imidazole, 0.005% LDAO pH 7.9) for 5CV, fractionate (5) elute with 6% LDAO elution buffer for 6.65CV, fractionate (6) elute with 100% LDAO elution buffer for 5CV, (8) re-equilibrate column with 5CV binding buffer for 5CV.

Pooled samples were dialyzed in 4 L PBS+0.005% LDAO, exchanged buffer after 2 hrs, and then dialyzed overnight.

h) LTA1-PaF

The PaF+dmLT vaccinated mice exhibited 100% survival with 44% sterilizing immunity against Pa challenge in a mouse lethal pulmonary model, while the PBS vaccinated mice exhibited 60% survival but all had >$10^{8-9}$ CFU/lung.

i) LTA1-PaF Purification

The mother plasmid is Novagen's pACYCDuet-1. The translocator for each fusion cannot be made without its cognate chaperone. Therefore, the complex of LTA1-PaF/Histag-PcrHI was produced from the plasmid pACYC-His-PcrHI-LTA1-PaF where the brcHI gene was inserted into the BamHI/HindIII sites allowing for expression of His-tag PcrHI (as set forth in SEQ ID NO: 30 and encoded by the nucleic acid sequence as set forth in SEQ ID NO: 29) and LTA1-PaF (as set forth in SEQ ID NO: 38 and encoded by the nucleic acid sequence as set forth in SEQ ID NO: 37) which was inserted at the NdeI-XhoI site. The PaF sequence had a 3' stop codon prior to the XhoI restriction site. The purification of LTA1-PaF was the same of for LTA1-22BF.

E. REFERENCES

Amuguni J H, Lee S, Kerstein K O, Brown D W, Belitsky B R, Herrmann J E, Keusch G T, Sonenshein A L, Tzipori S. Sublingually administered *Bacillus subtilis* cells expressing tetanus toxin C fragment induce protective systemic and mucosal antibodies against tetanus toxin in mice. Vaccine. 2011; 29(29-30):4778-84. Epub 2011/05/14. doi: S0264-410X(11)00638-4 [pii]

Bulir D C, Liang S, Lee A, Chong S, Simms E, Stone C, Kaushic C, Ashkar A, Mahony J B. Immunization with chlamydial type III secretion antigens reduces vaginal shedding and prevents fallopian tube pathology following live *C. muridarum* challenge. Vaccine. 2016; 34(34): 3979-85. doi: 10.1016/j.vaccine.2016.06.046. PubMed PMID: 27325352.

Chen X, Choudhari S P, Martinez-Becerra F J, Kim J H, Dickenson N E, Toth R Tt, Joshi S B, Greenwood J C, 2nd, Clements J D, Picking W D, Middaugh C R, Picking W L. Impact of Detergent on Biophysical Properties and Immune Response of the IpaDB Fusion Protein, a Candidate Subunit Vaccine against *Shigella* Species. Infect Immun. 201583(1):292-9. doi: 10.1128/IAI.02457-14. PubMed PMID: 25368115.

Fennelly N K, Sisti F, Higgins S C, Ross P J, van der Heide H, Mooi F R, Boyd A, Mills K H. *Bordetella pertussis* expresses a functional type III secretion system that subverts protective innate and adaptive immune responses. Infect Immun. 2008; 76(3):1257-66. doi: 10.1128/IAI.00836-07. PubMed PMID: 18195025; PMCID: PMC2258832.

Galan J E, Wolf-Watz H. Protein delivery into eukaryotic cells by type III secretion machines. Nature. 2006; 444 (7119):567-73. PubMed PMID: 17136086.

Higgs R, Higgins S C, Ross P J, Mills K H. Immunity to the respiratory pathogen *Bordetella pertussis*. Mucosal Immunol. 2012; 5(5):485-500. doi: 10.1038/mi.2012.54. PubMed PMID: 22718262.

Kilgore P E, Salim A M, Zervos M J, Schmitt H J. Pertussis: Microbiology, Disease, Treatment, and Prevention. Clin Microbiol Rev. 2016; 29(3):449-86. doi: 10.1128/CMR.00083-15. PubMed PMID: 27029594; PMCID: PMC4861987.

Martin S W, Pawloski L, Williams M, Weening K, DeBolt C, Qin X, Reynolds L, Kenyon C, Giambrone G, Kudish K, Miller L, Selvage D, Lee A, Skoff T H, Kamiya H, Cassiday P K, Tondella M L, Clark T A. Pertactin-negative *Bordetella pertussis* strains: evidence for a possible selective advantage. Clin Infect Dis. 2015; 60(2): 223-7. doi: 10.1093/cid/ciu788. PubMed PMID: 25301209.

Martinez-Becerra F J, Chen X, Dickenson N E, Choudhari S P, Harrison K, Clements J D, Picking W D, Van De Verg L L, Walker R I, Picking W L. Characterization of a novel fusion protein from IpaB and IpaD of *Shigella* spp. and its potential as a pan-*Shigella* vaccine. Infect Immun. 2013; 81(12):4470-7. doi: 10.1128/IAI.00859-13. PubMed PMID: 24060976; PMCID: 3837967.

Martinez-Becerra F J, Kissmann J M, Diaz-McNair J, Choudhari S P, Quick A M, Mellado-Sanchez G, Clements J D, Pasetti M F, Picking W L. Broadly protective *Shigella* vaccine based on type III secretion apparatus proteins. Infect Immun. 2012; 80(3):1222-31. doi: 10.1128/IAI.06174-11. PubMed PMID: 22202122; PMCID: 3294653.

Mattoo S, Cherry J D. Molecular pathogenesis, epidemiology, and clinical manifestations of respiratory infections due to *Bordetella pertussis* and other *Bordetella* subspecies. Clin Microbiol Rev. 2005; 18(2):326-82. doi: 10.1128/CMR.18.2.326-382.2005. PubMed PMID: 15831828; PMCID: PMC1082800.

Medhekar B, Shrivastava R, Mattoo S, Gingery M, Miller J F. *Bordetella* Bsp22 forms a filamentous type III secretion system tip complex and is immunoprotective in vitro and in vivo. Molecular microbiology. 2009;71(2):492-504. PubMed PMID: 19040642.

National Center for Immunization and Respiratory Diseases DoBD, CDC. 2015 Final Pertussis Surveillance Report 2017.

Nogawa H, A. Kuwae, T. Matsuzawa, and A. Abe. The type III secretion protein BopD in *Bordetella bronchiseptica* is complexed with BopB for pore formation on the host plasma membrane. J Bacteriol. 2004; 186(12):3806-13.

Norton E B, Lawson L B, Freytag L C, Clements J D. Characterization of a mutant *Escherichia coli* heat-labile toxin, LT(R192G/L211A), as a safe and effective oral adjuvant. Clinical and vaccine immunology: CVI. 2011; 18(4):546-51. doi: 10.1128/CVI.00538-10. PubMed PMID: 21288994; PMCID: 3122563.

Norton E B, Lawson L B, Mahdi Z, Freytag L C, Clements J D. The A subunit of *Escherichia coli* heat-labile enterotoxin functions as a mucosal adjuvant and promotes IgG2a, IgA, and Th17 responses to vaccine antigens. Infect Immun. 2012; 80(7):2426-35. doi: 10.1128/IAI.00181-12. PubMed PMID: 22526674; PMCID: 3416479.

Qin L, Gilbert P B, Corey L, McElrath M J, Self S G. A framework for assessing immunological correlates of protection in vaccine trials. J Infect Dis. 2007; 196(9): 1304-12. doi: 10.1086/522428. PubMed PMID: 17922394.

Ross P J, Sutton C E, Higgins S, Allen A C, Walsh K, Misiak A, Lavelle E C, McLoughlin R M, Mills K H. Relative contribution of Th1 and Th17 cells in adaptive immunity to *Bordetella pertussis*: towards the rational design of an improved acellular pertussis vaccine. PLoS Pathog. 2013; 9(4):e1003264. doi: 10.1371/journal.ppat.1003264. PubMed PMID: 23592988; PMCID: PMC3617212.

Sealey K L, Belcher T, Preston A. *Bordetella pertussis* epidemiology and evolution in the light of pertussis resurgence. Infect Genet Evol. 2016;40:136-43. doi: 10.1016/j.meegid.2016.02.032. PubMed PMID: 26932577.

Siegrist C A. Neonatal and early life vaccinology. Vaccine. 2001; 19(25-26):3331-46. PubMed PMID:11348697.

Villarino Romero R, Bibova I, Cerny O, Vecerek B, Wald T, Benada O, Zavadilova J, Osicka R, Sebo P. The *Bordetella pertussis* type III secretion system tip complex protein Bsp22 is not a protective antigen and fails to elicit serum antibody responses during infection of humans and mice. Infect Immun. 2013; 81(8):2761-7. doi: 10.1128/IAI.00353-13. PubMed PMID: 23690400; PMCID: PMC3719584.

Warfel J M, Zimmerman L I, Merkel T J. Acellular pertussis vaccines protect against disease but fail to prevent infection and transmission in a nonhuman primate model. Proc Nati Acad Sci USA. 2014111(2):787-92. doi: 10.1073/pnas.1314688110. PubMed PMID: 24277828; PMCID: PMC3896208.

Warfel J M, Zimmerman L I, Merkel T J. Comparison of Three Whole-Cell Pertussis Vaccines in the Baboon Model of Pertussis. Clin Vaccine Immunol. 2015; 23(1): 47-54. doi: 10.1128/CVI.00449-15. PubMed PMID: 26561389; PMCID: PMC4711092.

F. SEQUENCES

22BF Nucleotide Sequence

SEQ ID NO: 1

CATatgaccattgatctcggagtttcactcacgtcgcaggccggcggcctgcaaggcatcgacctcaagagcatggata tccagactctcatggtgtatgtgcagggtcgtcgcgccgaactcctcacggctcaaatgcagacccaggccgaagtggtgcagaagg -continued

```
ccaatgaacgcatggcgcagctcaacgaggtcctgtccgcgctgtcccgggccaaggccgagtttccgcccaatccgaagccggg
cgacaccatcccgggctgggacaaccagaaggtcagccggatcgaggttcctctcaatgatgcgctgcgcgctgccggcctgacg
ggcatgttcgaagcgcgcgatggccaagtgaccgcccccggcggccggggtacgcaggtcgtgaacggcacgggcgtcatggcc
ggttccacgacctataaggaactcgaaagtgcctacaccaccgtaaaggggatgctggatacggcgtccaatacgcaacagatggac
atgatcaggctgcaggccgccagcaacaagcgcaacgaggctttcgaggtcatgaccaacaccgagaagcggcgcagcgacctg
aacagttccatcaccaacaacatgcgcaagcttatgaccgtcatgagtacgaccatatccacagccccgagcggcgccgcgcttgcg
ccgtctcgcatagatatgcgggcaccggagcccgggagtgccggcgaaggcgccggcatcctggcgccggtgacgacgctggct
ctggcggcgggccggccggcttttccagcgtcaccgtcgctgcgcaccgcgcccgtcctggatccgccagtgcgcgatctcagccc
cgccgacttggccgacctgctgcgcgtcttgcgatccagggcggtggacgggcagttggccacggcgcgcgagaacctgcagga
cgcgcaagtcaaggcgaagcagaacacccaggcccagctcgacaagctggacgcatggttctcggaaggccgaagaggccgaga
gcaagggatggctgagcaaggtgttcggctggatcggcaaggtgctggcggtcgtggcatcggccctggcggtgggctttgccgcc
gtcgccagcgtggccaccggcgcggcggccacacccatgctgctgctcagcggcatggcactggtcagcgccgtgacatcgctgg
ccgaccagatatcgcaagaggcggaggccccgcctatcagcctgggcgggtttctctccgggctggccgacgtctgctgacagc
gttggggtggatcagtcgcaggccgaccaaattgccaagatcgtcgccggcctggccgtgcccgtcgtcttgctgatcgaaccccca
gatgctgggcgaaatggcgcaaggcgtggccaggctggctggcgccagcgatgccaccgcggggtacatagccatggcgatgtc
catcgtggcggcgatcgcggtcgccgcgatcaatgccgccggtacagccggcgcgggtagcgcttcggcgatcaaggggcctg
ggatcgggccgccgcggtagccacccaggtccttcaaggggggtacggcagtggcgcaaggcggcgtcggcgtgtcgatggcagt
cgatcgcaaacaggccgatctcctggtcgccgacaaggcggatctggcggcgagcctgacaaaactgcgggcggccatggagcg
tgaggcggacgatatcaagaagatcctggctcaattcgacgaggcctatcacatgatcgcgaagatgatcagcgatatggcgagtac
gcacagccaggtcagcgccaacctcgggcggcgccaggcggtgtagCTCGAG
```

22BF Amino Acid Sequence                                                         SEQ ID NO: 2

MTIDLGVSLTSQAGGLQGIDLKSMDIQTLMVYVQGRRAELLTAQMQTQAEV

VQKANERMAQLNEVLSALSRAKAEFPPNPKPGDTIPGWDNQKVSRIEVPLNDALRA

AGLTGMFEARDGQVTAPGGRGTQVVNGTGVMAGSTTYKELESAYTTVKGMLDTA

SNTQQMDMIRLQAASNKRNEAFEVMTNTEKRRSDLNSSITNNMRKLMTVMSTTIST

APSGAALAPSRIDMRAPEPGSAGEGAGILAPVTTLALAAGRPAFPASPSLRTAPVLDP

PVRDLSPADLADLLRVLRSRAVLGQLATARENLQDAQVKAKQNTQAQLDKLDAWF

RKAEEAESKGWLSKVFGWIGKVLAVVASALAVGFAAVASVATGAAATPMLLLSGM

ALVSAVTSLADQISQEAGGPPISLGGFLSGLAGRLLTALGVDQSQADQIAKIVAGLAV

PVVLLIEPQMLGEMAQGVARLAGASDATAGYIAMAMSIVAAIAVAAINAAGTAGAG

SASAIKGAWDRAAAVATQVLQGGTAVAQGGVGVSMAVDRKQADLLVADKADLA

ASLTKLRAAMEREADDIKKILAQFDEAYHMIAKMISDMASTHSQVSANLGRRQAV

Bsp22 Nucleotide Sequence                                                        SEQ ID NO: 3

```
CATatgaccattgatctcggagtttcactcacgtcgcaggccggcggcctgcaaggcatcgacctcaagagcatggata
tccagactctcatggtgtatgtgcagggtcgtcgcgccgaactcctcacggctcaaatgcagacccaggccgaagtggtgcagaagg
ccaatgaacgcatggcgcagctcaacgaggtcctgtccgcgctgtcccgggccaaggccgagtttccgcccaatccgaagccggg
cgacaccatcccgggctgggacaaccagaaggtcagccggatcgaggttcctctcaatgatgcgctgcgcgctgccggcctgacg
ggcatgttcgaagcgcgcgatggccaagtgaccgcccccggcggccggggtacgcaggtcgtgaacggcacgggcgtcatggcc
ggttccacgacctataaggaactcgaaagtgcctacaccaccgtaaaggggatgctggatacggcgtccaatacgcaacagatggac
atgatcaggctgcaggccgccagcaacaagcgcaacgaggctttcgaggtcatgaccaacaccgagaagcggcgcagcgacctg
aacagttccatcaccaacaacatgcgc
```

Bsp22 Amino Acid Sequence  SEQ ID NO: 4

MTIDLGVSLTSQAGGLQGIDLKSMDIQTLMVYVQGRRAELLTAQMQTQAEV

VQKANERMAQLNEVLSALSRAKAEFPPNPKPGDTIPGWDNQKVSRIEVPLNDALRA

AGLTGMFEARDGQVTAPGGRGTQVVNGTGVMAGSTTYKELESAYTTVKGMLDTA

SNTQQMDMIRLQAASNKRNEAFEVMTNTEKRRSDLNSSITNNMR

BopB Nucleotide Sequence  SEQ ID NO: 5

Atgaccgtcatgagtacgaccatatccacagccccgagcggcgccgcgcttgcgccgtctcgcatagatatgcgggcac cggagcccgggagtgccggcgaaggcgccggcatcctggcgccggtgacgacgctggctctggcggcgggccggccggcttttc cagcgtcaccgtcgctgcgcaccgcgcccgtcctggatccgccagtgcgcgatctcagccccgccgacttggccgacctgctgcgc gtcttgcgatccagggcggtggacgggcagttggccacggcgcgcgagaacctgcaggacgcgcaagtcaaggcgaagcagaa cacccaggcccagctcgacaagctggacgcatggtttcggaaggccgaagaggccgagagcaagggatggctgagcaaggtgtt cggctggatcggcaaggtgctggcggtcgtggcatcggccctggcggtgggctttgccgccgtcgccagcgtggccaccggcgcg gcggccacacccatgctgctgctcagcggcatggcactggtcagcgccgtgacatcgctggccgaccagatatcgcaagaggcgg gaggcccgcctatcagcctgggcgggtttctctccgggctggccggacgtctgctgacagcgttgggggtggatcagtcgcaggcc gaccaaattgccaagatcgtcgccggcctggccgtgcccgtcgtcttgctgatcgaaccccagatgctgggcgaaatggcgcaagg cgtggccaggctggctggcgccagcgatgccaccgcggggtacatagccatggcgatgtccatcgtggcggcgatcgcggtcgcc gcgatcaatgccgccggtacagccggcgcgggtagcgcttcggccgatcaaggggcctgggatcgggccgccgcggtagccacc caggtccttcaaggggggtacggcagtggcgcaaggcggcgtcggcgtgtcgatggcagtcgatcgcaaacaggccgatctcctggt cgccgacaaggcggatctggcggcgagcctgacaaaactgcgggcggccatggagcgtgaggcggacgatatcaagaagatcct ggctcaattcgacgaggcctatcacatgatcgcgaagatgatcagcgatatggcgagtacgcacagccaggtcagcgccaacctcg ggcggcgccaggcggtgtagCTCGAG BopB Amino Acid Sequence  SEQ ID NO: 6

MTVMSTTISTAPSGAALAPSRIDMRAPEPGSAGEGAGILAPVTTLALAAGRPA

FPASPSLRTAPVLDPPVRDLSPADLADLLRVLRSRAVDGQLATARENLQDAQVKAK

QNTQAQLDKLDAWFRKAEEAESKGWLSKVFGWIGKVLAVVASALAVGFAAVASV

ATGAAATPMLLLSGMALVSAVTSLADQISQEAGGPPISLGGFLSGLAGRLLTALGVD

QSQADQIAKIVAGLAVPVVLLIEPQMLGEMAQGVARLAGASDATAGYIAMAMSIVA

AIAVAAINAAGTAGAGSASAIKGAWDRAAAVATQVLQGGTAVAQGGVGVSMAVD

RKQADLLVADKADLAASLTKLRAAMEREADDIKKILAQFDEAYHMIAKMISDMAST

HSQVSANLGRRQAV

His-BcrH1 chaperone with histidine tag nucleotide sequence  SEQ ID NO: 7

ATGGGCAGCAGCCATCACCATCATCACCACAGCCAGGATCCGATGCCAAA

GTCAGCCGAGCAGGGCGGCTCCCCGGCGTCAGCTTCGCATGAGGCGTTGCGCCA

TATTCTCGACGCAGGCGCTTCGATGGGCAGCTTGCAGGGGTTGGACGAGGTGCA

ACAGCAGGCGTTGTACGCGATCGCTCATCK5CGCCTACGAACAGGGCCGCTATGC

CGACGCGTTGAAAATGTTCTGCCTGCTGGTCGCGTGCGATCCGCTGGAAGCCCGT

TATCTGCTGGCCCTGGGCGCCGCGGCCCAGGAGCTGGGGCTGTACGAGCATGCC

TTGCAGCAATACGCGGCCGCGGCGGCTTTGCAGTTGGACTCCCCCAGGCCCCTGT

TGCATGGCGCCGAGTGCCTGTATGCGTTGGGTCGTCGCCGCGACGCCCTGGATAC

GCTCGACATGGTGCTTGAGTTGTGCGGGTCGCCGGAGCATGCGGCCCTGCGCGA

ACGGGCCGAGTCGCTGCGCAGGAGCTATGCACGTGCCGACTGAAAGCTT

His-BcrH1 with histidine tag chaperone amino acid sequence
SEQ ID NO: 8

MGSSHHHHHHSQDPMPKSAEQGGSPASASHEALRHILDAGASMGSLQGLDE

VQQQALYAIAHGAYEQGRYADALKMFCLLVACDPLEARYLLALGAAAQELGLYEH

ALQQYAAAAALQLDSPRPLLHGAECLYALGRRRDALDTLDMVLELCGSPEHAALRE

RAESLRRSYARAD

BcrH1 amino acid sequence
SEQ ID NO: 9

MPKSAEQGGSPASASHEALRHILDAGASMGSLQGLDEVQQQALYAIAHGAY

EQGRYADALKMFCLLVACDPLEARYLLALGAAAQELGLYEHALQQYAAAAALQLD

SPRPLLHGAECLYALGRRRDALDTLDMVLELCGSPEHAALRERAESLRRSYARAD

IpgC Chaperone of DBF nucleic acidsequence
SEQ ID NO: 10

CCatgggcagcagccatcatcatcatcatcacagcagcggcctggtgccgcgcggcagccatatgctcgagatgtcttta aatatcaccgaaaatgaaagcatctctactgcagtaattgatgcaattaactctggcgctacactgaaagatattaatgcaattcctgatga tatgatggatgacatttattcatatgcttatgacttttacaacaaaggaagaatagaggaagctgaagttttcttcaggtttttatgtatatacg acttttacaatatagactacattatgggactcgcagctatttatcagataaaagaacagttccaacaagcagcagacctttatgctgtcgct tttgcattaggaaaaaatgactatacaccagtattccatactggacaatgccagcttcggttgaaagccccttaaaagctaaagagtgct tcgaactcgtaattcaacacagcaatgatgaaaaattaaaaataaaagcacaatcatacttggacgcaattcaggatatcaaggagtag

GATCC

IpgC Chaperone of DBF Amino Acid sequence
SEQ ID NO: 11

MSLNITENESISTAVIDAINSGATLKDINAIPDDMMDDIYSYAYDFYNKGRIEE

AEVFFRFLCIYDFYNVDYIMGLAAIYQIKEQFQQAADLYAVAFALGKNDYTPVFHTG

QCQLRLKAPLKAKECFELVIQHSNDEKLKIKAQSYLDAIQDIKE

LTA1 nucleic acid sequence
SEQ ID NO: 12

CATAtggacaatggcgatcgtttataccgtgccgactcgcgtcccccagatgagattaaacgtagcggtgggttaatgc cacgtgggcacaatgagtattttgaccgtggaacacagatgaacattaaccttacgatcatgcccgtgggacccagaccgggtttgtc cgttatgatgacgggtatgttagtacgagtttgtccttacgctccgcacaccttgcgggacaaagtattttatcaggctacagcacatatta catttatgtgatcgccactgccccaaacatgttcaatgtgaacgatgtgttggggtttacagcccccatccatatgaacaagaagtctcg gcccttgggggatcccatatagccagatttatggttggtaccgcgtaaattttggtgtgattgatgaacgtttgcatcgtaaccgtgaata ccgcgatcgctactaccgtaacttgaacattgcacctgccgaggacggctatcgtttagcgggattcccacccgatcatcaggcgtgg cgtgaggaaccgtggatccatcacgcccctcaggggtgcgggaacagtagtcgc LTA1 amino acid sequence
SEQ ID NO: 13

MDNGDRLYRADSRPPDEIKRSGGLMPRGHNEYFDRGTQMNINLYDHARGTQ

TGFVRYDDGYVSTSLSLRSAHLAGQSILSGYSTYYIYVIATAPNMFNVNDVLGVYSP

HPYEQEVSALGGIPYSQIYGWYRVNFGVIDERLHRNREYRDRYYRNLNIAPAEDGYR

LAGFPPDHQAWREEPWIHHAPQGCGNSSR

GSAAS Linker amino acid sequence
SEQ ID NO: 14

GSAAS

LTA1-GSAAS-DBF (IpaD-LE-IpaB) nucleic acid sequence
SEQ ID NO: 15

CATAtggacaatggcgatcgtttataccgtgccgactcgcgtcccccagatgagattaaacgtagcggtgggttaatgc cacgtgggcacaatgagtattttgaccgtggaacacagatgaacattaaccttacgatcatgcccgtgggacccagaccgggtttgtc cgttatgatgacgggtatgttagtacgagtttgtccttacgctccgcacaccttgcgggacaaagtattttatcaggctacagcacatatta catttatgtgatcgccactgccccaaacatgttcaatgtgaacgatgtgttggggtttacagcccccatccatatgaacaagaagtctcg -continued

```
gcccttgggggatcccatatagccagatttatggttggtaccgcgtaaattttggtgtgattgatgaacgtttgcatcgtaaccgtgaata ccgcgatcgctactaccgtaacttgaacattgcacctgccgaggacggctatcgtttagcgggattccacccgatcatcaggcgtgg cgtgaggaaccgtggatccatcacgcccctcaggggtgcgggaacagtagtcgcgggtccgcggcatccatgaatat aacaactctg actaatagta tttccacctc atcattcagt ccaaacaata ccaacggttc atcaaccgaa acagttaatt ctgatataaa acaacgacc agttctcatc ctgtaagttc ccttactatg ctcaacgaca cccttcataa tatcagaaca acaaatcagg cattaaagaa agagctttca caaaaaacgt tgactaaaac atcgctagaa gaaatagcat tacattcatc tcagattagc atggatgtaa ataaatccgc tcaactattg gatattcttt ccaggaacga atatccaatt aataaagacg caagagaatt attacattca gccccgaaag aagccgagct tgatggagat caaatgatat ctcatagaga actgtgggct aaaattgcaa actccatcaa tgatattaat gaacagtatc tgaaagtata tgaacatgcc gttagttcat atactcaaat gtatcaagat tttagcgctg ttctttccag tcttgccggc tggatctctc ccggaggtaa cgacggaaac tccgtgaaat tacaagtcaa ctcgcttaaa aaggcattgg aagaactcaa ggaaaaatat aaagataaac cgctatatcc agcaaataat actgttagtc aggaacaagc aaataaatgg cttacagaat taggtggaac aatcggcaag gtatctcaaa aaacggggg atatgttgtc agtataaaca tgaccccaat agacaatatg ttaaaaagct tagataatct aggtggaaat ggcgaggttg tgctagataa tgcaaaatat caggcatgga atgccggatt ctctgccgaa gatgaaacaa tgaaaaataa tcttcaaact ttagttcaaa aatacagtaa tgccaatagt attttttgata atrtagtaaa ggttttgagt agtacaataa gctcatgtac agatacagat aaactttttc tccatttc CTCGAG atgcataatgta agcaccacaa ccactggttt tcctcttgcc aaaatattga cttccactgagcttggagac aatactatcc aagctgcaaa tgatgcagct aacaaattat tttctcttacaattgctgat cttactgcta accaaaatat taatacaact aatgcacact caacttcaaatatattaatc cctgaactta agcaccaaa gtcattaaat gcaagttccc aactaacgcttttaattgga aaccttattc aaatactcgg tgaaaaatct ttaactgcat taacaaataaaattactgct tggaagtccc agcaacaggc aagacagcaa aaaacctag aattctccgataaaattaac actcttctat ctgaaactga aggactaacc agagactatg aaaaacaaattaataaacta aaaacgcag attctaaaat aaaagaccta gaaataaaa ttaaccaaattcaaacaaga ttatcgaacc tcgatccaga gtcaccagaa aagaaaaaat taagccgggaagaaatacaa ctcactatca aaaaagacgc agcagttaaa gacaggacat tgattgagcagaaaaccctg tcaattcata gcaaacttac agataaatca atgcaactcg aaaagaaatagactcttt tctgcatttt caaacacagc atctgctgaa cagctatcaa cccagcagaaatcattaacc ggacttgcca gtgttactca attgatggca acctttattc aactagttggaaaaaataat gaagaatctt taaaaaatga tctggctcta ttccagtctc tccaagaatcaagaaaaact gaaatggaga gaaatctga tgagtatgct gctgaagtac gtaaagcagaagaactcaac agagtaatgg gttgtgttgg gaaaatactt ggggcacttt taactatcgttagtgttgtt gcagcagctt tttctggagg agcctctcta gcactggcag ctgttggttt agctcttatg gttacggatg ctatagtaca agcagcgacc ggcaattcct tcatggaacaagccctgaat ccgatcatga aagcagtcat tgaaccctta atcaaactcc tttcagatgcatttacaaaa atgctcgaag gcttgggcgt cgactcgaaa aaagccaaaa tgattggctctattctgggg gcaatcgcag gcgctcttgt cctagttgca gcagtcgttc tcgtagccactgttggtaaa caggcagcag caaaacttgc agaaaatatt ggcaaaataa taggtaaaaccctcacagac cttataccaa agtttctcaa gaattttct tctcaactgg acgatttaatcactaatgct gttgccagat taaataaatt tcttggtgca gcgggtgatg aagtaatatccaaacaatt atttccaccc atttaaacca agcagtttta ttaggagaaa gtgttaactctgccacacaa gcgggaggaa gtgtcgcttc tgctgttttc cagaacagcg cgtcgacaaatctagcagac ctgacattat cgaaatatca agttgaacaa ctgtcaaaat atatcagtgaagcaatagaa aaattcggcc aattgcagga agtaattgca gatctattag cctcaatgtccaactctcag gctaatagaa ctgatgttgc aaaagcaatt ttgcaacaaa ctactgcttga GGATCC
```

LTA1-GSAAS-IpaD-LE-IpaB (DBF) Amino Acid sequence

SEQ ID NO: 16

MDNG

HPYEQEVSALGGIPYSQIYGWYRVNFGVIDERLHRNREYRDYYRNLNIAPAEDGYR

LAGFPPDHQAWREEPWIHHAPQGCGNSSRGSAASMNITTLTNSISTSSFSPNNTNGSS

TETVNSDIKTTTSSHPSSLTMLNDTLHNIRTTNQALKKELSQKTLRNEYPINKDAREL

LHSAPKEAELDGDQMISHRELWAKIANSINDINEQYLKVYEHAVSSYTQMYQDFSA

VLSSLAGWISPGGNDGNSVKLQVNSLKKALEELKEKYKDKPLYPANNTVSQEQANK

WLTELGGTIGKVSQKNGGYVVSINMTPIDNMLKSLDNLGGNGEVVLDNAKYQAWN

GFSAEDETMKNNLQTLVQKYSNANSIFDNLVKVLSSTISSCTDTDKLFLHFLEMHNV

STTTTGFPLAKILTSTELGDNTIQAANDAANKLFSLTIADLTANQNINTTNAHSTSNILI

PELKAPKSLNASSQLTLLIGNLIQILGEKSLTALTNKITAWKSQQQARQQKNLEFSDKI

NTLLSETEGLTRDYEKQINKLKNADSKIKDLENKINQIQTRLSNLDPESPEKKKLSREE

IQLTIKKDAAVKDRTLIEQKTLSIHSKLTDKSMQLEKEIDSFSAFSNTASAEQLSTQQK

SLTGLASVTQLMATFIQLVGKNNEESLKNDLALFQSLQESRKTEMERKSDEYAAEVR

KAEELNRVMGCVGKILGALLTIVSVVAAAFSGGASLALAAVGLALMVTDAIVQAAT

GNSFMEQALNPIMKAVIEPLIKLLSDAFTKMLEGLGVDSKKAKMIGSILGAIAGALVL

VAAVVLVATVGKQAAAKLAENIGKIIGKTLTDLIPKFLKNFSSQLDDLITNAVARLN

KFLGAAGDEVISKQIISTHLNQAVLLGESVNSATQAGGSVASAVFQNSASTNLADLT

LSKYQVEQLSKYISEAIEKFGQLQEVIADLLASMSNSQANRTDVAKAILQQTTA

LTA1-22BF nucleic acid sequence

SEQ ID NO: 17

CATAtggacaatggcgatcgtttataccgtgccgactcgcgtcccccagatgagattaaacgtagcggtgggttaatgc cacgtgggcacaatgagtattttgaccgtggaacacagatgaacattaacctttaegatcatgcccgtgggacccagaccgggtttgtc cgttatgatgacgggtatgttagtacgagtttgtccttacgctccgcacaccttgcgggacaaagtattttatcaggctacagcacatatta catttatgtgatcgccactgccccaaacatgttcaatgtgaacgatgtgttggggggtttacagcccccatccatatgaacaagaagtctcg gcccttgggggatcccatatagccagatttatggttggtaccgcgtaaattttggtgtgattgatgaacgtttgcatcgtaaccgtgaata ccgcgatcgctactaccgtaacttgaacattgcacctgccgaggacggctatcgtttagcgggattcccacccgatcatcaggcgtgg cgtgaggaaccgtggatccatcacgcccctcaggggtgcgggaacagtagtcgcatgaccattgatctcggagtttcactcacgtcgc aggccggcggcctgcaaggcatcgacctcaagagcatggatatccagactctcatggtgtatgtgcagggtcgtcgcgccgaactcc tcacggctcaaatgcagacccaggccgaagtggtgcagaaggccaatgaacgcatggcgcagctcaacgaggtcctgtccgcgct gtcccgggceaaggccgagtttccgcccaatccgaagccggggegacaccatcccgggctgggacaaccagaaggtcagccggat cgaggttcctctcaatgatgcgctgcgcgctgccggcctgacgggcatgttcgaagcgcgcgatggccaagtgaccgccccggcg gccggggtacgcaggtcgtgaacggcacgggcgtcatggccggttccacgacctataaggaactcgaaagtgcctacaccaccgta aaggggatgctggatacggcgtccaatacgcaacagatggacatgatcaggctgcaggccgccagcaacaagcgcaacgaggctt tcgaggtcatgaccaacaccgagaagcggcgcagcgacctgaacagttccatcaccaacaacatgcgcaagcttatgaccgtcatga gtacgaccatatccacagccccgagcggcgccgcgcttgcgccgtctcgcatagatatgcgggcaccggagcccgggagtgccgg cgaaggcgccggcatcctggcgccggtgacgacgctggctctggcggcgggccgccggcttttccagcgtcaccgtcgctgcgc accgcgcccgtcctggatccgccagtgcgcgatctcagccccgccgacttggccgacctgctgcgcgtcttgcgatccagggcggt ggacgggcagttggccacggcgcgcgagaacctgcaggacgcgcaagtcaaggcgaagcagaacacccaggcccagctcgac aagctggacgcatggtttcggaaggccgaagaggccgagagcaagggatggctgagcaaggtgttcggctggatcggcaaggtg ctggcggtcgtggcatcggccctggcggtgggctttgccgccgtcgccagcgtggccaccggcgcggcggccacaccatgctgc tgctcagcggcatggcactggtcagcgccgtgacatcgctggccgaccagatatcgcaagaggcgggaggcccgcctatcagcct gggcgggtttctctccgggctggccggacgtctgctgacagcgttggggtggatcagtcgcaggccgaccaaattgccaagatcgt cgccggcctggccgtgcccgtcgtcttgctgatcgaaccccagatgctgggcgaaatggcgcaaggcgtggccaggctggctggc -continued

```
gccagcgatgccaccgcggggtacatagccatggcgatgtccatcgtggcggcgatcgcggtcgccgcgatcaatgccgccggta cagccggegcgggtagcgcttcggcgatcaaggggcctgggatcgggccgccgcgtagccacccaggtccttcaaggggta cggcagtggcgcaaggcggcgtcggcgtgtcgatggcagtcgatcgcaaacaggccgatctcctggtcgccgacaaggcggatct ggcggcgagcctgacaaaactgcgggcggccatggagcgtgaggcggacgatatcaagaagatcctggctcaattcgacgaggc ctatcacatgatcgcgaagatgatcagcgatatggcgagtacgcacagccaggtcagcgccaacctcgggcggcgccaggcggtg tagCTCGAG
```

LTA1-22BF Amino acid sequence                                                        SEQ ID NO: 18

```
MDNGDRLYRADSRPPDEIKRSGGLMPRGHNEYFDRGTQMNINLYDHARGTQ

TGFVRYDDGYVSTSLSLRSAHLAGQSILSGYSTYYIYVIATAPNMFNVNDVLGVYSP

HPYEQEVSALGGIPYSQIYGWYRVNFGVIDERLHRNREYRDRYYRNLNIAPAEDGYR

LAGFPPDHQAWREEPWIHHAPQGCGNSSRMTIDLGVSLTSQAGGLQGIDLKSMDIQT

LMVYVQGRRAELLTAQMQTQAEVVQKANERMAQLNEVLSALSRAKAEFPPNPKPG

DTIPGWDNQKVSRIEVPLNDALRAAGLTGMFEARDGQVTAPGGRGTQVVNGTGVM

AGSTTYKELESAYTTVKGMLDTASNTQQMDMIRLQAASNKRNEAFEVMTNTEKRR

SDLNSSITNNMRKLMTVMSTTISTAPSGAALAPSRIDMRAPEPGSAGEGAGILAPVTT

LALAAGRPAFPASPSLRTAPVLDPPVRDLSPADLADLLRVLRSRAVDGQLATARENL

QDAQVKAKQNTQAQLDKLDAWFRKAEEEAESKGWLSKVFGWIGKVLAVVASALAV

GFAAVASVATGAAATPMLLLSGMALVSAVTSLADQISQEAGGPPISLGGFLSGLAGR

LLTALGVDQSQADQIAKIVAGLAVPVVLLIEPQMLGEMAQGVARLAGASDATAGYI

AMAMSIVAAIAVAAINAAGTAGAGSASAIKGAWDRAAAVATQVLQGGTAVAQGG

VGVSMAVDRKQADLLVADKADLAASLTKLRAAMEREADDIKKILAQFDEAYHMIA

KMISDMASTHSQVSANLGRRQAV*
```

His-BicA (Chaperone of BurkF) nucleic acid sequence                                          SEQ ID NO: 19

```
ATGGGCAGCAGCCATCACCATCATCACCACAGCCAGGATCCGATGACGCA

ACGCGACGTGAACATAGACGACATCGAGGCGCAGGAAATGGCGGCGGCGCTGCT

GGACGCGGTCCAGAACGGCGCGACGCTGAAGGACCTGCATCAGGTGCCGCAGGA

CCTGATGGACGGCATCTATGCGTTCGCGTACCGCTTCTACCAGCAGGGGCGGCTC

GACGACGCGGAGGTGTTCTTCCGCTTTCTGCGCATCTACGACTTCTACAACGCCG

AATACGCGATGGGGCTCGCGGCGGTGTGCCAGTTGAAGAAGGAGTACGCGCGGG

CGATCGATCTGTATGCACTCGCGTATTCGCTGTCGAAGGACGACCACCGGCCGAT

GTTCCACACCGGCCAATGCCATCTGCTGATGGGCAAGGCGGCGCTCGCGCGGCG

CTGCTTCGGCATCGTCGTCGAGCGCTCGCGCGACGAGCGCCTCGCGCAGAAGGC

GCAGTCCTATCTCGACGGGCTCGACGAAGTGGGCGCCGACGCGGCGCCCGCATC

CGCCGGGAACGACCACTGAGCGGCCGC
```

His-BicA (Chaperone of BurkF) Amino acid sequence                                          SEQ ID NO: 20

```
MGSSHHHHHHSQDPMTQRDVNIDDIEA

-continued

BipD nucleic acid sequence

SEQ ID NO: 21

CATATGAACATGCACGTGGACATGGGTCGTGCGCTGACCGTTCGTGATTG

GCCGGCGCTGGAGGCGCTGGCGAAAACCATGCCGGCGGATGCGGGTGCGCGTGC

GATGACCGATGATGACCTGCGTGCGGCGGGTGTGGACCGTCGTGTTCCGGAGCA

GAAGCTGGGTGCGGCGATTGATGAATTCGCGAGCCTGCGTCTGCCGGATCGTATC

GACGGTCGTTTCGTGGATGGCCGTCGTGCGAACCTGACCGTTTTTGATGATGCGC

GTGTTGCGGTTCGTGGTCATGCGCGTGCGCAACGTAACCTGCTGGAGCGTCTGGA

GACCGAACTGCTGGGTGGCACCCTGGATACCGCGGGTGACGAAGGTGGCATTCA

GCCGGACCCGATCCTGCAAGGCCTGGTGGATGTTATCGGTCAGGGCAAAAGCGA

TATTGACGCGTACGCGACCATCGTGGAAGGTCTGACCAAGTATTTTCAAAGCGTG

GCGGACGTTATGAGCAAACTGCAGGATTACATTAGCGCGAAGGATGACAAAAAC

ATGAAGATCGACGGTGGCAAGATCAAAGCGCTGATTCAGCAAGTGATCGACCAC

CTGCCGACCATGCAGCTGCCGAAGGGTGCGGATATTGCGCGTTGGCGTAAAGAG

CTGGGCGACGCGGTTAGCATCAGCGATAGCGGTGTGGTTACCATTAACCCGGAC

AAACTGATCAAGATGCGTGATAGCCTGCCGCCGGATGGCACCGTTTGGGATACC

GCGCGTTACCAAGCGTGGAACACCGCGTTCAGCGGTCAGAAAGGCCAGCATCCG

GAACGTCGTGCGGATGCGCGTCGTAAATATAGCCACCAGAACAGCAACTTTGAT

AACCTGGTGAAGGTTCTGAGCGGTGCGATTAGCACCCTGACCGACACCCAGAGC

TATCTGCAAATC

BipD amino acid sequence

SEQ ID NO: 22

MNMHVDMGRALTVRDWPALEALAKTMPADAGARAMTDDDLRAAGVDRR

VPEQKLGAAIDEFASLRLPDRIDGRFVDGRRANLTVFDDARVAVRGHARAQRNLLE

RLETELLGGTLDTAGDEGGIQPDPILQGLVDVIGQGKSDIDAYATIVEGLTKYFQSVA

DVMSKLQDYISAKDDKNMKIDGGKIKALIQQVIDHLPTMQLPKGADIARWRKELGD

AVSISDSGVVTINPDKLIKMRDSLPPDGTVWDTARYQAWNTAFSGQKGQHPERRAD

ARRKYSHQNSNFDNLVKVLSGAISTLTDTQSYLQI

BipB nucleic acid sequence

SEQ ID NO: 23

ATGAGCAGCGGTGTTCAAGGTGGCCCGGCGGCGAACGCGAACGCGTACC

AGACCCACCCGCTGCGTGATGCGGCGAGCGCGCTGGGCACCCTGAGCCCGCAGG

CGTATGTGGATGTGGTTAGCGCGGCGCAACGTAACTTCCTGGAGCGTATGAGCC

AACTGGCGAGCGAACAGTGCGATGCGCAACCGGCGGCGCATGATGCGCGTCTGG

ATGATCGTCCGGCGCTGCGTGCGCCGCAGGAACGTGACGCGCCGCCGCTGGGTG

CGAGCGATACCGGTAGCCGTGCGAGCGGTGCGGCGAAACTGACCGAGCTGCTGG

GTGTGCTGATGAGCGTTATTAGCGCGAGCAGCCTGGACGAACTGAAGCAACGTA

GCGATATCTGGAACCAGATGAGCAAAGCGGCGCAAGACAACCTGAGCCGTCTGA

GCGATGCGTTTCAGCGTGCGACCGACGAGGCGAAAGCGGCGGCGGATGCGGCGG

AACAGGCGGCGGCGGCGGCGAAGCAAGCGGGTGCGGACGCGAAAGCGGCGGAT

GCGGCGGTGGATGCGGCGCAAAAACGTTACGATGACGCGGTTAAGCAGGGCCTG

CCGGATGACCGTCTGCAAAGCCTGAAAGCGGCGCTGGAGCAGGCGCGTCAGCAA

GCGGGTGATGCGCATGGTCGTGCGGATGCGCTGCAGGCGGATGCGACCAAGAAA

CTGGACGCGGCGAGCGCGCTGGCGACCCAAGCGCGTGCGTGCGAACAGCAAGTG

-continued

```
GATGACGCGGTTAACCAGGCGACCCAGCAATATGGTGCGAGCGCGAGCCTGCGT
ACCCCGCAAAGCCCGCGTCTGAGCGGTGCGGCGGAGCTGACCGCGGTGCTGGGC
AAGCTGCAGGAACTGATTAGCAGCGGCAACGTTAAAGAGCTGGAAAGCAAGCA
GAAACTGTTCACCGAGATGCAAGCGAAGCGTGAGGCGGAACTGCAAAAGAAAA
GCGACGAATATCAGGCGCAAGTGAAGAAAGCGGAGGAAATGCAGAAAACGATG
GGTTGCATCGGCAAGATTGTGGGTTGGGTTATTACCGCGGTTAGCTTTGCGGCGG
CGGCGTTTACCGGTGGCGCGAGCCTGGCGCTGGCGGCGGTGGGCCTGGCGCTGG
CGGTTGGTGACGAGATTAGCCGTGCGACCACCGGTGTGAGCTTCATGGACAAGC
TGATGCAGCGGGTTATGGATGCGATGCTGAAACCGCTGATGGAGATGATTAGGA
GCCTGATCACCAAGGCGCTGGTTGCGTGCGGCGTTGATCAGCAAAAAGCGGAAC
TGGCGGGTGCGATTCTGGGTGCGGTTGTTACCGGTGTGGCGCTGGTTGCGGCGGC
GTTTGTTGGTGCGAGCGCGGTGAAAGCGGTTGCGAGCAAGGTTATCGACGCGAT
GGCGGGTCAGCTGACCAAGCTGATGGATAGCGCGATTGGCAAAATGCTGGTGCA
ACTGATCGAGAAATTCAGCGAAAAGAGCGGTCTGCAGGCGCTGGGTAGCCGTAC
CGCGACCGCGATGACCCGTATGCGTCGTGCGATTGGCGTTGAGGCGAAGGAAGA
CGGTATGCTGCTGGCGAACCGTTTTGAAAAAGCGGGCACCGTGATGAACGTTGG
TAACCAAGTGAGCCAAGCGGCGGGTGGCATTGTGGTTGGCGTTGAGCGTGCGAA
AGCGATGGGTCTGCTGGCGGATGTGAAAGAAGCGATGTATGACATCAAGCTGCT
GGGTGATCTGCTGAAACAGGCGGTGGACGCGTTTGCGGAGCACAACCGTGTTCT
GGCGCAACTGATGCAGCAAATGAGCGATGCGGGCGAAATGCAGACCAGCACCG
GCAAGCTGATCCTGCGTAACGCGCGTGCGGTTTAAGGATCC
```

BipB amino acid sequence

SEQ ID NO: 24

```
MSSGVQGGPAANANAYQTHPLRDAASALGTLSPQAYVDVVSAAQRNFLER
MSQLASEQCDAQPAAHDARLDDRPALRAPQERDAPPLGASDTGSRASGAAKLTELL
GVLMSVISASSLDELKQRSDIWNQMSKAAQDNLSRLSDAFQRATDEAKAAADAAEQ
AAAAAKQAGADAKAADAAVDAAQKRYDDAVKQGLPDDRLQSLKAALEQARQQA
GDAHGRADALQADATKKLDAASALATQARACEQQVDDAVNQATQQYGASASLRT
PQSPRLSGAAELTAVLGKLQELISSGNVKELESKQKLFTEMQAKREAELQKKSDEYQ
AQVKKAEEMQKTMGCIGKIVGWVITAVSFAAAAFTGGASLALAAVGLALAVGDEIS
RATTGVSFMDKLMQPVMDAILKPLMEMISSLITKALVACGVDQQKAELAGAILGAV
VTGVALVAAAFVGASAVKAVASKVIDAMAGQLTKLMDSAIGKMLVQLIEKFSEKS
GLQALGSRTATAMTRMRRAIGVEAKEDGMLLANRFEKAGTVMNVGNQVSQAAGG
IVVGVERAKAMGLLADVKEAMYDIKLLGDLLKQAVDAFAEHNRVLAQLMQQMSD
AGEMQTSTGKLILRNARAV
```

BurkF nucleic acid sequence

SEQ ID NO: 25

```
CATATGAACATGCACGTGGACATGGGTCGTGCGCTGACCGTTCGTGATTG
GCCGGCGCTGGAGGCGCTGGCGAAAACCATGCCGGCGGATGCGGGTGCGCGTGC
GATGACCGATGATGACCTGCGTGCGGCGGGTGTGGACCGTCGTGTTCCGGAGCA
GAAGCTGGGTGCGGCGATTGATGAATTCGCGAGCCTGCGTCTGCCGGATCGTATC
GACGGTCGTTTCGTGGATGGCCGTCGTGCGAACCTGACCGTTTTTGATGATGCGC
GTGTTGCGGTTCGTGGTCATGCGCGTGCGCAACGTAACCTGCTGGAGCGTCTGGA
```

-continued

```
GACCGAACTGCTGGGTGGCACCCTGGATACCGCGGGTGACGAAGGTGGCATTCA

GCCGGACCCGATCCTGCAAGGCCTGGTGGATGTTATCGGTCAGGGCAAAAGCGA

TATTGACGCGTACGCGACCATCGTGGAAGGTCTGACCAAGTATTTTCAAAGCGTG

GCGGACGTTATGAGCAAACTGCAGGATTACATTAGCGCGAAGGATGACAAAAAC

ATGAAGATCGACGGTGGCAAGATCAAAGCGCTGATTCAGCAAGTGATCGACCAC

CTGCCGACCATGCAGCTGCCGAAGGGTGCGGATATTGCGCGTTGGCGTAAAGAG

CTGGGCGACGCGGTTAGCATCAGCGATAGCGGTGTGGTTACCATTAACCCGGAC

AAACTGATCAAGATGCGTGATAGCCTGCCGCCGGATGGCACCGTTTGGGATACC

GCGCGTTACCAAGCGTGGAACACCGCGTTCAGCGGTCAGAAAGGCCAGCATCCG

GAACGTCGTGCGGATGCGCGTCGTAAATATAGCCACCAGAACAGCAACTTTGAT

AACCTGGTGAAGGTTCTGAGCGGTGCGATTAGCACCCTGACCGACACCCAGAGC

TATCTGCAAATCAAGCTTATGAGCAGCGGTGTTCAAGGTGGCCCGGCGGCGAAC

GCGAACGCGTACCAGACCCACCCGCTGCGTGATGCGGCGAGCGCGCTGGGCACC

CTGAGCCCGCAGGCGTATGTGGATGTGGTTAGCGCGGCGCAACGTAACTTCCTG

GAGCGTATGAGCCAACTGGCGAGCGAACAGTGCGATGCGCAACCGGCGGCGCAT

GATGCGCGTCTGGATGATCGTCCGGCGCTGCGTGCGCCGCAGGAACGTGACGCG

CCGCCGCTGGGTGCGAGCGATACCGGTAGCCGTGCGAGCGGTGCGGCGAAACTG

ACCGAGCTGCTGGGTGTGCTGATGAGCGTTATTAGCGCGAGCAGCCTGGACGAA

CTGAAGCAACGTAGCGATATCTGGAACCAGATGAGCAAAGCGGCGCAAGACAA

CCTGAGCCGTCTGAGCGATGCGTTTCAGCGTGCGACCGACGAGGCGAAAGCGGC

GGCGGATGCGGCGGAACAGGCGGCGGCGGCGAAGCAAGCGGGTGCGGACG

CGAAAGCGGCGGATGCGGCGGTGGATGCGGCGCAAAAACGTTACGATGACGCG

GTTAAGCAGGGCCTGCCGGATGACCGTCTGCAAAGCCTGAAAGCGGCGCTGGAG

CAGGCGCGTCAGCAAGCGGGTGATGCGCATGGTCGTGCGGATGCGCTGCAGGCG

GATGCGACCAAGAAACTGGACGCGGCGAGCGCGCTGGCGACCCAAGCGCGTGC

GTGCGAACAGCAAGTGGATGACGCGGTTAACCAGGCGACCCAGCAATATGGTGC

GAGCGCGAGCCTGCGTACCCCGCAAAGCCCGCGTCTGAGCGGTGCGGCGGAGCT

GACCGCGGTGCTGGGCAAGCTGCAGGAACTGATTAGCAGCGGCAACGTTAAAGA

GCTGGAAAGCAAGCAGAAACTGTTCACCGAGATGCAAGCGAAGCGTGAGGCGG

AACTGCAAAAGAAAGCGACGAATATCAGGCGCAAGTGAAGAAAGCGGAGGAA

ATGCAGAAAACGATGGGTTGCATCGGCAAGATTGTGGGTTGGGTTATTACCGCG

GTTAGCTTTGCGGCGGCGGCGTTTACCGGTGGCGCGAGCCTGGCGCTGGCGGCG

GTGGGCCTGGCGCTGGCGGTTGGTGACGAGATTAGCCGTGCGACCACCGGTGTG

AGCTTCATGGACAAGCTGATGCAGCCGGTTATGGATGCGATCCTGAAACCGCTG

ATGGAGATGATTAGCAGCCTGATCACCAAGGCGCTGGTTGCGTGCGGCGTTGAT

CAGCAAAAAGCGGAACTGGCGGGTGCGATTCTGGGTGCGGTTGTTACCGGTGTG

GCGCTGGTTGCGGCGGCGTTTGTTGGTGCGAGCGCGGTGAAAGCGGTTGCGAGC

AAGGTTATCGACGCGATGGCGGGTCAGCTGACCAAGCTGATGGATAGCGCGATT

GGCAAAATGCTGGTGCAACTGATCGAGAAATTCAGCGAAAAGAGCGGTCTGCAG

GCGCTGGGTAGCCGTACCGCGACCGCGATGACCCGTATGCGTCGTGCGATTGGC

GTTGAGGCGAAGGAAGACGGTATGCTGCTGGCGAACCGTTTTGAAAAAGCGGGC
```

```
ACCGTGATGAACGTTGGTAACCAAGTGAGCCAAGCGGCGGGTGGCATTGTGTT

GGCGTTGAGCGTGCGAAAGCGATGGGTCTGCTGGCGGATGTGAAAGAAGCGATG

TATGACATCAAGCTGCTGGGTGATCTGCTGAAACAGGCGGTGGACGCGTTTGCG

GAGCACAACCGTGTTCTGGCGCAACTGATGCAGCAAATGAGCGATGCGGGCGAA

ATGCAGACCAGCACCGGCAAGCTGATCCTGCGTAACGCGCGTGCGGTTTAAGGA

TCC
```

BurkF amino acid sequence            SEQ ID NO: 26

```
MNMHVDMGRALTVRDWPALEALAKTMPADAGARAMTDDDLRAAGVDRR

VPEQKLGAAIDEFASLRLPDRIDGRFVDGRRANLTVFDDARVAVRGHARAQRNLLE

RLETELLGGTLDTAGDEGGIQPDPILQGLVDVIGQGKSDIDAYATIVEGLTKYFQSVA

DVMSKLQDYISAKDDKNMKIDGGKIKALIQQVIDHLPTMQLPKGADIARWRKELGD

AVSISDSGVVTINPDKLIKMRDSLPPDGTVWDTARYQAWNTAFSGQKGQHPERRAD

ARRKYSHQNSNFDNLVKVLSGAISTLTDTQSYLQIKLMSSGVQGGPAANANAYQTH

PLRDAASALGTLSPQAYVDVVSAAQRNFLERMSQLASEQCDAQPAAHDARLDDRP

ALRAPQERDAPPLGASDTGSRASGAAKLTELLGVLMSVISASSLDELKQRSDIWNQM

SKAAQDNLSRLSDAFQRATDEAKAAADAAEQAAAAAKQAGADAKAADAAVDAA

QKRYDDAVKQGLPDDRLQSLKAALEQARQQAGDAHGRADALQADATKKLDAASA

LATQARACEQQVDDAVNQATQQYGASASLRTPQSPRLSGAAELTAVLGKLQELISS

GNVKELESKQKLFTEMQAKREAELQKKSDFYQAQVKKAEEMQKTMGCIGKIVGW

VITAVSFAAAAFTGGASLALAAVGLALAVGDEISRATTGVSFMDKLMQPVMDAILK

PLMEMISSLITKALVACGVDQQKAELAGAILGAVVTGVALVAAAFVGASAVKAVAS

KVIDAMAGQLTKLMDSAIGKMLVQLIEKFSEKSGLQALGSRTATAMTRMRRAIGVE

AKEDGMLLANRFEKAGTVMNVGNQVSQAAGGIVVGVERAKAMGLLADVKEAMY

DIKLLGDLLKQAVDAFAEHNRVLAQLMQQMSDAGEMQTSTGKLILRNARAV
```

LTA1-BurkF nucleic acid sequence            SEQ ID NO: 27

```
CATatggacaatggcgatcgtttataccgtgccgactcgcgtccccagatgagattaaacgtagcggtgggttaatgcc acgtgggcacaatgagtattttgaccgtggaacacagatgaacattaaccttacgatcatgcccgtgggacccagaccgggttttgtcc gttatgatgacgggtatgttagtacgagtttgtccttacgctccgcacaccttgcgggacaaagtattttatcaggctacagcacatattac atttatgtgatcgccactgccccaaacatgttcaatgtgaacgatgtgttgggggtttacagcccccatccatatgaacaagaagtctcg gcccttggggggatcccatatagccagatttatggttggtaccgcgtaaattttggtgtgattgatgaacgtttgcatcgtaaccgtgaata ccgcgatcgctactaccgtaacttgaacattgcacctgccgaggacggctatcgtttagcgggattcccacccgatcatcaggcgtgg cgtgaggaaccgtggatccatcacgcccctcaggggtgcgggaacagtagtcgcCATATGAACATGCACGTGGA

CATGGGTCGTGCGCTGACCGTTCGTGATTGGCCGGCGCTGGAGGCGCTGGCGAA

AACCATGCCGGCGGATGCGGGTGCGCGTGCGATGACCGATGATGACCTGCGTGC

GGCGGGTGTGGACCGTCGTGTTCCGGAGCAGAAGCTGGGTGCGGCGATTGATGA

ATTCGCGAGCCTGCGTCTGCCGGATCGTATCGACGGTCGTTTCGTGGATGGCCGT

CGTGCGAACCTGACCGTTTTTGATGATGCGCGTGTTGCGGTTCGTGGTCATGCGC

GTGCGCAACGTAACCTGCTGGAGCGTCTGGAGACCGAACTGCTGGGTGGCACCC

TGGATACCGCGGGTGACGAAGGTGGCATTCAGCCGGACCCGATCCTGCAAGGCC

TGGTGGATGTTATCGGTCAGGGCAAAAGCGATATTGACGCGTACGCGACCATCG

TGGAAGGTCTGACCAAGTATTTTCAAAGCGTGGCGGACGTTATGAGCAAACTGC
```

-continued

```
AGGATTACATTAGCGCGAAGGATGACAAAAACATGAAGATCGACGGTGGCAAG

ATCAAAGCGCTGATTCAGCAAGTGATCGACCACCTGCCGACCATGCAGCTGCCG

AAGGGTGCGGATATTGCGCGTTGGCGTAAAGAGCTGGGCGACGCGGTTAGGATC

AGCGATAGCGGTGTGGTTACCATTAACCCGGACAAACTGATCAAGATGCGTGAT

AGCCTGCCGCCGGATGGCACCGTTTGGGATACCGCGCGTTACCAAGCGTGGAAC

ACCGCGTTCAGCGGTCAGAAAGGCCAGCATCCGGAACGTCGTGCGGATGCGCGT

CGTAAATATAGCCACCAGAACAGCAACTTTGATAACCTGGTGAAGGTTCTGAGC

GGTGCGATTAGCACCCTGACCGACACCCAGAGCTATCTGCAAATCAAGCTTATG

AGCAGCGGTGTTCAAGGTGCCCGGCGGCGAACGCGAACGCGTACCAGACCCAC

CCGCTGCGTGATGCGGCGAGCGCGCTGGGCACCCTGAGCCCGCAGGCGTATGTG

GATGTGGTTAGCGCGGCGCAACGTAACTTCCTGGAGCGTATGAGCCAACTGGCG

AGCGAACAGTGCGATGCGCAACCGGCGGCGCATGATGCGCGTCTGGATGATCGT

CCGGCGCTGCGTGCGCCGCAGGAACGTGACGCGCCGCCGCTGGGTGCGAGCGAT

ACCGGTAGCCGTGCGAGCGGTGCGGCGAAACTGACCGAGCTGCTGGGTGTGCTG

ATGAGCGTTATTAGCGCGAGCAGCCTGGACGAACTGAAGCAACGTAGCGATATC

TGGAACCAGATGAGCAAAGCGGCGCAAGACAACCTGAGCCGTCTGAGCGATGCG

TTTCAGCGTGCGACCGACGAGGCGAAAGCGGCGGCGGATGCGGCGGAACAGGC

GGCGGCGGCGGCGAAGCAAGCGGGTGCGGACGCGAAAGCGGCGGATGCGGCGG

TGGATGCGGCGCAAAAACGTTACGATGACGCGGTTAAGCAGGGCCTGCCGGATG

ACCGTCTGCAAAGCCTGAAAGCGGCGCTGGAGCAGGCGCGTCAGCAAGCGGGTG

ATGCGCATGGTCGTGCGGATGCGCTGCAGGCGGATGCGACCAAGAAACTGGACG

CGGCGAGCGCGCTGGCGACCCAAGCGCGTGCGTGCGAACAGCAAGTGGATGACG

CGGTTAACCAGGCGACCCAGCAATATGGTGCGAGCGCGAGCCTGCGTACCCCGC

AAAGCCCGCGTCTGAGCGGTGCGGCGGAGCTGACCGCGGTGCTGGGCAAGCTGC

AGGAACTGATTAGCAGCGGCAACGTTAAAGAGCTGGAAAGCAAGCAGAAACTG

TTCACCGAGATGCAAGCGAAGCGTGAGGCGGAACTGCAAAAGAAAAGCGACGA

ATATCAGGCGCAAGTGAAGAAAGCGGAGGAAATGCAGAAAACGATGGGTTGCA

TCGGCAAGATTGTGGGTTGGGTTATTACCGCGGTTAGCTTTGCGGCGGCGGCGTT

TACCGGTGGCGCGAGCCTGGCGCTGGCGGCGGTGGGCCTGGCGCTGGCGGTTGG

TGACGAGATTAGCCGTGCGACCACCGGTGTGAGCTTCATGGACAAGCTGATGCA

GCCGGTTATGGATGCGATCCTGAAACCGCTGATGGAGATGATTAGCAGCCTGAT

CACCAAGGCGCTGGTTGCGTGCGGCGTTGATCAGCAAAAAGCGGAACTGGCGGG

TGCGATTCTGGGTGCGGTTGTTACCGGTGTGGCGCTGGTTGCGGCGGCGTTTGTT

GGTGCGAGCGCGGTGAAAGCGGTTGCGAGCAAGGTTATCGACGCGATGGCGGGT

CAGCTGACCAAGCTGATGGATAGCGCGATTGGCAAAATGCTGGTGCAACTGATC

GAGAAATTCAGCGAAAAGAGCGGTCTGCAGGCGCTGGGTAGCCGTACCGCGACC

GCGATGACCCGTATGCGTCGTGCGATTGGCGTTGAGGCGAAGGAAGACGGTATG

CTGCTGGCGAACCGTTTTGAAAAAGCGGGCACCGTGATGAACGTTGGTAACCAA

GTGAGCCAAGCGGCGGGTGGCATTGTGGTTGGCGTTGAGCGTGCGAAAGCGATG

GGTCTGCTGGCGGATGTGAAAGAAGCGATGTATGACATCAAGCTGCTGGGTGAT

CTGCTGAAACAGGCGGTGGACGCGTTTGCGGAGCACAACCGTGTTCTGGCGCAA
```

```
CTGATGCAGCAAATGAGCGATGCGGGCGAAATGCAGACCAGCACCGGCAAGCTG
ATCCTGCGTAACGCGCGTGCGGTTTAAGGATCC
```

LTA1-BurkF Amino acid sequence

SEQ ID NO: 28

```
MDNGDRLYRADSRPPDEIKRSGGLMPRGHNEYFDRGTQMNINLYDHARGTQ
TGFVRYDDGYVSTSLSLRSAHLAGQSILSGYSTYYIYVIATAPNMFNVNDVLGVYSP
HPYEQEVSALGGIPYSQIYGWYRVNFGVIDERLHRNREYRDRYYRNLNIAPAEDGYR
LAGFPPDHQAWREEPWIHHAPQGCGNSSRMNMHVDMGRALTVRDWPALEALAKT
MPADAGARAMTDDDLRAAGVDRRVPEQKLGAAIDEFASLRLPDRIDGRFVDGRRA
NLTVFDDARVAVRGHARAQRNLLERLETELLGGTLDTAGDEGGIQPDPILQGLVDVI
GQGKSDIDAYATIVEGLTKYFQSVADVMSKLQDYISAKDDKNMKIDGGKIKALIQQ
VIDHLPTMQLPKGADIARWRKELGDAVSISDSGVVTINPDKLIKMRDSLPPDGTVWD
TARYQAWNTAFSGQKGQHPERRADARRKYSHQNSNFDNLVKVLSGAISTLTDTQSY
LQIKLMSSGVQGGPAANANAYQTHPLRDAASALGTLSPQAYVDVVSAAQRNFLER
MSQLASEQCDAQPAAHDARLDDRPALRAPQERDAPPLGASDTGSRASGAAKLTELL
GVLMSVISASSLDELKQRSDIWNQMSKAAQDNLSRLSDAFQRATDEAKAAADAAEQ
AAAAAKQAGADAKAADAAVDAAQKRYDDAVKQGLPDDRLQSLKAALEQARQQA
GDAHGRADALQADATKKLDAASALATQARACEQQVDDAVNQATQQYGASASLRT
PQSPRLSGAAELTAVLGKLQELISSGNVKELESKQKLFTEMQAKREAELQKKSDEYQ
AQVKKAEEMQKTMGCIGKIVGWVITAVSFAAAAFTGGASLALAAVGLALAVGDEIS
RATTGVSFMDKLMQPVMDAILKPLMEMISSLITKALVACGVDQQKAELAGAILGAV
VTGVALVAAAFVGASAVKAVASKVIDAMAGQLTKLMDSAIGKMLVQLIEKFSEKS
GLQALGSRTATAMTRMRRAIGVEAKEDGMLLANRFEKAGTVMNVGNQVSQAAGG
IVVGVERAKAMGLLADVKEAMYDIKLLGDLLKQAVDAFAEHNRVLAQLMQQMSD
AGEMQTSTGKLILRNARAV-
```

His-PcrH (Chaperone of PaF) nucleic acid sequence

SEQ ID NO: 29

```
ATGGGCAGCAGCCATCACCATCATCACCACAGCCAGGATCCGATGAACCA
GCCGACCCCTTCCGACACCGACCAGCAACAGGCGCTGGAGGCCTTCCTGCGCGA
CGGCGGCACCCTGGCGATGCTTCGCGGACTCAGCGAGGACACCCTGGAGCAGCT
CTATGCGCTGGGCTTCAACCAGTACCAGGCGGGCAAGTGGGACGACGCGCAGAA
GATCTTCCAGGCACTGTGCATGCTCGACCACTACGACGCCCGCTACTTTCTCGGC
CTGGGCGCCTGCCGCCAGTCCCTCGGTCTCTATGAACAGGCCCTGCAGAGCTACA
GCTACGGCGCGCTGATGGACATCAACGAGCCGCGCTTTCCCTTCCATGCCGCCGA
GTGCCACCTGCAACTGGGTGATCTCGACGGAGCCGAGAGTGGCTTCTACTCGGCC
CGGGCCCTGGCCGCGGCACAGCCGGCGCACGAGGCCCTGGCCGCGCGTGCCGGC
GCCATGTTGGAAGCCGTAACCGCGAGAAAGGATCGAGCCTATGAATCCGATAAC
GCTTGAAAGCTT
```

His-PcrH (Chaperone of PaF) Amino acid sequence

SEQ ID NO: 30

```
MGSSHHHHHHSQDPMNQPTPSDTDQQQALEAFLRDGGTLAMLRGLSEDTLE
QLYALGFNQYQAGKWDDAQKIFQALCMLDHYDARYFLGLGACRQSLGLYEQALQS
YSYGALMDINEPRFPFHAAECHLQLGDLDGAESGFYSARALAAAQPAHEALAARAG
AMLEAVTARKDRAYESDNA-
```

PcrV nucleic acid sequence
SEQ ID NO: 31

CATATGGAAGTCAGAAACCTTAATGCCGCTCGCGAGCTGTTCCTGGACGA

GCTCCTGGCCGCGTCGGCGGCGCCTGCCAGTGCCGAGCAGGAGGAACTGCTGGC

CCTGTTGCGCAGCGAGCGGATCGTGCTGGCCCACGCCGGCCAGCCGCTGAGCGA

GGCGCAAGTGCTCAAGGCGCTCGCCTGGTTGCTCGCGGCCAATCCGTCCGCGCCT

CCGGGGCAGGGCCTCGAGGTACTCCGCGAAGTCCTGCAGGCACGTCGGCAGCCC

GGTGCGCAGTGGGATCTGCGTGAGTTCCTGGTGTCGGCCTATTTCAGCCTGCACG

GGCGTCTCGACGAGGATGTCATCGGTGTCTACAAGGATGTCCTGCAGACCCAGG

ACGGCAAGCGCAAGGCGCTGCTCGACGAGCTCAAGGCGCTGACCGCGGAGTTGA

AGGTCTACAGCGTGATCCAGTCGCAGATCAACGCCGCGCTGTCGGCCAGGCAGG

GCATCAGGATCGACGCTGGCGGTATCGATCTGGTCGACCCCACGCTATATGGCTA

TGCCGTCGGCGATCCCAGGTGGAAGGACAGCCCCGAGTATGCGCTGCTGAGCAA

TCTGGATACCTTCAGCGGCAAGCTGTCGATCAAGGATTTTCTCAGCGGCTCGCCG

AAGCAGAGCGGGGAACTCAAGGGCCTCAGCGATGAGTACCCCTTCGAGAAGGAC

AACAACCCGGTCGGCAATTTCGCCACCACGGTGAGCGACCGCTCGCGTCCGCTG

AACGACAAGGTCAACGAGAAGACCACCCTGCTCAACGACACCAGCTCCCGCTAC

AACTCGGCGGTCGAGGCGCTCAACCGCTTCATCCAGAAATACGACAGCGTCCTG

AGCGACATTCTCAGCGCGATC

PcrV amino acid sequence
SEQ ID NO: 32

MEVRNLNAARELFLDELLAASAAPASAEQEELLALLRSERIVLAHAGQPLSEA

QVLKALAWLLAANPSAPPGQGLEVLREVLQARRQPGAQWDLREFLVSAYFSLHGRL

DEDVIGVYKDVLQTQDGKRKALLDELKALTAELKVYSVIQSQINAALSARQGIRIDA

GGIDLVDPTLYGYAVGDPRWKDSPEYALLSNLDTFSGKLSIKDFLSGSPKQSGELKG

LSDEYPFEKDNNPVGNFATTVSDRSRPLNDKVNEKTTLLNDTSSRYNSAVEALNRFI

QKYDSVLSDILSAI

PopB nucleic acid sequence
SEQ ID NO: 33

ATGAACCCGATTACGCTGGAACGTGCTGGTCTGCCGTATGGTGTTGCCGA

TGCTGGTGACATCCCGGCTCTGGGTCGCCCGGTCGCACGTGATGTGGAAAGTCTG

CGTGTTGAACGTCTGGCAGCACCGGCAGCTGCAAGCGCATCTGGCACCGGTGTC

GCTCTGACGCCGCCGTCTGCAGCAAGTCAGCAACGTCTGGAAGTTGCTAACCGC

GCGGAAATTGCCTCACTGGTCCAGGCAGTGGGTGAAGACGTGGGTCTGGCACGT

CAAGTGGTTCTGGCAGGTGCATCGACCCTGCTGAGCGCAGGTCTGATGTCGCCGC

AGGCGTTCGAAATTGAACTGGCCAAAATCACCGGCGAAGTTGAAAATCAGCAGA

AAAAACTGAAACTGACGGAAATCGAACAGGCCCGTAAACAGAACCTGCAAAAA

ATGGAAGATAACCAGCAAAAAATCCGCGAATCGGAAGAAGCTGCGAAAGAAGC

GCAGAAAAGCGGCCTGGCCGCAAAAATTTTTGGTTGGATTTCTGCTATCGCGAGT

ATTATCGTGGGTGCAATCATGGTTGCAACCGGTGTCGGTGCTGCAGCAGGTGCAC

TGATGATTGCTGGCGGTGTCATGGGTGTCGTGAGTCAGTCCGTGCAGCAAGCAGC

TGCGGATGGTCTGATCTCAAAAGAAGTGATGGAAAAACTGGGCCCGGCCCTGAT

GGGTATTGAAATGGCCGTGGCACTGCTGGCCGCAGTTGTCTCCTTTGGTGGTTCA

GCAGTTGGTGGTCTGGCACGTCTGGGTGCAAAAATCGGCGGTAAAGCTGCGGAA

-continued

```
ATGACGGCATCCCTGGCTTCAAAAGTGGCAGACCTGGGCGGTAAATTCGGCTCTC

TGGCGGGCCAGTCACTGTCGCATAGCCTGAAACTGGGTGTGCAAGTTTCTGATCT

GACCCTGGACGTTGCAAACGGCGCCGCACAGGCTACGCACAGTGGTTTTCAAGC

GAAAGCTGCGAATCGTCAGGCCGATGTTCAAGAATCCCGTGCAGACCTGACCAC

GCTGCAGGGTGTCATTGAACGTCTGAAAGAAGAACTGAGCCGCATGCTGGAAGC

CTTTCAGGAAATTATGGAACGCATCTTCGCAATGCTGCAAGCGAAAGGCGAAAC

CCTGCACAATCTGTCTTCCCGTCCGGCGGCTATCTGAGGATCC
```

PopB amino acid sequence
SEQ ID NO: 34

```
MNPITLERAGLPYGVADAGDIPALGRPVARDVESLRVERLAAPAAASASGTG

VALTPPSAASQQRLEVANRAEIASLVQAVGEDVGLARQVVLAGASTLLSAGLMSPQ

AFEIELAKITGEVENQQKKLKLTEIEQARKQNLQKMEDNQQKIRESEEAAKEAQKSG

LAAKIFGWISAIASIIVGAIMVATGVGAAAGALMIAGGVMGVVSQSVQQAAADGLIS

KEVMEKLGPALMGIEMAVALLAAVVSFGGSAVGGLARLGAKIGGKAAEMTASLAS

KVADLGGKFGSLAGQSLSHSLKLGVQVSDLTLDVANGAAQATHSGFQAKAANRQA

DVQESRADLTTLQGVIERLKEELSRMLEAFQEIMERIFAMLQAKGETLHNLSSRPAAI
```

PaF nucleic acid sequence
SEQ ID NO: 35

```
CATATGGAAGTCAGAAACCTTAATGCCGCTCGCGAGCTGTTCCTGGACGA

GCTCCTGGCCGCGTCGGCGGCGCCTGCCAGTGCCGAGCAGGAGGAACTGCTGGC

CCTGTTGCGCAGCGAGCGGATCGTGCTGGCCCACGCCGGCCAGCCGCTGAGCGA

GGCGCAAGTGCTCAAGGCGCTCGCCTGGTTGCTCGCGGCCAATCCGTCCGCGCCT

CCGGGGCAGGGCCTCGAGGTACTCCGCGAAGTCCTGCAGGCACGTCGGCAGCCC

GGTGCGCAGTGGGATCTGCGTGAGTTCCTGGTGTCGGCCTATTTCAGCCTGCACG

GGCGTCTCGACGAGGATGTCATCGGTGTCTACAAGGATGTCCTGCAGACCCAGG

ACGGCAAGCGCAAGGCGCTGCTCGACGAGCTCAAGGCGCTGACCGCGGAGTTGA

AGGTCTACAGCGTGATCCAGTCGCAGATCAACGCCGCGCTGTCGGCCAGGCAGG

GCATCAGGATCGACGCTGGCGGTATCGATCTGGTCGACCCCACGCTATATGGCTA

TGCCGTCGGCGATCCCAGGTGGAAGGACAGCCCCGAGTATGCGCTGCTGAGCAA

TCTGGATACCTTCAGCGGCAAGCTGTCGATCAAGGATTTTCTCAGCGGCTCGCCG

AAGCAGAGCGGGGAACTCAAGGGCCTCAGCGATGAGTACCCCTTCGAGAAGGAC

AACAACCCGGTCGGCAATTTCGCCACCACGGTGAGCGACCGCTCGCGTCCGCTG

AACGACAAGGTCAACGAGAAGACCACCCTGCTCAACGACACCAGCTCCCGCTAC

AACTCGGCGGTCGAGGCGCTCAACCGCTTCATCCAGAAATACGACAGCGTCCTG

AGCGACATTCTCAGCGCGATCGGATCCATGAACCCGATTACGCTGGAACGTGCT

GGTCTGCCGTATGGTGTTGCCGATGCTGGTGACATCCCGGCTCTGGGTCGCCCGG

TCGCACGTGATGTGGAAAGTCTGCGTGTTGAACGTCTGGCAGCACCGGCAGCTG

CAAGCGCATCTGGCACCGGTGTCGCTCTGACGCCGCCGTCTGCAGCAAGTCAGC

AACGTCTGGAAGTTGCTAACCGCGCGGAAATTGCCTCACTGGTCCAGGCAGTGG

GTGAAGACGTGGGTCTGGCACGTCAAGTGGTTCTGGCAGGTGCATCGACCCTGCT

GAGCGCAGGTCTGATGTCGCCGCAGGCGTTCGAAATTGAACTGGCCAAAATCAC

CGGCGAAGTTGAAAATCAGCAGAAAAAACTGAAACTGACGGAAATCGAACAGG

CCCGTAAACAGAACCTGCAAAAAATGGAAGATAACCAGCAAAAAATCCGCGAA
```

-continued

TCGGAAGAAGCTGCGAAAGAAGCGCAGAAAAGCGGCCTGGCCGCAAAAATTTTT
GGTTGGATTTCTGCTATCGCGAGTATTATCGTGGGTGCAATCATGGTTGCAACCG
GTGTCGGTGCTGCAGCAGGTGCACTGATGATTGCTGGCGGTGTCATGGGTGTCGT
GAGTCAGTCCGTGCAGCAAGCAGCTGCGGATGGTCTGATCTCAAAAGAAGTGAT
GGAAAAACTGGGCCCGGCCCTGATGGGTATTGAAATGGCCGTGGCACTGCTGGC
CGCAGTTGTCTCCTTTGGTGGTTCAGCAGTTGGTGGTCTGGCACGTCTGGGTGCA
AAAATCGGCGGTAAAGCTGCGGAAATGACGGCATCCCTGGCTTCAAAAGTGGCA
GACCTGGGCGGTAAATTCGGCTCTCTGGCGGGCCAGTCACTGTCGCATAGCCTGA
AACTGGGTGTGCAAGTTTCTGATCTGACCCTGGACGTTGCAAACGGCGCCGCACA
GGCTACGCACAGTGGTTTTCAAGCGAAAGCTGCGAATCGTCAGGCCGATGTTCA
AGAATCCCGTGCAGACCTGACCACGCTGCAGGGTGTCATTGAACGTCTGAAAGA
AGAACTGAGCCGCATGCTGGAAGCCTTTCAGGAAATTATGGAACGCATCTTCGC
AATGCTGCAAGCGAAAGGCGAAACCCTGCACAATCTGTCTTCCCGTCCGGCGGC
TATCTGAGGATCC

PaF amino acid sequence

SEQ ID NO: 36

MEVRNLNAARELFLDELLAASAAPASAEQEELLALLRSERIVLAHAGQPLSEA
QVLKALAWLLAANPSAPPGQGLEVLREVLQARRQPGAQWDLREFLVSAYFSLHGRL
DEDVIGVYKDVLQTQDGKRKALLDELKALTAELKVYSVIQSQINAALSARQGIRIDA
GGIDLVDPTLYGYAVGDPRWKDSPEYALLSNLDTFSGKLSIKDFLSGSPKQSGELKG
LSDEYPFEKDNNPVGNFATTVSDRSRPLNDKVNEKTTLLNDTSSRYNSAVEALNRFI
QKYDSVLSDILSAIGSMNPITLERAGLPYGVADAGDIPALGRPVARDVESLRVERLAA
PAAASASGTGVALTPPSAASQQRLEVANRAEIASLVQAVGEDVGLARQVVLAGAST
LLSAGLMSPQAFEIELAKITGEVENQQKKLKLTEIEQARKQNLQKMEDNQQKIRESE
EAAKEAQKSGLAAKIFGWISAIASIIVGAIMVATGVGAAAGALMIAGGVMGVVSQS
VQQAAADGLISKEVMEKLGPALMGIEMAVALLAAVVSFGGSAVGGLARLGAKIGG
KAAEMTASLASKVADLGGKFGSLAGQSLSHSLKLGVQVSDLTLDVANGAAQATHS
GFQAKAANRQADVQESRADLTTLQGVIERLKEELSRMLEAFQEIMERIFAMLQAKG
ETLHNLSSRPAAI

LTA1-PaF nucleic acid sequence

SEQ ID NO: 37

CATatggacaatggcgatcgtttataccgtgccgactcgcgtcccccagatgagattaaacgtagcggtgggttaatgcc acgtgggcacaatgagtattttgaccgtggaacacagatgaacattaacctttacgatcatgcccgtgggacccagaccgggtttgtcc gttatgatgacgggtatgttagtacgagtttgtccttacgctccgcacaccttgcgggacaaagtattttatcaggctacagcacatattac atttatgtgatcgccactgccccaaacatgttcaatgtgaacgatgtgttgggggtttacagcccccatccatatgaacaagaagtctcg gcccttgggggggatcccatatagccagatttatggttggtaccgcgtaaattttggtgtgattgatgaacgtttgcatcgtaaccgtgaata ccgcgatcgctactaccgtaacttgaacattgcacctgccgaggacggctatcgtttagcgggattcccacccgatcatcaggcgtgg cgtgaggaaccgtggatccatcacgcccctcaggggtgcgggaacagtagtcgcCATATGGAAGTCAGAAACCT

TAATGCCGCTCGCGAGCTGTTCCTGGACGAGCTCCTGGCCGCGTCGGCGGCGCCT

GCCAGTGCCGAGCAGGAGGAACTGCTGGCCCTGTTGCGCAGCGAGCGGATCGTG

CTGGCCCACGCCGGCCAGCCGCTGAGCGAGGCGCAAGTGCTCAAGGCGCTCGCC

TGGTTGCTCGCGGCCAATCCGTCCGCGCCTCCGGGGCAGGGCCTCGAGGTACTCC

GCGAAGTCCTGCAGGCACGTCGGCAGCCCGGTGCGCAGTGGGATCTGCGTGAGT

-continued

```
TCCTGGTGTCGGCCTATTTCAGCCTGCACGGGCGTCTCGACGAGGATGTCATCGG

TGTCTACAAGGATGTCCTGCAGACCCAGGACGGCAAGCGCAAGGCGCTGCTCGA

CGAGCTCAAGGCGCTGACCGCGGAGTTGAAGGTCTACAGCGTGATCCAGTCGCA

GATCAACGCCGCTGTCGGCCAGGCAGGGCATCAGGATCGACGCTGGCGGTAT

CGATCTGGTCGACCCCACGCTATATGGCTATGCCGTCGGCGATCCCAGGTGGAAG

GACAGCCCCGAGTATGCGCTGCTGAGCAATCTGGATACCTTCAGCGGCAAGCTG

TCGATCAAGGATTTTCTCAGCGGCTCGCCGAAGCAGAGCGGGGAACTCAAGGGC

CTCAGCGATGAGTACCCCTTCGAGAAGGACAACAACCCGGTCGGCAATTTCGCC

ACCACGGTGAGCGACCGCTCGCGTCCGCTGAACGACAAGGTCAACGAGAAGACC

ACCCTGCTCAACGACACCAGCTCCCGCTACAACTCGGCGGTCGAGGCGCTCAAC

CGCTTCATCCAGAAATACGACAGCGTCCTGAGCGACATTCTCAGCGCGATCGGAT

CCATGAACCCGATTACGCTGGAACGTGCTGGTCTGCCGTATGGTGTTGCCGATGC

TGGTGACATCCCGGCTCTGGGTCGCCCGGTCGCACGTGATGTGGAAAGTCTGCGT

GTTGAACGTCTGGCAGCACCGGCAGCTGCAAGCGCATCTGGCACCGGTGTCGCT

CTGACGCCGCCGTCTGCAGCAAGTCAGCAACGTCTGGAAGTTGCTAACCGCGCG

GAAATTGCCTCACTGGTCCAGGCAGTGGGTGAAGACGTGGGTCTGGCACGTCAA

GTGGTTCTGGCAGGTGCATCGACCCTGCTGAGGGCAGGTCTGATGTCGCCGCAGG

CGTTCGAAATTGAACTGGCCAAAATCACCGGCGAAGTTGAAAATCAGCAGAAAA

AACTGAAACTGACGGAAATCGAACAGGCCCGTAAACAGAACCTGCAAAAAATG

GAAGATAACCAGCAAAAAATCCGCGAATCGGAAGAAGCTGCGAAAGAAGCGCA

GAAAAGCGGCCTGGCCGCAAAAATTTTTGGTTGGATTTCTGCTATCGCGAGTATT

ATCGTGGGTGCAATCATGGTTGCAACCGGTGTCGGTGCTGCAGCAGGTGCACTG

ATGATTGCTGGCGGTGTCATGGGTGTCGTGAGTCAGTCCGTGCAGCAAGCAGCTG

CGGATGGTCTGATCTCAAAAGAAGTGATGGAAAAACTGGGCCCGGCCCTGATGG

GTATTGAAATGGCCGTGGCACTGCTGGCCGCAGTTGTCTCCTTTGGTGGTTCAGC

AGTTGGTGGTCTGGCACGTCTGGGTGCAAAAATCGGCGGTAAAGCTGCGGAAAT

GACGGCATCCCTGGCTTCAAAAGTGGCAGACCTGGGCGGTAAATTCGGCTCTCTG

GCGGGCCAGTCACTGTCGCATAGCCTGAAACTGGGTGTGCAAGTTTCTGATCTGA

CCCTGGACGTTGCAAACGGCGCCGCACAGGCTACGCACAGTGGTTTTCAAGCGA

AAGCTGCGAATCGTCAGGCCGATGTTCAAGAATCCCGTGCAGACCTGACCACGC

TGCAGGGTGTCATTGAACGTCTGAAAGAAGAACTGAGCCGCATGCTGGAAGCCT

TTCAGGAAATTATGGAACGCATCTTCGCAATGCTGCAAGCGAAAGGCGAAACCC

TGCACAATCTGTCTTCCCGTCCGGCGGCTATCTGAGGATCC
```

LTA1-PaF Amino acid sequence

SEQ ID NO: 38

```
MDNGDRLYRADSRPPDEIKRSGGLMPRGHNEYFDRGTQMNINLYDHARGTQ

TGFVRYDDGYVSTSLSLRSAHLAGQSILSGYSTYYIYVIATAPNMFNVNDVLGVYSP

HPYEQEVSALGGIPYSQIYGWYRVNFGVIDERLHRNREYRDRYYRNLNIAPAEDGYR

LAGFPPDHQAWREEPWIHHAPQGCGNSSRMEVRNLNAARELFLDELLAASAAPASA

EQEELLALLRSERIVLAHAGQPLSEAQVLKALAWLLAANPSAPPGQGLEVLREVLQA

RRQPGAQWDLREFLVSAYFSLHGRLDEDVIGVYKDVLQTQDGKRKALLDELKALT

AELKVYSVIQSQINAALSARQGIRDAGGIDLVDPTLYGYAVGDPRWKDSPEYALLS
```

NLDTFSGKLSIKDFLSGSPKQSGELKGLSDEYPFEKDNNPVGNFATTVSDRSRPLNDK

VNEKTTLLNDTSSRYNSAVEALNRFIQKYDSVLSDILSAIGSMNPITLERAGLPYGVA

DAGDLPALGRPVARDVESLRVERLAAPAAASASGTGVALTPPSAASQQRLEVANRAE

IASLVQAVGEDVGLARQVVLAGASTLLSAGLMSPQAFEIELAKITGEVENQQKKLKL

TEIEQARKQNLQKMEDNQQKIRESEEAAKEAQKSGLAAKIFGWISAIASIIVGAIMVA

TGVGAAAGALMIAGGVMGVVSQSVQQAAADGLISKEVMEKLGPALMGIEMAVAL

LAAVVSFGGSAVGGLARLGAKIGGKAAEMTASLASKVADLGGKFGSLAGQSLSHSL

KLGVQVSDLTLDVANGAAQATHSGFQAKAANRQADVQESRADLTTLQGVIERLKE

ELSRMLEAFQEIMERIFAMLQAKGETLHNLSSRPAAI-

SycD (Chaperone for YerF) nucleic acid sequence        SEQ ID NO: 39

ATGGGCAGCAGCCATCACCATCATCACCACAGCCAGGATCCGatgcaacaagag acgacagacactcaagaataccagctggcaatggaatccttcctaaaaggagggggaactatcgccatgctcaacgaaatttcaagtg acactttagagcaactctactctcttgcgtttaaccaataccagtcaggaaaatacgaggatgctcacaaggtctttcaagctctctgtgtg ctagaccactatgattcacgtttcttttagggctaggcgcttgtcgtcaagccatggggcaatacgacttagcgattcatagctacagcta tggcgccataatggatataaaagaacctcgttttccgtttcatgctgccgaatgtttactgcaaaagggagagcttgctgaagcagaaag tggcttgttcttggctcaagagcttatcgcagacaaacctgagtttaaggagcttccacccgagttagctcaatgttagaagcaattaaat tgaaaaaggagatggaacatgagtgcgttgataacccatgaAAGCTT

SycD (Chaperone for YerF) Amino acid sequence         SEQ ID NO: 40

MGSSHHHHHHSSGLVPRGSHMQQETTDTQEYQLAMESFLKGGGTIAMLNEIS

SDTLEQLYSLAFNQYQSGKYEDAHKVFQALCVLDHYDSRFFLGLGACRQAMGQYD

LAIHSYSYGAIMDIKEPRFPFHAAECLLQKGELAEAESGLFLAQELIADKPEFKELSTR

VSSMLEAIKLKKEMEHECVDNP-

LcrV amino acid sequence                              SEQ ID NO: 41

CATATGATTAGAGCCTACGAACAAAACCCACAACATTTTATTGAGGATCT

AGAAAAAGTTAGGGTGGAACAACTTACTGGTCATGGTTCTTCAGTTTTAGAAGA

ATTGGTTCAGTTAGTCAAAGATAAAAATATAGATATTTCCATTAAATATGATCCC

AGAAAAGATTCGGAGGTTTTTGCCAATAGAGTAATTACTGATGATATCGAATTGC

TCAAGAAAATCCTAGCTTATTTTCTACCCGAGGATGCCATTCTTAAAGGCGGTCA

TTATGACAACCAACTGCAAAATGGCATCAAGCGAGTAAAAGAGTTCCTTGAATC

ATCGCCGAATACACAATGGGAATTGCGGGCGTTCATGGCAGTAATGCATTTCTCT

TTAACCGCCGATCGTATCGATGATGATATTTTGAAAGTGATTGTTGATTCAATGA

ATCATCATGGTGATGCCCGTAGCAAGTTGCGTGAAGAATTAGCTGAGCTTACCGC

CGAATTAAAGATTTATTCAGTTATTCAAGCCGAAATTAATAAGCATCTGTCTAGT

AGTGGCACCATAAATATCCATGATAAATCCATTAATCTCATGGATAAAAATTTAT

ATGGTTATACAGATGAAGAGATTTTTAAAGCCAGCGCAGAGTACAAAATTCTCG

AGAAAATGCCTCAAACCACCATTCAGGTGGATGGGAGCGAGAAAAAAATAGTCT

CGATAAAGGACTTTCTTGGAAGTGAGAATAAAAGAACCGGGGCGTTGGGTAATC

TGAAAAACTCATACTCTTATAATAAAGATAATAATGAATTATCTCACTTTGCCAC

CACCTGCTCGGATAAGTCCAGGCCGCTCAACGACTTGGTTAGCCAAAAAACAAC

TCAGCTGTCTGATATTACATCACGTTTTAATTCAGCTATTGAAGCACTGAACCGTT

-continued

TCATTCAGAAATATGATTCAGTGATGCAACGTCTGCTAGATGACACGTCTGGTAA
A

LcrV amino acid sequence

SEQ ID NO: 42

MIRAYEQNPQHFIEDLEKVRVEQLTGHGSSVLEELVQLVKDKNIDISIKYDPR

KDSEVFANRVITDDIELLKKILAYFLPEDAILKGGHYDNQLQNGIKRVKEFLESSPNT

QWELRAFMAVMHFSLTADRIDDDILKVIVDSMNHHGDARSKLREELAELTAELKIYS

VIQAEINKHLSSSGTINIHDKSINLMDKNLYGYTDEEIFKASAEYKILEKMPQTTIQVD

GSEKKIVSIKDFLGSENKRTGALGNLKNSYSYNKDNNELSHFATTCSDKSRPLNDLV

SQKTTQLSDITSRFNSAIEALNRFIQKYDSVMQRLLDDTSGK

YopB nucleic acid sequence

SEQ ID NO: 43

ATGAGTGCGTTGATAACCCATGATCGCTCAACGCCAGTAACTGGAAGTCT

ACTTCCCTACGTCGAGACACCAGCGCCCGCCCCCCTTCAGACTCAACAAGTCGCG

GGAGAACTGAAGGATAAAAATGGTGGGGTGAGTTCTCAGGGCGTACAGCTCCCT

GCACCACTAGCAGTGGTTGCCAGCCAAGTCACTGAAGGACAACAGCAAGAAATC

ACTAAATTATTGGAGTCGGTCACCCGCGGCACGGCAGGATCTCAACTGATATCA

AATTATGTTTCAGTGCTAACGAATTTTACGCTCGCTTCACCTGATACATTTGAGAT

TGAGTTAGGTAAGCTAGTTTCTAATTTAGAAGAAGTACGCAAAGACATAAAAAT

CGCTGATATTCAGCGTCTTCATGAACAAAACATGAAGAAAATTGAAGAGAATCA

AGAGAAAATCAAAGAAACAGAAGAGAATGCCAAGCAAGTCAAGAAATCCGGCA

TGGCATCAAAGATTTTTGGCTGGCTCAGCGCCATAGCCTCAGTGGTTATCGGTGC

CATCATGGTGGCCTCAGGGGTAGGAGCCGTTGCCGGTGCAATGATGATTGCCTCA

GGCGTAATTGGGATGGCGAATATGGCTGTGAAACAAGCGGCGGAAGATGGCCTG

ATATCCCAAGAGGCAATGCAAGTATTAGGGCCGATACTCACTGCGATTGAAGTC

GCATTGACTGTAGTTTCAACCGTAATGACCTTTGGCGGTTCGGCACTAAAATGCC

TGGCTGATATTGGCGCAAAACTCGGTGCTAACACCGCAAGTCTTGCTGCTAAAGG

AGCCGAGTTTTCGGCCAAAGTTGCCCAAATTTCGACAGGCATATCAAACACTGTC

GGGAATGCAGTGACTAAATTAGGGGGCAGTTTTGGTAGTTTAACAATGAGCCAT

GTAATCCGTACAGGATCACAGGCAACACAAGTCGCCGTTGGTGTGGGCAGCGGA

ATAACTCAGACCATCAATAATAAAAAACAAGCTGATTTACAACATAATAACGCT

GATTTGGCCTTGAACAAGGCAGACATGGCAGCGTTACAAAGTATTATTGACCGA

CTCAAAGAAGAGTTATCCCATTTGTCAGAGTCACATCAACAAGTGATGGAACTG

ATTTTCCAGATGATTAATGCAAAAGGTGACATGCTGCATAATTTGGCCGGCAGAC

CCCATACTGTTTAAGGTACC

YopB amino acid sequence

SEQ ID NO: 44

MSALITHDRSTPVTGSLLPYVETPAPAPLQTQQVAGELKDKNGGVSSQGVQL

PAPLAVVASQVTEGQQQEITKLLESVTRGTAGSQLISNYVSVLTNFTLASPDTFEIELG

KLVSNLEEVRKDIKIADIQRLHEQNMKKIEENQEKIKETEENAKQVKKSGMASKIFG

WLSAIASVVIGAIMVASGVGAVAGAMMIASGVIGMANMAVKQAAEDGLISQEAMQ

VLGPILTAEVALTVVSTVMTFGGSALKCLADIGAKLGANTASLAAKGAEFSAKVAQ

ISTGISNTVGNAVTKLGGSFGSLTMSHVIRTGSQATQVAVGVGSGITQTINNKKQADL

-continued

QHNNADLALNKADMAALQSIIDRLKEELSHLSESHQQVMELIFQMINAKGDMLHNL

AGRPHTV

YerF nucleic acid sequence

SEQ ID NO: 45

CATATGATTAGAGCCTACGAACAAAACCCACAACATTTTATTGAGGATCT

AGAAAAAGTTAGGGTGGAACAACTTACTGGTCATGGTTCTTCAGTTTTAGAAGA

ATTGGTTCAGTTAGTCAAAGATAAAAATATAGATATTTCCATTAAATATGATCCC

AGAAAAGATTCGGAGGTTTTTGCCAATAGAGTAATTACTGATGATATCGAATTGC

TCAAGAAAATCCTAGCTTATTTTCTACCCGAGGATGCCATTCTTAAAGGCGGTCA

TTATGACAACCAACTGCAAAATGGCATCAAGCGAGTAAAAGAGTTCCTTGAATC

ATCGCCGAATACACAATGGGAATTGCGGGCGTTCATGGCAGTAATGCATTTCTCT

TTAACCGCCGATCGTATCGATGATGATATTTTGAAAGTGATTGTTGATTCAATGA

ATCATCATGGTGATGCCCGTAGCAAGTTGCGTGAAGAATTAGCTGAGCTTACCGC

CGAATTAAAGATTTATTCAGTTATTCAAGCCGAAATTAATAAGCATCTGTCTAGT

AGTGGCACCATAAATATCCATGATAAATCCATTAATCTCATGGATAAAAATTTAT

ATGGTTATACAGATGAAGAGATTTTTAAAGCCAGCGCAGAGTACAAAATTCTCG

AGAAAATGCCTCAAACCACCATTCAGGTGGATGGGAGCGAGAAAAAAATAGTCT

CGATAAAGGACTTTCTTGGAAGTGAGAATAAAAGAACCGGGGCGTTGGGTAATC

TGAAAAACTCATACTCTTATAATAAAGATAATAATGAATTATCTCACTTTGCCAC

CACCTGCTCGGATAAGTCCAGGCCGCTCAACGACTTGGTTAGCCAAAAAACAAC

TCAGCTGTCTGATATTACATCACGTTTTAATTCAGCTATTGAAGCACTGAACCGTT

TCATTCAGAAATATGATTCAGTGATGCAACGTCTGCTAGATGACACGTCTGGTAA

AGGATCCATGAGTGCGTTGATAACCCATGATCGCTCAACGCCAGTAACTGGAAG

TCTACTTCCCTACGTCGAGACACCAGCGCCCGCCCCCCTTCAGACTCAACAAGTC

GCGGGAGAACTGAAGGATAAAAATGGTGGGGTGAGTTCTCAGGGCGTACAGCTC

CCTGCACCACTAGCAGTGGTTGCCAGCCAAGTCACTGAAGGACAACAGCAAGAA

ATCACTAAATTATTGGAGTCGGTCACCCGCGGCACGGCAGGATCTCAACTGATAT

CAAATTATGTTTCAGTGCTAACGAATTTTACGCTCGCTTCACCTGATACATTTGAG

ATTGAGTTAGGTAAGCTAGTTTCTAATTTAGAAGAAGTACGCAAAGACATAAAA

ATCGCTGATATTCAGCGTCTTCATGAACAAAACATGAAGAAAATTGAAGAGAAT

CAAGAGAAAATCAAAGAAACAGAAGAGAATGCCAAGCAAGTCAAGAAATCCGG

CATGGCATCAAAGATTTTTGGCTGGCTCAGCGCCATAGCCTCAGTGGTTATCGGT

GCCATCATGGTGGCCTCAGGGGTAGGAGCCGTTGCCGGTGCAATGATGATTGCCT

CAGGCGTAATTGGGATGGCGAATATGGCTGTGAAACAAGCGGCGGAAGATGGCC

TGATATCCCAAGAGGCAATGCAAGTATTAGGGCCGATACTCACTGCGATTGAAG

TCGCATTGACTGTAGTTTCAACCGTAATGACCTTTGGCGGTTCGGCACTAAAATG

CCTGGCTGATATTGGCGCAAAACTCGGTGCTAACACCGCAAGTCTTGCTGCTAAA

GGAGCCGAGTTTTCGGCCAAAGTTGCCCAAATTTCGACAGGCATATCAAACACT

GTCGGGAATGCAGTGACTAAATTAGGGGGCAGTTTTGGTAGTTTAACAATGAGC

CATGTAATCCGTACAGGATCACAGGCAACACAAGTCGCCGTTGGTGTGGGCAGC

GGAATAACTCAGACCATCAATAATAAAAAACAAGCTGATTTACAACATAATAAC

GCTGATTTGGCCTTGAACAAGGCAGACATGGCAGCGTTACAAAGTATTATTGACC

-continued

GACTCAAAGAAGAGTTATCCCATTTGTCAGAGTCACATCAACAAGTGATGGAAC

TGATTTTCCAGATGATTAATGCAAAAGGTGACATGCTGCATAATTTGGCCGGCAG

ACCCCATACTGTTTAAGGTACC

YerF amino acid sequence

SEQ ID NO: 46

MIRAYEQNPQHFIEDLEKVRVEQLTGHGSSVLEELVQLVKDKNIDISIKYDPR

KDSEVFANRVITDDIELLKKILAYFLPEDAILKGGHYDNQLQNGIKRVKEFLESSPNT

QWELRAFMAVMHFSLTADRIDDDILKVIVDSMNHHGDARSKLREELAELTAELKIYS

VIQAEINKHLSSSGTINIHDKSINLMDKNLYGYTDEEIFKASAEYKILEKMPQTTIQVD

GSEKKIVSIKDFLGSENKRTGALGNLKNSYSYNKDNNELSHFATTCSDKSRPLNDLV

SQKTTQLSDITSRFNSAIEALNRFIQKYDSVMQRLLDDTSGKGSMSALITHDRSTPVT

GSLLPYVETPAPAPLQTQQVAGELKDKNGGVSSQGVQLPAPLAVVASQVTEGQQQE

ITKLLESVTRGTAGSQLISNYVSVLTNFTLASPDTFEIELGKLVSNLEEVRKDIKIADIQ

RLHEQNMKKIEENQEKIKETEENAKQVKKSGMASKIFGWLSAIASVVIGAIMVASGV

GAVAGAMMIASGVIGMANMAVKQAAEDGLISQEAMQVLGPILTAIEVALTVVSTV

MTFGGSALKCLADIGAKLGANTASLAAKGAEFSAKVAQISTGISNTVGNAVTKLGGS

FGSLTMSHVIRTGSQATQVAVGVGSGITQTINNKKQADLQHNNADLALNKADMAA

LQSIIDRLKEELSHLSESHQQVMELIFQMINAKGDMLHNLAGRPHTV

LTA1-YerF nucleic acid sequence

SEQ ID NO: 47

CATatggacaatggcgatcgtttataccgtgccgactcgcgtcccccagatgagattaaacgtagcggtgggttaatgcc acgtgggcacaatgagtattttgaccgtggaacacagatgaacattaacctttacgatcatgcccgtgggacccagaccgggtttgtcc gttatgatgacgggtatgttagtacgagtttgtccttacgctccgcacaccttgcgggacaaagtattttatcaggctacagcacatattac atttatgtgatcgccactgccccaaacatgttcaatgtgaacgatgtgttgggggtttacagcccccatccatatgaacaagaagtctcg gcccttgggggatcccatatagccagatttatggttggtaccgcgtaaattttggtgtgattgatgaacgtttgcatcgtaaccgtgaata ccgcgatcgctactaccgtaacttgaacattgcacctgccgaggacggctatcgtttagcgggattcccacccgatcatcaggcgtgg cgtgaggaaccgtggatccatcacgcccctcaggggtgcgggaacagtagtcgcCATATGATTAGAGCCTACGA

ACAAAACCCACAACATTTTATTGAGGATCTAGAAAAAGTTAGGGTGGAACAACT

TACTGGTCATGGTTCTTCAGTTTTAGAAGAATTGGTTCAGTTAGTCAAAGATAAA

AATATAGATATTTCCATTAAATATGATCCCAGAAAAGATTCGGAGGTTTTTGCCA

ATAGAGTAATTACTGATGATATCGAATTGCTCAAGAAAATCCTAGCTTATTTTCT

ACCCGAGGATGCCATTCTTAAAGGCGGTCATTATGACAACCAACTGCAAAATGG

CATCAAGCGAGTAAAAGAGTTCCTTGAATCATCGCCGAATACACAATGGGAATT

GCGGGCGTTCATGGCAGTAATGCATTTCTCTTTAACCGCCGATCGTATCGATGAT

GATATTTTGAAAGTGATTGTTGATTCAATGAATCATCATGGTGATGCCCGTAGCA

AGTTGCGTGAAGAATTAGCTGAGCTTACCGCCGAATTAAAGATTTATTCAGTTAT

TCAAGCCGAAATTAATAAGCATCTGTCTAGTAGTGGCACCATAAATATCCATGAT

AAATCCATTAATCTCATGGATAAAAATTTATATGGTTATACAGATGAAGAGATTT

TTAAAGCCAGCGCAGAGTACAAAATTCTCGAGAAAATGCCTCAAACCACCATTC

AGGTGGATGGGAGCGAGAAAAAAATAGTCTCGATAAAGGACTTTCTTGGAAGTG

AGAATAAAAGAACCGGGGCGTTGGGTAATCTGAAAAACTCATACTCTTATAATA

AAGATAATAATGAATTATCTCACTTTGCCACCACCTGCTCGGATAAGTCCAGGCC

GCTCAACGACTTGGTTAGCCAAAAAACAACTCAGCTGTCTGATATTACATCACGT

```
                                                       -continued
TTTAATTCAGCTATTGAAGCACTGAACCGTTTCATTCAGAAATATGATTCAGTGA
TGCAACGTCTGCTAGATGACACGTCTGGTAAAGGATCCATGAGTGCGTTGATAAC
CCATGATCGCTCAACGCCAGTAACTGGAAGTCTACTTCCCTACGTCGAGACACCA
GCGCCCGCCCCCCTTCAGACTCAACAAGTCGCGGGAGAACTGAAGGATAAAAAT
GGTGGGGTGAGTTCTCAGGGCGTACAGCTCCCTGCACCACTAGCAGTGGTTGCCA
GCCAAGTCACTGAAGGACAACAGCAAGAAATCACTAAATTATTGGAGTCGGTCA
CCCGCGGCACGGCAGGATCTCAACTGATATCAAATTATGTTTCAGTGCTAACGAA
TTTTACGCTCGCTTCACCTGATACATTTGAGATTGAGTTAGGTAAGCTAGTTTCTA
ATTTAGAAGAAGTACGCAAAGACATAAAAATCGCTGATATTCAGCGTCTTCATG
AACAAAACATGAAGAAAATTGAAGAGAATCAAGAGAAAATCAAAGAAACAGAA
GAGAATGCCAAGCAAGTCAAGAAATCCGGCATGGCATCAAAGATTTTTGGCTGG
CTCAGCGCCATAGCCTCAGTGGTTATCGGTGCCATCATGGTGGCCTCAGGGGTAG
GAGCCGTTGCCGGTGCAATGATGATTGCCTCAGGCGTAATTGGGATGGCGAATA
TGGCTGTGAAACAAGCGGCGGAAGATGGCCTGATATCCCAAGAGGCAATGCAAG
TATTAGGGCCGATACTCACTGCGATTGAAGTCGCATTGACTGTAGTTTCAACCGT
AATGACCTTTGGCGGTTCGGCACTAAAATGCCTGGCTGATATTGGCGCAAAACTC
GGTGCTAACACCGCAAGTCTTGCTGCTAAAGGAGCCGAGTTTTCGGCCAAAGTTG
CCCAAATTTCGACAGGCATATCAAACACTGTCGGGAATGCAGTGACTAAATTAG
GGGGCAGTTTTGGTAGTTTAACAATGAGCCATGTAATCCGTACAGGATCACAGG
CAACACAAGTCGCCGTTGGTGTGGGCAGCGGAATAACTCAGACCATCAATAATA
AAAAACAAGCTGATTTACAACATAATAACGCTGATTTGGCCTTGAACAAGGCAG
ACATGGCAGCGTTACAAAGTATTATTGACCGACTCAAAGAAGAGTTATCCCATTT
GTCAGAGTCACATCAACAAGTGATGGAACTGATTTTCCAGATGATTAATGCAAA
AGGTGACATGCTGCATAATTTGGCCGGCAGACCCCATACTGTTTAAGGTACC
```

LTA1-YerF Amino acid sequence                                                  SEQ ID NO: 48

```
MDNGDRLYRADSRPPDEIKRSGGLMPRGHNEYFDRGTQMNINLYDHARGTQ
TGFVRYDDGYVSTSLSLRSAHLAGQSILSGYSTYYIYVIATAPNMFNVNDVLGVYSP
HPYEQEVSALGGIPYSQIYGWYRVNFGVIDERLHRNREYRDRYYRNLNIAPAEDGYR
LAGFPPDHQAWREEPWIHHAPQGCGNSSRMIRAYEQNPQHFIEDLEKVRVEQLTGH
GSSVLEELVQLVKDKNIDISIKYDPRKDSEVFANRVITDDIELLKKILAYFLPEDAILK
GGHYDNQLQNGIKRVKEFLESSPNTQWELRAFMAVMHFSLTADRIDDDILKVIVDS
MNHHGDARSKLREELAELTAELKIYSVIQAEINKHLSSSGTINIHDKSINLMDKNLYG
YTDEEIFKASAEYKILEKMPQTTIQVDGSEKKIVSIKDFLGSENKRTGALGNLKNSYS
YNKDNNELSHFATTCSDKSRPLNDLVSQKTTQLSDITSRFNSAIEALNRFIQKYDSVM
QRLLDDTSGKGSMSALITHDRSTPVTGSLLPYVETPAPAPLQTQQVAGELKDKNGGV
SSQGVQLPAPLAVVASQVTEGQQQEITKLLESVTRGTAGSQLISNYVSVLTNFTLASP
DTFEIELGKLVSNLEEVRKDIKIADIQRLHEQNMKKIEENQEKIKETEENAKQVKKSG
MASKIFGWLSAIASVVIGAIMVASGVGAVAGAMMIASGVIGMANMAVKQAAEDGL
ISQEAMQVLGPILTAIEVALTVVSTVMTFGGSALKCLADIGAKLGANTASLAAKGAE
FSAKVAQISTGISNTVGNAVTKLGGSFGSLTMSHVIRTGSQATQVAVGVGSGITQTIN
```

NKKQADLQHNNADLALNKADMAALQSIIDRLKEELSHLSESHQQVMELIFQMINAK
GDMLHNLAGRPHTV-

His-SicA chaperone for S1 nucleic sequence

SEQ ID NO: 49

ATGGGCAGCAGCCATCACCATCATCACCACAGCCAGGATCCGatggactaccaga
acaacgtcagcgaagaacgtgttgcggaaatgatttgggatgccgttagtgaaggcgccacgctaaaagacgttcatggaatccctca
agatatgatggacggtttatatgctcatgcttatgagttttataaccagggacgactggatgaagctgagacgttctttcgtttcttatgcatt
tatgattttttacaatcccgattacaccatgggactggcggcagtatgccaactgaaaaaacaatttcagaaagcatgtgacctttatgcag
tagcgtttacgttacttaaaaatgattatcgccccgtttttttttaccggcagtgtcaattattaatgcgtaaggcagcaaaagccagacagt
gttttgaacttgtcaatgaacgtactgaagatgagtctctgcgggcaaaagcgttggtctatctggaggcgctaaaaacggcggagaca
gagcagcacagcgagcaggagaaggagtaaAAGCTT His-SicA chaperone for S1 Amino acid sequence

SEQ ID NO: 50

MGSSHHHHHHSQDPMDYQNNVSEERVAEMIWDAVSEGATLKDVHGIPQDM
MDGLYAHAYEFYNQGRLDEAETFFRFLCIYDFYNPDYTMGLAAVCQLKKQFQKAC
DLYAVAFTLLKNDYRPVFFTGQCQLLMRKAAKARQCFELVNERTEDESLRAKALVY
LEALKTAETEQHSEQEKE*

SipD nucleic acid sequence

SEQ ID NO: 51 atgcttaatattcaaaattattccgcttctcctcatccggggatcgttgccgaacggccgcagactccctcggcgagcgagc
acgtcgagactgccgtggtaccgtctaccacagaacatcgcggtacagatatcatttcattatcgcaggcggctactaaaatccaccag
gcacagcagacgctgcagtcaacgccaccgatctctgaagagaataatgacgagcgcacgctggcgcgccagcagttgaccagca
gcctgaatgcgctggcgaagtccggcgtgtcattatccgcagaacaaaatgagaacctgcggagcgcgttttctgcgccgacgtcgg
ccttatttagcgcttcgcctatggcgcagccgagaacaaccatttctgatgctgagatttgggatatggtttcccaaaatatatcggcgata
ggtgacagctatctgggcgtttatgaaaacgttgtcgcagtctataccgattttatcaggccttcagtgatattctttccaaaatgggagg
ctggttattaccaggtaaggacggtaataccgttaagctagatgttacctcactcaaaaatgatttaaacagtttagtcaataaatataatca
aataaacagtaataccgttttatttccagcgcagtcaggcagcggcgttaaagtagccactgaagcggaagcgagacagtggctcagt
gaattgaatttaccgaatagctgcctgaaatcttatggatccggttatgtcgtcaccgttgatctgacgccattacaaaaaatggttcagga
tattgatggtttaggcgcgccgggaaaagactcaaaactcgaaatggataacgccaaatatcaagcctggcagtcgggttttaaagcg
caggaagaaaatatgaaaaccacattacagacgctgacgcaaaaatatagcaatgccaattcattgtacgacaacctggtaaaagtgct
gagcagtacgataagtagcagcctggaaaccgccaaaagcttcctgcaagga SipD amino acid sequence

SEQ ID NO: 52

MLNIQNYSASPHPGIVAERPQTPSASEHVETAVVPSTTEHRGTDIISLSQAATKI
HQAQQTLQSTPPISEENNDERTLARQQLTSSLNALAKSGVSLSAEQNENLRSAFSAPT
SALFSASPMAQPRTTISDAEIWDMVSQNISAIGDSYLGVYENVVAVYTDFYQAFSDIL
SKMGGWLLPGKDGNTVKLDVTSLKNDLNSLVNKYNQINSNTVLFPAQSGSGVKVA
TEAEARQWLSELNLPNSCLKSYGSGYVVTVDLTPLQKMVQDIDGLGAPGKDSKLEM
DNAKYQAWQSGFKAQEENMKTTLQTLTQKYSNANSLYDNLVKVLSSTISSSLETAK
SFLQG

SipB nucleic acid sequence

SEQ ID NO: 53 atggtaaatgacgcaagtagcattagccgtagcggatatacccaaaatccgcgcctcgctgaggcggcttttgaaggcgtt
cgtaagaacacggactttttaaaagcggcggataaagcttttaaagatgtggtggcaacgaaagcgggcgaccttaaagccggaaca
aagtccggcgagagcgctattaatacggtgggtctaaagccgcctacggacgccgccgggaaaaactctccagcgaagggcaatt
gacattactgcttggcaagttaatgaccctactgggcgatgtttcgctgtctcaactggagtctcgtctggcggtatggcaggcgatgatt -continued

```
gagtcacaaaaagagatggggattcaggtatcgaaagaattccagacggctctgggagaggctcaggaggcgacggatctctatga agccagtatcaaaaagacggataccgccaagagtgtttatgacgctgcgaccaaaaaactgacgcaggcgcaaaataaattgcaatc gctggacccggctgaccccggctatgcacaagctgaagccgcggtagaacaggccggaaaagaagcgacagaggcgaaagagg ccttagataaggccacggatgcgacggttaaagcaggcacagacgccaaagcgaaagccgagaaagcggataacattctgaccaa attccagggaacggctaatgccgcctctcagaatcaggtttcccagggtgagcaggataatctgtcaaatgtcgcccgcctcactatgc tcatggccatgtttattgagattgtgggcaaaaatacggaagaaagcctgcaaaacgatcttgcgcttttcaacgccttgcaggaaggg cgtcaggcggagatggaaaagaaatcggctgaattccaggaagagacgcgcaaagccgaggaaacgaaccgcattatgggatgta tcgggaaagtcctcggcgcgctgctaaccattgtcagcgttgtggccgctgttttttaccggtggggcgagtctggcgctggctgcggt gggacttgcggtaatggtggccgatgaaattgtgaaggcggcgacgggagtgtcgtttattcagcaggcgctaaacccgattatgga gcatgtgctgaagccgttaatggagctgattggcaaggcgattaccaaagcgctggaaggattaggcgtcgataagaaaacggcag agatggccggcagcattgttggtgcgattgtcgccgctattgccatggtggcggtcattgtggtggtcgcagttgtcgggaaaggcgc ggcggcgaaactggggtaacgcgctgagcaaaatgatgggcgaaacgattaagaagttggtgcctaacgtgctgaaacagttggcgc aaaacggcagcaaactctttacccaggggatgcaacgtattactagcggtctgggtaatgtgggtagcaagatgggcctgcaaacga atgccttaagtaaagagctggtaggtaatacccctaaataaagtggcgttgggcatggaagtcacgaataccgcagcccagtcagccg gtggtgttgccgagggcgtatttattaaaaatgccagcgaggcgcttgctgattttatgctcgcccgttttgccatggatcagattcagca gtggcttaaacaatccgtagaaatatttggtgaaaaccagaaggtaacggcggaactgcaaaaagccatgtcttctgcggtacagcaa aatgcggatgcttcgcgttttattctgcgccagagtcgcgcataa
```

SipB amino acid sequence

SEQ ID NO: 54

MVNDASSISRSGYTQNPRLAEAAFEGVRKNTDFLKAADKAFKDVVATKAGD

LKAGTKSGESAINTVGLKPPTDAAREKLSSEGQLTLLLGKLMTLLGDVSLSQLESRL

AVWQAMIESQKEMGIQVSKEFQTALGEAQEATDLYEASIKKTDTAKSVYDAATKKL

TQAQNKLQSLDPADPGYAQAEAAVEQAGKEATEAKEALDKATDATVKAGTDAKA

KAEKADNILTKFQGTANAASQNQVSQGEQDNLSNVARLTMLMAMFIEIVGKNTEES

LQNDLALFNALQEGRQAEMEKKSAEFQEETRKAEETNRIMGCIGKVLGALLTIVSVV

AAVFTGGASLALAAVGLAVMVADEIVKAATGVSFIQQALNPIMEHVLKPLMELIGK

AITKALEGLGVDKKTAEMAGSIVGAIVAAIAMVAVIVVVAVVGKGAAAKLGNALS

KMMGETIKKLVPNVLKQLAQNGSKLFTQGMQRITSGLGNVGSKMGLQTNALSKEL

VGNTLNKVALGMEVTNTAAQSAGGVAEGVFIKNASEALADFMLARFAMDQIQQWL

KQSVEIFGENQKVTAELQKAMSSAVQQNADASRFILRQSRA

S1 nucleic acid sequence

SEQ ID NO: 55

```
atgcttaatattcaaaattattccgcttctcctcatccggggatcgttgccgaacggccgcagactccctcggcgagcgagc acgtcgagactgccgtggtaccgtctaccacagaacatcgcggtacagatatcatttcattatcgcaggcggctactaaaatccaccag gcacagcagacgctgcagtcaacgccaccgatctctgaagagaataatgacgagcgcacgctggcgcgccagcagttgaccagca gcctgaatgcgctggcgaagtccggcgtgtcattatccgcagaacaaaatgagaacctgcgggagcgcgttttctgcgccgacgtcgg ccttatttagcgcttcgcctatggcgcagccgagaacaaccatttctgatgctgagatttgggatatggtttcccaaaatatatcggcgata ggtgacagctatctgggcgtttatgaaaacgttgtcgcagtctataccgattttttatcaggccttcagtgatattctttccaaaatggggagg ctggttattaccaggtaaggacggtaataccgttaagctagatgttacctcactcaaaaatgatttaaacagtttagtcaataaatataatca aataaacagtaataccgttttatttccagcgcagtcaggcagcggcgttaaagtagccactgaagcggaagcgagacagtggctcagt gaattgaatttaccgaatagctgcctgaaatcttatggatccggttatgtcgtcaccgttgatctgacgccattacaaaaatggttcagga tattgatggtttaggcgcgccgggaaaagactcaaaactcgaaatggataacgccaaatatcaagcctggcagtcgggttttaaagcg caggaagaaaatatgaaaaccacattacagacgctgacgcaaaaatatagcaatgccaattcattgtacgacaacctggtaaaagtgct
```

-continued

```
gagcagtacgataagtagcagcctggaaaccgccaaaagcttcctgcaaggagtcgacatggtaaatgacgcaagtagcattagcc gtagcggatatacccaaaatccgcgcctcgctgaggcggttttgaaggcgttcgtaagaacacggacttttaaaagcggcggataa agcttttaaagatgtggtggcaacgaaagcgggcgaccttaaagccggaacaaagtccggcgagagcgctattaatacggtgggtct aaagccgcctacggacgccgcccgggaaaaactctccagcgaagggcaattgacattactgcttggcaagttaatgaccctactggg cgatgtttcgctgtctcaactggagtctcgtctggcggtatggcaggcgatgattgagtcacaaaaagagatggggattcaggtatcga aagaattccagacggctctgggagaggctcaggaggcgacggatctctatgaagccagtatcaaaaagacggataccgccaagagt gtttatgacgctgcgaccaaaaaactgacgcaggcgcaaaataaattgcaatcgctggacccggctgaccccggctatgcacaagct gaagccgcggtagaacaggccggaaaagaagcgacagaggcgaaagaggccttagataaggccacggatgcgacggttaaagc aggcacagacgccaaagcgaaagccgagaaagcggataacattctgaccaaattccagggaacggctaatgccgcctctcagaatc aggtttcccagggtgagcaggataatctgtcaaatgtcgcccgcctcactatgctcatggccatgtttattgagattgtgggcaaaaatac ggaagaaagcctgcaaaacgatcttgcgcttttcaacgccttgcaggaagggcgtcaggcggagatggaaaagaaatcggctgaatt ccaggaagagacgcgcaaagccgaggaaacgaaccgcattatgggatgtatcgggaaagtcctcggcgcgctgctaaccattgtca gcgttgtggccgctgttttaccggtggggcgagtctggcgctggctgcggtgggacttgcggtaatggtggccgatgaaattgtgaa ggcggcgacgggagtgtcgtttattcagcaggcgctaaaccgattatggagcatgtgctgaagccgttaatggagctgattggcaag gcgattaccaaagcgctggaaggattaggcgtcgataagaaaacggcagagatggccggcagcattgttggtgcgattgtcgccgct attgccatggtggcggtcattgtggtggtcgcagttgtcgggaaaggcgcggcggcgaaactgggtaacgcgctgagcaaaatgat gggcgaaacgattaagaagttggtgcctaacgtgctgaaacagttggcgcaaaacggcagcaaactctttacccaggggatgcaac gtattactagcggtctgggtaatgtgggtagcaagatgggcctgcaaacgaatgccttaagtaaagagctggtaggtaatacccctaaat aaagtggcgttgggcatggaagtcacgaataccgcagcccagtcagccggtggtgttgccgagggcgtatttattaaaaatgccagc gaggcgcttgctgattttatgctcgcccgttttgccatggatcagattcagcagtggcttaaacaatccgtagaaatatttggtgaaaacc agaaggtaacggcggaactgcaaaaagccatgtcttctgcggtacagcaaaatgcggatgcttcgcgttttattctgcgccagagtcg cgcataa
```

S1 amino acid sequence

SEQ ID NO: 56

MLNIQNYSASPHPGIVAERPQTPSASEHVETAVVPSTTEHRGTDIISLSQAATKI

HQAQQTLQSTPPISEENNDERTLARQQLTSSLNALAKSGVSLSAEQNENLRSAFSAPT

SALFSASPMAQPRTTISDAEIWDMVSQNISAIGDSYLGVYENVVAVYTDFYQAFSDIL

SKMGGWLLPGKDGNTVKLDVTSLKNDLNSLVNKYNQINSNTVLFPAQSGSGVKVA

TEAEARQWLSELNLPNSCLKSYGSGYVVTVDLTPLQKMVQDIDGLGAPGKDSKLEM

DNAKYQAWQSGFKAQEENMKTTLQTLTQKYSNANSLYDNLVKVLSSTISSSLETAK

SFLQGVDMVNDASSISRSGYTQNPRLAEAAFEGVRKNTDFLKAADKAFKDVVATKA

GDLKAGTKSGESAINTVGLKPPTDAAREKLSSEGQLTLLLGKLMTLLGDVSLSQLES

RLAVWQAMIESQKEMGIQVSKEFQTALGEAQEATDLYEASIKKTDTAKSVYDAATK

KLTQAQNKLQSLDPADPGYAQAEAAVEQAGKEATEAKEALDKATDATVKAGTDA

KAKAEKADNILTKFQGTANAASQNQVSQGEQDNLSNVARLTMLMAMFIEIVGKNTE

ESLQNDLALFNALQEGRQAEMEKKSAEFQEETRKAEETNRIMGCIGKVLGALLTIVS

VVAAVFTGGASLALAAVGLAVMVADEIVKAATGVSFIQQALNPIMEHVLKPLMELI

GKAITKALEGLGVDKKTAEMAGSIVGAIVAAIAMVAVIVVVAVVGKGAAAKLGNA

LSKMMGETIKKLVPNVLKQLAQNGSKLFTQGMQRITSGLGNVGSKMGLQTNALSKE

LVGNTLNKVALGMEVTNTAAQSAGGVAEGVFIKNASEALADFMLARFAMDQIQQW

LKQSVEIFGENQKVTAELQKAMSSAVQQNADASRFILRQSRA

LTA1-GSAAS-S1 Nucleic acid sequence

SEQ ID NO: 57

CATatggacaatggcgatcgtttataccgtgccgactcgcgtcccccagatgagattaaacgtagcggtgggttaatgcc acgtgggcacaatgagtattttgaccgtggaacacagatgaacattaacctttacgatcatgcccgtgggacccagaccgggtttgtcc gttatgatgacgggtatgttagtacgagtttgtccttacgctccgcacaccttgcgggacaaagtattttatcaggctacagcacatattac atttatgtgatcgccactgccccaaacatgttcaatgtgaacgatgtgttgggggtttacagcccccatccatatgaacaagaagtctcg gcccttgggggatcccatatagccagatttatggttggtaccgcgtaaattttggtgtgattgatgaacgtttgcatcgtaaccgtgaata ccgcgatcgctactaccgtaacttgaacattgcacctgccgaggacggctatcgtttagcgggattcccacccgatcatcaggcgtgg cgtgaggaaccgtggatccatcacgcccctcaggggtgcgggaacagtagtcgcgggtccgcggcatccatgcttaatattcaaaatt attccgcttctcctcatccggggatcgttgccgaacggccgcagactccctcggcgagcgagcacgtcgagactgccgtggtaccgt ctaccacagaacatcgcggtacagatatcatttcattatcgcaggcggctactaaaatccaccaggcacagcagacgctgcagtcaac gccaccgatctctgaagagaataatgacgagcgcacgctggcgcgccagcagttgaccagcagcctgaatgcgctggcgaagtcc ggcgtgtcattatccgcagaacaaaatgagaacctgcgggagcgcgttttctgcgccgacgtcggccttatttagcgcttcgcctatggc gcagccgagaacaaccatttctgatgctgagatttgggatatggtttcccaaaatatatcggcgataggtgacagctatctgggcgtttat gaaaacgttgtcgcagtctataccgattttttatcaggccttcagtgatattctttccaaaatggggagctggttattaccaggtaaggacgg taataccgttaagctagatgttacctcactcaaaaatgatttaaacagtttagtcaataaatataatcaaataaacagtaataccgttttatttc cagcgcagtcaggcagcggcgttaaagtagccactgaagcggaagcgagacagtggctcagtgaattgaatttaccgaatagctgc ctgaaatcttatggatccggttatgtcgtcaccgttgatctgacgccattacaaaaaatggttcaggatattgatggtttaggcgcgccgg gaaaagactcaaaactcgaaatggataacgccaaatatcaagcctggcagtcgggttttaaagcgcaggaagaaaatatgaaaacca cattacagacgctgacgcaaaaatatagcaatgccaattcattgtacgacaacctggtaaaagtgctgagcagtacgataagtagcagc ctggaaccgccaaaagcttcctgcaaggagtcgacatggtaaatgacgcaagtagcattagccgtagcggatatacccaaaatccg cgcctcgctgaggcggcttttgaaggcgttcgtaagaacacggactttttaaaagcggcggataaagcttttaaagatgtggtggcaac gaaagcgggcgaccttaaagccggaacaaagtccggcgagagcgctattaatacggtgggtctaaagccgcctacggacgccgcc cgggaaaaactctccagcgaagggcaattgacattactgcttggcaagttaatgaccctactgggcgatgtttcgctgtctcaactgga gtctcgtctggcggtatggcaggcgatgattgagtcacaaaaagagatggggattcaggtatcgaaagaattccagacggctctggg agaggctcaggaggcgacggatctctatgaagccagtatcaaaaagacggataccgccaagagtgtttatgacgctgcgaccaaaa aactgacgcaggcgcaaaataaattgcaatcgctggacccggctgaccccggctatgcacaagctgaagccgcggtagaacaggc cggaaaagaagcgacagaggcgaaagaggccttagataaggccacggatgcgacggttaaagcaggcacagacgccaaagcga aagccgagaaagcggataacattctgaccaaattccagggaacggctaatgccgcctctcagaatcaggtttcccagggtgagcagg ataatctgtcaaatgtcgcccgcctcactatgctcatggccatgtttattgagattgtgggcaaaaatacggaagaaagcctgcaaaacg atcttgcgcttttcaacgccttgcaggaagggcgtcaggcggagatggaaaagaaatcggctgaattccaggaagagacgcgcaaa gccgaggaaacgaaccgcattatgggatgtatcgggaaagtcctcggcgcgctgctaaccattgtcagcgttgtggccgctgttttac cggtggggcgagtctggcgctggctgcggtgggacttgcggtaatggtggccgatgaaattgtgaaggcggcgacgggagtgtcgt ttattcagcaggcgctaaacccgattatggagcatgtgctgaagccgttaatggagctgattggcaaggcgattaccaaagcgctgga aggattaggcgtcgataagaaaaeggcagagatggccggcagcattgttggtgcgattgtcgccgctattgccatggtggcggtcatt gtggtggtcgcagttgtcgggaaaggcgcggcggcgaaactgggtaacgcgctgagcaaaatgatgggcgaaacgattaagaagt tggtgcctaacgtgctgaaacagttggcgcaaaacggcagcaaactctttacccaggggatgeaacgtattactagcggtctgggtaa tgtgggtagcaagatgggcctgcaaacgaatgccttaagtaaagagctggtaggtaatacectaaataaagtggcgttgggcatggaa gtcacgaataccgcagcccagtcagccggtggtgttgccgagggcgtatttattaaaaatgccagcgaggcgcttgctgattttatgct cgcccgttttgccatggatcagattcagcagtggcttaaacaatccgtagaaatatttggtgaaaaccagaaggtaacggcggaactgc aaaaagccatgtcttctgcggtacagcaaaatgcggatgcttcgcgttttattctgcgccagagtcgcgcataaCTCGAG LTA1-GSAAS-S1 Amino acid sequence

SEQ ID NO: 58

MDNGDRLYRADSRPPDEIKRSGGLMPRGHNEYFDRGTQMNINLYDHARGTQ
TGFVRYDDGYVSTSLSLRSAHLAGQSILSGYSTYYIYVIATAPNMFNVNDVLGVYSP
HPYEQEVSALGGIPYSQIYGWYRVNFGVIDERLHRNREYRDRYYRNLNIAPAEDGYR
LAGFPPDHQAWREEPWIHHAPQGCGNSSRGSAASMLNIQNYSASPHPGIVAERPQTP
SASEHVETAVVPSTTEHRGTDIISLSQAATKIHQAQQTLQSTPPISEENNDERTLARQQ
LTSSLNALAKSGVSLSAEQNENLRSAFSAPTSALFSASPMAQPRTTISDAEIWDMVSQ
NISAIGDSYLGVYENVVAVYTDFYQAFSDILSKMGGWLLPGKDGNTVKLDVTSLKN
DLNSLVNKYNQINSNTVLFPAQSGSGVKVATEAEARQWLSELNLPNSCLKSYGSGY
VVTVDLTPLQKMVQDIDGLGAPGKDSKLEMDNAKYQAWQSGFKAQEENMKTTLQ
TLTQKYSNANSLYDNLVKVLSSTISSSLETAKSFLQGVDMVNDASSISRSGYTQNPRL
AEAAFEGVRKNTDFLKAADKAFKDVVATKAGDLKAGTKSGESAINTVGLKPPTDA
AREKLSSEGQLTLLLGKLMTLLGDVSLSQLESRLAVWQAMIESQKEMGIQVSKEFQT
ALGEAQEATDLYEASIKKTDTAKSVYDAATKKLTQAQNKLQSLDPADPGYAQAEA
AVEQAGKEATEAKEALDKATDATVKAGTDAKAKAEKADNILTKFQGTANAASQNQ
VSQGEQDNLSNVARLTMLMAMFIEIVGKNTEESLQNDLALFNALQEGRQAEMEKKS
AEFQEETRKAEETNRIMGCIGKVLGALLTIVSVVAAVFTGGASLALAAVGLAVMVA
DEIVKAATGVSFIQQALNPIMEHVLKPLMELIGKAITKALEGLGVDKKTAEMAGSIV
GAIVAAIAMVAVIVVVAVVGKGAAAKLGNALSKMMGETIKKLVPNVLKQLAQNGS
KLFTQGMQRITSGLGNVGSKMGLQTNALSKELVGNTLNKVALGMEVTNTAAQSAG
GVAEGVFIKNASEALADFMLARFAMDQIQQWLKQSVEIFGENQKVTAELQKAMSSA
VQQNADASRFILRQSRA*

His-SscA chaperone for S2 nucleic acid sequence

SEQ ID NO: 59

ATGGGCAGCAGCCATCACCATCATCACCACAGCCAGGATCCGatgaaaaaagac
ccgaccctacaacaggcacatgacacgatgcggttttttccggcgtggcggctcgctgcgtatgttgttggatgacgatgttacacagcc
gcttaatactctgtatcgctatgccacgcagcttatggaggtaaaagaattcgccggcgcagcgcgactttttcaattgctgacgatatat
gatgcctggtcatttgactactggtttcggttaggggaatgctgccaggctcaaaaacattgggggaagcgatatacgcttatggacg
cgcggcacaaattaagattgatgcgccgcaggcgccatgggccgcagcggaatgctatctcgcgtgtgataacgtctgttatgcaatc
aaagcgttaaaggccgtggtgcgtatttgcggcgaggtcagtgaacatcaaattctccgacagcgtgcagaaaagatgttacagcaac
tttctgacaggagctaaAAGCTT His-SscA chaperone for S2 Amino acid sequence

SEQ ID NO: 60

MGSSHHHHHHSQDPMKKDPTLQQAHDTMRFFRRGGSLRMLLDDDVTQPLN
TLYRYATQLMEVKEFAGAARLFQLLTIYDAWSFDYWFRLGECCQAQKHWGEAIYA
YGRAAQIKIDAPQAPWAAAECYLACDNVCYAIKALKAVVRICGEVSEHQILRQRAE
KMLQQLSDRS*

SseB nucleic acid sequence

SEQ ID NO: 61

Atgtcttcaggaaacatcttatggggaagtcaaaaccctattgtgtttaaaaatagcttcggcgtcagcaacgctgataccgg
gagccaggatgacttatcccagcaaaatccgtttgccgaagggtatggtgttttgcttattctccttatggttattcaggctatcgcaaataa
taaatttattgaagtccagaagaacgctgaacgtgccagaaatacccaggaaaagtcaaatgagatggatgaggtgattgctaaagca
gccaaaggggatgctaaaaccaaagaggaggtgcctgaggatgtaattaaatacatgcgtgataatggtattctcatcgatggtatgac
cattgatgattatatggctaaatatggcgatcatgggaagctggataaaggtggcctacaggcgatcaaagcggctttggataatgacg -continued ccaaccggaataccgatcttatgagtcaggggcagataacaattcaaaaaatgtctcaggagcttaacgctgtccttacccaactgaca gggcttatcagtaagtgggggaaatttccagtatgatagcgcagaaaacgtactca SseB amino acid sequence

SEQ ID NO: 62

MSSGNILWGSQNPIVFKNSFGVSNADTGSQDDLSQQNPFAEGYGVLLILLMVI

QAIANNKFIEVQKNAERARNTQEKSNEMDEVIAKAAKGDAKTKEEVPEDVIKYMRD

NGILIDGMTIDDYMAKYGDHGKLDKGGLQAIKAALDNDANRNTDLMSQGQITIQK

MSQELNAVLTQLTGLISKWGEISSMIAQKTYS

SseC nucleic acid sequence

SEQ ID NO: 63 atgaatcgaattcacagtaatagcgacagcgccgcaggagtaaccgccttaacacatcatcacttaagcaatgtcagttgcg tttcctcgggttcgctgggaaagcgccagcatcgtgtgaattctacttttggcgatggcaacgccgcgtgtctgctatccgggaaatta gtcttcaggaggcaagcaatgcgttgaagcaactgcttgatgccgtacccgaaatcataagcgtccatcattgcctgacttttgcaga ccaatcccgcggttttatcaatgatgatgacgtcattaatactcaacgtctttggtaataacgctcaatcgttatgccaacagcttgagcgg gcaactgaggtgcaaaatgcattacgtaataagcaggtaaaggagtatcaggagcagatccagaaagcgatagagcaggaggataa agcgcgtaaagcgggtatttrtggcgctattttgactggattaccggcatatttgaaaccgtgattggcgccttaaaagttgtggaaggtt ttctgtccggaaatcccgcagaaatggctagcggcgtagcttatatggccgcaggttgtgcaggaatggttaaagccggagccgaaa cggcaatgatgtgcggtgctgaccacgatacctgtcaggcaattattgacgtgacaagtaagattcaatttggttgtgaagccgtcgcg ctggcactggatgttttccagattggccgtgcttttatggcgacgagaggtttatctggcgcagctgcaaaagtgcttgactccggttttg gcgaggaagtggttgagcgtatggtaggtgcaggggaagcagaaatagaggagttggctgaaaagtttggcgaagaagtgagcga aagtttttccaaacaatttgagccgcttgaacgtgaaatggctatggcgaatgagatggcagaggaggctgccgagttttctcgtaacgt agaaaataatatgacgcgaagcgcgggaaaaagctttacgaaagagggggtgaaagcaatggcaaaagaagcggcaaagaagc cctggaaaaatgtgtgcaagaaggtggaaagttcctgttaaaaaaattccgtaataaagttctcttcaatatgttcaaaaaaatcctgtatg ccttactgagggattgttcatttaaaggcttacaggctatcagatgtgcaaccgagggcgccagtcagatgaatactggcatggttaaca cagaaaaagcgaagatcgaaagaaaatagagcaattaataactcagcaacggtttctggatttcataatgcaacaaacagaaaccca gaaaaagatagaacaaaaacgcttagaggagctttataaggggagcggtgccgcgcttagagatgtattagataccattgatcactata gtagcgttcaggcgagaatagctggctatcgcgcttaa SseC amino acid sequence

SEQ ID NO: 64

MNRIHSNSDSAAGVTALTHHHLSNVSCVSSGSLGKRQHRVNSTFGDGNAAC

LLSGKISLQEASNALKQLLDAVPGNHKRPSLPDFLQTNPAVLSMMMTSLILNVFGNN

AQSLCQQLERATEVQNALRNKQVKEYQEQIQKAIEQEDKARKAGIFGAIFDWITGIFE

TVIGALKVVEGFLSGNPAEMASGVAYMAAGCAGMVKAGAETAMMCGADHDTCQ

AIIDVTSKIQFGCEAVALALDVFQIGRAFMATRGLSGAAAKVLDSGFGEEVVERMVG

AGEAEIEELAEKFGEEVSESFSKQFEPLEREMAMANEMAEEAAEFSRNVENNMTRSA

GKSFTKEGVKAMAKEAAKEALEKCVQEGGKFLLKKFRNKVLFNMFKKILYALLRD

CSFKGLQAIRCATEGASQMNTGMVNTEKAKIEKKIEQLITQQRFLDFIMQQTENQKKI

EQKRLEELYKGSGAALRDVLDTIDHYSSVQARIAGYRA

S2 nucleic acid sequence

SEQ ID NO: 65 atgtcttcaggaaacatcttatggggaagtcaaaaccctattgtgtttaaaaatagcttcggcgtcagcaacgctgataccgg gagccaggatgacttatcccagcaaaatccgtttgccgaagggtatggtgttttgcttattctccttatggttattcaggctatcgcaaataa taaatttattgaagtccagaagaacgctgaacgtgccagaaatacccaggaaaagtcaaatgagatggatgaggtgattgctaaagca gccaaagggggatgctaaaaccaaagaggaggtgcctgaggatgtaattaaatacatgcgtgataatggtattctcatcgatggtatgac cattgatgattatatggctaaatatggcgatcatgggaagctggataaaggtggcctacaggcgatcaaagcggctttggataatgacg -continued

```
ccaaccggaataccgatcttatgagtcaggggcagataacaattcaaaaaatgtctcaggagcttaacgctgtccttacccaactgaca
gggcttatcagtaagtgggggaaatttccagtatgatagcgcagaaaacgtactcaGAGCTcatgaatcgaattcacagtaata
gcgacagcgccgcaggagtaaccgccttaacacatcatcacttaagcaatgtcagttgcgtttcctcgggttcgctgggaaagcgcca
gcatcgtgtgaattctacttttggcgatggcaacgccgcgtgtctgctatccgggaaaattagtcttcaggaggcaagcaatgcgttgaa
gcaactgcttgatgccgtacccggaaatcataagcgtccatcattgcctgacttttgcagaccaatcccgcggttttatcaatgatgatg
acgtcattaatactcaacgtctttggtaataacgctcaatcgttatgccaacagcttgagcgggcaactgaggtgcaaaatgcattacgta
ataagcaggtaaaggagtatcaggagcagatccagaaagcgatagagcaggaggataaagcgcgtaaagcgggtattttggcgct
atttttgactggattaccggcatatttgaaaccgtgattggcgccttaaaagttgtggaaggttttctgtccggaaatcccgcagaaatggc
tagcggcgtagcttatatgccgcaggttgtgcaggaatggttaaagccggagccgaaacggcaatgatgtgcggtgctgaccacga
tacctgtcaggcaattattgacgtgacaagtaagattcaatttggttgtgaagccgtcgcgctggcactggatgttttccagattggccgt
gcttttatggcgacgagaggtttatctggcgcagctgcaaaagtgcttgactccggttttggcgaggaagtggttgagcgtatggtaggt
gcaggggaagcagaaatagaggagttggctgaaaagtttggcgaagaagtgagcgaaagttttttccaaacaatttgagccgcttgaa
cgtgaaatggctatggcgaatgagatggcagaggaggctgccgagttttctcgtaacgtagaaaataatatgacgcgaagcgcggga
aaaagctttacgaaagaggggtgaaagcaatggcaaaagaagcggcaaaagaagccctggaaaatgtgtgcaagaaggtgga
aagttcctgttaaaaaaattccgtaataaagtctcttcaatatgttcaaaaaatcctgtatgccttactgagggattgttcatttaaaggctt
acaggctatcagatgtgcaaccgagggcgccagtcagatgaatactggcatggttaacacagaaaaagcgaagatcgaaagaaaa
tagagcaattaataactcagcaacggtttctggatttcataatgcaacaaacagaaaaccagaaaaagatagaacaaaaacgcttagag
gagctttataaggggagcggtgccgcgcttagagatgtattagataccattgatcactatagtagcgttcaggcgagaatagctggctat
cgcgcttaa
```

S2 amino acid sequence                                                                SEQ ID NO: 66

```
MSSGNILWGSQNPIVFKNSFGVSNADTGSQDDLSQQNPFAEGYGVLLILLMVI
QAIANNKFIEVQKNAERARNTQEKSNEMDEVIAKAAKGDAKTKEEVPEDVIKYMRD
NGILIDGMTIDDYMAKYGDHGKLDKGGLQAIKAALDNDANRNTDLMSQGQITIQK
MSQELNAVLTQLTGLISKWGEISSMIAQKTYSELMNRIHSNSDSAAGVTALTHHHLS
NVSCVSSGSLGKRQHRVNSTFGDGNAACLLSGKISLQEASNALKQLLDAVPGNHKR
PSLPDFLQTNPAVLSMMMTSLILNVFGNNAQSLCQQLERATEVQNALRNKQVKEYQ
EQIQKAIEQEDKARKAGIFGAIFDWITGIFETVIGALKVVEGFLSGNPAEMASGVAYM
AAGCAGMVKAGAETAMMCGADHDTCQAIIDVTSKIQFGCEAVALALDVFQIGRAF
MATRGLSGAAAKVLDSGFGEEVVERMVGAGEAEIEELAEKFGEEVSESFSKQFEPLE
REMAMANEMAEEAAEFSRNVENNMTRSAGKSFTKEGVKAMAKEAAKEALEKCVQ
EGGKFLLKKFRNKVLFNMFKKILYALLRDCSFKGLQAIRCATEGASQMNTGMVNTE
KAKIEKKIEQLITQQRFLDFIMQQTENQKKIEQKRLEELYKGSGAALRDVLDTIDHYS
SVQARIAGYRA
```

LTA1-GSAAS-S2 nucleic acid s

-continued

```
cttatggggaagtcaaaaccctattgtgtttaaaaatagcttcggcgtcagcaacgctgataccgggagccaggatgacttatcccagc aaaatccgtttgccgaagggtatggtgttttgcttattctccttatggttattcaggctatcgcaaataataaatttattgaagtccagaagaa cgctgaacgtgccagaaatacccaggaaaagtcaatgagatggatgaggtgattgctaaagcagccaaaggggatgctaaaacca aagaggaggtgcctgaggatgtaattaaatacatgcgtgataatggtattctcatcgatggtatgaccattgatgattatatggctaaatat ggcgatcatgggaagctggataaaggtggcctacaggcgatcaaagcggctttggataatgacgccaaccggaataccgatcttatg agtcaggggcagataacaattcaaaaaatgtctcaggagcttaacgctgtccttacccaactgacagggcttatcagtaagtgggggg aaatttccagtatgatagcgcagaaaacgtactcaGAGCTCatgaatcgaattcacagtaatagcgacagcgccgcaggagtaa ccgccttaacacatcatcacttaagcaatgtcagttgcgtttcctcgggttcgctgggaaagcgccagcatcgtgtgaattctacttttggc gatggcaacgccgcgtgtctgctatccgggaaaattagtcttcaggaggcaagcaatgcgttgaagcaactgcttgatgccgtacccg gaaatcataagcgtccatcattgcctgacttttttgcagaccaatcccgcggttttatcaatgatgatgacgtcattaatactcaacgtctttg gtaataacgctcaatcgttatgccaacagcttgagcgggcaactgaggtgcaaaatgcattacgtaataagcaggtaaaggagtatca ggagcagatccagaaagcgatagagcaggaggataaagcgcgtaaagcgggtattttttggcgctatttttgactggattaccggcata tttgaaaccgtgattggcgccttaaaagttgtggaaggttttctgtccggaaatcccgcagaaatggctagcggcgtagcttatatggcc gcaggttgtgcaggaatggttaaagccggagccgaaacggcaatgatgtgcggtgctgaccacgatacctgtcaggcaattattgac gtgacaagtaagattcaatttggttgtgaagccgtcgcgctggcactggatgttttccagattggccgtgcttttatggcgacgagaggtt tatctggcgcagctgcaaaagtgcttgactccggttttggcgaggaagtggttgagcgtatggtaggtgcaggggaagcagaaatag aggagttggctgaaaagtttggcgaagaagtgagcgaaagttttttccaaacaatttgagccgcttgaacgtgaaatggctatggcgaat gagatggcagaggaggctgccgagttttctcgtaacgtagaaaataatatgacgcgaagcgcgggaaaaagctttacgaaagaggg ggtgaaagcaatggcaaaagaagcggcaaaagaagccctggaaaaatgtgtgcaagaaggtggaaagttcctgttaaaaaaattcc gtaataaagttctcttcaatatgttcaaaaaaatcctgtatgccttactgagggattgttcatttaaaggcttacaggctatcagatgtgcaac cgagggcgccagtcagatgaatactggcatggttaacacagaaaaagcgaagatcgaaagaaaatagagcaattaataactcagc aacggtttctggatttcataatgcaacaaacagaaaaccagaaaaagatagaacaaaaacgcttagaggagctttataaggggagcgg tgccgcgcttagagatgtattagataccattgatcactatagtagcgttcaggcgagaatagctggctatcg LTA1-SseB Nucleic acid sequence

SEQ ID NO: 69

ATGGGCAGCAGCCATCATCATCATCATCACAGCAGCGGCCTGGTGCCGCG
CGGCAGCCATatggacaatggcgatcgtttataccgtgccgactcgcgtcccccagatgagattaaacgtagcggtgggtta
atgccacgtgggcacaatgagtattttgaccgtggaacacagatgaacattaacctttacgatcatgcccgtgggacccagaccgggtt
tgtccgttatgatgacgggtatgttagtacgagtttgtccttacgctccgcacaccttgcgggacaaagtattttatcaggctacagcacat
attacatttatgtgatcgccactgccccaaacatgttcaatgtgaacgatgtgttggggggtttacagcccccatccatatgaacaagaagt
ctcggcccttgggggatcccatatagccagatttatggttggtaccgcgtaaattttggtgtgattgatgaacgtttgcatcgtaaccgtg
aataccgcgatcgctactaccgtaacttgaacattgcacctgccgaggacggctatcgtttagcgggattcccacccgatcatcaggcg
tggcgtgaggaaccgtggatccatcacgcccctcaggggtgcgggaacagtagtcgcgggtccgcggcatccatgtcttcaggaaa
catcttatggggaagtcaaaaccctattgtgttaaaaatagcttcggcgtcagcaacgctgataccgggagccaggatgacttatccca
gcaaaatccgtttgccgaagggtatggtgttttgcttattctccttatggttattcaggctatcgcaaataataaatttattgaagtccagaag
aacgctgaacgtgccagaaatacccaggaaagtcaaatgagatggatgaggtgattgctaaagcagccaaggggatgctaaaac
caaagaggaggtgcctgaggatgtaattaaatacatgcgtgataatggtattctcatcgatggtatgaccattgatgattatatggctaaat
atggcgatcatgggaagctggataaaggtggcctacaggcgatcaaagcggctttggataatgacgccaaccggaataccgatcttat
gagtcaggggcagataacaattcaaaaaatgtctcaggagcttaacgctgtccttacccaactgacagggcttatcagtaagtggggg
gaaatttccagtatgatagcgcagaaaacgtactcataaGGATCC LTA1-SseB Amino acid sequence

SEQ ID NO: 70

MGSSHHHHHHSSGLVPRGSHMDNGDRLYRADSRPPDEIKRSGG

CT053 nucleic acid sequence

SEQ ID NO: 73

Aaaagtgagcgtttaaaaaaattagaatcagagcttcatgatcttacccagtggatgcaacttggccttgttcctaaaaaga aatcgagagacaccaggaagaaatccgtctgctagaaagcaaaatccttgaagagaaagaacgtctacaacttctcaaagaaagcgg tgagatcaaagagtacgtaaccccctcgaagaactccagctaaaaccatttacccagatggccccagcgtttcagacgttgagtttgtag aatcctcggatacagaagtggatctcgatgccggtgacacaattgagattgacctaggtgatgaggcaagagaagaaagcggaaac gaactcgactactctagtgaagacgatgaggatccttttcagcgatcgcaatcgttggcgccgaggaggcatcatagatcctgacgcga atgaatgg CT053 amino acid sequence

SEQ ID NO: 74

MKSERLKKLESELHDLTQWMQLGLVPKKEIERHQEEIRLLESKILEEKERLQL

LKESGEIKEYVTPRRTPAKTIYPDGPSVSDVEFVESSDTEVDLDAGDTIEIDLGDEARE

ESGNELDYSSEDDEDPFSDRNRWRRGGIIDPDANEW

CopB nucleic acid sequence

SEQ ID NO: 75 atgagcttgtcatccagcagcagctcggatagttcgaatctgaaaaatgtgttatctcaggtcatcgcgtctacaccAcagg gggttcctaatgctgacaaattaaccgacaatcaggtaaaacaagtccagcagaccgtcaaaaccgtgatgatctgtccatggagag cgacgtcgcggtggcgggaacagccggaaaagatcgtgctgcgtcggcgtcccagatcgagggacaagagctgattgagcaaca gggacttgcggctgggaaagagacggcttctgctgatgctacatcattgacccagtcggcatccaaaggcgcttccagtcagcagtgt attgaggataccagtaagtccctggagctttcttcgctttcgagcctgtcaagcgtagatgcgacacatttgcaggaaatccaatcgatc gtgtcttcagcaatgggcgccaccaacgaattgtcattgacgaacttagagacaccgggattaccaaagccgagtaccactccAcgc caggaagttatggagatcagccttgccttagcgaaggccatcactgcattgggtgagagcactcaggctgccttggaaaattttcagtc cactcagagtcagtccgcgaacatgaataagatgagtttggaatcccaaggcttgaaaatcgacaaggagcgtgaagaatttaagaaa atgcaggagattcagcaaaagagcggcacaaattcaaccatggatactgtgaataaagttatgattggcgtgacagtggcaattacagt aatctctgttgtttcagcattgtttacctgcggtttgggcttgattggcacagccgctgcgggtgccacagccgccaccgctggggcaac ggccgccgccacgaccgctacctctgtgacgaccacagtcgctacccaggtgacgatgcaagcggtggtccaagtcgttaagcagg ctattatccaagcagtaaaacgcgccatcgtccaagcgattaaacaggggattaagcaaggcattaaacaagcgatcaaacaggcag tcaaggcaagcgtgaagacacttgccaaaaatgtaggcaagattttcagcgcaggcaagaacgctgtgagtaagtccttcccAaaatt gtctaaggtgattaatacacttggttccaaatgggttactcttggcgtgggggcccttacagcggtgccgcagttagtcagtggcattac ctcccttcaattgtctgatatgcaaaaagaacttgcacaaatccaaaaggaagtgggtgcacttacggcgcagagtgagatgatgaaa gcgtttacactgttctggcagcaagcttcgaaaatcgcggccaaacaaacggaatcaccttcagagacgcaacaacaggcagctaag accggcgcccagatcgctaaagcgttgtccgccatttcgggtgctttagctgctgctgctTAG CopB amino acid sequence

SEQ ID NO: 76

MSLSSSSSSDSSNLKNVLSQVIASTPQGVPNADKLTDNQVKQVQQTRQNRDD

LSMESDVAVAGTAGKDRAASASQIEGQELIEQQGLAAGKETASADATSLTQSASKG

ASSQQCIEDTSKSLELSSLSSLSSVDATHLQEIQSIVSSAMGATNELSLTNLETPGLPKP

STTPRQEVMEISLALAKAITALGESTQAALENFQSTQSQSANMNKMSLESQGLKIDK

EREEFKKMQEIQQKSGTNSTMDTVNKVMIGVTVAITVISVVSALFTCGLGLIGTAAA

GATAATAGATAAATTATSVTTTVATQVTMQAVVQVVKQAIIQAVKRAIVQAIKQGI

KQGIKQAIKQAVKASVKTLAKNVGKIFSAGKNAVSKSFPKLSKVINTLGSKWVTLGV

GALTAVPQLVSGITSLQLSDMQKELAQIQKEVGALTAQSEMMKAFTLFWQQASKIA

AKQTESPSETQQQAAKTGAQIAKALSAISGALAAAA

CT053-CopB nucleic acid sequence

SEQ ID NO: 77 aaaagtgagcgtttaaaaaaattagaatcagagcttcatgatcttacccagtggatgcaacttggccttgttcctaaaaagaa atcgagagacaccaggaagaaatccgtctgctagaaagcaaaatccttgaagagaaagaaegtctacaacttctcaaagaaagcggt gagatcaaagagtacgtaacccctcgaagaactccagctaaaaccatttacccagatggccccagcgtttcagacgttgagtttgtaga atcctcggatacagaagtggatctcgatgccggtgacacaattgagattgacctaggtgatgaggcaagagaagaaagcggaaacg aactcgactactctagtgaagacgatgaggatccttttcagcgatcgcaatcgttggcgccgaggaggcatcatagatcctgacgcgaa tgaatggGGTTCAGCTGCTTCAatgagcttgtcatccagcagcagctcggatagttcgaatctgaaaaatgtgttatctca ggtcatcgcgtctacaccAcagggggttcctaatgctgacaaattaaccgacaatcaggtaaaacaagtccagcagacccgtcaaaa ccgtgatgatctgtccatggagagcgacgtcgcggtggcgggaacagccggaaaagatcgtgctgcgtcggcgtcccagatcgag ggacaagagctgattgagcaacagggacttgcggctgggaaagagacggcttctgctgatgctacatcattgacccagtcggcatcc aaaggcgcttccagtcagcagtgtattgaggataccagtaagtccctggagctttcttcgctttcgagcctgtcaagcgtagatgcgaca catttgcaggaaatccaatcgatcgtgtcttcagcaatgggcgccaccaacgaattgtcattgacgaacttagagacaccgggattacc aaagccgagtaccactccAcgccaggaagttatggagatcagccttgccttagcgaaggccatcactgcattgggtgagagcactca ggctgccttggaaaattttcagtccactcagagtcagtccgcgaacatgaataagatgagtttggaatcccaaggcttgaaaatcgaca aggagcgtgaagaatttaagaaaatgcaggagattcagcaaaagagcggcacaaattcaaccatggatactgtgaataaagttatgat tggcgtgacagtggcaattacagtaatctctgttgtttcagcattgtttacctgcggtttgggcttgattggcacagccgctgcgggtgcc acagccgccaccgctggggcaacgccgccgccacgaccgctacctctgtgacgaccacagtcgctacccaggtgacgatgcaag cggtggtccaagtcgttaagcaggctattatccaagcagtaaaacgcgccatcgtccaagcgattaaacaggggattaagcaaggcat taaacaagcgatcaaacaggcagtcaaggcaagcgtgaagacacttgccaaaaatgtaggcaagattttcagcgcaggcaagaacg ctgtgagtaagtccttcccAaaattgtctaaggtgattaatacacttggttccaaatgggttactcttggcgtgggggcccttacagcggt gccgcagttagtcagtggcattacctcccttcaattgtctgatatgcaaaaagaacttgcacaaatccaaaaggaagtgggtgcacttac ggcgcagagtgagatgatgaaagcgtttacactgttctggcagcaagcttcgaaaatcgcggccaaacaaacggaatcaccttcaga gacgcaacaacaggcagctaagaccggcgcccagatcgctaaagcgttgtccgccatttcgggtgctttagctgctgctgctTAG CT053-CopB amino acid sequence

SEQ ID NO: 78

MKSERLKKLESELHDLTQWMQLGLVPKKEIERHQEEIRLLESKILEEKERLQL

LKESGEIKEYVTPRRTPAKTIYPDGPSVSDVEFVESSDTEVDLDAGDTIEIDLGDEARE

ESGNELDYSSEDDEDPFSDRNRWRRGGIIDPDANEWGSAASMSLSSSSSSDSSNLKN

YTSQVIASTPQGYTNADKLTDNQVKQVQQTRQNRDDLSMESDVAVAGTAGKDRAA

SASQIEGQELIEQQGLAAGKETASADATSLTQSASKGASSQQCIEDTSKSLELSSLSSL

SSVDATHLQEIQSIVSSAMGATNELSLTNLETPGLPKPSTTPRQEVMEISLALAKAITA

LGESTQAALENFQSTQSQSANMNKMSLESQGLKIDKEREEFKKMQEIQQKSGTNST

MDTVNKVMIGVTVAITVISVVSALFTCGLGLIGTAAAGATAATAGATAAATTATSVT

TTVATQVTMQAVVQVVKQAIIQAVKRAIVQAIKQGIKQGIKQAIKQAVKASVKTLA

KNVGKIFSAGKNAVSKSFPKLSKVINTLGSKWVTLGVGALTAVPQLVSGITSLQLSD

MQKELAQIQKEVGALTAQSEMMKAFTLFWQQASKIAAKQTESPSETQQQAAKTGA

QIAKALSAISGALAAAA

LTA1-CT053-CopB nucleic acid sequence

SEQ ID NO: 79

CATatggacaatggcgatcgtttataccgtgccgactcgcgtcccccagatgagattaaacgtagcggtgggttaatgcc acgtgggcacaatgagtattttgaccgtggaacacagatgaacattaaccttacgatcatgcccgtgggacccagaccgggttgtcc gttatgatgacgggtatgttagtacgagtttgtccttacgctccgcacaccttgcgggacaaagtattttatcaggctacagcacatattac atttatgtgatcgccactgccccaaacatgttcaatgtgaacgatgtgttgggggtttacagcccccatccatatgaacaagaagtctcg -continued gcccttgggggatcccatatagccagatttatggttggtaccgcgtaaattttggtgtgattgatgaacgtttgcatcgtaaccgtgaata ccgcgatcgctactaccgtaacttgaacattgcacctgccgaggacggctatcgtttagcgggattcccacccgatcatcaggcgtgg cgtgaggaaccgtggatccatcacgcccctcaggggtgcgggaacagtagtcgcCATatgaaaagtgagcgtttaaaaaaattag aatcagagcttcatgatcttacccagtggatgcaacttggccttgttcctaaaaaagaaatcgagagacaccaggaagaaatccgtctg ctagaaagcaaaatccttgaagagaaagaacgtctacaacttctcaaagaaagcggtgagatcaaagagtacgtaaccccctcgaaga actccagctaaaaccatttacccagatggccccagcgttttcagacgttgagtttgtagaatcctcggatacagaagtggatctcgatgcc ggtgacacaattgagattgacctaggtgatgaggcaagagaagaaagcggaaacgaactcgactactctagtgaagacgatgagga tcctttcagcgatcgcaatcgttggcgccgaggaggcatcatagatcctgacgcgaatgaatggGGTTCAGCTGCTTCA atgagcttgtcatccagcagcagctcggatagttcgaatctgaaaaatgtgttatctcaggtcatcgcgtctacaccAcaggggttcct aatgctgacaaattaaccgacaatcaggtaaaacaagtccagcagacccgtcaaaaccgtgatgatctgtccatggagagcgacgtc gcggtggcgggaacagccgaaaagatcgtgctgcgtcggcgtcccagatcgagggacaagagctgattgagcaacagggactt gcggctgggaaagagacggcttctgctgatgctacatcattgacccagtcggcatccaaaggcgcttccagtcagcagtgtattgagg ataccagtaagtccctggagctttcttcgctttcgagcctgtcaagcgtagatgcgacacatttgcaggaaatccaatcgatcgtgtcttc agcaatgggcgccaccaacgaattgtcattgacgaacttagagacaccgggattaccaaagccgagtaccactccAcgccaggaa gttatggagatcagccttgccttagcgaaggccatcactgcattgggtgagagcactcaggctgccttggaaaattttcagtccactcag agtcagtccgcgaacatgaataagatgagtttggaatcccaaggcttgaaaatcgacaaggagcgtgaagaatttaagaaaatgcag gagattcagcaaaagagcggcacaaattcaaccatggatactgtgaataaagttatgattggcgtgacagtggcaattacagtaatctct gttgtttcagcattgtttacctgcggtttgggcttgattggcacagccgctgcgggtgccacagccgccaccgctggggcaacggccg ccgccacgaccgctacctctgtgacgaccacagtcgctacccaggtgacgatgcaagcggtggtccaagtcgttaagcaggctattat ccaagcagtaaaacgcgccatcgtccaagcgattaaacaggggattaagcaaggcattaaacaagcgatcaaacaggcagtcaagg caagcgtgaagacacttgccaaaaatgtaggcaagattttcagcgcaggcaagaacgctgtgagtaagtccttcccAaaattgtctaa ggtgattaatacacttggttccaaatgggttactcttggcgtgggggcccttacagcggtgccgcagttagtcagtggcattacctcccctt caattgtctgatatgcaaaaagaacttgcacaaatccaaaaggaagtgggtgcacttacggcgcagagtgagatgatgaaagcgttta cactgttctggcagcaagcttcgaaaatcgcggccaaacaaacggaatcaccttcagagacgcaacaacaggcagctaagaccggc gcccagatcgctaaagcgttgtccgccatttcgggtgctttagctgctgctgctTAGCTCGAG LTA1-CT053-CopB Amino acid sequence
                                                                                          SEQ ID NO: 80
MDNGDRLYRADSRPPDEIKRSGGLMPRGHNEYFDRGTQMNINLYDHARGTQ

TGFVRYDDGYVSTSLSLRSAHLAGQSILSGYSTYYIYVIATAPNMFNVNDVLGVYSP

HPYEQEVSALGGIPYSQIYGWYRVNFGVIDERLHRNREYRDRYYRNLNIAPAEDGYR

LAGFPPDHQAWREEPWIHHAPQGCGNSSRMKSERLKKLESELHDLTQWMQLGLVP

KKEIERHQEEIRLLESKILEEKERLQLLKESGEIKEYVTPRRTPAKTIYPDGPSVSDVEF

VESSDTEVDLDAGDTIEIDLGDEAREESGNELDYSSEDDEDPFSDRNRWRRGGIIDPD

ANEWGSAASMSLSSSSSDSSNLKNVLSQVIASTPQGVPNADKLTDNQVKQVQQTR

QNRDDLSMESDVAVAGTAGKDRAASASQIEGQELIEQQGLAAGKETASADATSLTQ

SASKGASSQQCIEDTSKSLELSSLSSLSSVDATHLQEIQSIVSSAMGATNELSLTNLETP

GLPKPSTTPRQEVMEISLALAKAITALGESTQAALENFQSTQSQSANMNKMSLESQG

LKIDKEREEFKKMQEIQQKSGTNSTMDTVNKVMIGVTVAITVISVVSALFTCGLGLIG

TAAAGATAATAGATAAATTATSVTTTVATQVTMQAVVQVVKQAIIQAVKRAIVQAI

KQGIKQGIKQAIKQAVKASVKTLAKNVGKIFSAGKNAVSKSFPKLSKVINTLGSKWV

TLGVGALTAVPQLVSGITSLQLSDMQKELAQIQKEVGALTAQSEMMKAFTLFWQQA

SKIAAKQTESPSETQQQAAKTGAQIAKALSAISGALAAAA*

HisScc2 chaperone for LTA1-CT668-CopB nucleic acid sequence

SEQ ID NO: 81

ATGGGCAGCAGCCATCACCATCATCACCACAGCCAGGATCCGatgagcactccat
cttctaataattctaaaaaaccttcggcctcttttaataaaaaatcacgtagccgcttggccgagattgctgcacaaaaaaaagcaaaagc
tgaggatttggaacaaaaatatcctgttcctacggaagaggagacaaaacaagttctcatggacatcctacaggggttaagcaacgga
ttaactcttcagcaaattttaggtctctccgacgtcctccttgaagagatctacaccgtagcatataccttctactcccaagggaaatatcg
ggaagctatcggtcttttccaaatcttaacagcctccaaacctcaatgctacaaatacatcttaggtcttagctcttgctatcaccagctaaa
aatgtatgatgaagccgcttttggtttcttcctagctttcgatgctcaacccgaaaaccccatccctccttactacatcgccgatagcttgat
gaagctaaaccaacccgaagaatctcaagacttcctcgatattacgatcgatatgtgtaagaacaagccggaatataaagttcttaaaga
tcgctgcagcattatgaagcaatctttagatgccgtgctgaaaaaagagaaatctgcaaaaggctctgaaacacaagcctcctctcctaa
aaacacaaaagctaaaaaagctgcttctaacaagaaaaaagcaaagtaaGCGGCCGC HisScc2 chaperone for LTA1-CT668-CopB Amino acid sequence

SEQ ID NO: 82

MGSSHHHHHHSQDPMSTPSSNNSKKPSASFNKKSRSELAEIAAQKKAKAEDL
EQKYPVPTEEETKQVLMDILQGLSNGLTLQQILGLSDVTLEEIYTVAYTFYSQGKYRE
AIGLFQILTASKPQCYKYILGLSSCYHQLKMYDEAAFGFFLAFDAQPENPIPPYYIADS
LMKLNQPEESQDFLDITIDMCKNKPEYKVLKDRCSIMKQSLDAVLKKEKSAKGSETQ
ASSPKNTKAKKAASNKKKAK*

CT668 nucleic acid sequence

SEQ ID NO: 83

Atagatcctcttaagctttttccaaattttgatggggataaggagagtgctgcggtgaataaaccttcagcatctcctatgccc
agcgaattaagtaaaaatgttgcctcattctctttagggggtggaggtgctgcgttggattcgacagtgtccacagaaaagctatcgttga
tggctatgatgcaggataaaaattcgcagttgatcgatcctgagttggaggaagctctgaactctgaagagttacaagagcagatccatt
tgttaaaaaagtcgtttgtgggatgcacaaacgcagatgcaaatgcaagatcccgacaagttggcctctgagcatgtagatgctttagga
gtcattgttgatttaatcaatggggattttcaagcgatagctgaacatacacaacagacggtcaagcagggtaatggtgacgaagaaaa
atctgttacacgcaagatagtcgattgggtctcttcaggagaagaaattttgaatcgtgctttgttgtatttctccgatcgtaatggagaaag
agaaacattagccgatttcttaaaagttcagtatgccgttcaaagagctacacaacgcgccgagttatttgccagtattctaggtgccacg
gtgagtagtgtaaaaacgattatgacaacccagttaggt CT668 amino acid sequence

SEQ ID NO: 84

MIDPLKLFPNFDGDKESAAVNKPSASPMPSELSKNVASFSLGGGGAALDSTVS
TEKLSLMAMMQDKNSQLIDPELEEALNSEELQEQIHLLKSRLVVDAQTQMQMQDPD
KLASEHVDALGVIVDLINGDFQAIAEHTQQTVKQGNGDEEKSVTRKIVDWVSSGEEI
LNRALLYFSDRNGERETLADFLKVQYAVQRATQRAELFASELGATVSSVKTIMTTQL

CT668-CopB nucleic acid sequence

SEQ ID NO: 85 atagatcctcttaagctttttccaaattttgatggggataaggagagtgctgcggtgaataaaccttcagcatctcctatgccca
gcgaattaagtaaaaatgttgcctcattctctttagggggtggaggtgctgcgttggattcgacagtgtccacagaaaagctatcgttgat
ggctatgatgcaggataaaaattcgcagttgatcgatcctgagttggaggaagctctgaactctgaagagttacaagagcagatccattt
gttaaaaaagtcgtttgtgggatgcacaaacgcagatgcaaatgcaagatcccgacaagttggcctctgagcatgtagatgctttaggag
tcattgttgatttaatcaatggggattttcaagcgatagctgaacatacacaacagacggtcaagcagggtaatggtgacgaagaaaaat
ctgttacacgcaagatagtcgattgggtctcttcaggagaagaaattttgaatcgtgctttgttgtatttctccgatcgtaatggagaaaga
gaaacattagccgatttcttaaaagttcagtatgccgttcaaagagctacacaacgcgccgagttatttgccagtattctaggtgccacgg
tgagtagtgtaaaaacgattatgacaacccagttaggtGGTTCAGCTGCTTCAatgagcttgtcatccagcagcagctcg
gatagttcgaatctgaaaaatgtgttatctcaggtcatcgcgtctacaccAcagggggttcctaatgctgacaaattaaccgacaatcag
gtaaaacaagtccagcagacccgtcaaaaccgtgatgatctgtccatggagagcgacgtcgcggtggcgggaacagccggaaaag -continued

```
atcgtgctgcgtcggcgtcccagatcgagggacaagagctgattgagcaacaggacttgcggctgggaagagacggcttctgct
gatgctacatcattgacccagtcggcatccaaaggcgcttccagtcagcagtgtattgaggataccagtaagtccctggagctttcttcg
ctttcgagcctgtcaagcgtagatgcgacacatttgcaggaaatccaatcgatcgtgtcttcagcaatgggcgccaccaacgaattgtc
attgacgaacttagagacaccgggattaccaaagccgagtaccactccAcgccaggaagttatgagatcagccttgccttagcgaa
ggccatcactgcattgggtgagagcactcaggctgccttggaaaattttcagtccactcagagtcagtccgcgaacatgaataagatga
gtttggaatcccaaggcttgaaaatcgacaaggagcgtgaagaatttaagaaaatgcaggagattcagcaaaagagcggcacaaatt
caaccatggatactgtgaataaagttatgattggcgtgacagtggcaattacagtaatctctgttgtttcagcattgtttacctgcggtttgg
gcttgattggcacagccgctgcgggtgccacagccgccaccgctggggcaacggccgccgccacgaccgctacctctgtgacgac
cacagtcgctacccaggtgacgatgcaagcggtggtccaagtcgttaagcaggctattatccaagcagtaaaacgcgccatcgtcca
agcgattaaacaggggattaagcaaggcattaaacaagcgatcaaacaggcagtcaaggcaagcgtgaagacacttgccaaaaatg
taggcaagattttcagcgcaggcaagaacgctgtgagtaagtccttcccAaaattgtctaaggtgattaatacacttggttccaaatggg
ttactcttggcgtgggggccctt tacagcggtgccgcagttagtcagtggcattacctcccttcaattgtctgatatgcaaaaagaacttgc
acaaatccaaaaggaagtgggtgcacttacgcgcagagtgagatgatgaaagcgtttacactgttctggcagcaagcttcgaaaatc
gcggccaaacaaacggaatcaccttcagagacgcaacaacaggcagctaagaccggcgcccagatcgctaaagcgttgtccgcca
tttcgggtgctttagctgctgctgctTAG
```

CT668-CopB amino acid sequence

SEQ ID NO: 86

```
MIDPLKLFPNFDGDKESAAVNKPSASPMPSELSKNVASFSLGGGGAALDSTVS
TEKLSLMAMMQDKNSQLIDPELEEALNSEELQEQIHLLKSRLWDAQTQMQMQDPD
KLASEHVDALGVIVDLINGDFQAIAEHTQQTVKQGNGDEEKSVTRKIVDWVSSGEEI
LNRALLYFSDRNGERETLADFLKVQYAVQRATQRAELFASILGATVSSVKTIMTTQL
GGSAASMSLSSSSSSDSSNLKNVLSQVIASTPQGVPNADKLTDNQVKQVQQTRQNRD
DLSMESDVAVAGTAGKDRAASASQIEGQELIEQQGLAAGKETASADATSLTQSASK
GASSQQCIEDTSKSLELSSLSSLSSVDATHLQEIQSIVSSAMGATNELSLTNLETPGLPK
PSTTPRQEVMEISLALAKAITALGESTQAALENFQSTQSQSANMNKMSLESQGLKIDK
EREEFKKMQEIQQKSGTNSTMDTVNKVMIGVTVAITVISVVSALFTCGLGLIGTAAA
GATAATAGATAAATTATSVTTTVATQVTMQAVVQVVKQAIIQAVKRAIVQAIKQGI
KQGIKQAIKQAVKASVKTLAKNVGKIFSAGKNAVSKSFPKLSKVINTLGSKWVTLGV
GALTAVPQLVSGITSLQLSDMQKELAQIQKEVGALTAQSEMMKAFTLFWQQASKIA
AKQTESPSETQQQAAKTGAQIAKALSAISGALAAAA
```

LTA1-CT668-CopB nucleic acid sequence

SEQ ID NO: 87

```
CATatggacaatggcgatcgtttataccgtgccgactcgcgtcccccagatgagattaaacgtagcggtgggttaatgcc
acgtgggcacaatgagtattttgaccgtgaacacagatgaacattaaccttacgatcatgcccgtgggacccagaccgggtttgtcc
gttatgatgacgggtatgttagtacgagtttgtccttacgctccgcacaccttgcgggacaaagtattttatcaggctacagcacatattac
atttatgtgatcgccactgccccaaacatgttcaatgtgaacgatgtgttggggtttacagcccccatccatgaacaagaagtctcg
gcccttgggggatcccatatagccagatttatggttggtaccgcgtaaattttggtgtgattgatgaacgtttgcatcgtaaccgtgaata
ccgcgatcgctactaccgtaacttgaacattgcacctgccgaggacggctatcgtttagcgggattcccacccgatcatcaggcgtgg
cgtgaggaaccgtggatccatcacgcccctcaggggtgcgggaacagtagtcgcCATatgatagatcctcttaagcttttttccaaatt
ttgatggggataaggagagtgctgcggtgaataaaccttcagcatctcctatgcccagcgaattaagtaaaaatgttgcctcattctcttta
gggggtggaggtgctgcgttggattcgacagtgtccacagaaaagctatcgttgatggctatgatgcaggataaaaattcgcagttgat
cgatcctgagttggaggaagctctgaactctgaagagttacaagagcagatcccatttgttaaaaagtcgtttgtgggatgcacaaacgc
agatgcaaatgcaagatcccgacaagttggcctctgagcatgtagatgctttaggagtcattgttgatttaatcaatgggggattttcaagc
```

-continued

```
gatagctgaacatacacaacagacggtcaagcagggtaatggtgacgaagaaaatctgttacacgcaagatagtcgattgggtctct tcaggagaagaaattttgaatcgtgctttgttgtatttctccgatcgtaatggagaaagagaaacattagccgatttcttaaaagttcagtat gccgttcaaagagctacacaacgcgccgagttatttgccagtattctaggtgccacggtgagtagtgtaaaaacgattatgacaaccca gttaggtGGTTCAGCTGCTTCAatgagcttgtcatccagcagcagctcggatagttcgaatctgaaaaatgtgttatctcag gtcatcgcgtctacaccAcaggggttcctaatgctgacaaattaaccgacaatcaggtaaaacaagtccagcagacccgtcaaaac cgtgatgatctgtccatggagagcgacgtcgcggtggcgggaacagccgaaaagatcgtgctgcgtcggcgtcccagatcgagg gacaagagctgattgagcaacagggacttgcggctgggaaagagacggcttctgctgatgctacatcattgacccagtcggcatcca aaggcgcttccagtcagcagtgtattgaggataccagtaagtccctggagctttcttcgctttcgagcctgtcaagcgtagatgcgacac atttgcaggaaatccaatcgatcgtgtcttcagcaatgggcgccaccaacgaattgtcattgacgaacttagagacaccgggattacca aagccgagtaccactccAcgccaggaagttatggagatcagccttgccttagcgaaggccatcactgcattgggtgagagcactca ggctgccttggaaaattttcagtccactcagagtcagtccgcgaacatgaataagatgagtttggaatcccaaggcttgaaaatcgaca aggagcgtgaagaatttaagaaaatgcaggagattcagcaaaagagcggcacaaattcaaccatggatactgtgaataaagttatgat tggcgtgacagtggcaattacagtaatctctgttgtttcagcattgtttacctgcggtttgggcttgattggcacagccgctgcgggtgcc acagccgccaccgctggggcaacggccgccgccacgaccgctacctctgtgacgaccacagtcgctacccaggtgacgatgcaag cggtggtccaagtcgttaagcaggctattatccaagcagtaaaacgcgccatcgtccaagcgattaaacaggggattaagcaaggcat taaacaagcgatcaaacaggcagtcaaggcaagcgtgaagacacttgccaaaaatgtaggcaagattttcagcgcaggcaagaacg ctgtgagtaagtccttcccAaaattgtctaaggtgattaatacacttggttccaaatgggttactcttggcgtggggccct tacagcggt gccgcagttagtcagtggcattacctcccttcaattgtctgatatgcaaaaagaacttgcacaaatccaaaaggaagtgggtgcacttac ggcgcagagtgagatgatgaaagcgtttacactgttctggcagcaagcttcgaaaatcgcggccaaacaaacggaatccccttcaga gacgcaacaacaggcagctaagaccggcgcccagatcgctaaagcgttgtccgccatttcgggtgctttagctgctgctgctTAG

CTCGAG
```

LTA1-CT668-CopB Amino acid sequence                                                                 SEQ ID NO: 88

```
MDNGDRLYRADSRPPDEIKRSGGLMPRGHNEYFDRGTQMNINLYDHARGTQ

TGFVRYDDGYVSTSLSLRSAHLAGQSILSGYSTYYIYVIATAPNMFNVNDVLGVYSP

HPYEQEVSALGGIPYSQIYGWYRVNFGVIDERLHRNREYRDRYYRNLNIAPAEDGYR

LAGFPPDHQAWREEPWIHHAPQGCGNSSRMIDPLKLFPNFDGDKESAAVNKPSASP

MPSELSKNVASFSLGGGGAALDSTVSTEKLSLMAMMQDKNSQLIDPELEEALNSEEL

QEQIHLLKSRLWDAQTQMQMQDPDKLASEHVDALGVIVDLINGDFQAIAEHTQQTV

KQGNGDEEKSVTRKIVDWVSSGEEILNRALLYFSDRNGERETLADFLKVQYAVQRA

TQRAELFASILGATVSSVKTIMTTQLGGSAASMSLSSSSSSDSSNLKNVLSQVIASTPQ

GVPNADKLTDNQVKQVQQTRQNRDDLSMESDVAVAGTAGKDRAASASQIEGQELI

EQQGLAAGKETASADATSLTQSASKGASSQQCIEDTSKSLELSSLSSLSSVDATHLQEI

QSIVSSAMGATNELSLTNLETPGLPKPSTTPRQEVMEISLALAKAITALGESTQAALEN

FQSTQSQSANMNKMSLESQGLKIDKEREEFKKMQEIQQKSGTNSTMDTVNKVMIGV

TVAITVISVVSALFTCGLGLIGTAAAGATAATAGATAAATTATSVTTTVATQVTMQA

VVQVVKQAIIQAVKRAIVQAIKQGIKQGIKQAIKQAVKASVKTLAKNVGKIFSAGKN

AVSKSFPKLSKVINTLGSKWVTLGVGALTAVPQLVSGITSLQLSDMQKELAQIQKEV

GALTAQSEMMKAFTLFWQQASKIAAKQTESPSETQQQAAKTGAQIAKALSAISGAL

AAAA*
```

-continued

HisScc3 chaperone for CT053-CopB2 Nucleic acid sequence

SEQ ID NO: 89

ATGGGCAGCAGCCATCACCATCATCACCACAGCCAGGATCCGatgccaccaagc aagatccaatgtcttgaaacttttgaaagaacttatggacacctttatctacaacatgcgtccctaatgcgtcatttagcctatctactcgata aaattgctcgctcttaccctcatatgtgtccgcttcccgataatatggaagcgtactttgagaattatatccccaataaagatatccctctgg acacctatcaaaaaattttcaaactgtcctcagaagatcttgaacaagtctacaaggaaggatacaacgcctatttacaaggagactatg aggaaagttctaccgctttttactggttgattttctttaacccatttgtgtctaaattttggttttcattaggagcttcgctccatatgcgccaaaa atatcaacaagctcttcatgcttatggtgtagctgctttgctaagagaaaaagacccttatcctcattactatgcctacatctgctacaccct gctcaataatcctgaagaagctgaaaaagctcttgatcttgcttggcaaaaagtaaaaacaagctctgcctatagctcttaaaagaaga aattttagcgatcaaatcgtacgcctaaGCGGCCGC HisScc3 chaperone for CT053-CopB2 amino acid sequence

SEQ ID NO: 90

MGSSHHHHHHSQDPMPPSKIQCLETFERTYGHLYLQHASLMRHLAYLLDKIA

RSYPHMCPLPDNMEAYFENYIPNKDIPLDTYQKIFKLSSEDLEQVYKEGYNAYLQGD

YEESSTAFYWLIFFNPFVSKFWFSLGASLHMRQKYQQALHAYGVAALLREKDPYPH

YYAYICYTLLNNPEEAEKALDLAWQKVKTSSAYSSLKEEILAIKSYA*

CopB2 nucleic acid sequence

SEQ ID NO: 91 atgagctcttggtttgcacaggcgacggacgtcgctttgagccagacccttgatctgcctgacgcttcattggcggttcaaac cgaaaaatttccAtacagctgttcaatctctaaggaatccgccccAtcatgtattcgtaaaatcttcgcccatttagcatctcagaaggaa agtgctccgctgtcttttttctcgtttacaaccgactactccgaaagaacgcatcctgttttttcgggtcatcgccttcctcccaattgtcctcga ctgtccgcaccacaacctcttctccatggaatctttttagcaactcccaggcacgcaactcgacccgtaaattgtcggagaagcttcattt gagctcagagttatccgcccgtgactccactaagccttcgtcgagcgaaccggttaaaccatcggaaaatcttttgcacacccctgagc atcataaggaatccttctcaagtttgaaaaaggataacttatctcctatcatggaggagatcgactcattctctgcagagacagagtccctt gaagagcgtttggtcacccagaaaaaggaggagacggtggcccaggagcaaaagcacccAttgctgcgtacatctactccgccat caaaggccagcggggaatcacaagattctagcgaacacagctcaaggaagatcctatagtcaacaaccgagccataaaatccaac gccgtaaagagcgtgctaagcgcgtcgtcccAattattactccgccaacggtgggtatctttagtttgagctaccttcttacaaaacagg ggatcttagcggatttcagcgcctattcggcatacaaggataatttagaaacaactcagcaagagctgaccatgttgcatcaagaacgta tcgagcaagtccaaaaaGatcgtggataaaagtaagacaatgcgcttttgggattcattagcatccattgtggccacaatcattccatgga tcgaaatgggtgttgcagtaaccatcatcgcactgggaggtggaatcctttcctggtgctctcttttttgctgcgcttatcatgattgtaatttc attattggaagcattcgacgggtggcgtgcaatcgctaagcatttaccaggtaacgatcttgaaaagaagatgcgttatttaggttacgta aagttggccttaactgtgttctcgtgcttactgagtttaagcgccttgtatgtagcaaaattaggaatgagtccgcttttggaggggttgtg aagagtatcgcaccAgcattaagtggtatgctgggtttgactcaaggcgtagcactgtatttacaatcttcatcgcaaaagattcgtgcc cgctgcactcagatcgacgcacgcattgaattgattaactgggaacgcgatgagtatttcttgcgtgctgaacaacttcttgattcaatgc aaacgtccttcgaacaacttactgaaacattacagttacaacgtgaaattgatcagacatttacagacgctttgcgcTAG CopB2 amino acid sequence

SEQ ID NO: 92

MSSWFAQATDVALSQTLDLPDASLAVQTEKFPYSCSISKESAPSCIRKIFAHLA

SQKESAPLSFSRLQPTTPKERILFFGSSPSSQLSSTVRTTTSSPWNLFSNSQARNSTRKL

SEKLHLSSELSARDSTKPSSSEPVKPSENLLHTPEHHKESFSSLKKDNLSPIMEEIDSFS

AETESLEERLVTQKKEETVAQEQKHPLLRTSTPPSKASGESQDSSEHSSKEDPYSQQP

SHKIQRRKERAKRVVPIITPPTVGIFSLSYLLTKQGILADFSAYSAYKDNLETTQQELT

MLHQERIEQVQKIVDKSKTMRFWDSLASIVATIIPWIEMGVAVTIIALGGGILSWCSLF

AALIMIVISLLEAFDGWRAIAKHLPGNDLEKKMRYLGYVKLALTVFSCLLSLSALYV

AKLGMSPLLEGVVKSIAPALSGMLGLTQGVALYLQSSSQKIRARCTQIDARIELINWE
RDEYFLRAEQLLDSMQTSFEQLTETLQLQREIDQTFTDALR

CT053-CopB2 nucleic acid sequence

SEQ ID NO: 93 aaaagtgagcgtttaaaaaaattagaatcagagcttcatgatcttacccagtggatgcaacttggccttgttcctaaaaaagaa atcgagagacaccaggaagaaatccgtctgctagaaagcaaaatccttgaagagaaagaacgtctacaacttctcaaagaaagcggt gagatcaaagagtacgtaacccctcgaagaactccagctaaaaccatttacccagatggccccagcgtttcagacgttgagtttgtaga atcctcggatacagaagtggatctcgatgccggtgacacaattgagattgacctaggtgatgaggcaagagaagaaagcggaaacg aactcgactactctagtgaagacgatgaggatcctttcagcgatcgcaatcgttggcgccgaggaggcatcatagatcctgacgcgaa tgaatggGGTTCAGGTGCTTCAatgagctcttggtttgcacaggcgacgacgtcgctttgagccagacccttgatctgc ctgacgcttcattggcggttcaaaccgaaaaatttccAtacagctgttcaatctctaaggaatccgccccAtcatgtattcgtaaaatctt cgcccatttagcatctcagaaggaaagtgctccgctgtcttttctcgtttacaaccgactactccgaaagaacgcatcctgtttttcgggt catcgccttcctcccaattgtcctcgactgtccgcaccacaacctcttctccatggaatcttttagcaactcccaggcacgcaactcgac ccgtaaattgtcggagaagcttcatttgagctcagagttatccgccgtgactccactaagccttcgtcgagcgaaccggttaaaccatc ggaaaatcttttgcacacccctgagcatcataaggaatccttctcaagtttgaaaaaggataacttatctcctatcatggaggagatcgac tcattctctgcagagacagagtcccttgaagagcgtttggtcacccagaaaaaggaggagacggtggcccaggagcaaaagcaccc Attgctgcgtacatctactccgccatcaaaggccagcggggaatcacaagattctagcgaacacagctcaaaggaagatccttatagt caacaaccgagccataaaatccaacgccgtaaagagcgtgctaagcgcgtcgtcccAattattactccgccaacggtgggtatcttta gtttgagctaccttcttacaaaacaggggatcttagcggatttcagcgcctattcggcatacaaggataatttagaaacaactcagcaag agctgaccatgttgcatcaagaacgtatcgagcaagtccaaaaGatcgtggataaaagtaagacaatgcgcttttgggattcattagca tccattgtggccacaatcattccatggatcgaaatgggtgttgcagtaaccatcatcgcactgggaggtggaatcctttcctggtgctctc ttttgctgcgcttatcatgattgtaatttcattattggaagcattcgacgggtggcgtgcaatcgctaagcatttaccaggtaacgatcttga aaagaagatgcgttatttaggttacgtaaagttggccttaactgtgttctcgtgcttactgagtttaagcgccttgtatgtagcaaaattagg aatgagtccgcttttggaggggggttgtgaagagtatcgcaccAgcattaagtggtatgctgggtttgactcaaggcgtagcactgtattt acaatcttcatcgcaaaagattcgtgcccgctgcactcagatcgacgcacgcattgaattgattaactgggaacgcgatgagtatttcttg cgtgctgaacaacttcttgattcaatgcaaacgtccttcgaacaacttactgaaacattacagttacaacgtgaaattgatcagacatttac agacgctttgcgcTAG CT053-CopB2 amino acid sequence

SEQ ID NO: 94

MKSERLKKLESELHDLTQWMQLGLVPKKEIERHQEEIRLLESKILEEKERLQL

LKESGEIKEYVTPRRTPAKTIYPDGPSVSDVEFVESSDTEVDLDAGDTIEIDLGDEARE

ESGNELDYSSEDDEDPFSDRNRWRRGGIIDPDANEWGSAASMSSWFAQATDVALSQ

TLDLPDASLAVQTEKFPYSCSISKESAPSCIRKIFAHLASQKESAPLSFSRLQPTTPKERI

LFFGSSPSSQLSSTVRTTTSSPWNLFSNSQARNSTRKLSEKLHLSSELSARDSTKPSSSE

PVKPSENLLHTPEHHKESFSSLKKDNLSPIMEEIDSFSAETESLEERLVTQKKEETVAQ

EQKHPLLRTSTPPSKASGESQDSSEHSSKEDPYSQQPSHKIQRRKERAKRVVPIITPPT

VGIFSLSYLLTKQGILADFSAYSAYKDNLETTQQELTMLHQERIEQVQKIVDKSKTM

RFWDSLASIVATIIPWIEMGVAVTIIALGGGILSWCSLFAALIMIVISLLEAFDGVVRAIA

KHLPGNDLEKKMRYLGYVKLALTVFSCLLSLSALYVAKLGMSPLLEGVVKSIAPALS

GMLGLTQGVALYLQSSSQKIRARCTQIDARIELINWERDEYFLRAEQLLDSMQTSFE

QLTETLQLQREIDQTFTDALR

LTA1-CT053-CopB2 nucleic acid sequence
SEQ ID NO: 95

CATatggacaatggcgatcgtttataccgtgccgactcgcgtcccccagatgagattaaacgtagcggtgggttaatgcc acgtgggcacaatgagtattttgaccgtggaacacagatgaacattaacctttacgatcatgcccgtgggacccagaccgggtttgtcc gttatgatgacgggtatgttagtacgagtttgtccttacgctccgcacaccttgcgggacaaagtattttatcaggctacagcacatattac atttatgtgatcgccactgccccaaacatgttcaatgtgaacgatgtgttgggggtttacagcccccatccatatgaacaagaagtctcg gcccttgggggatcccatatagccagatttatggttggtaccgcgtaaattttggtgtgattgatgaacgtttgcatcgtaaccgtgaata ccgcgatcgctactaccgtaacttgaacattgcacctgccgaggacggctatcgtttagcgggattcccacccgatcatcaggcgtgg cgtgaggaaccgtggatccatcacgcccctcaggggtgcgggaacagtagtcgcCATatgaaagtgagcgtttaaaaaaattag aatcagagcttcatgatcttacccagtggatgcaacttggccttgttcctaaaaaagaaatcgagagacaccaggaagaaatccgtctg ctagaaagcaaaatccttgaagagaaagaacgtctacaacttctcaaagaaagcggtgagatcaaagagtacgtaaccccctcgaaga actccagctaaaaccatttacccagatggccccagcgtttcagacgttgagtttgtagaatcctcggatacagaagtggatctcgatgcc ggtgacacaattgagattgacctaggtgatgaggcaagagaagaaagcggaaacgaactcgactactctagtgaagacgatgagga tccttttcagcgatcgcaatcgttggcgccgaggaggcatcatagatcctgacgcgaatgaatggGGTTCAGCTGCTTCA atgagctcttggtttgcacaggcgacggacgtcgctttgagccagacccttgatctgcctgacgcttcattggcggttcaaaccgaaaa atttccAtacagctgttcaatctctaaggaatccgccccAtcatgtattcgtaaaatcttcgcccatttagcatctcagaaggaaagtgct ccgctgtcttttttctcgtttacaaccgactactccgaaagaacgcatcctgttttttcgggtcatcgccttcctcccaattgtcctcgactgtcc gcaccacaacctcttctccatggaatcttttagcaactcccaggcacgcaactcgaccgtaaattgtcggagaagcttcatttgagctc agagttatccgcccgtgactccactaagccttgtcgagcgaaccggttaaaccatcggaaaatctttgcacacccctgagcatcataa ggaatccttctcaagtttgaaaaaggataacttatctcctatcatggaggagatcgactcattctctgcagagacagagtcccttgaagag cgtttggtcacccagaaaaggaggagacggtggcccaggagcaaaagcacccAttgctgcgtacatctactccgccatcaaaggc cagcggggaatcacaagattctagcgaacacagctcaaaggaagatcctttatagtcaacaaccgagccataaaatccaacgccgtaa agagcgtgctaagcgcgtcgtcccAattattactccgccaacggtgggtatctttagtttgagctaccttcttacaaaacaggggatctta gcggatttcagcgcctattcggcatacaaggataatttagaaacaactcagcaagagctgaccatgttgcatcaagaacgtatcgagca agtccaaaaGatcgtggataaaagtaagacaatgcgcttttgggattcattagcatccattgtggccacaatcattccatggatcgaaat gggtgttgcagtaaccatcatcgcactgggaggtggaatcctttcctggtgctctctttttgctgcgcttatcatgattgtaatttcattattgg aagcattcgacgggtggcgtgcaatcgctaagcatttaccaggtaacgatcttgaaaagaagatgcgttatttaggttacgtaaagttgg ccttaactgtgttctcgtgcttactgagtttaagcgccttgtatgtagcaaaattaggaatgagtccgcttttggagggggttgtgaagagt atcgcaccAgcattaagtggtatgctgggtttgactcaaggcgtagcactgtatttacaatcttcatcgcaaaagattcgtgcccgctgc actcagatcgacgcacgcattgaattgattaactgggaacgcgatgagtatttcttgcgtgctgaacaacttcttgattcaatgcaaacgt ccttcgaacaacttactgaaacattacagttacaacgtgaaattgatcagacatttacagacgctttgcgcTAGCTCGAG LTA1-CT053-CopB2 Amino acid sequence
SEQ ID NO: 96

MDNGDRLYRADSRPPDEIKRSGGLMPRGHNEYFDRGTQMNINLYDHARGTQ

TGFVRYDDGYVSTSLSLRSAHLAGQSILSGYSTYYIYVIATAPNMFNVNDVLGVYSP

HPYEQEVSALGGIPYSQIYGWYRVNFGVIDERLHRNREYRDRYYRNLNIAPAEDGYR

LAGFPPDHQAWREEPWIHHAPQGCGNSSRMKSERLKKLESELHDLTQWMQLGLVP

KKEIERHQEEIRLLESKILEEKERLQLLKESGEIKEYVTPRRTPAKTIYPDGPSVSDVEF

VESSDTEVDLDAGDTIEIDLGDEAREESGNELDYSSEDDEDPFSDRNRWRRGGIIDPD

ANEWGSAASMSSWFAQATDVALSQTLDLPDASLAVQTEKFPYSCSISKESAPSCIRKI

FAHLASQKESAPLSFSRLQPTTPKERILFFGSSPSSQLSSTVRTTTSSPWNLFSNSQARN

STRKLSEKLHLSSELSARDSTKPSSSEPVKPSENLLHTPEHHKESFSSLKKDNLSPIMEE

IDSFSAETESLEERLVTQKKEETVAQEQKHPLLRTSTPPSKASGESQDSSEHSSKEDPY

SQQPSHKIQRRKERAKRVVPIITPPTVGIFSLSYLLTKQGILADFSAYSAYKDNLETTQ

QELTMLHQERIEQVQKIVDKSKTMRFWDSLASIVATIIPWIEMGVAVTIIALGGGILS

WCSLFAALIMIVISLLEAFDGWRAIAKHLPGNDLEKKMRYLGYVKLALTVFSCLLSL

SALYVAKLGMSPLLEGVVKSIAPALSGMLGLTQGVALYLQSSSQKIRARCTQIDARIE

LINWERDEYFLRAEQLLDSMQTSFEQLTETLQLQREIDQTFTDALR*

HisScc3 chaperone for CT668-CopB2 nucleic acid sequence  SEQ ID NO: 97

ATGGGCAGCAGCCATCACCATCATCACCACAGCCAGGATCCGatgccaccaagc aagatccaatgtcttgaaacttttgaaagaacttatggacaccttctctacaacatgcgtccctaatgcgtcatttagcctatctactcgata aaattgctcgctcttaccctcatatgtgtccgcttcccgataatatggaagcgtactttgagaattatatccccaataaagatatccctctgg acacctatcaaaaaattttcaaactgtcctcagaagatcttgaacaagtctacaaggaaggatacaacgcctatttacaaggagactatg aggaaagttctaccgcttttttactggttgattttctttaacccatttgtgtctaaattttggttttcattaggagcttcgctccatatgcgccaaaa atatcaacaagctcttcatgcttatgGTgtagctgctttgctaagagaaaaagacccctatccctcattactatgcctacatctgctacaccct gctcaataatcctgaagaagctgaaaaagctcttgatcttgcttggcaaaaagtaaaaacaagctctgcctatagctcttttaaaagaaga aattttagcgatcaaatcgtacgcctaaGCGGCCGC HisScc3 chaperone for CT668-CopB2 Amino acid sequence  SEQ ID NO: 98

MGSSHHHHHHSQDPMPPSKIQCLETFERTYGHLYLQHASLMRHLAYLLDKIA

RSYPHMCPLPDNMEAYFENYIPNKDIPLDTYQKIFKLSSEDLEQVYKEGYNAYLQGD

YEESSTAFYWLIFFNPFVSKFWFSLGASLHMRQKYQQALHAYGVAALLREKDPYPH

YYAYICYTLLNNPEEAEKALDLAWQKVKTSSAYSSLKEEILAIKSYA*

CT668-CopB2 nucleic acid sequence  SEQ ID NO: 99 aaaagtgagcgtttaaaaaaattagaatcagagcttcatgatcttacccagtggatgcaacttggccttgttcctaaaaaagaa atcgagagacaccaggaagaaatccgtctgctagaaagcaaaatccttgaagagaaagaacgtctacaacttctcaaagaaagcggt gagatcaaagagtacgtaaccctcgaagaactccagctaaaaccatttacccagatggccccagcgtttcagacgttgagtttgtaga atcctcggatacagaagtggatctcgatgccggtgacacaattgagattgacctaggtgatgaggcaagagaagaaagcggaaacg aactcgactactctagtgaagacgatgaggatcctttcagcgatcgcaatcgttggcgccgaggaggcatcatagatcctgacgcgaa tgaatggGGTTCAGCTGCTTCAatgagctcttggtttgcacaggcgacggacgtcgctttgagccagacccttgatctgc ctgacgcttcattggcggttcaaaccgaaaaatttccAtacagctgttcaatctctaaggaatccgccccAtcatgtattcgtaaaatctt cgcccatttagcatctcagaaggaaagtgrtccgctgtcttttttctcgtttacaaccgactactccgaaagaacgcatcctgtttttcgggt catcgccttcctcccaattgtcctcgactgtccgcaccacaacctcttctccatggaatcttttttagcaactcccaggcacgcaactcgac ccgtaaattgtcggagaagcttcatttgagctcagagttatccgcccgtgactccactaagccttcgtcgagcgaaccggttaaaccatc ggaaaatcttttgcacacccctgagcatcataaggaatccttctcaagtttgaaaaaggataacttatctcctatcatggaggagatcgac tcattctctgcagagacagagtcccttgaagagcgtttggtcacccagaaaaaggaggagacggtggcccaggagcaaaagcaccc Attgctgcgtacatctactccgccatcaaaggccagcggggaatcacaagattctagcgaacacagctcaaaggaagatccttatagt caacaaccgagccataaaatccaacgccgtaaagagcgtgctaagcgcgtcgtcccAattattactccgccaacggtgggtatcttta gtttgagctaccttcttacaaaacaggggatcttagcggatttcagcgcctattcggcatacaaggataatttagaaacaactcagcaag agctgaccatgttgcatcaagaacgtatcgagcaagtccaaaaGatcgtggataaaagtaagacaatgcgcttttgggattcattagca tccattgtggccacaatcattccatggatcgaaatgggtgttgcagtaaccatcatcgcactgggaggtggaatcctttcctggtgctctc ttttttgctgcgcttatcatgattgtaatttcattattggaagcattcgacggtggcgtgcaatcgctaagcatttaccaggtaacgatcttga aaagaagatgcgttatttaggttacgtaaagttggccttaactgtgttctcgtgcttactgagtttaagcgccttgtatgtagcaaaattagg aatgagtccgcttttggaggggttgtgaagagtatcgcaccAgcattaagtggtatgctgggtttgactcaaggcgtagcactgtatttt acaatcttcatcgcaaaagattcgtgcccgctgcactcagatcgacgcacgcattgaattgattaactgggaacgcgatgagtatttcttg -continued cgtgctgaacaacttcttgattcaatgcaaacgtccttcgaacaacttactgaaacattacagttacaacgtgaaattgatcagacatttac agacgctttgcgcTAG CT668-CopB2 amino acid sequence

SEQ ID NO: 100

MKSERLKKLESELHDLTQWMQLGLVPKKEIERHQEEIRLLESKILEEKERLQL

LKESGEIKEYVTPRRTPAKTIYPDGPSVSDVEFVESSDTEVDLDAGDTIEIDLGDEARE

ESGNELDYSSEDDEDPFSDRNRWRRGGIIDPDANEWGSAASMSSWFAQATDVALSQ

TLDLPDASLAVQTEKFPYSCSISKESAPSCIRKIFAHLASQKESAPLSFSRLQPTTPKERI

LFFGSSPSSQLSSTVRTTTSSPWNLFSNSQARNSTRKLSEKLHLSSELSARDSTKPSSSE

PVKPSENLLHTPEHHKESFSSLKKDNLSPIMEEIDSFSAETESLEERLVTQKKEETVAQ

EQKHPLLRTSTPPSKASGESQDSSEHSSKEDPYSQQPSHKIQRRKERAKRVVPIITPPT

VGIFSLSYLLTKQGILADFSAYSAYKDNLETTQQELTMLHQERIEQVQKIVDKSKTM

RFWDSLASIVATIIPWIEMGVAVTIIALGGGILSWCSLFAALIMIVISLLEAFDGWRAIA

KHLPGNDLEKKMRYLGYVKLALTVFSCLLSLSALYVAKLGMSPLLEGVVKSIAPALS

GMLGLTQGVALYLQSSSQKIRARCTQIDARIELINWERDEYFLRAEQLLDSMQTSFE

QLTETLQLQREIDQTFTDALR

LTA1-CT668-CopB2 nucleic acid sequence

SEQ ID NO: 101

CATatggacaatggcgatcgtttataccgtgccgactcgcgtcccccagatgagattaaacgtagcggtgggttaatgcc acgtgggcacaatgagtattttgaccgtggaacacagatgaacattaacctttacgatcatgcccgtgggacccagaccgggtttgtcc gttatgatgacgggtatgttagtacgagtttgtccttacgctccgcacaccttgcgggacaaagtattttatcaggctacagcacatattac atttatgtgatcgccactgccccaaacatgttcaatgtgaacgatgtgttgggggtttacagcccccatccatatgaacaagaagtctcg gcccttgggggatcccatatagccagattatggttggtaccgcgtaaattttggtgtgattgatgaacgtttgcatcgtaaccgtgaata ccgcgatcgctactaccgtaacttgaacattgcacctgccgaggacggctatcgtttagcgggattcccacccgatcatcaggcgtgg cgtgaggaaccgtggatccatcacgcccctcaggggtgcgggaacagtagtcgcCATatgaaaagtgagcgtttaaaaaaattag aatcagagcttcatgatcttacccagtggatgcaacttggccttgttcctaaaaaagaaatcgagagacaccaggaagaaatccgtctg ctagaaagcaaaatccttgaagagaaagaacgtctacaacttctcaaagaaagcggtgagatcaaagagtacgtaaccctcgaaga actccagctaaaaccatttacccagatggccccagcgtttcagacgttgagtttgtagaatcctcggatacagaagtggatctcgatgcc ggtgacacaattgagattgacctaggtgatgaggcaagagaagaaagcggaaacgaactcgactactctagtgaagacgatgagga tccttttcagcgatcgcaatcgttggcgccgaggaggcatcatagatcctgacgcgaatgaatggGGTTCAGCTGCTTCA atgagctcttggtttgcacaggcgacggacgtcgctttgagccagaccttgatctgcctgacgcttcattggcggttcaaaccgaaaa atttccAtacagctgttcaatctctaaggaatccgccccAtcatgtattcgtaaaatcttcgcccatttagcatctcagaaggaaagtgct ccgctgtcttttctcgtttacaaccgactactccgaaagaacgcatcctgttttttcgggtcatcgccttcctcccaattgtcctcgactgtcc gcaccacaacctcttctccatggaatctttttagcaactcccaggcacgcaactcgacccgtaaattgtcggagaagcttcatttgagctc agagttatccgcccgtgactccactaagccttcgtcgagcgaaccggttaaaccatcggaaaatcttttgcacaccctgagcatcataa ggaatccttctcaagtttgaaaaaggataacttatctcctatcatggaggagatcgactcattctctgcagagacagagtcccttgaagag cgtttggtcacccagaaaaggaggagacggtggcccaggagcaaaagcacccAttgctgcgtacatctactccgccatcaaaggc cagcggggaatcacaagattctagcgaacacagctcaaaggaagatccttatagtcaacaaccgagccataaaatccaacgccgtaa agagcgtgctaagcgcgtcgtcccAattattactccgccaacggtgggtatctttagtttgagctaccttcttacaaaacaggggatctta gcggatttcagcgcctattcggcatacaaggataatttagaaacaactcagcaagagctgaccatgttgcatcaagaacgtatcgagca agtccaaaaGatcgtggataaaagtaagacaatgcgcttttgggattcattagcatccattgtggccacaatcattccatggatcgaaat gggtgttgcagtaaccatcatcgcactgggaggtggaatcctttcctggtgctctctttttgctgcgcttatcatgattgtaatttcattattgg aagcattcgacgggtggcgtgcaatcgctaagcatttaccaggtaacgatcttgaaaagaagatgcgttatttaggttacgtaaagttgg -continued ccttaactgtgttctcgtgcttactgagtttaagcgccttgtatgtagcaaaattaggaatgagtccgcttttggaggggttgtgaagagt atcgcaccAgcattaagtggtatgctgggtttgactcaaggcgtagcactgtatttacaatcttcatcgcaaaagattcgtgccgctgc actcagatcgacgcacgcattgaattgattaactgggaacgcgatgagtatttcttgcgtgctgaacaacttcttgattcaatgcaaacgt ccttcgaacaacttactgaaacattacagttacaacgtgaaattgatcagacatttacagacgctttgcgcTAGCTCGAG LTA1-CT668-CopB2 Amino acid sequence

SEQ ID NO: 102

MDNGDRLYRADSRPPDEIKRSGGLMPRGHNEYFDRGTQMNINLYDHARGTQ

TGFVRYDDGYVSTSLSLRSAHLAGQSILSGYSTYYIYVIATAPNMFNVNDVLGVYSP

HPYEQEVSALGGIPYSQIYGWYRVNFGVIDERLHRNREYRDRYYRNLNLAPAEDGYR

LAGFPPDHQAWREEPWIHHAPQGCGNSSRMKSERLKKLESELHDLTQWMQLGLVP

KKEIERHQEEIRLLESKILEEKERLQLLKESGEIKEYVTPRRTPAKTIYPDGPSVSDVEF

VESSDTEVDLDAGDTIEIDLGDEAREESGNELDYSSEDDEDPFSDRNRWRRGGIIDPD

ANEWGSAASMSSWFAQATDVALSQTLDLPDASLAVQTEKFPYSCSISKESAPSCIRKI

FAHLASQKESAPLSFSRLQPTTPKERILFFGSSPSSQLSSTVRTTTSSPWNLFSNSQARN

STRKLSEKLHLSSELSARDSTKPSSSEPVKPSENLLHTPEHHKESFSSLKKDNLSPIMEE

IDSFSAETESLEERLVTQKKEETVAQEQKHPLLRTSTPPSKASGESQDSSEHSSKEDPY

SQQPSHKIQRRKERAKRVVPIITPPTVGIFSLSYLLTKQGILADFSAYSAYKDNLETTQ

QELTMLHQERIEQVQKIVDKSKTMRFWDSLASIVATIIPWIEMGVAVTIIALGGGILS

WCSLFAALIMIVISLLEAFDGWRAIAKHLPGNDLEKKMRYLGYVKLALTVFSCLLSL

SALYVAKLGMSPLLEGVVKSIAPALSGMLGLTQGVALYLQSSSQKIRARCTQIDARIE

LINWERDEYFLRAEQLLDSMQTSFEQLTETLQLQREIDQTFTDALR dmLT eltA (LTa) nucleic acid sequence

SEQ ID NO: 113 atgattgaca tcatgttgca tataggttag ataaaacaag tggttatctt ccggattgt cttcttgtat gatatataag ttttcctcga tgaaaaatat aactttcatt tttttatttt tattagcatc gccattatat gcaaatggcg acagattata ccgtgctgac tctagacccc cagatgaaat aaaacgtttc cggagtctta tgcccagagg taatgagtac ttcgatagag aactcaaat gaatattaat ctttatgatc acgcgagagg aacacaaacc ggctttgtca gatatgatga cggatatgtt ccacttctc ttagtttgag aagtgctcac ttagcaggac agtatatatt tcaggatat tcacttacta tatatatcgt tatagcaaat atgtttaatg ttaatgatgt aattagcgta tacagccctc acccatatga acaggaggtt tctgcgttag gtggaatacc atattctcag atatatggat ggtatcgtgt taatttggt gtgattgatg aacgattaca tcgtaacagg aatatagag accggtatta cagaaatctg aatatagctc cggcagagga tggttacaga ttagcaggtt tccaccgga tcaccaagct tggagagaag aaccctggat tcatcatgca ccacaaggtt gtggagattc atcaGgaaca atcacaggtg atacttgtaa tgaggagacc cagaatctga gcacaatata tGCcagggaa tatcaatcaa aagttaagag cagatatttt cagactatc agtcagaggt tgacatatat aacagaattc gggatgaatt atgaataaag taaaatgt eltB (LTb) nucleic acid sequence

SEQ ID NO: 114 gttgacatat ataacagaat tcgggatgaa ttatgaataa agtaaaatgt tatgttttat ttacggcgtt actatcctct ctatatgcac acggagctcc ccagactatt acagaactat gttcggaata tcgcaacaca caatatata cgataaatga caagatacta tcatatacgg aatcgatggc aggcaaaaga gaatggttta tcattacatt taagagcggc gaaacatttc aggtcgaagt cccgggcagt caacatatag actcccagaa aaaagccatt gaaaggatga aggacacatt aagaatcaca tatctgaccg agaccaaaat tgataaatta tgtgtatgga ataataaaac ccccaattca attgcggcaa tcagtatgaa aaactagttt gcttttaaaag catgtctaat gctaggaacc tatataacaa ctactgtact tatactaatg agccttatgc tgcatttgaa aaggcggtag aggaggcaat accgatcctt aaactgtaac actataacag cttccactac agggagctgt tatagcacac agaaaaaact aagctaggct ggaggggcaa gctt

What is claimed is:

1. A fusion polypeptide comprising a fusion of a needle tip protein or an antigenic fragment thereof and a translocator protein or an antigenic fragment thereof from a Type III secretion system (T3SS) of *Pseudomonas* spp.; wherein the needle tip protein comprises PcrV as set forth in SEQ ID NO: 32 and the translocator protein comprises PopB as set forth in SEQ ID NO: 34; and wherein the fusion further comprises a double mutant labile toxin (dmLT) comprising the active moiety LTA1 or an antigenic fragment thereof from Enterotoxigenic *Escherichia coli* or cholera toxin or an antigenic fragment thereof.

2. The polypeptide of claim 1, wherein the fusion polypeptide is arranged so that the needle tip protein is 5' of the translocator protein.

3. The polypeptide of claim 1, wherein the dmLT retains its ADP ribosylation activity.

4. The polypeptide of claim 1, wherein the dmLT is 5' of the needle tip protein and translocator protein fusion.

5. A vaccine comprising the fusion polypeptide of claim 1.

6. The vaccine of claim 5, further comprising one or more components of an acellular pertussis vaccine.

7. A method of eliciting an immune response against *Pseudomonas* sp. in a subject in need thereof comprising administering to the subject a composition comprising the fusion polypeptide of claim 1 in an amount sufficient to elicit the immune response against said *Pseudomonas* sp.

* * * * *

SEQUENCE LISTING

<160> NUMBER OF SEQ ID NOS: 118

<210> SEQ ID NO 1
<211> LENGTH: 1833
<212> TYPE: DNA
<213> ORGANISM: Artificial Sequence
<220> FEATURE:
<223> OTHER INFORMATION: synthetic construct

<400> SEQUENCE: 1

| | | | | | |
|---|---|---|---|---|---|
| catatgacca | ttgatctcgg | agtttcactc | acgtcgcagg | ccggcggcct | gcaaggcatc | 60 |
| gacctcaaga | gcatggatat | ccagactctc | atggtgtatg | tgcagggtcg | tcgcgccgaa | 120 |
| ctcctcacgg | ctcaaatgca | gacccaggcc | gaagtggtgc | agaaggccaa | tgaacgcatg | 180 |
| gcgcagctca | acgaggtcct | gtccgcgctg | tcccgggcca | aggccgagtt | ccgcccaat | 240 |
| ccgaagccgg | cgacaccat | cccgggctgg | gacaaccaga | aggtcagccg | gatcgaggtt | 300 |
| cctctcaatg | atgcgctgcg | cgctgccggc | ctgacgggca | tgttcgaagc | gcgcgatggc | 360 |
| caagtgaccg | ccccggcgg | ccggggtacg | caggtcgtga | acggcacggg | cgtcatggcc | 420 |
| ggttccacga | cctataagga | actcgaaagt | gcctacacca | ccgtaaaggg | gatgctggat | 480 |
| acggcgtcca | atacgcaaca | gatggacatg | atcaggctgc | aggccgccag | caacaagcgc | 540 |
| aacgaggctt | tcgaggtcat | gaccaacacc | gagaagcggc | gcagcgacct | gaacagttcc | 600 |
| atcaccaaca | acatgcgcaa | gcttatgacc | gtcatgagta | cgaccatatc | cacagccccg | 660 |
| agcggcgccg | cgcttgcgcc | gtctcgcata | gatatgcggg | caccggagcc | cgggagtgcc | 720 |
| ggcgaaggcg | ccggcatcct | ggcgccggtg | acgacgctgg | ctctggcggc | gggccggccg | 780 |
| gcttttccag | cgtcaccgtc | gctgcgcacc | gcgcccgtcc | tggatccgcc | agtgcgcgat | 840 |
| ctcagccccg | ccgacttggc | cgacctgctg | cgcgtcttgc | gatccagggc | ggtggacggg | 900 |
| cagttggcca | cggcgcgcga | gaacctgcag | gacgcgcaag | tcaaggcgaa | gcagaacacc | 960 |
| caggcccagc | tcgacaagct | ggacgcatgg | tttcggaagg | ccgaagaggc | cgagagcaag | 1020 |
| ggatggctga | gcaaggtgtt | cggctggatc | ggcaaggtgc | tggcggtcgt | ggcatcggcc | 1080 |
| ctggcggtgg | gctttgccgc | cgtcgccagc | gtggccaccg | gcgcggcggc | cacacccatg | 1140 |
| ctgctgctca | gcggcatggc | actggtcagc | gccgtgacat | cgctggccga | ccagatatcg | 1200 |
| caagaggcgg | gaggcccgcc | tatcagcctg | ggcgggtttc | tctccgggct | ggccggacgt | 1260 |
| ctgctgacag | cgttgggggt | ggatcagtcg | caggccgacc | aaattgccaa | gatcgtcgcc | 1320 |
| ggcctggccg | tgcccgtcgt | cttgctgatc | gaacccagga | tgctgggcga | aatggcgcaa | 1380 |
| ggcgtggcca | gctggctgg | cgccagcgat | gccaccgcgg | ggtacatagc | catggcgatg | 1440 |
| tccatcgtgg | cggcgatcgc | ggtcgccgcg | atcaatgccg | ccggtacagc | cggcgcgggt | 1500 |
| agcgcttcgg | cgatcaaggg | ggcctggat | cgggccgccg | cggtagccac | ccaggtcctt | 1560 |
| caaggggta | cggcagtggc | gcaaggcggc | gtcggcgtgt | cgatgcagt | cgatcgcaaa | 1620 |
| caggccgatc | tcctggtcgc | cgacaaggcg | gatctggcgg | cgagcctgac | aaaactgcgg | 1680 |
| gcggccatgg | agcgtgaggc | ggacgatatc | aagaagatcc | tggctcaatt | cgacgaggcc | 1740 |
| tatcacatga | tcgcgaagat | gatcagcgat | atggcgagta | cgcacagcca | ggtcagcgcc | 1800 |
| aacctcgggc | ggcgccaggc | ggtgtagctc | gag | | | 1833 |

<210> SEQ ID NO 2
<211> LENGTH: 607
<212> TYPE: PRT
<213> ORGANISM: Artificial Sequence

```
<220> FEATURE:
<223> OTHER INFORMATION: synthetic construct

<400> SEQUENCE: 2

Met Thr Ile Asp Leu Gly Val Ser Leu Thr Ser Gln Ala Gly Gly Leu
1               5                   10                  15

Gln Gly Ile Asp Leu Lys Ser Met Asp Ile Gln Thr Leu Met Val Tyr
            20                  25                  30

Val Gln Gly Arg Arg Ala Glu Leu Leu Thr Ala Gln Met Gln Thr Gln
        35                  40                  45

Ala Glu Val Val Gln Lys Ala Asn Glu Arg Met Ala Gln Leu Asn Glu
    50                  55                  60

Val Leu Ser Ala Leu Ser Arg Ala Lys Ala Glu Phe Pro Pro Asn Pro
65                  70                  75                  80

Lys Pro Gly Asp Thr Ile Pro Gly Trp Asp Asn Gln Lys Val Ser Arg
                85                  90                  95

Ile Glu Val Pro Leu Asn Asp Ala Leu Arg Ala Gly Leu Thr Gly
            100                 105                 110

Met Phe Glu Ala Arg Asp Gly Gln Val Thr Ala Pro Gly Gly Arg Gly
        115                 120                 125

Thr Gln Val Val Asn Gly Thr Gly Val Met Ala Gly Ser Thr Thr Tyr
    130                 135                 140

Lys Glu Leu Glu Ser Ala Tyr Thr Thr Val Lys Gly Met Leu Asp Thr
145                 150                 155                 160

Ala Ser Asn Thr Gln Gln Met Asp Met Ile Arg Leu Gln Ala Ala Ser
                165                 170                 175

Asn Lys Arg Asn Glu Ala Phe Glu Val Met Thr Asn Thr Glu Lys Arg
            180                 185                 190

Arg Ser Asp Leu Asn Ser Ser Ile Thr Asn Asn Met Arg Lys Leu Met
        195                 200                 205

Thr Val Met Ser Thr Thr Ile Ser Thr Ala Pro Ser Gly Ala Ala Leu
210                 215                 220

Ala Pro Ser Arg Ile Asp Met Arg Ala Pro Glu Pro Gly Ser Ala Gly
225                 230                 235                 240

Glu Gly Ala Gly Ile Leu Ala Pro Val Thr Thr Leu Ala Leu Ala Ala
                245                 250                 255

Gly Arg Pro Ala Phe Pro Ala Ser Pro Ser Leu Arg Thr Ala Pro Val
            260                 265                 270

Leu Asp Pro Pro Val Arg Asp Leu Ser Pro Ala Asp Leu Ala Asp Leu
        275                 280                 285

Leu Arg Val Leu Arg Ser Arg Ala Val Asp Gly Gln Leu Ala Thr Ala
290                 295                 300

Arg Glu Asn Leu Gln Asp Ala Gln Val Lys Ala Lys Gln Asn Thr Gln
305                 310                 315                 320

Ala Gln Leu Asp Lys Leu Asp Ala Trp Phe Arg Lys Ala Glu Glu Ala
                325                 330                 335

Glu Ser Lys Gly Trp Leu Ser Lys Val Phe Gly Trp Ile Gly Lys Val
            340                 345                 350

Leu Ala Val Val Ala Ser Ala Leu Ala Val Gly Phe Ala Ala Val Ala
        355                 360                 365

Ser Val Ala Thr Gly Ala Ala Thr Pro Met Leu Leu Leu Ser Gly
    370                 375                 380

Met Ala Leu Val Ser Ala Val Thr Ser Leu Ala Asp Gln Ile Ser Gln
385                 390                 395                 400
```

Glu Ala Gly Gly Pro Pro Ile Ser Leu Gly Phe Leu Ser Gly Leu
                405                 410                 415

Ala Gly Arg Leu Leu Thr Ala Leu Gly Val Asp Gln Ser Gln Ala Asp
        420                 425                 430

Gln Ile Ala Lys Ile Val Ala Gly Leu Ala Val Pro Val Val Leu Leu
    435                 440                 445

Ile Glu Pro Gln Met Leu Gly Glu Met Ala Gln Gly Val Ala Arg Leu
450                 455                 460

Ala Gly Ala Ser Asp Ala Thr Ala Gly Tyr Ile Ala Met Ala Met Ser
465                 470                 475                 480

Ile Val Ala Ala Ile Ala Val Ala Ala Ile Asn Ala Ala Gly Thr Ala
                485                 490                 495

Gly Ala Gly Ser Ala Ser Ala Ile Lys Gly Ala Trp Asp Arg Ala Ala
            500                 505                 510

Ala Val Ala Thr Gln Val Leu Gln Gly Gly Thr Ala Val Ala Gln Gly
        515                 520                 525

Gly Val Gly Val Ser Met Ala Val Asp Arg Lys Gln Ala Asp Leu Leu
    530                 535                 540

Val Ala Asp Lys Ala Asp Leu Ala Ala Ser Leu Thr Lys Leu Arg Ala
545                 550                 555                 560

Ala Met Glu Arg Glu Ala Asp Asp Ile Lys Lys Ile Leu Ala Gln Phe
                565                 570                 575

Asp Glu Ala Tyr His Met Ile Ala Lys Met Ile Ser Asp Met Ala Ser
            580                 585                 590

Thr His Ser Gln Val Ser Ala Asn Leu Gly Arg Arg Gln Ala Val
        595                 600                 605

<210> SEQ ID NO 3
<211> LENGTH: 618
<212> TYPE: DNA
<213> ORGANISM: Bordetella spp

<400> SEQUENCE: 3
catatgacca ttgatctcgg agtttcactc acgtcgcagg ccggcggcct gcaaggcatc      60
gacctcaaga gcatggatat ccagactctc atggtgtatg tgcagggtcg tcgcgccgaa     120
ctcctcacgg ctcaaatgca gacccaggcc gaagtggtgc agaaggccaa tgaacgcatg     180
gcgcagctca cgaggtcct gtccgcgctg tcccgggcca aggccgagtt ccgcccaat      240 ccgaagccgg gcgacaccat cccgggctgg gacaaccaga aggtcagccg gatcgaggtt     300
cctctcaatg atgcgctgcg cgctgccggc ctgacgggca tgttcgaagc gcgcgatggc     360
caagtgaccg cccccggcgg ccggggtacg caggtcgtga acggcacggg cgtcatggcc     420
ggttccacga cctataagga actcgaaagt gcctacacca ccgtaaaggg gatgctggat     480
acggcgtcca atacgcaaca gatggacatg atcaggctgc aggccgccag caacaagcgc     540
aacgaggctt tcgaggtcat gaccaacacc gagaagcggc gcagcgacct gaacagttcc     600
atcaccaaca acatgcgc                                                  618

<210> SEQ ID NO 4
<211> LENGTH: 205
<212> TYPE: PRT
<213> ORGANISM: Bordetella spp

<400> SEQUENCE: 4

Met Thr Ile Asp Leu Gly Val Ser Leu Thr Ser Gln Ala Gly Gly Leu

```
Gln Gly Ile Asp Leu Lys Ser Met Asp Ile Gln Thr Leu Met Val Tyr
            20                  25                  30

Val Gln Gly Arg Arg Ala Glu Leu Leu Thr Ala Gln Met Gln Thr Gln
        35                  40                  45

Ala Glu Val Val Gln Lys Ala Asn Glu Arg Met Ala Gln Leu Asn Glu
    50                  55                  60

Val Leu Ser Ala Leu Ser Arg Ala Lys Ala Glu Phe Pro Pro Asn Pro
65                  70                  75                  80

Lys Pro Gly Asp Thr Ile Pro Gly Trp Asp Asn Gln Lys Val Ser Arg
                85                  90                  95

Ile Glu Val Pro Leu Asn Asp Ala Leu Arg Ala Ala Gly Leu Thr Gly
            100                 105                 110

Met Phe Glu Ala Arg Asp Gly Gln Val Thr Ala Pro Gly Gly Arg Gly
        115                 120                 125

Thr Gln Val Val Asn Gly Thr Gly Val Met Ala Gly Ser Thr Thr Tyr
    130                 135                 140

Lys Glu Leu Glu Ser Ala Tyr Thr Thr Val Lys Gly Met Leu Asp Thr
145                 150                 155                 160

Ala Ser Asn Thr Gln Gln Met Asp Met Ile Arg Leu Gln Ala Ala Ser
                165                 170                 175

Asn Lys Arg Asn Glu Ala Phe Glu Val Met Thr Asn Thr Glu Lys Arg
            180                 185                 190

Arg Ser Asp Leu Asn Ser Ser Ile Thr Asn Asn Met Arg
        195                 200                 205
```

<210> SEQ ID NO 5
<211> LENGTH: 1209
<212> TYPE: DNA
<213> ORGANISM: Bordetella spp

<400> SEQUENCE: 5

```
atgaccgtca tgagtacgac catatccaca gccccgagcg gcgccgcgct tgcgccgtct     60
cgcatagata tgcgggcacc ggagcccggg agtgccggcg aaggcgccgg catcctggcg    120
ccggtgacga cgctggctct ggcggcgggc cggccggctt ttccagcgtc accgtcgctg    180
cgcaccgcgc ccgtcctgga tccgccagtg cgcgatctca gccccgccga cttggccgac    240
ctgctgcgcg tcttgcgatc cagggcggtg gacgggcagt tggccacggc gcgcgagaac    300
ctgcaggacg cgcaagtcaa ggcgaagcag aacacccagg cccagctcga caagctggac    360
gcatggtttc ggaaggccga agaggccgag agcaagggat ggctgagcaa ggtgttcggc    420
tggatcggca aggtgctggc ggtcgtggca tcggccctgg cggtgggctt tgccgccgtc    480
gccagcgtgg ccaccggcgc ggcggccaca cccatgctgc tgctcagcgg catggcactg    540
gtcagcgccg tgacatcgct ggccgaccag atatcgcaag aggcgggagg cccgcctatc    600
agcctgggcg ggtttctctc cgggctggcc ggacgtctgc tgacagcgtt gggggtggat    660
cagtcgcagg ccgaccaaat tgccaagatc gtcgccggcc tggccgtgcc cgtcgtcttg    720
ctgatcgaac cccagatgct gggcgaaatg gcgcaaggcg tggccaggct ggctggcgcc    780
agcgatgcca ccgcggggta catagccatg gcgatgtcca tcgtggcggc gatcgcggtc    840
gccgcgatca atgccgccgg tacagccggc gcgggtagcg cttcggcgat caagggggcc    900
tgggatcggg ccgccgcggt agccacccag gtccttcaag gggtacggc agtggcgcaa     960 ggcggcgtcg gcgtgtcgat ggcagtcgat cgcaaacagg ccgatctcct ggtcgccgac   1020
```

-continued

```
aaggcggatc tggcggcgag cctgacaaaa ctgcgggcgg ccatggagcg tgaggcggac    1080
gatatcaaga agatcctggc tcaattcgac gaggcctatc acatgatcgc gaagatgatc    1140
agcgatatgg cgagtacgca cagccaggtc agcgccaacc tcgggcggcg ccaggcggtg    1200
tagctcgag                                                             1209
```

<210> SEQ ID NO 6
<211> LENGTH: 400
<212> TYPE: PRT
<213> ORGANISM: Bordetella spp

<400> SEQUENCE: 6

```
Met Thr Val Met Ser Thr Thr Ile Ser Thr Ala Pro Ser Gly Ala Ala
1               5                   10                  15

Leu Ala Pro Ser Arg Ile Asp Met Arg Ala Pro Glu Pro Gly Ser Ala
            20                  25                  30

Gly Glu Gly Ala Gly Ile Leu Ala Pro Val Thr Thr Leu Ala Leu Ala
        35                  40                  45

Ala Gly Arg Pro Ala Phe Pro Ala Ser Pro Ser Leu Arg Thr Ala Pro
    50                  55                  60

Val Leu Asp Pro Val Arg Asp Leu Ser Pro Ala Asp Leu Ala Asp
65                  70                  75                  80

Leu Leu Arg Val Leu Arg Ser Arg Ala Val Asp Gly Gln Leu Ala Thr
                85                  90                  95

Ala Arg Glu Asn Leu Gln Asp Ala Gln Val Lys Ala Lys Gln Asn Thr
            100                 105                 110

Gln Ala Gln Leu Asp Lys Leu Asp Ala Trp Phe Arg Lys Ala Glu Glu
        115                 120                 125

Ala Glu Ser Lys Gly Trp Leu Ser Lys Val Phe Gly Trp Ile Gly Lys
    130                 135                 140

Val Leu Ala Val Val Ala Ser Ala Leu Ala Val Gly Phe Ala Ala Val
145                 150                 155                 160

Ala Ser Val Ala Thr Gly Ala Ala Ala Thr Pro Met Leu Leu Ser
                165                 170                 175

Gly Met Ala Leu Val Ser Ala Val Thr Ser Leu Ala Asp Gln Ile Ser
            180                 185                 190

Gln Glu Ala Gly Gly Pro Pro Ile Ser Leu Gly Gly Phe Leu Ser Gly
        195                 200                 205

Leu Ala Gly Arg Leu Leu Thr Ala Leu Gly Val Asp Gln Ser Gln Ala
    210                 215                 220

Asp Gln Ile Ala Lys Ile Val Ala Gly Leu Ala Val Pro Val Val Leu
225                 230                 235                 240

Leu Ile Glu Pro Gln Met Leu Gly Glu Met Ala Gln Gly Val Ala Arg
                245                 250                 255

Leu Ala Gly Ala Ser Asp Ala Thr Ala Gly Tyr Ile Ala Met Ala Met
            260                 265                 270

Ser Ile Val Ala Ala Ile Ala Val Ala Ala Ile Asn Ala Ala Gly Thr
        275                 280                 285

Ala Gly Ala Gly Ser Ala Ser Ala Ile Lys Gly Ala Trp Asp Arg Ala
    290                 295                 300

Ala Ala Val Ala Thr Gln Val Leu Gln Gly Gly Thr Ala Val Ala Gln
305                 310                 315                 320

Gly Gly Val Gly Val Ser Met Ala Val Asp Arg Lys Gln Ala Asp Leu
                325                 330                 335
```

-continued

```
Leu Val Ala Asp Lys Ala Asp Leu Ala Ala Ser Leu Thr Lys Leu Arg
            340                 345                 350

Ala Ala Met Glu Arg Glu Ala Asp Asp Ile Lys Lys Ile Leu Ala Gln
            355                 360                 365

Phe Asp Glu Ala Tyr His Met Ile Ala Lys Met Ile Ser Asp Met Ala
370                 375                 380

Ser Thr His Ser Gln Val Ser Ala Asn Leu Gly Arg Arg Gln Ala Val
385                 390                 395                 400
```

<210> SEQ ID NO 7
<211> LENGTH: 534
<212> TYPE: DNA
<213> ORGANISM: Artificial Sequence
<220> FEATURE:
<223> OTHER INFORMATION: synthetic construct

<400> SEQUENCE: 7

```
atgggcagca gccatcacca tcatcaccac agccaggatc cgatgccaaa gtcagccgag      60
cagggcggct ccccggcgtc agcttcgcat gaggcgttgc gccatattct cgacgcaggc     120
gcttcgatgg gcagcttgca ggggttggac gaggtgcaac agcaggcgtt gtacgcgatc     180
gctcatggcg cctacgaaca gggccgctat gccgacgcgt tgaaaatgtt ctgcctgctg     240
gtcgcgtgcg atccgctgga agcccgttat ctgctggccc tgggcgccgc ggcccaggag     300
ctggggctgt acgagcatgc cttgcagcaa tacgcggccg cggcggcttt gcagttggac     360
tcccccaggc ccctgttgca tggcgccgag tgcctgtatg cgttgggtcg tcgccgcgac     420
gccctggata cgctcgacat ggtgcttgag ttgtgcgggt cgccggagca tgcggccctg     480
cgcgaacggg ccgagtcgct gcgcaggagc tatgcacgtg ccgactgaaa gctt           534
```

<210> SEQ ID NO 8
<211> LENGTH: 175
<212> TYPE: PRT
<213> ORGANISM: Artificial Sequence
<220> FEATURE:
<223> OTHER INFORMATION: synthetic construct

<400> SEQUENCE: 8

```
Met Gly Ser Ser His His His His His Ser Gln Asp Pro Met Pro
1               5                   10                  15

Lys Ser Ala Glu Gln Gly Gly Ser Pro Ala Ser Ala Ser His Glu Ala
            20                  25                  30

Leu Arg His Ile Leu Asp Ala Gly Ala Ser Met Gly Ser Leu Gln Gly
            35                  40                  45

Leu Asp Glu Val Gln Gln Gln Ala Leu Tyr Ala Ile Ala His Gly Ala
50                  55                  60

Tyr Glu Gln Gly Arg Tyr Ala Asp Ala Leu Lys Met Phe Cys Leu Leu
65                  70                  75                  80

Val Ala Cys Asp Pro Leu Glu Ala Arg Tyr Leu Leu Ala Leu Gly Ala
            85                  90                  95

Ala Ala Gln Glu Leu Gly Leu Tyr Glu His Ala Leu Gln Gln Tyr Ala
            100                 105                 110

Ala Ala Ala Ala Leu Gln Leu Asp Ser Pro Arg Pro Leu Leu His Gly
            115                 120                 125

Ala Glu Cys Leu Tyr Ala Leu Gly Arg Arg Arg Asp Ala Leu Asp Thr
            130                 135                 140

Leu Asp Met Val Leu Glu Leu Cys Gly Ser Pro Glu His Ala Ala Leu
145                 150                 155                 160
```

Arg Glu Arg Ala Glu Ser Leu Arg Arg Ser Tyr Ala Arg Ala Asp
                165                 170                 175

<210> SEQ ID NO 9
<211> LENGTH: 161
<212> TYPE: PRT
<213> ORGANISM: Artificial Sequence
<220> FEATURE:
<223> OTHER INFORMATION: synthetic construct

<400> SEQUENCE: 9

Met Pro Lys Ser Ala Glu Gln Gly Gly Ser Pro Ala Ser Ala Ser His
1               5                   10                  15

Glu Ala Leu Arg His Ile Leu Asp Ala Gly Ala Ser Met Gly Ser Leu
            20                  25                  30

Gln Gly Leu Asp Glu Val Gln Gln Gln Ala Leu Tyr Ala Ile Ala His
        35                  40                  45

Gly Ala Tyr Glu Gln Gly Arg Tyr Ala Asp Ala Leu Lys Met Phe Cys
    50                  55                  60

Leu Leu Val Ala Cys Asp Pro Leu Glu Ala Arg Tyr Leu Leu Ala Leu
65                  70                  75                  80

Gly Ala Ala Ala Gln Glu Leu Gly Leu Tyr Glu His Ala Leu Gln Gln
                85                  90                  95

Tyr Ala Ala Ala Ala Leu Gln Leu Asp Ser Pro Arg Pro Leu Leu
            100                 105                 110

His Gly Ala Glu Cys Leu Tyr Ala Leu Gly Arg Arg Arg Asp Ala Leu
        115                 120                 125

Asp Thr Leu Asp Met Val Leu Glu Leu Cys Gly Ser Pro Glu His Ala
    130                 135                 140

Ala Leu Arg Glu Arg Ala Glu Ser Leu Arg Arg Ser Tyr Ala Arg Ala
145                 150                 155                 160

Asp

<210> SEQ ID NO 10
<211> LENGTH: 544
<212> TYPE: DNA
<213> ORGANISM: Artificial Sequence
<220> FEATURE:
<223> OTHER INFORMATION: synthetic construct

<400> SEQUENCE: 10
ccatgggcag cagccatcat catcatcatc acagcagcgg cctggtgccg cgcggcagcc      60
atatgctcga gatgtcttta aatatcaccg aaaatgaaag catctctact gcagtaattg     120
atgcaattaa ctctggcgct acactgaaag atattaatgc aattcctgat gatatgatgg     180
atgacattta ttcatatgct tatgactttt acaacaaagg aagaatagag gaagctgaag     240
ttttcttcag ttttttatgt atatacgact tttacaatat agactacatt atgggactcg     300
cagctattta tcagataaaa gaacagttcc aacaagcagc agacctttat gctgtcgctt     360
ttgcattagg aaaaaatgac tatacaccag tattccatac tggacaatgc agcttcggt     420 tgaaagcccc cttaaaagct aaagagtgct cgaactcgt aattcaacac agcaatgatg     480
aaaaattaaa aataaaagca caatcatact tggacgcaat tcaggatatc aaggagtagg     540
atcc                                                                  544

<210> SEQ ID NO 11
<211> LENGTH: 155

<212> TYPE: PRT
<213> ORGANISM: Artificial Sequence
<220> FEATURE:
<223> OTHER INFORMATION: synthetic construct

<400> SEQUENCE: 11

```
Met Ser Leu Asn Ile Thr Glu Asn Glu Ser Ile Ser Thr Ala Val Ile
1               5                   10                  15

Asp Ala Ile Asn Ser Gly Ala Thr Leu Lys Asp Ile Asn Ala Ile Pro
            20                  25                  30

Asp Asp Met Met Asp Asp Ile Tyr Ser Tyr Ala Tyr Asp Phe Tyr Asn
        35                  40                  45

Lys Gly Arg Ile Glu Glu Ala Glu Val Phe Phe Arg Phe Leu Cys Ile
    50                  55                  60

Tyr Asp Phe Tyr Asn Val Asp Tyr Ile Met Gly Leu Ala Ala Ile Tyr
65                  70                  75                  80

Gln Ile Lys Glu Gln Phe Gln Gln Ala Ala Asp Leu Tyr Ala Val Ala
                85                  90                  95

Phe Ala Leu Gly Lys Asn Asp Tyr Thr Pro Val Phe His Thr Gly Gln
            100                 105                 110

Cys Gln Leu Arg Leu Lys Ala Pro Leu Lys Ala Lys Glu Cys Phe Glu
        115                 120                 125

Leu Val Ile Gln His Ser Asn Asp Glu Lys Leu Lys Ile Lys Ala Gln
130                 135                 140

Ser Tyr Leu Asp Ala Ile Gln Asp Ile Lys Glu
145                 150                 155
```

<210> SEQ ID NO 12
<211> LENGTH: 585
<212> TYPE: DNA
<213> ORGANISM: Escherichia coli

<400> SEQUENCE: 12

```
catatggaca atggcgatcg tttataccgt gccgactcgc gtcccccaga tgagattaaa    60
cgtagcggtg ggttaatgcc acgtgggcac aatgagtatt ttgaccgtgg aacacagatg   120
aacattaacc tttacgatca tgcccgtggg acccagaccg ggtttgtccg ttatgatgac   180
gggtatgtta gtacgagttt gtccttacgc tccgcacacc ttgcgggaca agtatttta   240 tcaggctaca gcacatatta catttatgtg atcgccactg ccccaaacat gttcaatgtg   300
aacgatgtgt tggggtttta cagcccccat ccatatgaac aagaagtctc ggcccttggg   360
gggatcccat atagccagat ttatggttgg taccgcgtaa attttggtgt gattgatgaa   420
cgtttgcatc gtaaccgtga ataccgcgat cgctactacc gtaacttgaa cattgcacct   480
gccgaggacg gctatcgttt agcgggattc ccacccgatc atcaggcgtg gcgtgaggaa   540
ccgtggatcc atcacgcccc tcaggggtgc gggaacagta gtcgc                   585
```

<210> SEQ ID NO 13
<211> LENGTH: 194
<212> TYPE: PRT
<213> ORGANISM: Escherichia coli

<400> SEQUENCE: 13

```
Met Asp Asn Gly Asp Arg Leu Tyr Arg Ala Asp Ser Arg Pro Pro Asp
1               5                   10                  15

Glu Ile Lys Arg Ser Gly Gly Leu Met Pro Arg Gly His Asn Glu Tyr
            20                  25                  30
```

```
Phe Asp Arg Gly Thr Gln Met Asn Ile Asn Leu Tyr Asp His Ala Arg
             35                  40                  45

Gly Thr Gln Thr Gly Phe Val Arg Tyr Asp Asp Gly Tyr Val Ser Thr
 50                  55                  60

Ser Leu Ser Leu Arg Ser Ala His Leu Ala Gly Gln Ser Ile Leu Ser
 65                  70                  75                  80

Gly Tyr Ser Thr Tyr Tyr Ile Tyr Val Ile Ala Thr Ala Pro Asn Met
                 85                  90                  95

Phe Asn Val Asn Asp Val Leu Gly Val Tyr Ser Pro His Pro Tyr Glu
            100                 105                 110

Gln Glu Val Ser Ala Leu Gly Ile Pro Tyr Ser Gln Ile Tyr Gly
            115                 120                 125

Trp Tyr Arg Val Asn Phe Gly Val Ile Asp Glu Arg Leu His Arg Asn
130                 135                 140

Arg Glu Tyr Arg Asp Arg Tyr Tyr Arg Asn Leu Asn Ile Ala Pro Ala
145                 150                 155                 160

Glu Asp Gly Tyr Arg Leu Ala Gly Phe Pro Asp His Gln Ala Trp
            165                 170                 175

Arg Glu Glu Pro Trp Ile His His Ala Pro Gln Gly Cys Gly Asn Ser
            180                 185                 190

Ser Arg

<210> SEQ ID NO 14
<211> LENGTH: 5
<212> TYPE: PRT
<213> ORGANISM: Artificial Sequence
<220> FEATURE:
<223> OTHER INFORMATION: synthetic construct

<400> SEQUENCE: 14

Gly Ser Ala Ala Ser
 1               5

<210> SEQ ID NO 15
<211> LENGTH: 3351
<212> TYPE: DNA
<213> ORGANISM: Artificial Sequence
<220> FEATURE:
<223> OTHER INFORMATION: synthetic construct

<400> SEQUENCE: 15
catatggaca atggcgatcg tttataccgt gccgactcgc gtcccccaga tgagattaaa      60
cgtagcggtg ggttaatgcc acgtgggcac aatgagtatt ttgaccgtgg aacacagatg     120
aacattaacc tttacgatca tgcccgtggg acccagaccg gtttgtccg ttatgatgac      180 gggtatgtta gtacgagttt gtccttacgc tccgcacacc ttgcgggaca agtatttta     240 tcaggctaca gcacatatta catttatgtg atcgccactg ccccaaacat gttcaatgtg     300
aacgatgtgt tggggttta cagcccccat ccatatgaac aagaagtctc ggcccttggg     360
gggatcccat atagccagat ttatggttgg taccgcgtaa attttggtgt gattgatgaa     420
cgtttgcatc gtaaccgtga ataccgcgat cgctactacc gtaacttgaa cattgcacct     480
gccgaggacg gctatcgttt agcgggattc ccacccgatc atcaggcgtg gcgtgaggaa     540
ccgtggatcc atcacgcccc tcaggggtgc gggaacagta gtcgcgggtc cgcggcatcc     600
atgaatataa caactctgac taatagtatt tccacctcat cattcagtcc aaacaatacc     660
aacggttcat caaccgaaac agttaattct gatataaaaa caacgaccag ttctcatcct     720
```

| | |
|---|---|
| gtaagttccc ttactatgct caacgacacc cttcataata tcagaacaac aaatcaggca | 780 |
| ttaaagaaag agcttttcaca aaaaacgttg actaaaacat cgctagaaga aatagcatta | 840 |
| cattcatctc agattagcat ggatgtaaat aaatccgctc aactattgga tattctttcc | 900 |
| aggaacgaat atccaattaa taaagacgca agagaattat tacattcagc cccgaaagaa | 960 |
| gccgagcttg atggagatca aatgatatct catagagaac tgtgggctaa aattgcaaac | 1020 |
| tccatcaatg atattaatga acagtatctg aaagtatatg aacatgccgt tagttcatat | 1080 |
| actcaaatgt atcaagattt tagcgctgtt ctttccagtc ttgccggctg gatctctccc | 1140 |
| ggaggtaacg acggaaactc cgtgaaatta caagtcaact cgcttaaaaa ggcattggaa | 1200 |
| gaactcaagg aaaaatataa agataaaccg ctatatccag caaataatac tgttagtcag | 1260 |
| gaacaagcaa ataaatggct tacagaatta ggtggaacaa tcggcaaggt atctcaaaaa | 1320 |
| aacgggggat atgttgtcag tataaacatg accccaatag acaatatgtt aaaaagctta | 1380 |
| gataatctag gtggaaatgg cgaggttgtg ctagataatg caaaatatca ggcatggaat | 1440 |
| gccggattct ctgccgaaga tgaaacaatg aaaaataatc ttcaaacttt agttcaaaaa | 1500 |
| tacagtaatg ccaatagtat ttttgataat ttagtaaagg ttttgagtag tacaataagc | 1560 |
| tcatgtacag atacagataa actttttctc catttcctcg agatgcataa tgtaagcacc | 1620 |
| acaaccactg gttttcctct tgccaaaata ttgacttcca ctgagcttgg agacaatact | 1680 |
| atccaagctg caaatgatgc agctaacaaa ttattttctc ttacaattgc tgatcttact | 1740 |
| gctaaccaaa atattaatac aactaatgca cactcaactt caaatatatt aatccctgaa | 1800 |
| cttaaagcac caaagtcatt aaatgcaagt tcccaactaa cgcttttaat tggaaacctt | 1860 |
| attcaaatac tcggtgaaaa atctttaact gcattaacaa ataaaattac tgcttggaag | 1920 |
| tcccagcaac aggcaagaca gcaaaaaaac ctagaattct ccgataaaat taacactctt | 1980 |
| ctatctgaaa ctgaaggact aaccagagac tatgaaaaac aaattaataa actaaaaaac | 2040 |
| gcagattcta aaataaaaga cctagaaaat aaaattaacc aaattcaaac aagattatcg | 2100 |
| aacctcgatc cagagtcacc agaaaagaaa aaattaagcc gggaagaaat acaactcact | 2160 |
| atcaaaaaag acgcagcagt taaagacagg acattgattg agcagaaaac cctgtcaatt | 2220 |
| catagcaaac ttacagataa atcaatgcaa ctcgaaaaag aaatagactc tttttctgca | 2280 |
| ttttcaaaca cagcatctgc tgaacagcta tcaacccagc agaaatcatt aaccggactt | 2340 |
| gccagtgtta ctcaattgat ggcaaccttt attcaactag ttggaaaaaa taatgaagaa | 2400 |
| tcttaaaaaa atgatctggc tctattccag tctctccaag aatcaagaaa aactgaaatg | 2460 |
| gagagaaaat ctgatgagta tgctgctgaa gtacgtaaag cagaagaact caacagagta | 2520 |
| atgggttgtg ttgggaaaat acttggggca cttttaacta tcgttagtgt tgttgcagca | 2580 |
| gcttttttctg gaggagcctc tctagcactg gcagctgttg gtttagctct tatggttacg | 2640 |
| gatgctatag tacaagcagc gaccggcaat tccttcatgg aacaagccct gaatccgatc | 2700 |
| atgaaagcag tcattgaacc cttaatcaaa ctcctttcag atgcatttac aaaaatgctc | 2760 |
| gaaggcttgg gcgtcgactc gaaaaaagcc aaaatgattg gctctattct gggggcaatc | 2820 |
| gcaggcgctc ttgtcctagt tgcagcagtc gttctcgtag ccactgttgg taaacaggca | 2880 |
| gcagcaaaac ttgcagaaaa tattggcaaa ataataggta aaaccctcac agaccttata | 2940 |
| ccaaagtttc tcaagaattt ttcttctcaa ctggacgatt taatcactaa tgctgttgcc | 3000 |
| agattaaata aatttcttgg tgcagcgggt gatgaagtaa tatccaaaca aattatttcc | 3060 |
| acccatttaa accaagcagt tttattagga gaaagtgtta actctgccac acaagcggga | 3120 |

```
ggaagtgtcg cttctgctgt tttccagaac agcgcgtcga caaatctagc agacctgaca   3180
ttatcgaaat atcaagttga acaactgtca aatatatca gtgaagcaat agaaaaattc    3240
ggccaattgc aggaagtaat tgcagatcta ttagcctcaa tgtccaactc tcaggctaat   3300
agaactgatg ttgcaaaagc aattttgcaa caaactactg cttgaggatc c            3351
```

<210> SEQ ID NO 16
<211> LENGTH: 1081
<212> TYPE: PRT
<213> ORGANISM: Artificial Sequence
<220> FEATURE:
<223> OTHER INFORMATION: synthetic construct

<400> SEQUENCE: 16

```
Met Asp Asn Gly Asp Arg Leu Tyr Arg Ala Asp Ser Arg Pro Pro Asp
1               5                   10                  15

Glu Ile Lys Arg Ser Gly Gly Leu Met Pro Arg Gly His Asn Glu Tyr
                20                  25                  30

Phe Asp Arg Gly Thr Gln Met Asn Ile Asn Leu Tyr Asp His Ala Arg
            35                  40                  45

Gly Thr Gln Thr Gly Phe Val Arg Tyr Asp Asp Gly Tyr Val Ser Thr
        50                  55                  60

Ser Leu Ser Leu Arg Ser Ala His Leu Ala Gly Gln Ser Ile Leu Ser
65                  70                  75                  80

Gly Tyr Ser Thr Tyr Tyr Ile Tyr Val Ile Ala Thr Ala Pro Asn Met
                85                  90                  95

Phe Asn Val Asn Asp Val Leu Gly Val Tyr Ser Pro His Pro Tyr Glu
            100                 105                 110

Gln Glu Val Ser Ala Leu Gly Gly Ile Pro Tyr Ser Gln Ile Tyr Gly
        115                 120                 125

Trp Tyr Arg Val Asn Phe Gly Val Ile Asp Glu Arg Leu His Arg Asn
130                 135                 140

Arg Glu Tyr Arg Asp Arg Tyr Tyr Arg Asn Leu Asn Ile Ala Pro Ala
145                 150                 155                 160

Glu Asp Gly Tyr Arg Leu Ala Gly Phe Pro Pro Asp His Gln Ala Trp
                165                 170                 175

Arg Glu Glu Pro Trp Ile His His Ala Pro Gln Gly Cys Gly Asn Ser
            180                 185                 190

Ser Arg Gly Ser Ala Ala Ser Met Asn Ile Thr Thr Leu Thr Asn Ser
        195                 200                 205

Ile Ser Thr Ser Ser Phe Ser Pro Asn Asn Thr Asn Gly Ser Ser Thr
    210                 215                 220

Glu Thr Val Asn Ser Asp Ile Lys Thr Thr Ser Ser His Pro Ser
225                 230                 235                 240

Ser Leu Thr Met Leu Asn Asp Thr Leu His Asn Ile Arg Thr Asn
                245                 250                 255

Gln Ala Leu Lys Lys Glu Leu Ser Gln Lys Thr Leu Arg Asn Glu Tyr
            260                 265                 270

Pro Ile Asn Lys Asp Ala Arg Glu Leu Leu His Ser Ala Pro Lys Glu
        275                 280                 285

Ala Glu Leu Asp Gly Asp Gln Met Ile Ser His Arg Glu Leu Trp Ala
    290                 295                 300

Lys Ile Ala Asn Ser Ile Asn Asp Ile Asn Glu Gln Tyr Leu Lys Val
305                 310                 315                 320
```

```
Tyr Glu His Ala Val Ser Ser Tyr Thr Gln Met Tyr Gln Asp Phe Ser
            325                 330                 335

Ala Val Leu Ser Ser Leu Ala Gly Trp Ile Ser Pro Gly Gly Asn Asp
            340                 345                 350

Gly Asn Ser Val Lys Leu Gln Val Asn Ser Leu Lys Lys Ala Leu Glu
            355                 360                 365

Glu Leu Lys Glu Lys Tyr Lys Asp Lys Pro Leu Tyr Pro Ala Asn Asn
370                 375                 380

Thr Val Ser Gln Glu Gln Ala Asn Lys Trp Leu Thr Glu Leu Gly Gly
385                 390                 395                 400

Thr Ile Gly Lys Val Ser Gln Lys Asn Gly Gly Tyr Val Val Ser Ile
                405                 410                 415

Asn Met Thr Pro Ile Asp Asn Met Leu Lys Ser Leu Asp Asn Leu Gly
            420                 425                 430

Gly Asn Gly Glu Val Val Leu Asp Asn Ala Lys Tyr Gln Ala Trp Asn
            435                 440                 445

Gly Phe Ser Ala Glu Asp Glu Thr Met Lys Asn Asn Leu Gln Thr Leu
    450                 455                 460

Val Gln Lys Tyr Ser Asn Ala Asn Ser Ile Phe Asp Asn Leu Val Lys
465                 470                 475                 480

Val Leu Ser Ser Thr Ile Ser Ser Cys Thr Asp Thr Asp Lys Leu Phe
                485                 490                 495

Leu His Phe Leu Glu Met His Asn Val Ser Thr Thr Thr Gly Phe
            500                 505                 510

Pro Leu Ala Lys Ile Leu Thr Ser Thr Glu Leu Gly Asp Asn Thr Ile
            515                 520                 525

Gln Ala Ala Asn Asp Ala Ala Asn Lys Leu Phe Ser Leu Thr Ile Ala
    530                 535                 540

Asp Leu Thr Ala Asn Gln Asn Ile Asn Thr Thr Asn Ala His Ser Thr
545                 550                 555                 560

Ser Asn Ile Leu Ile Pro Glu Leu Lys Ala Pro Lys Ser Leu Asn Ala
                565                 570                 575

Ser Ser Gln Leu Thr Leu Leu Ile Gly Asn Leu Ile Gln Ile Leu Gly
            580                 585                 590

Glu Lys Ser Leu Thr Ala Leu Thr Asn Lys Ile Thr Ala Trp Lys Ser
            595                 600                 605

Gln Gln Gln Ala Arg Gln Gln Lys Asn Leu Glu Phe Ser Asp Lys Ile
    610                 615                 620

Asn Thr Leu Leu Ser Glu Thr Glu Gly Leu Thr Arg Asp Tyr Glu Lys
625                 630                 635                 640

Gln Ile Asn Lys Leu Lys Asn Ala Asp Ser Lys Ile Lys Asp Leu Glu
                645                 650                 655

Asn Lys Ile Asn Gln Ile Gln Thr Arg Leu Ser Asn Leu Asp Pro Glu
            660                 665                 670

Ser Pro Glu Lys Lys Lys Leu Ser Arg Glu Ile Gln Leu Thr Ile
            675                 680                 685

Lys Lys Asp Ala Ala Val Lys Asp Arg Thr Leu Ile Glu Gln Lys Thr
    690                 695                 700

Leu Ser Ile His Ser Lys Leu Thr Asp Lys Ser Met Gln Leu Glu Lys
705                 710                 715                 720

Glu Ile Asp Ser Phe Ser Ala Phe Ser Asn Thr Ala Ser Ala Glu Gln
                725                 730                 735

Leu Ser Thr Gln Gln Lys Ser Leu Thr Gly Leu Ala Ser Val Thr Gln
```

740                 745                 750
Leu Met Ala Thr Phe Ile Gln Leu Val Gly Lys Asn Asn Glu Glu Ser
                755                 760                 765
Leu Lys Asn Asp Leu Ala Leu Phe Gln Ser Leu Gln Glu Ser Arg Lys
                770                 775                 780
Thr Glu Met Glu Arg Lys Ser Asp Glu Tyr Ala Ala Glu Val Arg Lys
785                 790                 795                 800
Ala Glu Glu Leu Asn Arg Val Met Gly Cys Val Gly Lys Ile Leu Gly
                    805                 810                 815
Ala Leu Leu Thr Ile Val Ser Val Ala Ala Ala Phe Ser Gly Gly
                    820                 825                 830
Ala Ser Leu Ala Leu Ala Ala Val Gly Leu Ala Leu Met Val Thr Asp
                    835                 840                 845
Ala Ile Val Gln Ala Ala Thr Gly Asn Ser Phe Met Glu Gln Ala Leu
                    850                 855                 860
Asn Pro Ile Met Lys Ala Val Ile Glu Pro Leu Ile Lys Leu Leu Ser
865                 870                 875                 880
Asp Ala Phe Thr Lys Met Leu Glu Gly Leu Gly Val Asp Ser Lys Lys
                    885                 890                 895
Ala Lys Met Ile Gly Ser Ile Leu Gly Ala Ile Ala Gly Ala Leu Val
                    900                 905                 910
Leu Val Ala Ala Val Leu Val Ala Thr Val Gly Lys Gln Ala Ala
                    915                 920                 925
Ala Lys Leu Ala Glu Asn Ile Gly Lys Ile Ile Gly Lys Thr Leu Thr
                    930                 935                 940
Asp Leu Ile Pro Lys Phe Leu Lys Asn Phe Ser Ser Gln Leu Asp Asp
945                 950                 955                 960
Leu Ile Thr Asn Ala Val Ala Arg Leu Asn Lys Phe Leu Gly Ala Ala
                    965                 970                 975
Gly Asp Glu Val Ile Ser Lys Gln Ile Ile Ser Thr His Leu Asn Gln
                    980                 985                 990
Ala Val Leu Leu Gly Glu Ser Val Asn Ser Ala Thr Gln Ala Gly Gly
                    995                1000                1005
Ser Val Ala Ser Ala Val Phe Gln Asn Ser Ala Ser Thr Asn Leu
                   1010                1015                1020
Ala Asp Leu Thr Leu Ser Lys Tyr Gln Val Glu Gln Leu Ser Lys
                   1025                1030                1035
Tyr Ile Ser Glu Ala Ile Glu Lys Phe Gly Gln Leu Gln Glu Val
                   1040                1045                1050
Ile Ala Asp Leu Leu Ala Ser Met Ser Asn Ser Gln Ala Asn Arg
                   1055                1060                1065
Thr Asp Val Ala Lys Ala Ile Leu Gln Gln Thr Thr Ala
                   1070                1075                1080

<210> SEQ ID NO 17
<211> LENGTH: 2415
<212> TYPE: DNA
<213> ORGANISM: Artificial Sequence
<220> FEATURE:
<223> OTHER INFORMATION: synthetic construct

<400> SEQUENCE: 17
catatggaca atggcgatcg tttataccgt gccgactcgc gtcccccaga tgagattaaa    60
cgtagcggtg ggttaatgcc acgtgggcac aatgagtatt ttgaccgtgg aacacagatg   120

```
aacattaacc tttacgatca tgcccgtggg acccagaccg ggtttgtccg ttatgatgac    180
gggtatgtta gtacgagttt gtccttacgc tccgcacacc ttgcgggaca aagtatttta    240
tcaggctaca gcacatatta catttatgtg atcgccactg ccccaaacat gttcaatgtg    300
aacgatgtgt tggggtttta cagcccccat ccatatgaac aagaagtctc ggcccttggg    360
gggatcccat atagccagat ttatggttgg taccgcgtaa attttggtgt gattgatgaa    420
cgtttgcatc gtaaccgtga ataccgcgat cgctactacc gtaacttgaa cattgcacct    480
gccgaggacg gctatcgttt agcgggattc ccacccgatc atcaggcgtg gcgtgaggaa    540
ccgtggatcc atcacgcccc tcaggggtgc gggaacagta gtcgcatgac cattgatctc    600
ggagtttcac tcacgtcgca ggccggcggc ctgcaaggca tcgacctcaa gagcatggat    660
atccagactc tcatggtgta tgtgcagggt cgtcgcgccg aactcctcac ggctcaaatg    720
cagacccagg ccgaagtggt gcagaaggcc aatgaacgca tggcgcagct caacgaggtc    780
ctgtccgcgc tgtcccgggc caaggccgag tttccgccca atccgaagcc gggcgacacc    840
atcccgggct gggacaacca aaggtcagcc ggatcgagg ttcctctcaa tgatgcgctg    900
cgcgctgccg gcctgacggg catgttcgaa gcgcgcgatg gccaagtgac cgcccccggc    960
ggccggggta cgcaggtcgt gaacggcacg ggcgtcatgg ccggttccac gacctataag   1020
gaactcgaaa gtgcctacac caccgtaaag gggatgctgg atacggcgtc caatacgcaa   1080
cagatggaca tgatcaggct gcaggccgcc agcaacaagc gcaacgaggc tttcgaggtc   1140
atgaccaaca ccgagaagcg gcgcagcgac ctgaacagtt ccatcaccaa caacatgcgc   1200
aagcttatga ccgtcatgag tacgaccata tccacagccc cgagcggcgc cgcgcttgcg   1260
ccgtctcgca tagatatgcg ggcaccggag cccgggagtg ccggcgaagg cgccggcatc   1320
ctggcgccgg tgacgacgct ggctctggcg gcgggccggc cggcttttcc agcgtcaccg   1380
tcgctgcgca ccgcgcccgt cctggatccg ccagtgcgcg atctcagccc cgccgacttg   1440
gccgacctgc tgcgcgtctt gcgatccagg gcggtggacg ggcagttggc cacggcgcgc   1500
gagaacctgc aggacgcgca agtcaaggcg aagcagaaca cccaggccca gctcgacaag   1560
ctggacgcat ggtttcggaa ggccgaagag gccgagagca agggatggct gagcaaggtg   1620
ttcggctgga tcggcaaggt gctggcggtc gtggcatcgg ccctggcggt gggctttgcc   1680
gccgtcgcca gcgtggccac cggcgcgcg ccacacccca tgctgctgct cagcggcatg   1740
gcactggtca gcgccgtgac atcgctggcc gaccagatat cgcaagaggc gggaggcccg   1800
cctatcagcc tgggcgggtt tctctccggg ctggccggac gtctgctgac agcgttgggg   1860
gtggatcagt cgcaggccga ccaaattgcc aagatcgtcg ccggcctggc cgtgcccgtc   1920
gtcttgctga tcgaaccccca gatgctgggc gaaatgcgc aaggcgtggc caggctggct   1980
ggcgccagcg atgccaccgc ggggtacata gccatggcga tgtccatcgt ggcggcgatc   2040
gcggtcgccg cgatcaatgc cgccggtaca gccggcgcgg gtagcgcttc ggcgatcaag   2100
ggggcctggg atcgggccgc cgcggtagcc acccaggtcc ttcaaggggg tacggcagtg   2160
gcgcaaggcg gcgtcggcgt gtcgatggca gtcgatcgca acaggccga tctcctggtc   2220
gccgacaagg cggatctggc ggcgagcctg acaaaactgc gggcggccat ggagcgtgag   2280
gcggacgata tcaagaagat cctggctcaa ttcgacgagg cctatcacat gatcgcgaag   2340
atgatcagcg atatggcgag tacgcacagc caggtcagcg ccaacctcgg gcggcgccag   2400
gcggtgtagc tcgag                                                    2415
```

<210> SEQ ID NO 18
<211> LENGTH: 801
<212> TYPE: PRT
<213> ORGANISM: Artificial Sequence
<220> FEATURE:
<223> OTHER INFORMATION: synthetic construct

<400> SEQUENCE: 18

```
Met Asp Asn Gly Asp Arg Leu Tyr Arg Ala Asp Ser Arg Pro Pro Asp
1               5                   10                  15

Glu Ile Lys Arg Ser Gly Gly Leu Met Pro Arg Gly His Asn Glu Tyr
            20                  25                  30

Phe Asp Arg Gly Thr Gln Met Asn Ile Asn Leu Tyr Asp His Ala Arg
        35                  40                  45

Gly Thr Gln Thr Gly Phe Val Arg Tyr Asp Asp Gly Tyr Val Ser Thr
    50                  55                  60

Ser Leu Ser Leu Arg Ser Ala His Leu Ala Gly Gln Ser Ile Leu Ser
65                  70                  75                  80

Gly Tyr Ser Thr Tyr Tyr Ile Tyr Val Ile Ala Thr Ala Pro Asn Met
                85                  90                  95

Phe Asn Val Asn Asp Val Leu Gly Val Tyr Ser Pro His Pro Tyr Glu
            100                 105                 110

Gln Glu Val Ser Ala Leu Gly Gly Ile Pro Tyr Ser Gln Ile Tyr Gly
        115                 120                 125

Trp Tyr Arg Val Asn Phe Gly Val Ile Asp Glu Arg Leu His Arg Asn
    130                 135                 140

Arg Glu Tyr Arg Asp Arg Tyr Tyr Arg Asn Leu Asn Ile Ala Pro Ala
145                 150                 155                 160

Glu Asp Gly Tyr Arg Leu Ala Gly Phe Pro Pro Asp His Gln Ala Trp
                165                 170                 175

Arg Glu Glu Pro Trp Ile His His Ala Pro Gln Gly Cys Gly Asn Ser
            180                 185                 190

Ser Arg Met Thr Ile Asp Leu Gly Val Ser Leu Thr Ser Gln Ala Gly
        195                 200                 205

Gly Leu Gln Gly Ile Asp Leu Lys Ser Met Asp Ile Gln Thr Leu Met
    210                 215                 220

Val Tyr Val Gln Gly Arg Arg Ala Glu Leu Leu Thr Ala Gln Met Gln
225                 230                 235                 240

Thr Gln Ala Glu Val Val Gln Lys Ala Asn Glu Arg Met Ala Gln Leu
                245                 250                 255

Asn Glu Val Leu Ser Ala Leu Ser Arg Ala Lys Ala Glu Phe Pro Pro
            260                 265                 270

Asn Pro Lys Pro Gly Asp Thr Ile Pro Gly Trp Asp Asn Gln Lys Val
        275                 280                 285

Ser Arg Ile Glu Val Pro Leu Asn Asp Ala Leu Arg Ala Ala Gly Leu
    290                 295                 300

Thr Gly Met Phe Glu Ala Arg Asp Gly Gln Val Thr Ala Pro Gly Gly
305                 310                 315                 320

Arg Gly Thr Gln Val Val Asn Gly Thr Gly Val Met Ala Gly Ser Thr
                325                 330                 335

Thr Tyr Lys Glu Leu Glu Ser Ala Tyr Thr Thr Val Lys Gly Met Leu
            340                 345                 350

Asp Thr Ala Ser Asn Thr Gln Gln Met Asp Met Ile Arg Leu Gln Ala
        355                 360                 365

Ala Ser Asn Lys Arg Asn Glu Ala Phe Glu Val Met Thr Asn Thr Glu
```

```
            370                 375                 380
Lys Arg Arg Ser Asp Leu Asn Ser Ser Ile Thr Asn Asn Met Arg Lys
385                 390                 395                 400

Leu Met Thr Val Met Ser Thr Thr Ile Ser Thr Ala Pro Ser Gly Ala
                405                 410                 415

Ala Leu Ala Pro Ser Arg Ile Asp Met Arg Ala Pro Glu Pro Gly Ser
            420                 425                 430

Ala Gly Glu Gly Ala Gly Ile Leu Ala Pro Val Thr Thr Leu Ala Leu
            435                 440                 445

Ala Ala Gly Arg Pro Ala Phe Pro Ala Ser Pro Ser Leu Arg Thr Ala
            450                 455                 460

Pro Val Leu Asp Pro Pro Val Arg Asp Leu Ser Pro Ala Asp Leu Ala
465                 470                 475                 480

Asp Leu Leu Arg Val Leu Arg Ser Arg Ala Val Asp Gly Gln Leu Ala
                485                 490                 495

Thr Ala Arg Glu Asn Leu Gln Asp Ala Gln Val Lys Ala Lys Gln Asn
            500                 505                 510

Thr Gln Ala Gln Leu Asp Lys Leu Asp Ala Trp Phe Arg Lys Ala Glu
            515                 520                 525

Glu Ala Glu Ser Lys Gly Trp Leu Ser Lys Val Phe Gly Trp Ile Gly
            530                 535                 540

Lys Val Leu Ala Val Val Ala Ser Ala Leu Ala Val Gly Phe Ala Ala
545                 550                 555                 560

Val Ala Ser Val Ala Thr Gly Ala Ala Thr Pro Met Leu Leu Leu
                565                 570                 575

Ser Gly Met Ala Leu Val Ser Ala Val Thr Ser Leu Ala Asp Gln Ile
                580                 585                 590

Ser Gln Glu Ala Gly Gly Pro Pro Ile Ser Leu Gly Gly Phe Leu Ser
            595                 600                 605

Gly Leu Ala Gly Arg Leu Leu Thr Ala Leu Gly Val Asp Gln Ser Gln
            610                 615                 620

Ala Asp Gln Ile Ala Lys Ile Val Ala Gly Leu Ala Val Pro Val Val
625                 630                 635                 640

Leu Leu Ile Glu Pro Gln Met Leu Gly Glu Met Ala Gln Gly Val Ala
                645                 650                 655

Arg Leu Ala Gly Ala Ser Asp Ala Thr Ala Gly Tyr Ile Ala Met Ala
            660                 665                 670

Met Ser Ile Val Ala Ala Ile Ala Val Ala Ala Ile Asn Ala Ala Gly
            675                 680                 685

Thr Ala Gly Ala Gly Ser Ala Ser Ala Ile Lys Gly Ala Trp Asp Arg
            690                 695                 700

Ala Ala Ala Val Ala Thr Gln Val Leu Gln Gly Gly Thr Ala Val Ala
705                 710                 715                 720

Gln Gly Gly Val Gly Val Ser Met Ala Val Asp Arg Lys Gln Ala Asp
            725                 730                 735

Leu Leu Val Ala Asp Lys Ala Asp Leu Ala Ala Ser Leu Thr Lys Leu
            740                 745                 750

Arg Ala Ala Met Glu Arg Glu Ala Asp Asp Ile Lys Lys Ile Leu Ala
            755                 760                 765

Gln Phe Asp Glu Ala Tyr His Met Ile Ala Lys Met Ile Ser Asp Met
            770                 775                 780

Ala Ser Thr His Ser Gln Val Ser Ala Asn Leu Gly Arg Arg Gln Ala
785                 790                 795                 800
```

Val

<210> SEQ ID NO 19
<211> LENGTH: 566
<212> TYPE: DNA
<213> ORGANISM: Artificial Sequence
<220> FEATURE:
<223> OTHER INFORMATION: synthetic construct

<400> SEQUENCE: 19

```
atgggcagca gccatcacca tcatcaccac agccaggatc cgatgacgca acgcgacgtg      60
aacatagacg acatcgaggc gcaggaaatg gcggcggcgc tgctggacgc ggtccagaac     120
ggcgcgacgc tgaaggacct gcatcaggtg ccgcaggacc tgatggacgg catctatgcg     180
ttcgcgtacc gcttctacca gcaggggcgg ctcgacgacg cggaggtgtt cttccgcttt     240
ctgcgcatct acgacttcta caacgccgaa tacgcgatgg gctcgcggc ggtgtgccag      300
ttgaagaagg agtacgcgcg ggcgatcgat ctgtatgcac tcgcgtattc gctgtcgaag     360
gacgaccacc ggccgatgtt ccacaccggc caatgccatc tgctgatggg caaggcggcg     420
ctcgcgcggc gctgcttcgg catcgtcgtc gagcgctcgc gcgacgagcg cctcgcgcag     480
aaggcgcagt cctatctcga cgggctcgac gaagtgggcg ccgacgcggc gcccgcatcc     540
gccgggaacg accactgagc ggccgc                                          566
```

<210> SEQ ID NO 20
<211> LENGTH: 185
<212> TYPE: PRT
<213> ORGANISM: Artificial Sequence
<220> FEATURE:
<223> OTHER INFORMATION: synthetic construct

<400> SEQUENCE: 20

```
Met Gly Ser Ser His His His His His His Ser Gln Asp Pro Met Thr
1               5                   10                  15

Gln Arg Asp Val Asn Ile Asp Ile Glu Ala Gln Glu Met Ala Ala
            20                  25                  30

Ala Leu Leu Asp Ala Val Gln Asn Gly Ala Thr Leu Lys Asp Leu His
        35                  40                  45

Gln Val Pro Gln Asp Leu Met Asp Gly Ile Tyr Ala Phe Ala Tyr Arg
    50                  55                  60

Phe Tyr Gln Gln Gly Arg Leu Asp Asp Ala Glu Val Phe Phe Arg Phe
65                  70                  75                  80

Leu Arg Ile Tyr Asp Phe Tyr Asn Ala Glu Tyr Ala Met Gly Leu Ala
                85                  90                  95

Ala Val Cys Gln Leu Lys Lys Glu Tyr Ala Arg Ala Ile Asp Leu Tyr
            100                 105                 110

Ala Leu Ala Tyr Ser Leu Ser Lys Asp Asp His Arg Pro Met Phe His
        115                 120                 125

Thr Gly Gln Cys His Leu Leu Met Gly Lys Ala Ala Leu Ala Arg Arg
    130                 135                 140

Cys Phe Gly Ile Val Val Glu Arg Ser Arg Asp Glu Arg Leu Ala Gln
145                 150                 155                 160

Lys Ala Gln Ser Tyr Leu Asp Gly Leu Asp Glu Val Gly Ala Asp Ala
                165                 170                 175

Ala Pro Ala Ser Ala Gly Asn Asp His
            180                 185
```

<210> SEQ ID NO 21
<211> LENGTH: 930
<212> TYPE: DNA
<213> ORGANISM: Burkholderia spp

<400> SEQUENCE: 21
catatgaaca tgcacgtgga catgggtcgt gcgctgaccg ttcgtgattg gccggcgctg 60
gaggcgctgg cgaaaaccat gccggcggat gcgggtgcgc gtgcgatgac cgatgatgac 120
ctgcgtgcgg cgggtgtgga ccgtcgtgtt ccggagcaga agctgggtgc ggcgattgat 180
gaattcgcga gcctgcgtct gccggatcgt atcgacggtc gtttcgtgga tggccgtcgt 240
gcgaacctga ccgtttttga tgatgcgcgt gttgcggttc gtggtcatgc gcgtgcgcaa 300
cgtaacctgc tggagcgtct ggagaccgaa ctgctgggtg gcaccctgga taccgcgggt 360
gacgaaggtg gcattcagcc ggacccgatc ctgcaaggcc tggtggatgt tatcggtcag 420
ggcaaaagcg atattgacgc gtacgcgacc atcgtggaag gtctgaccaa gtattttcaa 480
agcgtggcgg acgttatgag caaactgcag gattacatta gcgcgaagga tgacaaaaac 540
atgaagatcg acggtggcaa gatcaaagcg ctgattcagc aagtgatcga ccacctgccg 600
accatgcagc tgccgaaggg tgcggatatt gcgcgttggc gtaaagagct gggcgacgcg 660
gttagcatca gcgatagcgg tgtggttacc attaacccgg acaaactgat caagatgcgt 720
gatagcctgc cgccggatgg caccgtttgg gataccgcgc gttaccaagc gtggaacacc 780
gcgttcagcg gtcagaaagg ccagcatccg gaacgtcgtg cggatgcgcg tcgtaaatat 840
agccaccaga acagcaactt tgataacctg gtgaaggttc tgagcggtgc gattagcacc 900
ctgaccgaca cccagagcta tctgcaaatc 930

<210> SEQ ID NO 22
<211> LENGTH: 309
<212> TYPE: PRT
<213> ORGANISM: Burkholderia spp

<400> SEQUENCE: 22

Met Asn Met His Val Asp Met Gly Arg Ala Leu Thr Val Arg Asp Trp
1 5 10 15

Pro Ala Leu Glu Ala Leu Ala Lys Thr Met Pro Ala Asp Ala Gly Ala
20 25 30

Arg Ala Met Thr Asp Asp Asp Leu Arg Ala Ala Gly Val Asp Arg Arg
35 40 45

Val Pro Glu Gln Lys Leu Gly Ala Ala Ile Asp Glu Phe Ala Ser Leu
50 55 60

Arg Leu Pro Asp Arg Ile Asp Gly Arg Phe Val Asp Gly Arg Arg Ala
65 70 75 80

Asn Leu Thr Val Phe Asp Asp Ala Arg Val Ala Val Arg Gly His Ala
85 90 95

Arg Ala Gln Arg Asn Leu Leu Glu Arg Leu Glu Thr Glu Leu Leu Gly
100 105 110

Gly Thr Leu Asp Thr Ala Gly Asp Glu Gly Gly Ile Gln Pro Asp Pro
115 120 125

Ile Leu Gln Gly Leu Val Asp Val Ile Gly Gln Gly Lys Ser Asp Ile
130 135 140

Asp Ala Tyr Ala Thr Ile Val Glu Gly Leu Thr Lys Tyr Phe Gln Ser
145 150 155 160

Val Ala Asp Val Met Ser Lys Leu Gln Asp Tyr Ile Ser Ala Lys Asp

```
              165                 170                 175
Asp Lys Asn Met Lys Ile Asp Gly Gly Lys Ile Lys Ala Leu Ile Gln
                180                 185                 190

Gln Val Ile Asp His Leu Pro Thr Met Gln Leu Pro Lys Gly Ala Asp
            195                 200                 205

Ile Ala Arg Trp Arg Lys Glu Leu Gly Asp Ala Val Ser Ile Ser Asp
        210                 215                 220

Ser Gly Val Val Thr Ile Asn Pro Asp Lys Leu Ile Lys Met Arg Asp
225                 230                 235                 240

Ser Leu Pro Pro Asp Gly Thr Val Trp Asp Thr Ala Arg Tyr Gln Ala
                245                 250                 255

Trp Asn Thr Ala Phe Ser Gly Gln Lys Gly Gln His Pro Glu Arg Arg
            260                 265                 270

Ala Asp Ala Arg Arg Lys Tyr Ser His Gln Asn Ser Asn Phe Asp Asn
        275                 280                 285

Leu Val Lys Val Leu Ser Gly Ala Ile Ser Thr Leu Thr Asp Thr Gln
    290                 295                 300

Ser Tyr Leu Gln Ile
305
```

<210> SEQ ID NO 23
<211> LENGTH: 1869
<212> TYPE: DNA
<213> ORGANISM: Burkholderia spp

<400> SEQUENCE: 23

```
atgagcagcg gtgttcaagg tgcccggcg gcgaacgcga acgcgtacca gacccacccg      60
ctgcgtgatg cggcgagcgc gctgggcacc ctgagcccgc aggcgtatgt ggatgtggtt    120
agcgcggcgc aacgtaactt cctggagcgt atgagccaac tggcgagcga acagtgcgat    180
gcgcaaccgg cggcgcatga tgcgcgtctg gatgatcgtc cggcgctgcg tgcgccgcag    240
gaacgtgacg cgccgccgct gggtgcgagc gataccggta ccgtgcgag cggtgcggcg    300
aaactgaccg agctgctggg tgtgctgatg agcgttatta gcgcgagcag cctggacgaa    360
ctgaagcaac gtagcgatat ctggaaccag atgagcaaag cggcgcaaga caacctgagc    420
cgtctgagcg atgcgtttca gcgtgcgacc gacgaggcga agcggcggc ggatgcggcg    480
gaacaggcgc ggcggcggc gaagcaagcg ggtgcgacg cgaaagcggc ggatgcggcg    540
gtggatgcgg cgcaaaaacg ttacgatgac gcggttaagc agggcctgcc ggatgaccgt    600
ctgcaaagcc tgaaagcggc gctggagcag gcgcgtcagc aagcgggtga tgcgcatggt    660
cgtgcggatg cgctgcaggc ggatgcgacc aagaaactgg acgcggcgag cgcgctggcg    720
acccaagcgc gtgcgtgcga acagcaagtg gatgacgcgg ttaaccaggc gacccagcaa    780
tatggtgcga gcgcgagcct gcgtaccccg caaagcccgc gtctgagcgg tgcggcggag    840
ctgaccgcgg tgctgggcaa gctgcaggaa ctgattagca gcggcaacgt taaagagctg    900
gaaagcaagc agaaactgtt caccgagatg caagcgaagc gtgaggcgga actgcaaaag    960
aaaagcgacg aatatcaggc gcaagtgaag aaagcggagg aaatgcagaa acgatgggt   1020
tgcatcggca agattgtggg ttgggttatt accgcggtta gctttgcggc ggcggcgttt   1080
accggtggcg cgagcctggc gctggcggcg gtgggcctgg cgctggcggt tggtgacgag   1140
attagccgtg cgaccaccgg tgtgagcttc atggacaagc tgatgcagcc ggttatggat   1200
gcgatcctga accgctgat ggagatgatt agcagcctga tcaccaaggc gctggttgcg   1260
```

-continued

```
tgcggcgttg atcagcaaaa agcggaactg gcgggtgcga ttctgggtgc ggttgttacc    1320
ggtgtggcgc tggttgcggc ggcgtttgtt ggtgcgagcg cggtgaaagc ggttgcgagc    1380
aaggttatcg acgcgatggc gggtcagctg accaagctga tggatagcgc gattggcaaa    1440
atgctggtgc aactgatcga gaaattcagc gaaaagagcg tcctgcaggc gctgggtagc    1500
cgtaccgcga ccgcgatgac ccgtatgcgt cgtgcgattg gcgttgaggc gaaggaagac    1560
ggtatgctgc tggcgaaccg ttttgaaaaa gcgggcaccg tgatgaacgt tggtaaccaa    1620
gtgagccaag cggcgggtgg cattgtggtt ggcgttgagc gtgcgaaagc gatgggtctg    1680
ctggcggatg tgaaagaagc gatgtatgac atcaagctgc tggtgatctg ctgaaacag    1740 gcggtggacg cgtttgcgga gcacaaccgt gttctggcgc aactgatgca gcaaatgagc    1800
gatgcgggcg aaatgcagac cagcaccggc aagctgatcc tgcgtaacgc gcgtgcggtt    1860
taaggatcc                                                            1869
```

<210> SEQ ID NO 24
<211> LENGTH: 620
<212> TYPE: PRT
<213> ORGANISM: Burkholderia spp

<400> SEQUENCE: 24

```
Met Ser Ser Gly Val Gln Gly Gly Pro Ala Ala Asn Ala Asn Ala Tyr
1               5                   10                  15

Gln Thr His Pro Leu Arg Asp Ala Ala Ser Ala Leu Gly Thr Leu Ser
            20                  25                  30

Pro Gln Ala Tyr Val Asp Val Val Ser Ala Ala Gln Arg Asn Phe Leu
        35                  40                  45

Glu Arg Met Ser Gln Leu Ala Ser Glu Gln Cys Asp Ala Gln Pro Ala
    50                  55                  60

Ala His Asp Ala Arg Leu Asp Asp Arg Pro Ala Leu Arg Ala Pro Gln
65                  70                  75                  80

Glu Arg Asp Ala Pro Pro Leu Gly Ala Ser Asp Thr Gly Ser Arg Ala
                85                  90                  95

Ser Gly Ala Ala Lys Leu Thr Glu Leu Leu Gly Val Leu Met Ser Val
            100                 105                 110

Ile Ser Ala Ser Ser Leu Asp Glu Leu Lys Gln Arg Ser Asp Ile Trp
        115                 120                 125

Asn Gln Met Ser Lys Ala Ala Gln Asp Asn Leu Ser Arg Leu Ser Asp
    130                 135                 140

Ala Phe Gln Arg Ala Thr Asp Glu Ala Lys Ala Ala Asp Ala Ala
145                 150                 155                 160

Glu Gln Ala Ala Ala Ala Lys Gln Ala Gly Ala Asp Ala Lys Ala
                165                 170                 175

Ala Asp Ala Ala Val Asp Ala Gln Lys Arg Tyr Asp Asp Ala Val
            180                 185                 190

Lys Gln Gly Leu Pro Asp Asp Arg Leu Gln Ser Leu Lys Ala Ala Leu
        195                 200                 205

Glu Gln Ala Arg Gln Gln Ala Gly Asp Ala His Gly Arg Ala Asp Ala
    210                 215                 220

Leu Gln Ala Asp Ala Thr Lys Lys Leu Asp Ala Ser Ala Leu Ala
225                 230                 235                 240

Thr Gln Ala Arg Ala Cys Glu Gln Gln Val Asp Asp Ala Val Asn Gln
                245                 250                 255

Ala Thr Gln Gln Tyr Gly Ala Ser Ala Ser Leu Arg Thr Pro Gln Ser
```

```
                260               265                270
Pro Arg Leu Ser Gly Ala Ala Glu Leu Thr Ala Val Leu Gly Lys Leu
        275                 280                 285
Gln Glu Leu Ile Ser Ser Gly Asn Val Lys Glu Leu Glu Ser Lys Gln
        290                 295                 300
Lys Leu Phe Thr Glu Met Gln Ala Lys Arg Glu Ala Glu Leu Gln Lys
305                 310                 315                 320
Lys Ser Asp Glu Tyr Gln Ala Gln Val Lys Lys Ala Glu Glu Met Gln
                325                 330                 335
Lys Thr Met Gly Cys Ile Gly Lys Ile Val Gly Trp Val Ile Thr Ala
                340                 345                 350
Val Ser Phe Ala Ala Ala Ala Phe Thr Gly Gly Ala Ser Leu Ala Leu
            355                 360                 365
Ala Ala Val Gly Leu Ala Leu Ala Val Gly Asp Glu Ile Ser Arg Ala
        370                 375                 380
Thr Thr Gly Val Ser Phe Met Asp Lys Leu Met Gln Pro Val Met Asp
385                 390                 395                 400
Ala Ile Leu Lys Pro Leu Met Glu Met Ile Ser Ser Leu Ile Thr Lys
                405                 410                 415
Ala Leu Val Ala Cys Gly Val Asp Gln Gln Lys Ala Glu Leu Ala Gly
                420                 425                 430
Ala Ile Leu Gly Ala Val Val Thr Gly Val Ala Leu Val Ala Ala Ala
            435                 440                 445
Phe Val Gly Ala Ser Ala Val Lys Ala Val Ala Ser Lys Val Ile Asp
        450                 455                 460
Ala Met Ala Gly Gln Leu Thr Lys Leu Met Asp Ser Ala Ile Gly Lys
465                 470                 475                 480
Met Leu Val Gln Leu Ile Glu Lys Phe Ser Lys Ser Gly Leu Gln
                485                 490                 495
Ala Leu Gly Ser Arg Thr Ala Thr Ala Met Thr Arg Met Arg Arg Ala
                500                 505                 510
Ile Gly Val Glu Ala Lys Glu Asp Gly Met Leu Leu Ala Asn Arg Phe
            515                 520                 525
Glu Lys Ala Gly Thr Val Met Asn Val Gly Asn Gln Val Ser Gln Ala
        530                 535                 540
Ala Gly Gly Ile Val Val Gly Val Glu Arg Ala Lys Ala Met Gly Leu
545                 550                 555                 560
Leu Ala Asp Val Lys Glu Ala Met Tyr Asp Ile Lys Leu Leu Gly Asp
                565                 570                 575
Leu Leu Lys Gln Ala Val Asp Ala Phe Ala Glu His Asn Arg Val Leu
                580                 585                 590
Ala Gln Leu Met Gln Met Ser Asp Ala Gly Glu Met Gln Thr Ser
            595                 600                 605
Thr Gly Lys Leu Ile Leu Arg Asn Ala Arg Ala Val
        610                 615                 620

<210> SEQ ID NO 25
<211> LENGTH: 2805
<212> TYPE: DNA
<213> ORGANISM: Artificial Sequence
<220> FEATURE:
<223> OTHER INFORMATION: synthetic construct

<400> SEQUENCE: 25
catatgaaca tgcacgtgga catgggtcgt gcgctgaccg ttcgtgattg gccggcgctg    60
```

```
gaggcgctgg cgaaaaccat gccggcggat gcgggtgcgc gtgcgatgac cgatgatgac    120
ctgcgtgcgg cgggtgtgga ccgtcgtgtt ccggagcaga agctgggtgc ggcgattgat    180
gaattcgcga gcctgcgtct gccggatcgt atcgacggtc gtttcgtgga tggccgtcgt    240
gcgaacctga ccgtttttga tgatgcgcgt gttgcggttc gtggtcatgc gcgtgcgcaa    300
cgtaacctgc tggagcgtct ggagaccgaa ctgctgggtg caccctggga taccgcgggt    360
gacgaaggtg gcattcagcc ggacccgatc ctgcaaggcc tggtggatgt tatccggtcag   420 ggcaaaagcg atattgacgc gtacgcgacc atcgtggaag gtctgaccaa gtatttcaa    480 agcgtggcg acgttatgag caaactgcag gattacatta gcgcgaagga tgacaaaaac    540
atgaagatcg acggtggcaa gatcaaagcg ctgattcagc aagtgatcga ccacctgccg    600
accatgcagc tgccgaaggg tgcggatatt gcgcgttggc gtaaagagct gggcgacgcg    660
gttagcatca gcgatagcgg tgtggttacc attaacccgg acaaactgat caagatgcgt    720
gatagcctgc cgccggatgg caccgtttgg gataccgcgc gttaccaagc gtggaacacc    780
gcgttcagcg gtcagaaagg ccagcatccg gaacgtcgtg cggatgcgcg tcgtaaatat    840
agccaccaga acagcaactt tgataacctg gtgaaggttc tgagcggtgc gattagcacc    900
ctgaccgaca cccagagcta tctgcaaatc aagcttatga gcagcggtgt tcaaggtggc    960
ccggcggcga acgcgaacgc gtaccagacc cacccgctgc gtgatgcggc gagcgcgctg   1020
ggcaccctga gcccgcaggc gtatgtggat gtggttagcg cggcgcaacg taacttcctg   1080
gagcgtatga gccaactggc gagcgaacag tgcgatgcgc aaccggcggc gcatgatgcg   1140
cgtctggatg atcgtccggc gctgcgtgcg ccgcaggaac gtgacgcgcc gccgctgggt   1200
gcgagcgata ccggtagccg tgcgagcggt gcggcgaaac tgaccgagct gctgggtgtg   1260
ctgatgagcg ttattagcgc gagcagcctg gacgaactga agcaacgtag cgatatctgg   1320
aaccagatga gcaaagcggc gcaagacaac ctgagccgtc tgagcgatgc gtttcagcgt   1380
gcgaccgacg aggcgaaagc ggcggcggat gcggcggaac aggcggcggc ggcggcgaag   1440
caagcgggtg cggacgcgaa agcggcggat gcggcgtgg atgcggcgca aaaacgttac   1500
gatgacgcgg ttaagcaggg cctgccggat gaccgtctgc aaagcctgaa agcggcgctg   1560
gagcaggcgc gtcagcaagc gggtgatgcg catggtcgtg cggatgcgct gcaggcggat   1620
gcgaccaaga aactggacgc ggcgagcgcg ctggcgaccc aagcgcgtgc gtgcgaacag   1680
caagtggatg acgcggttaa ccaggcgacc cagcaatatg tgcgagcgc gagcctgcgt   1740 accccgcaaa gcccgcgtct gagcggtgcg gcggagctga ccgcggtgct gggcaagctg   1800
caggaactga ttagcagcgg caacgttaaa gagctggaaa gcaagcagaa actgttcacc   1860
gagatgcaag cgaagcgtga ggcggaactg caaaagaaaa gcgacgaata tcaggcgcaa   1920
gtgaagaaag cggaggaaat gcagaaaacg atgggttgca tcggcaagat tgtgggttgg   1980
gttattaccg cggttagctt tgcggcgcg cgtttaccg gtggcgcgag cctggcgctg   2040
gcggcggtgg gcctggcgct ggcggttggt gacgagatta gccgtgcgac caccggtgtg   2100
agcttcatgg acaagctgat gcagccggtt atgatgcga tcctgaaacc gctgatggag   2160
atgattagca gcctgatcac caaggcgctg gttgcgtgcg gcgttgatca gcaaaaagcg   2220
gaactggcgg gtgcgattct gggtgcggtt gttaccggtg tggcgctggt tgcggcggcg   2280
tttgttggtg cgagcgcggt gaaagcggtt gcgagcaagg ttatcgacgc gatgcgggt   2340 cagctgacca agctgatgga tagcgcgatt ggcaaaatgc tggtgcaact gatcgagaaa   2400
```

-continued

```
ttcagcgaaa agagcggtct gcaggcgctg ggtagccgta ccgcgaccgc gatgacccgt    2460
atgcgtcgtg cgattggcgt tgaggcgaag gaagacggta tgctgctggc gaaccgtttt    2520
gaaaaagcgg gcaccgtgat gaacgttggt aaccaagtga gccaagcggc gggtggcatt    2580
gtggttggcg ttgagcgtgc gaaagcgatg ggtctgctgg cggatgtgaa agaagcgatg    2640
tatgacatca agctgctggg tgatctgctg aaacaggcgg tggacgcgtt tgcggagcac    2700
aaccgtgttc tggcgcaact gatgcagcaa atgagcgatg cgggcgaaat gcagaccagc    2760
accggcaagc tgatcctgcg taacgcgcgt gcggtttaag gatcc                    2805
```

<210> SEQ ID NO 26
<211> LENGTH: 931
<212> TYPE: PRT
<213> ORGANISM: Artificial Sequence
<220> FEATURE:
<223> OTHER INFORMATION: synthetic construct

<400> SEQUENCE: 26

```
Met Asn Met His Val Asp Met Gly Arg Ala Leu Thr Val Arg Asp Trp
1               5                   10                  15

Pro Ala Leu Glu Ala Leu Ala Lys Thr Met Pro Ala Asp Ala Gly Ala
            20                  25                  30

Arg Ala Met Thr Asp Asp Leu Arg Ala Ala Gly Val Asp Arg Arg
        35                  40                  45

Val Pro Glu Gln Lys Leu Gly Ala Ala Ile Asp Glu Phe Ala Ser Leu
    50                  55                  60

Arg Leu Pro Asp Arg Ile Asp Gly Arg Phe Val Asp Gly Arg Arg Ala
65                  70                  75                  80

Asn Leu Thr Val Phe Asp Asp Ala Arg Val Ala Val Arg Gly His Ala
                85                  90                  95

Arg Ala Gln Arg Asn Leu Leu Glu Arg Leu Glu Thr Glu Leu Leu Gly
            100                 105                 110

Gly Thr Leu Asp Thr Ala Gly Asp Glu Gly Ile Gln Pro Asp Pro
        115                 120                 125

Ile Leu Gln Gly Leu Val Asp Val Ile Gly Gln Gly Lys Ser Asp Ile
130                 135                 140

Asp Ala Tyr Ala Thr Ile Val Glu Gly Leu Thr Lys Tyr Phe Gln Ser
145                 150                 155                 160

Val Ala Asp Val Met Ser Lys Leu Gln Asp Tyr Ile Ser Ala Lys Asp
                165                 170                 175

Asp Lys Asn Met Lys Ile Asp Gly Gly Lys Ile Lys Ala Leu Ile Gln
            180                 185                 190

Gln Val Ile Asp His Leu Pro Thr Met Gln Leu Pro Lys Gly Ala Asp
        195                 200                 205

Ile Ala Arg Trp Arg Lys Glu Leu Gly Asp Ala Val Ser Ile Ser Asp
    210                 215                 220

Ser Gly Val Val Thr Ile Asn Pro Asp Lys Leu Ile Lys Met Arg Asp
225                 230                 235                 240

Ser Leu Pro Pro Asp Gly Thr Val Trp Asp Thr Ala Arg Tyr Gln Ala
                245                 250                 255

Trp Asn Thr Ala Phe Ser Gly Gln Lys Gly Gln His Pro Glu Arg Arg
            260                 265                 270

Ala Asp Ala Arg Arg Lys Tyr Ser His Gln Asn Ser Asn Phe Asp Asn
        275                 280                 285

Leu Val Lys Val Leu Ser Gly Ala Ile Ser Thr Leu Thr Asp Thr Gln
```

```
            290                 295                 300
Ser Tyr Leu Gln Ile Lys Leu Met Ser Ser Gly Val Gln Gly Gly Pro
305                 310                 315                 320

Ala Ala Asn Ala Asn Ala Tyr Gln Thr His Pro Leu Arg Asp Ala Ala
                325                 330                 335

Ser Ala Leu Gly Thr Leu Ser Pro Gln Ala Tyr Val Asp Val Val Ser
                340                 345                 350

Ala Ala Gln Arg Asn Phe Leu Glu Arg Met Ser Gln Leu Ala Ser Glu
            355                 360                 365

Gln Cys Asp Ala Gln Pro Ala Ala His Asp Ala Arg Leu Asp Asp Arg
        370                 375                 380

Pro Ala Leu Arg Ala Pro Gln Glu Arg Asp Ala Pro Pro Leu Gly Ala
385                 390                 395                 400

Ser Asp Thr Gly Ser Arg Ala Ser Gly Ala Ala Lys Leu Thr Glu Leu
                405                 410                 415

Leu Gly Val Leu Met Ser Val Ile Ser Ala Ser Ser Leu Asp Glu Leu
                420                 425                 430

Lys Gln Arg Ser Asp Ile Trp Asn Gln Met Ser Lys Ala Ala Gln Asp
            435                 440                 445

Asn Leu Ser Arg Leu Ser Asp Ala Phe Gln Arg Ala Thr Asp Glu Ala
        450                 455                 460

Lys Ala Ala Ala Asp Ala Ala Glu Gln Ala Ala Ala Ala Ala Lys Gln
465                 470                 475                 480

Ala Gly Ala Asp Ala Lys Ala Asp Ala Ala Val Asp Ala Ala Gln
            485                 490                 495

Lys Arg Tyr Asp Asp Ala Val Lys Gln Gly Leu Pro Asp Asp Arg Leu
                500                 505                 510

Gln Ser Leu Lys Ala Ala Leu Glu Gln Ala Arg Gln Ala Gly Asp
            515                 520                 525

Ala His Gly Arg Ala Asp Ala Leu Gln Ala Asp Ala Thr Lys Lys Leu
        530                 535                 540

Asp Ala Ala Ser Ala Leu Ala Thr Gln Ala Arg Ala Cys Glu Gln Gln
545                 550                 555                 560

Val Asp Asp Ala Val Asn Gln Ala Thr Gln Gln Tyr Gly Ala Ser Ala
                565                 570                 575

Ser Leu Arg Thr Pro Gln Ser Pro Arg Leu Ser Gly Ala Ala Glu Leu
                580                 585                 590

Thr Ala Val Leu Gly Lys Leu Gln Glu Leu Ile Ser Ser Gly Asn Val
            595                 600                 605

Lys Glu Leu Glu Ser Lys Gln Lys Leu Phe Thr Glu Met Gln Ala Lys
        610                 615                 620

Arg Glu Ala Glu Leu Gln Lys Lys Ser Asp Glu Tyr Gln Ala Gln Val
625                 630                 635                 640

Lys Lys Ala Glu Glu Met Gln Lys Thr Met Gly Cys Ile Gly Lys Ile
                645                 650                 655

Val Gly Trp Val Ile Thr Ala Val Ser Phe Ala Ala Ala Phe Thr
            660                 665                 670

Gly Gly Ala Ser Leu Ala Leu Ala Ala Val Gly Leu Ala Leu Ala Val
        675                 680                 685

Gly Asp Glu Ile Ser Arg Ala Thr Thr Gly Val Ser Phe Met Asp Lys
            690                 695                 700

Leu Met Gln Pro Val Met Asp Ala Ile Leu Lys Pro Leu Met Glu Met
705                 710                 715                 720
```

| | | | | | | | | | | | |
|---|---|---|---|---|---|---|---|---|---|---|---|
| Ile | Ser | Ser | Leu | Ile | Thr | Lys | Ala | Leu | Val | Ala | Cys | Gly | Val | Asp | Gln |
| | | | 725 | | | | 730 | | | | 735 |

Ile Ser Ser Leu Ile Thr Lys Ala Leu Val Ala Cys Gly Val Asp Gln
                725                 730                 735

Gln Lys Ala Glu Leu Ala Gly Ala Ile Leu Gly Ala Val Val Thr Gly
            740                 745                 750

Val Ala Leu Val Ala Ala Phe Val Gly Ala Ser Ala Val Lys Ala
        755                 760                 765

Val Ala Ser Lys Val Ile Asp Ala Met Ala Gly Gln Leu Thr Lys Leu
        770                 775                 780

Met Asp Ser Ala Ile Gly Lys Met Leu Val Gln Leu Ile Glu Lys Phe
785                 790                 795                 800

Ser Glu Lys Ser Gly Leu Gln Ala Leu Gly Ser Arg Thr Ala Thr Ala
                805                 810                 815

Met Thr Arg Met Arg Arg Ala Ile Gly Val Glu Ala Lys Glu Asp Gly
                820                 825                 830

Met Leu Leu Ala Asn Arg Phe Glu Lys Ala Gly Thr Val Met Asn Val
                835                 840                 845

Gly Asn Gln Val Ser Gln Ala Ala Gly Gly Ile Val Val Gly Val Glu
    850                 855                 860

Arg Ala Lys Ala Met Gly Leu Leu Ala Asp Val Lys Glu Ala Met Tyr
865                 870                 875                 880

Asp Ile Lys Leu Leu Gly Asp Leu Leu Lys Gln Ala Val Asp Ala Phe
                885                 890                 895

Ala Glu His Asn Arg Val Leu Ala Gln Leu Met Gln Gln Met Ser Asp
                900                 905                 910

Ala Gly Glu Met Gln Thr Ser Thr Gly Lys Leu Ile Leu Arg Asn Ala
            915                 920                 925

Arg Ala Val
    930

<210> SEQ ID NO 27
<211> LENGTH: 3390
<212> TYPE: DNA
<213> ORGANISM: Artificial Sequence
<220> FEATURE:
<223> OTHER INFORMATION: synthetic construct

<400> SEQUENCE: 27

| | | |
|---|---|---|
| catatggaca atggcgatcg tttataccgt gccgactcgc gtcccccaga tgagattaaa | 60 |
| cgtagcggtg ggttaatgcc acgtgggcac aatgagtatt ttgaccgtgg aacacagatg | 120 |
| aacattaacc tttacgatca tgcccgtggg acccagaccg ggtttgtccg ttatgatgac | 180 |
| gggtatgtta gtacgagttt gtccttacgc tccgcacacc ttgcgggaca agtatttta | 240 |
| tcaggctaca gcacatatta catttatgtg atcgccactg ccccaaacat gttcaatgtg | 300 |
| aacgatgtgt gggggtttta cagcccccat ccatatgaac aagaagtctc ggcccttggg | 360 |
| gggatcccat atagccagat ttatggttgg taccgcgtaa attttggtgt gattgatgaa | 420 |
| cgtttgcatc gtaaccgtga ataccgcgat cgctactacc gtaacttgaa cattgcacct | 480 |
| gccgaggacg gctatcgttt agcgggattc ccacccgatc atcaggcgtg gcgtgaggaa | 540 |
| ccgtggatcc atcacgcccc tcaggggtgc gggaacagta gtcgccatat gaacatgcac | 600 |
| gtggacatgg tcgtgcgct accgttcgt gattggccgg cgctggaggc gctggcgaaa | 660 |
| accatgccgg cggatgcggg tgcgcgtgcg atgaccgatg atgacctgcg tgcggcgggt | 720 |
| gtggaccgtc gtgttccgga gcagaagctg ggtgcggcga ttgatgaatt cgcgagcctg | 780 |

```
cgtctgccgg atcgtatcga cggtcgtttc gtggatggcc gtcgtgcgaa cctgaccgtt    840
tttgatgatg cgcgtgttgc ggttcgtggt catgcgcgtg cgcaacgtaa cctgctggag    900
cgtctggaga ccgaactgct gggtggcacc ctggataccg cgggtgacga aggtggcatt    960
cagccggacc cgatcctgca aggcctggtg gatgttatcg gtcagggcaa aagcgatatt   1020
gacgcgtacg cgaccatcgt ggaaggtctg accaagtatt tcaaagcgt ggcggacgtt   1080 atgagcaaac tgcaggatta cattagcgcg aaggatgaca aaaacatgaa gatcgacggt   1140
ggcaagatca aagcgctgat tcagcaagtg atcgaccacc tgccgaccat gcagctgccg   1200
aagggtgcgg atattgcgcg ttggcgtaaa gagctgggcg acgcggttag catcagcgat   1260
agcggtgtgg ttaccattaa cccggacaaa ctgatcaaga tgcgtgatag cctgccgccg   1320
gatggcaccg tttgggatac cgcgcgttac aagcgtgga acaccgcgtt cagcggtcag   1380
aaaggccagc atccggaacg tcgtgcggat gcgcgtcgta atatagcca ccagaacagc   1440 aactttgata acctggtgaa ggttctgagc ggtgcgatta gcaccctgac cgacacccag   1500
agctatctgc aaatcaagct tatgagcagc ggtgttcaag gtggcccggc ggcgaacgcg   1560
aacgcgtacc agacccaccc gctgcgtgat gcggcgagcg cgctgggcac cctgagcccg   1620
caggcgtatg tggatgtggt tagcgcggcg caacgtaact tcctggagcg tatgagccaa   1680
ctggcgagcg aacagtgcga tgcgcaaccg gcggcgcatg atgcgcgtct ggatgatcgt   1740
ccggcgctgc gtgcgccgca ggaacgtgac gcgccgccgc tgggtgcgag cgataccggt   1800
agccgtgcga gcggtgcggc gaaactgacc gagctgctgg gtgtgctgat gagcgttatt   1860
agcgcgagca gcctggacga actgaagcaa cgtagcgata tctggaacca gatgagcaaa   1920
gcggcgcaag acaacctgag ccgtctgagc gatgcgtttc agcgtgcgac cgacgaggcg   1980
aaagcggcgc cggatgcggc ggaacaggcg cggcggcgg cgaagcaagc gggtgcggac   2040
gcgaaagcgg cggatgcggc ggtggatgcg gcgcaaaaac gttacgatga cgcggttaag   2100
cagggcctgc cggatgaccg tctgcaaagc ctgaaagcgg cgctggagca ggcgcgtcag   2160
caagcgggtg atgcgcatgg tcgtgcggat gcgctgcagg cggatgcgac caagaaactg   2220
gacgcggcga gcgcgctggc gacccaagcg cgtgcgtgcg aacagcaagt ggatgacgcg   2280
gttaaccagg cgacccagca atatggtgcg agcgcgagcc tgcgtacccc gcaaagcccg   2340
cgtctgagcg gtgcggcgga gctgaccgcg gtgctgggca agctgcagga actgattagc   2400
agcggcaacg ttaaagagct ggaaagcaag cagaaactgt tcaccgagat gcaagcgaag   2460
cgtgaggcgg aactgcaaaa gaaaagcgac gaatatcagg cgcaagtgaa gaaagcggag   2520
gaaatgcaga aaacgatggg ttgcatcggc aagattgtgg gttgggttat taccgcggtt   2580
agctttgcgg cggcggcgtt taccggtggc gcgagcctgg cgctggcggc ggtgggcctg   2640
gcgctggcgg ttggtgacga gattagccgt gcgaccaccg gtgtgagctt catggacaag   2700
ctgatgcagc cggttatgga tgcgatcctg aaaccgctga tggagatgat tagcagcctg   2760
atcaccaagg cgctggttgc gtgcggcgtt gatcagcaaa aagcggaact ggcgggtgcg   2820
attctgggtg cggttgttac cggtgtggcg ctggttgcgg cggcgtttgt tggtgcgagc   2880
gcggtgaaag cggttgcgag caaggttatc gacgcgatgg cgggtcagct gaccaagctg   2940
atggatagcg cgattggcaa aatgctggtg caactgatcg agaaattcag cgaaaagagc   3000
ggtctgcagg cgctgggtag ccgtaccgcg accgcgatga cccgtatgcg tcgtgcgatt   3060
ggcgttgagg cgaaggaaga cggtatgctg ctggcgaacc gttttgaaaa agcgggcacc   3120
gtgatgaacg ttggtaacca agtgagccaa gcggcgggtg gcattgtggt tggcgttgag   3180
```

-continued

```
cgtgcgaaag cgatgggtct gctggcggat gtgaaagaag cgatgtatga catcaagctg   3240
ctgggtgatc tgctgaaaca ggcggtggac gcgtttgcgg agcacaaccg tgttctggcg   3300
caactgatgc agcaaatgag cgatgcgggc gaaatgcaga ccagcaccgg caagctgatc   3360
ctgcgtaacg cgcgtgcggt ttaaggatcc                                    3390
```

<210> SEQ ID NO 28
<211> LENGTH: 1125
<212> TYPE: PRT
<213> ORGANISM: Artificial Sequence
<220> FEATURE:
<223> OTHER INFORMATION: synthetic construct

<400> SEQUENCE: 28

```
Met Asp Asn Gly Asp Arg Leu Tyr Arg Ala Asp Ser Arg Pro Pro Asp
1               5                  10                  15

Glu Ile Lys Arg Ser Gly Gly Leu Met Pro Arg Gly His Asn Glu Tyr
            20                  25                  30

Phe Asp Arg Gly Thr Gln Met Asn Ile Asn Leu Tyr Asp His Ala Arg
        35                  40                  45

Gly Thr Gln Thr Gly Phe Val Arg Tyr Asp Asp Gly Tyr Val Ser Thr
    50                  55                  60

Ser Leu Ser Leu Arg Ser Ala His Leu Ala Gly Gln Ser Ile Leu Ser
65                  70                  75                  80

Gly Tyr Ser Thr Tyr Tyr Ile Tyr Val Ile Ala Thr Ala Pro Asn Met
                85                  90                  95

Phe Asn Val Asn Asp Val Leu Gly Val Tyr Ser Pro His Pro Tyr Glu
            100                 105                 110

Gln Glu Val Ser Ala Leu Gly Gly Ile Pro Tyr Ser Gln Ile Tyr Gly
        115                 120                 125

Trp Tyr Arg Val Asn Phe Gly Val Ile Asp Glu Arg Leu His Arg Asn
130                 135                 140

Arg Glu Tyr Arg Asp Arg Tyr Tyr Arg Asn Leu Asn Ile Ala Pro Ala
145                 150                 155                 160

Glu Asp Gly Tyr Arg Leu Ala Gly Phe Pro Pro Asp His Gln Ala Trp
                165                 170                 175

Arg Glu Glu Pro Trp Ile His His Ala Pro Gln Gly Cys Gly Asn Ser
            180                 185                 190

Ser Arg Met Asn Met His Val Asp Met Gly Arg Ala Leu Thr Val Arg
        195                 200                 205

Asp Trp Pro Ala Leu Glu Ala Leu Ala Lys Thr Met Pro Ala Asp Ala
    210                 215                 220

Gly Ala Arg Ala Met Thr Asp Asp Leu Arg Ala Ala Gly Val Asp
225                 230                 235                 240

Arg Arg Val Pro Glu Gln Lys Leu Gly Ala Ala Ile Asp Glu Phe Ala
                245                 250                 255

Ser Leu Arg Leu Pro Asp Arg Ile Asp Gly Arg Phe Val Asp Gly Arg
            260                 265                 270

Arg Ala Asn Leu Thr Val Phe Asp Asp Ala Arg Val Ala Val Arg Gly
        275                 280                 285

His Ala Arg Ala Gln Arg Asn Leu Leu Glu Arg Leu Glu Thr Glu Leu
    290                 295                 300

Leu Gly Gly Thr Leu Asp Thr Ala Gly Asp Glu Gly Gly Ile Gln Pro
305                 310                 315                 320
```

-continued

```
Asp Pro Ile Leu Gln Gly Leu Val Asp Val Ile Gly Gln Gly Lys Ser
                325                 330                 335
Asp Ile Asp Ala Tyr Ala Thr Ile Val Glu Gly Leu Thr Lys Tyr Phe
            340                 345                 350
Gln Ser Val Ala Asp Val Met Ser Lys Leu Gln Asp Tyr Ile Ser Ala
        355                 360                 365
Lys Asp Asp Lys Asn Met Lys Ile Asp Gly Gly Lys Ile Lys Ala Leu
    370                 375                 380
Ile Gln Gln Val Ile Asp His Leu Pro Thr Met Gln Leu Pro Lys Gly
385                 390                 395                 400
Ala Asp Ile Ala Arg Trp Arg Lys Glu Leu Gly Asp Ala Val Ser Ile
                405                 410                 415
Ser Asp Ser Gly Val Val Thr Ile Asn Pro Asp Lys Leu Ile Lys Met
            420                 425                 430
Arg Asp Ser Leu Pro Pro Asp Gly Thr Val Trp Asp Thr Ala Arg Tyr
        435                 440                 445
Gln Ala Trp Asn Thr Ala Phe Ser Gly Gln Lys Gly Gln His Pro Glu
    450                 455                 460
Arg Arg Ala Asp Ala Arg Arg Lys Tyr Ser His Gln Asn Ser Asn Phe
465                 470                 475                 480
Asp Asn Leu Val Lys Val Leu Ser Gly Ala Ile Ser Thr Leu Thr Asp
                485                 490                 495
Thr Gln Ser Tyr Leu Gln Ile Lys Leu Met Ser Ser Gly Val Gln Gly
            500                 505                 510
Gly Pro Ala Ala Asn Ala Asn Ala Tyr Gln Thr His Pro Leu Arg Asp
        515                 520                 525
Ala Ala Ser Ala Leu Gly Thr Leu Ser Pro Gln Ala Tyr Val Asp Val
    530                 535                 540
Val Ser Ala Ala Gln Arg Asn Phe Leu Glu Arg Met Ser Gln Leu Ala
545                 550                 555                 560
Ser Glu Gln Cys Asp Ala Gln Pro Ala Ala His Asp Ala Arg Leu Asp
                565                 570                 575
Asp Arg Pro Ala Leu Arg Ala Pro Gln Glu Arg Asp Ala Pro Pro Leu
            580                 585                 590
Gly Ala Ser Asp Thr Gly Ser Arg Ala Ser Gly Ala Ala Lys Leu Thr
        595                 600                 605
Glu Leu Leu Gly Val Leu Met Ser Val Ile Ser Ala Ser Ser Leu Asp
    610                 615                 620
Glu Leu Lys Gln Arg Ser Asp Ile Trp Asn Gln Met Ser Lys Ala Ala
625                 630                 635                 640
Gln Asp Asn Leu Ser Arg Leu Ser Asp Ala Phe Gln Arg Ala Thr Asp
                645                 650                 655
Glu Ala Lys Ala Ala Asp Ala Ala Glu Gln Ala Ala Ala Ala Ala Ala
            660                 665                 670
Lys Gln Ala Gly Ala Asp Ala Lys Ala Asp Ala Ala Val Asp Ala
        675                 680                 685
Ala Gln Lys Arg Tyr Asp Asp Ala Val Lys Gln Gly Leu Pro Asp Asp
    690                 695                 700
Arg Leu Gln Ser Leu Lys Ala Ala Leu Glu Ala Arg Gln Gln Ala
705                 710                 715                 720
Gly Asp Ala His Gly Arg Ala Asp Ala Leu Gln Ala Asp Ala Thr Lys
                725                 730                 735
Lys Leu Asp Ala Ala Ser Ala Leu Ala Thr Gln Ala Arg Ala Cys Glu
```

```
                     740                 745                 750
Gln Gln Val Asp Asp Ala Val Asn Gln Ala Thr Gln Gln Tyr Gly Ala
            755                 760                 765
Ser Ala Ser Leu Arg Thr Pro Gln Ser Pro Arg Leu Ser Gly Ala Ala
        770                 775                 780
Glu Leu Thr Ala Val Leu Gly Lys Leu Gln Glu Leu Ile Ser Ser Gly
785                 790                 795                 800
Asn Val Lys Glu Leu Glu Ser Lys Gln Lys Leu Phe Thr Glu Met Gln
                805                 810                 815
Ala Lys Arg Glu Ala Glu Leu Gln Lys Lys Ser Asp Glu Tyr Gln Ala
            820                 825                 830
Gln Val Lys Lys Ala Glu Glu Met Gln Lys Thr Met Gly Cys Ile Gly
        835                 840                 845
Lys Ile Val Gly Trp Val Ile Thr Ala Val Ser Phe Ala Ala Ala Ala
    850                 855                 860
Phe Thr Gly Gly Ala Ser Leu Ala Leu Ala Ala Val Gly Leu Ala Leu
865                 870                 875                 880
Ala Val Gly Asp Glu Ile Ser Arg Ala Thr Thr Gly Val Ser Phe Met
                885                 890                 895
Asp Lys Leu Met Gln Pro Val Met Asp Ala Ile Leu Lys Pro Leu Met
            900                 905                 910
Glu Met Ile Ser Ser Leu Ile Thr Lys Ala Leu Val Ala Cys Gly Val
        915                 920                 925
Asp Gln Gln Lys Ala Glu Leu Ala Gly Ala Ile Leu Gly Ala Val Val
    930                 935                 940
Thr Gly Val Ala Leu Val Ala Ala Ala Phe Val Gly Ala Ser Ala Val
945                 950                 955                 960
Lys Ala Val Ala Ser Lys Val Ile Asp Ala Met Ala Gly Gln Leu Thr
                965                 970                 975
Lys Leu Met Asp Ser Ala Ile Gly Lys Met Leu Val Gln Leu Ile Glu
            980                 985                 990
Lys Phe Ser Glu Lys Ser Gly Leu  Gln Ala Leu Gly Ser  Arg Thr Ala
        995                 1000                1005
Thr Ala  Met Thr Arg Met Arg  Arg Ala Ile Gly Val  Glu Ala Lys
    1010                1015                1020
Glu Asp  Gly Met Leu Leu Ala  Asn Arg Phe Glu Lys  Ala Gly Thr
    1025                1030                1035
Val Met  Asn Val Gly Asn Gln  Val Ser Gln Ala Ala  Gly Gly Ile
    1040                1045                1050
Val Val  Gly Val Glu Arg Ala  Lys Ala Met Gly Leu  Leu Ala Asp
    1055                1060                1065
Val Lys  Glu Ala Met Tyr Asp  Ile Lys Leu Leu Gly  Asp Leu Leu
    1070                1075                1080
Lys Gln  Ala Val Asp Ala Phe  Ala Glu His Asn Arg  Val Leu Ala
    1085                1090                1095
Gln Leu  Met Gln Gln Met Ser  Asp Ala Gly Glu Met  Gln Thr Ser
    1100                1105                1110
Thr Gly  Lys Leu Ile Leu Arg  Asn Ala Arg Ala Val
    1115                1120                1125

<210> SEQ ID NO 29
<211> LENGTH: 552
<212> TYPE: DNA
<213> ORGANISM: Artificial Sequence
```

<220> FEATURE:
<223> OTHER INFORMATION: synthetic construct

<400> SEQUENCE: 29

```
atgggcagca gccatcacca tcatcaccac agccaggatc cgatgaacca gccgacccct      60
tccgacaccg accagcaaca ggcgctggag gccttcctgc gcgacggcgg caccctggcg     120
atgcttcgcg gactcagcga ggacaccctg gagcagctct atgcgctggg cttcaaccag     180
taccaggcgg gcaagtggga cgacgcgcag aagatcttcc aggcactgtg catgctcgac     240
cactacgacg cccgctactt tctcggcctg ggcgcctgcc gccagtccct cggtctctat     300
gaacaggccc tgcagagcta cagctacggc gcgctgatgg acatcaacga gccgcgcttt     360
ccctccatg ccgccgagtg ccacctgcaa ctgggtgatc tcgacggagc cgagagtggc     420
ttctactcgg cccgggccct ggccgcggca gccggcgc acgaggccct ggccgcgcgt      480
gccggcgcca tgttggaagc cgtaaccgcg agaaaggatc gagcctatga atccgataac     540
gcttgaaagc tt                                                          552
```

<210> SEQ ID NO 30
<211> LENGTH: 181
<212> TYPE: PRT
<213> ORGANISM: Artificial Sequence
<220> FEATURE:
<223> OTHER INFORMATION: synthetic construct

<400> SEQUENCE: 30

```
Met Gly Ser Ser His His His His His Ser Gln Asp Pro Met Asn
1               5                   10                  15

Gln Pro Thr Pro Ser Asp Thr Asp Gln Gln Gln Ala Leu Glu Ala Phe
            20                  25                  30

Leu Arg Asp Gly Gly Thr Leu Ala Met Leu Arg Gly Leu Ser Glu Asp
        35                  40                  45

Thr Leu Glu Gln Leu Tyr Ala Leu Gly Phe Asn Gln Tyr Gln Ala Gly
    50                  55                  60

Lys Trp Asp Asp Ala Gln Lys Ile Phe Gln Ala Leu Cys Met Leu Asp
65                  70                  75                  80

His Tyr Asp Ala Arg Tyr Phe Leu Gly Leu Gly Ala Cys Arg Gln Ser
                85                  90                  95

Leu Gly Leu Tyr Glu Gln Ala Leu Gln Ser Tyr Ser Tyr Gly Ala Leu
            100                 105                 110

Met Asp Ile Asn Glu Pro Arg Phe Pro Phe His Ala Ala Glu Cys His
        115                 120                 125

Leu Gln Leu Gly Asp Leu Asp Gly Ala Glu Ser Gly Phe Tyr Ser Ala
    130                 135                 140

Arg Ala Leu Ala Ala Ala Gln Pro Ala His Glu Ala Leu Ala Ala Arg
145                 150                 155                 160

Ala Gly Ala Met Leu Glu Ala Val Thr Ala Arg Lys Asp Arg Ala Tyr
                165                 170                 175

Glu Ser Asp Asn Ala
            180
```

<210> SEQ ID NO 31
<211> LENGTH: 885
<212> TYPE: DNA
<213> ORGANISM: Pseudomonas spp

<400> SEQUENCE: 31

-continued

```
catatggaag tcagaaacct taatgccgct cgcgagctgt tcctggacga gctcctggcc    60
gcgtcggcgg cgcctgccag tgccgagcag gaggaactgc tggccctgtt gcgcagcgag   120
cggatcgtgc tggcccacgc cggccagccg ctgagcgagg cgcaagtgct caaggcgctc   180
gcctggttgc tcgcggccaa tccgtccgcg cctccggggc agggcctcga ggtactccgc   240
gaagtcctgc aggcacgtcg gcagcccggt gcgcagtggg atctgcgtga gttcctggtg   300
tcggcctatt tcagcctgca cgggcgtctc gacgaggatg tcatcggtgt ctacaaggat   360
gtcctgcaga cccaggacgg caagcgcaag gcgctgctcg acgagctcaa ggcgctgacc   420
gcggagttga aggtctacag cgtgatccag tcgcagatca acgccgcgct gtcggccagg   480
cagggcatca ggatcgacgc tggcggtatc gatctggtcg accccacgct atatggctat   540
gccgtcggcg atcccaggtg gaaggacagc cccgagtatg cgctgctgag caatctggat   600
accttcagcg gcaagctgtc gatcaaggat tttctcagcg gctcgccgaa gcagagcggg   660
gaactcaagg gcctcagcga tgagtacccc ttcgagaagg acaacaaccc ggtcggcaat   720
ttcgccacca cggtgagcga ccgctcgcgt ccgctgaacg acaaggtcaa cgagaagacc   780
accctgctca acgacaccag ctcccgctac aactcggcgg tcgaggcgct caaccgcttc   840
atccagaaat acgacagcgt cctgagcgac attctcagcg cgatc              885
```

<210> SEQ ID NO 32
<211> LENGTH: 294
<212> TYPE: PRT
<213> ORGANISM: Pseudomonas spp

<400> SEQUENCE: 32

```
Met Glu Val Arg Asn Leu Asn Ala Ala Arg Glu Leu Phe Leu Asp Glu
1               5                   10                  15

Leu Leu Ala Ala Ser Ala Ala Pro Ala Ser Ala Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
        115                 120                 125

Lys Ala Leu Leu Asp Glu Leu Lys Ala Leu Thr Glu Leu Lys Val
    130                 135                 140

Tyr Ser Val Ile Gln Ser Gln Ile Asn Ala Ala Leu Ser Ala Arg Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
        195                 200                 205

Asp Phe Leu Ser Gly Ser Pro Lys Gln Ser Gly Glu Leu Lys Gly Leu
    210                 215                 220
```

Ser Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
            245                 250                 255

Glu Lys Thr Thr Leu Leu Asn Asp Thr Ser Ser Arg Tyr Asn Ser Ala
        260                 265                 270

Val Glu Ala Leu Asn Arg Phe Ile Gln Lys Tyr Asp Ser Val Leu Ser
    275                 280                 285

Asp Ile Leu Ser Ala Ile
    290

<210> SEQ ID NO 33
<211> LENGTH: 1179
<212> TYPE: DNA
<213> ORGANISM: Pseudomonas spp

<400> SEQUENCE: 33
atgaacccga ttacgctgga acgtgctggt ctgccgtatg gtgttgccga tgctggtgac      60
atcccggctc tgggtcgccc ggtcgcacgt gatgtggaaa gtctgcgtgt gaacgtctg     120 gcagcaccgg cagctgcaag cgcatctggc accggtgtcg ctctgacgcc gccgtctgca    180
gcaagtcagc aacgtctgga agttgctaac cgcgcggaaa ttgcctcact ggtccaggca    240
gtgggtgaag acgtgggtct ggcacgtcaa gtggttctgg caggtgcatc gaccctgctg    300
agcgcaggtc tgatgtcgcc gcaggcgttc gaaattgaac tggccaaaat caccggcgaa    360
gttgaaaatc agcagaaaaa actgaaactg acggaaatcg aacaggcccg taaacagaac    420
ctgcaaaaaa tggaagataa ccagcaaaaa atccgcgaat cggaagaagc tgcgaaagaa    480
gcgcagaaaa gcggcctggc cgcaaaaatt tttggttgga tttctgctat cgcgagtatt    540
atcgtgggtg caatcatggt tgcaaccggt gtcggtgctg cagcaggtgc actgatgatt    600
gctggcggtg tcatgggtgt cgtgagtcag tccgtgcagc aagcagctgc ggatggtctg    660
atctcaaaag aagtgatgga aaaactgggc ccggccctga tgggtattga atggccgtg     720 gcactgctgg ccgcagttgt ctcctttggt ggttcagcag ttggtggtct ggcacgtctg    780
ggtgcaaaaa tcggcggtaa agctgcggaa atgacggcat ccctggcttc aaaagtggca    840
gacctgggcg gtaaattcgg ctctctggcg ggccagtcac tgtcgcatag cctgaaactg    900
ggtgtgcaag tttctgatct gaccctggac gttgcaaacg cgccgcaca ggctacgcac     960 agtggttttc aagcgaaagc tgcgaatcgt caggccgatg ttcaagaatc ccgtgcagac   1020
ctgaccacgc tgcagggtgt cattgaacgt ctgaaagaag aactgagccg catgctggaa   1080
gcctttcagg aaattatgga acgcatcttc gcaatgctgc aagcgaaagg cgaaaccctg   1140
cacaatctgt cttcccgtcc ggcggctatc tgaggatcc                         1179

<210> SEQ ID NO 34
<211> LENGTH: 390
<212> TYPE: PRT
<213> ORGANISM: Pseudomonas spp

<400> SEQUENCE: 34

Met Asn Pro Ile Thr Leu Glu Arg Ala Gly Leu Pro Tyr Gly Val Ala
1               5                   10                  15

Asp Ala Gly Asp Ile Pro Ala Leu Gly Arg Pro Val Ala Arg Asp Val
            20                  25                  30

Glu Ser Leu Arg Val Glu Arg Leu Ala Ala Pro Ala Ala Ala Ser Ala

```
                35                  40                  45
Ser Gly Thr Gly Val Ala Leu Thr Pro Pro Ser Ala Ala Ser Gln Gln
 50                  55                  60

Arg Leu Glu Val Ala Asn Arg Ala Glu Ile Ala Ser Leu Val Gln Ala
 65                  70                  75                  80

Val Gly Glu Asp Val Gly Leu Ala Arg Gln Val Leu Ala Gly Ala
                 85                  90                  95

Ser Thr Leu Leu Ser Ala Gly Leu Met Ser Pro Gln Ala Phe Glu Ile
            100                 105                 110

Glu Leu Ala Lys Ile Thr Gly Glu Val Glu Asn Gln Gln Lys Lys Leu
            115                 120                 125

Lys Leu Thr Glu Ile Glu Gln Ala Arg Lys Gln Asn Leu Gln Lys Met
        130                 135                 140

Glu Asp Asn Gln Gln Lys Ile Arg Glu Ser Glu Ala Ala Lys Glu
145                 150                 155                 160

Ala Gln Lys Ser Gly Leu Ala Ala Lys Ile Phe Gly Trp Ile Ser Ala
                165                 170                 175

Ile Ala Ser Ile Ile Val Gly Ala Ile Met Val Ala Thr Gly Val Gly
            180                 185                 190

Ala Ala Ala Gly Ala Leu Met Ile Ala Gly Val Met Gly Val Val
        195                 200                 205

Ser Gln Ser Val Gln Gln Ala Ala Asp Gly Leu Ile Ser Lys Glu
    210                 215                 220

Val Met Glu Lys Leu Gly Pro Ala Leu Met Gly Ile Glu Met Ala Val
225                 230                 235                 240

Ala Leu Leu Ala Ala Val Val Ser Phe Gly Gly Ser Ala Val Gly Gly
                245                 250                 255

Leu Ala Arg Leu Gly Ala Lys Ile Gly Gly Lys Ala Ala Glu Met Thr
            260                 265                 270

Ala Ser Leu Ala Ser Lys Val Ala Asp Leu Gly Gly Lys Phe Gly Ser
        275                 280                 285

Leu Ala Gly Gln Ser Leu Ser His Ser Leu Lys Leu Gly Val Gln Val
    290                 295                 300

Ser Asp Leu Thr Leu Asp Val Ala Asn Gly Ala Ala Gln Ala Thr His
305                 310                 315                 320

Ser Gly Phe Gln Ala Lys Ala Ala Asn Arg Gln Ala Asp Val Gln Glu
                325                 330                 335

Ser Arg Ala Asp Leu Thr Thr Leu Gln Gly Val Ile Glu Arg Leu Lys
            340                 345                 350

Glu Glu Leu Ser Arg Met Leu Glu Ala Phe Gln Glu Ile Met Glu Arg
        355                 360                 365

Ile Phe Ala Met Leu Gln Ala Lys Gly Glu Thr Leu His Asn Leu Ser
    370                 375                 380

Ser Arg Pro Ala Ala Ile
385                 390

<210> SEQ ID NO 35
<211> LENGTH: 2070
<212> TYPE: DNA
<213> ORGANISM: Artificial Sequence
<220> FEATURE:
<223> OTHER INFORMATION: synthetic construct

<400> SEQUENCE: 35
catatggaag tcagaaacct taatgccgct cgcgagctgt tcctggacga gctcctggcc    60
```

```
gcgtcggcgg cgcctgccag tgccgagcag gaggaactgc tggccctgtt gcgcagcgag      120
cggatcgtgc tggcccacgc cggccagccg ctgagcgagg cgcaagtgct caaggcgctc      180
gcctggttgc tcgcggccaa tccgtccgcg cctccggggc agggcctcga ggtactccgc      240
gaagtcctgc aggcacgtcg gcagcccggt gcgcagtggg atctgcgtga gttcctggtg      300
tcggcctatt tcagcctgca cgggcgtctc gacgaggatg tcatcggtgt ctacaaggat      360
gtcctgcaga cccaggacgg caagcgcaag gcgctgctcg acgagctcaa ggcgctgacc      420
gcggagttga aggtctacag cgtgatccag tcgcagatca acgccgcgct gtcggccagg      480
cagggcatca ggatcgacgc tggcggtatc gatctggtcg accccacgct atatggctat      540
gccgtcggcg atcccaggtg gaaggacagc cccgagtatg cgctgctgag caatctggat      600
accttcagcg gcaagctgtc gatcaaggat tttctcagcg gctcgccgaa gcagagcggg      660
gaactcaagg gcctcagcga tgagtacccc ttcgagaagg acaacaaccc ggtcggcaat      720
ttcgccacca cggtgagcga ccgctcgcgt ccgctgaacg acaaggtcaa cgagaagacc      780
accctgctca acgacaccag ctcccgctac aactcggcgg tcgaggcgct caaccgcttc      840
atccagaaat acgacagcgt cctgagcgac attctcagcg cgatcggatc catgaacccg      900
attacgctgg aacgtgctgg tctgccgtat ggtgttgccg atgctggtga catcccggct      960
ctgggtcgcc cggtcgcacg tgatgtggaa agtctgcgtg ttgaacgtct ggcagcaccg     1020
gcagctgcaa gcgcatctgg caccggtgtc gctctgacgc cgccgtctgc agcaagtcag     1080
caacgtctgg aagttgctaa ccgcgcgaa attgcctcac tggtccaggc agtgggtgaa     1140
gacgtgggtc tggcacgtca agtggttctg gcaggtgcat cgaccctgct gagcgcaggt     1200
ctgatgtcgc cgcaggcgtt cgaaattgaa ctggccaaaa tcaccggcga agttgaaaat     1260
cagcagaaaa aactgaaact gacggaaatc gaacaggccc gtaaacagaa cctgcaaaaa     1320
atggaagata ccagcaaaaa atccgcgaaa tcggaagaag ctgcgaaaga agcgcagaaa     1380
agcggcctgg ccgcaaaaat ttttggttgg atttctgcta tcgcgagtat tatcgtgggt     1440
gcaatcatgg ttgcaaccgg tgtcggtgct gcagcaggtg cactgatgat tgctggcggt     1500
gtcatgggtg tcgtgagtca gtccgtgcag caagcagctg cggatggtct gatctcaaaa     1560
gaagtgatgg aaaaactggg cccggccctg atgggtattg aaatggccgt ggcactgctg     1620
gccgcagttg tctcctttgg tggttcagca gttggtggtc tggcacgtct gggtgcaaaa     1680
atcggcggta agctgcggaa aatgacggca tccctggctt caaaagtggc agacctgggc     1740
ggtaaattcg gctctctggc gggccagtca ctgtcgcata gcctgaaact gggtgtgcaa     1800
gtttctgatc tgaccctgga cgttgcaaac ggcgccgcac aggctacgca cagtggtttt     1860
caagcgaaag ctgcgaatcg tcaggccgat gttcaagaat cccgtgcaga cctgaccacg     1920
ctgcagggtg tcattgaacg tctgaaagaa gaactgagcc gcatgctgga agcctttcag     1980
gaaattatgg aacgcatctt cgcaatgctg caagcgaaag cgaaaccct gcacaatctg     2040 tcttcccgtc cggcggctat ctgaggatcc                                      2070
```

<210> SEQ ID NO 36
<211> LENGTH: 686
<212> TYPE: PRT
<213> ORGANISM: Artificial Sequence
<220> FEATURE:
<223> OTHER INFORMATION: synthetic construct

<400> SEQUENCE: 36

```
Met Glu Val Arg Asn Leu Asn Ala Ala Arg Glu Leu Phe Leu Asp Glu
1               5                   10                  15
Leu Leu Ala Ala Ser Ala Ala Pro Ala Ser Ala Glu Gln Glu Glu Leu
            20                  25                  30
Leu Ala Leu Leu Arg Ser Glu Arg Ile Val Leu Ala His Ala Gly Gln
        35                  40                  45
Pro Leu Ser Glu Ala Gln Val Leu Lys Ala Leu Ala Trp Leu Leu Ala
    50                  55                  60
Ala Asn Pro Ser Ala Pro Gly Gln Gly Leu Glu Val Leu Arg Glu
65                  70                  75                  80
Val Leu Gln Ala Arg Arg Gln Pro Gly Ala Gln Trp Asp Leu Arg Glu
                85                  90                  95
Phe Leu Val Ser Ala Tyr Phe Ser Leu His Gly Arg Leu Asp Glu Asp
            100                 105                 110
Val Ile Gly Val Tyr Lys Asp Val Leu Gln Thr Gln Asp Gly Lys Arg
            115                 120                 125
Lys Ala Leu Leu Asp Glu Leu Lys Ala Leu Thr Ala Glu Leu Lys Val
        130                 135                 140
Tyr Ser Val Ile Gln Ser Gln Ile Asn Ala Ala Leu Ser Ala Arg Gln
145                 150                 155                 160
Gly Ile Arg Ile Asp Ala Gly Gly Ile Asp Leu Val Asp Pro Thr Leu
                165                 170                 175
Tyr Gly Tyr Ala Val Gly Asp Pro Arg Trp Lys Asp Ser Pro Glu Tyr
            180                 185                 190
Ala Leu Leu Ser Asn Leu Asp Thr Phe Ser Gly Lys Leu Ser Ile Lys
        195                 200                 205
Asp Phe Leu Ser Gly Ser Pro Lys Gln Ser Gly Glu Leu Lys Gly Leu
    210                 215                 220
Ser Asp Glu Tyr Pro Phe Glu Lys Asp Asn Asn Pro Val Gly Asn Phe
225                 230                 235                 240
Ala Thr Thr Val Ser Asp Arg Ser Arg Pro Leu Asn Asp Lys Val Asn
                245                 250                 255
Glu Lys Thr Thr Leu Leu Asn Asp Thr Ser Ser Arg Tyr Asn Ser Ala
            260                 265                 270
Val Glu Ala Leu Asn Arg Phe Ile Gln Lys Tyr Asp Ser Val Leu Ser
        275                 280                 285
Asp Ile Leu Ser Ala Ile Gly Ser Met Asn Pro Ile Thr Leu Glu Arg
    290                 295                 300
Ala Gly Leu Pro Tyr Gly Val Asp Ala Gly Asp Ile Pro Ala Leu
305                 310                 315                 320
Gly Arg Pro Val Ala Arg Asp Val Glu Ser Leu Arg Val Glu Arg Leu
                325                 330                 335
Ala Ala Pro Ala Ala Ser Ala Ser Gly Thr Gly Val Ala Leu Thr
            340                 345                 350
Pro Pro Ser Ala Ala Ser Gln Gln Arg Leu Glu Val Ala Asn Arg Ala
        355                 360                 365
Glu Ile Ala Ser Leu Val Gln Ala Val Gly Glu Asp Val Gly Leu Ala
    370                 375                 380
Arg Gln Val Val Leu Ala Gly Ala Ser Thr Leu Leu Ser Ala Gly Leu
385                 390                 395                 400
Met Ser Pro Gln Ala Phe Glu Ile Glu Leu Ala Lys Ile Thr Gly Glu
                405                 410                 415
Val Glu Asn Gln Gln Lys Lys Leu Lys Leu Thr Glu Ile Glu Gln Ala
```

```
                420             425             430
Arg Lys Gln Asn Leu Gln Lys Met Glu Asp Asn Gln Gln Lys Ile Arg
            435                 440                 445
Glu Ser Glu Glu Ala Ala Lys Glu Ala Gln Lys Ser Gly Leu Ala Ala
        450                 455                 460
Lys Ile Phe Gly Trp Ile Ser Ala Ile Ala Ser Ile Ile Val Gly Ala
465                 470                 475                 480
Ile Met Val Ala Thr Gly Val Gly Ala Ala Gly Ala Leu Met Ile
                485                 490                 495
Ala Gly Gly Val Met Gly Val Val Ser Gln Ser Val Gln Gln Ala Ala
            500                 505                 510
Ala Asp Gly Leu Ile Ser Lys Glu Val Met Glu Lys Leu Gly Pro Ala
        515                 520                 525
Leu Met Gly Ile Glu Met Ala Val Ala Leu Leu Ala Ala Val Val Ser
        530                 535                 540
Phe Gly Gly Ser Ala Val Gly Gly Leu Ala Arg Leu Gly Ala Lys Ile
545                 550                 555                 560
Gly Gly Lys Ala Ala Glu Met Thr Ala Ser Leu Ala Ser Lys Val Ala
                565                 570                 575
Asp Leu Gly Gly Lys Phe Gly Ser Leu Ala Gly Gln Ser Leu Ser His
            580                 585                 590
Ser Leu Lys Leu Gly Val Gln Val Ser Asp Leu Thr Leu Asp Val Ala
        595                 600                 605
Asn Gly Ala Ala Gln Ala Thr His Ser Gly Phe Gln Ala Lys Ala Ala
        610                 615                 620
Asn Arg Gln Ala Asp Val Gln Glu Ser Arg Ala Asp Leu Thr Thr Leu
625                 630                 635                 640
Gln Gly Val Ile Glu Arg Leu Lys Glu Glu Leu Ser Arg Met Leu Glu
                645                 650                 655
Ala Phe Gln Glu Ile Met Glu Arg Ile Phe Ala Met Leu Gln Ala Lys
            660                 665                 670
Gly Glu Thr Leu His Asn Leu Ser Ser Arg Pro Ala Ala Ile
        675                 680                 685

<210> SEQ ID NO 37
<211> LENGTH: 2655
<212> TYPE: DNA
<213> ORGANISM: Artificial Sequence
<220> FEATURE:
<223> OTHER INFORMATION: synthetic construct

<400> SEQUENCE: 37
catatggaca atggcgatcg tttataccgt gccgactcgc gtcccccaga tgagattaaa      60
cgtagcggtg ggttaatgcc acgtgggcac aatgagtatt ttgaccgtgg aacacagatg     120
aacattaacc tttacgatca tgcccgtggg acccagaccg ggtttgtccg ttatgatgac     180
gggtatgtta gtacgagttt gtccttacgc tccgcacacc ttgcgggaca agtattttta     240
tcaggctaca gcacatatta catttatgtg atcgccactg ccccaaacat gttcaatgtg     300
aacgatgtgt ggggttta cagcccccat ccatatgaac aagaagtctc ggcccttggg     360
gggatcccat atagccagat ttatggttgg taccgcgtaa attttggtgt gattgatgaa     420
cgtttgcatc gtaaccgtga ataccgcgat cgctactacc gtaacttgaa cattgcacct     480
gccgaggacg gctatcgttt agcgggattc ccacccgatc atcaggcgtg gcgtgaggaa     540
ccgtggatcc atcacgcccc tcaggggtgc gggaacagta gtcgccatat ggaagtcaga     600
```

```
aaccttaatg ccgctcgcga gctgttcctg gacgagctcc tggccgcgtc ggcggcgcct      660
gccagtgccg agcaggagga actgctggcc ctgttgcgca gcgagcggat cgtgctggcc      720
cacgccggcc agccgctgag cgaggcgcaa gtgctcaagg cgctcgcctg gttgctcgcg      780
gccaatccgt ccgcgcctcc ggggcagggc ctcgaggtac tccgcgaagt cctgcaggca      840
cgtcggcagc ccggtgcgca gtgggatctg cgtgagttcc tggtgtcggc ctatttcagc      900
ctgcacgggg tctcgacgga ggatgtcatc ggtgtctaca aggatgtcct gcagacccag      960
gacggcaagc gcaaggcgct gctcgacgag ctcaaggcgc tgaccgcgga gttgaaggtc     1020
tacagcgtga tccagtcgca gatcaacgcc gcgctgtcgg ccaggcaggg catcaggatc     1080
gacgctggcg gtatcgatct ggtcgacccc acgctatatg ctatgccgt cggcgatccc      1140 aggtggaagg acagcccga gtatgcgctg ctgagcaatc tggatacctt cagcggcaag      1200
ctgtcgatca aggattttct cagcggctcg ccgaagcaga gcgggaact caagggcctc      1260 agcgatgagt acccccttcga gaaggacaac aacccggtcg gcaatttcgc caccacggtg    1320
agcgaccgct cgcgtccgct gaacgacaag gtcaacgaga agaccaccct gctcaacgac    1380
accagctccc gctacaactc ggcggtcgag gcgctcaacc gcttcatcca gaaatacgac    1440
agcgtcctga gcgacattct cagcgcgatc ggatccatga acccgattac gctggaacgt    1500
gctggtctgc cgtatggtgt tgccgatgct ggtgacatcc cggctctggg tcgcccggtc    1560
gcacgtgatg tggaaagtct gcgtgttgaa cgtctggcag caccggcagc tgcaagcgca   1620
tctggcaccg gtgtcgctct gacgccgccg tctgcagcaa gtcagcaacg tctggaagtt   1680
gctaaccgcg cggaaattgc ctcactggtc caggcagtgg gtgaagacgt gggtctggca   1740
cgtcaagtgg ttctggcagg tgcatcgacc ctgctgagcg caggtctgat gtcgccgcag   1800
gcgttcgaaa ttgaactggc caaaatcacc ggcgaagttg aaaatcagca gaaaaaactg   1860
aaactgacgg aaatcgaaca ggcccgtaaa cagaacctgc aaaaaatgga agataaccag   1920
caaaaaatcc gcgaatcgga agaagctgcg aaagaagcgc agaaaagcgg cctggccgca   1980 aaaattttg gttggatttc tgctatcgcg agtattatcg tgggtgcaat catggttgca    2040
accggtgtcg gtgctgcagc aggtgcactg atgattgctg gcggtgtcat gggtgtcgtg    2100
agtcagtccg tgcagcaagc agctgcggat ggtctgatct caaaagaagt gatgaaaaaa    2160
ctgggcccgg ccctgatggg tattgaaatg gccgtggcac tgctggccgc agttgtctcc    2220
tttggtggtt cagcagttgg tggtctggca cgtctgggtg caaaaatcgg cggtaaagct    2280
gcggaaatga cggcatccct ggcttcaaaa gtggcagacc tgggcggtaa attcggctct    2340
ctggcgggcc agtcactgtc gcatagcctg aaactgggtg tgcaagtttc tgatctgacc    2400
ctggacgttg caaacggcgc cgcacaggct acgcacagtg gttttcaagc gaaagctgcg    2460
aatcgtcagg ccgatgttca agaatcccgt gcagacctga ccacgctgca gggtgtcatt    2520
gaacgtctga agaagaact gagccgcatg ctggaagcct tcaggaaat tatgaacgc      2580 atcttcgcaa tgctgcaagc gaaaggcgaa accctgcaca atctgtcttc ccgtccggcg    2640
gctatctgag gatcc                                                      2655
```

<210> SEQ ID NO 38
<211> LENGTH: 880
<212> TYPE: PRT
<213> ORGANISM: Artificial Sequence
<220> FEATURE:
<223> OTHER INFORMATION: synthetic construct

```
<400> SEQUENCE: 38

Met Asp Asn Gly Asp Arg Leu Tyr Arg Ala Asp Ser Arg Pro Pro Asp
 1               5                  10                  15

Glu Ile Lys Arg Ser Gly Gly Leu Met Pro Arg Gly His Asn Glu Tyr
             20                  25                  30

Phe Asp Arg Gly Thr Gln Met Asn Ile Asn Leu Tyr Asp His Ala Arg
         35                  40                  45

Gly Thr Gln Thr Gly Phe Val Arg Tyr Asp Asp Gly Tyr Val Ser Thr
     50                  55                  60

Ser Leu Ser Leu Arg Ser Ala His Leu Ala Gly Gln Ser Ile Leu Ser
 65                  70                  75                  80

Gly Tyr Ser Thr Tyr Tyr Ile Tyr Val Ile Ala Thr Ala Pro Asn Met
                 85                  90                  95

Phe Asn Val Asn Asp Val Leu Gly Val Tyr Ser Pro His Pro Tyr Glu
            100                 105                 110

Gln Glu Val Ser Ala Leu Gly Gly Ile Pro Tyr Ser Gln Ile Tyr Gly
            115                 120                 125

Trp Tyr Arg Val Asn Phe Gly Val Ile Asp Glu Arg Leu His Arg Asn
130                 135                 140

Arg Glu Tyr Arg Asp Arg Tyr Tyr Arg Asn Leu Asn Ile Ala Pro Ala
145                 150                 155                 160

Glu Asp Gly Tyr Arg Leu Ala Gly Phe Pro Asp His Gln Ala Trp
                165                 170                 175

Arg Glu Glu Pro Trp Ile His His Ala Pro Gln Gly Cys Gly Asn Ser
                180                 185                 190

Ser Arg Met Glu Val Arg Asn Leu Asn Ala Ala Arg Glu Leu Phe Leu
            195                 200                 205

Asp Glu Leu Leu Ala Ala Ser Ala Ala Pro Ala Ser Ala Glu Gln Glu
            210                 215                 220

Glu Leu Leu Ala Leu Leu Arg Ser Glu Arg Ile Val Leu Ala His Ala
225                 230                 235                 240

Gly Gln Pro Leu Ser Glu Ala Gln Val Leu Lys Ala Leu Ala Trp Leu
                245                 250                 255

Leu Ala Ala Asn Pro Ser Ala Pro Pro Gly Gln Gly Leu Glu Val Leu
            260                 265                 270

Arg Glu Val Leu Gln Ala Arg Arg Gln Pro Gly Ala Gln Trp Asp Leu
            275                 280                 285

Arg Glu Phe Leu Val Ser Ala Tyr Phe Ser Leu His Gly Arg Leu Asp
        290                 295                 300

Glu Asp Val Ile Gly Val Tyr Lys Asp Val Leu Gln Thr Gln Asp Gly
305                 310                 315                 320

Lys Arg Lys Ala Leu Leu Asp Glu Leu Lys Ala Leu Thr Ala Glu Leu
                325                 330                 335

Lys Val Tyr Ser Val Ile Gln Ser Gln Ile Asn Ala Ala Leu Ser Ala
            340                 345                 350

Arg Gln Gly Ile Arg Ile Asp Ala Gly Gly Ile Asp Leu Val Asp Pro
        355                 360                 365

Thr Leu Tyr Gly Tyr Ala Val Gly Asp Pro Arg Trp Lys Asp Ser Pro
    370                 375                 380

Glu Tyr Ala Leu Leu Ser Asn Leu Asp Thr Phe Ser Gly Lys Leu Ser
385                 390                 395                 400

Ile Lys Asp Phe Leu Ser Gly Ser Pro Lys Gln Ser Gly Glu Leu Lys
                405                 410                 415
```

```
Gly Leu Ser Asp Glu Tyr Pro Phe Glu Lys Asp Asn Pro Val Gly
            420                 425                 430

Asn Phe Ala Thr Thr Val Ser Asp Arg Ser Arg Pro Leu Asn Asp Lys
            435                 440                 445

Val Asn Glu Lys Thr Thr Leu Leu Asn Asp Thr Ser Ser Arg Tyr Asn
450                 455                 460

Ser Ala Val Glu Ala Leu Asn Arg Phe Ile Gln Lys Tyr Asp Ser Val
465                 470                 475                 480

Leu Ser Asp Ile Leu Ser Ala Ile Gly Ser Met Asn Pro Ile Thr Leu
            485                 490                 495

Glu Arg Ala Gly Leu Pro Tyr Gly Val Ala Asp Ala Gly Asp Ile Pro
            500                 505                 510

Ala Leu Gly Arg Pro Val Ala Arg Asp Val Glu Ser Leu Arg Val Glu
            515                 520                 525

Arg Leu Ala Ala Pro Ala Ala Ser Ala Ser Gly Thr Gly Val Ala
530                 535                 540

Leu Thr Pro Pro Ser Ala Ala Ser Gln Gln Arg Leu Glu Val Ala Asn
545                 550                 555                 560

Arg Ala Glu Ile Ala Ser Leu Val Gln Ala Val Gly Glu Asp Val Gly
            565                 570                 575

Leu Ala Arg Gln Val Val Leu Ala Gly Ala Ser Thr Leu Leu Ser Ala
            580                 585                 590

Gly Leu Met Ser Pro Gln Ala Phe Glu Ile Glu Leu Ala Lys Ile Thr
            595                 600                 605

Gly Glu Val Glu Asn Gln Gln Lys Lys Leu Lys Leu Thr Glu Ile Glu
            610                 615                 620

Gln Ala Arg Lys Gln Asn Leu Gln Lys Met Glu Asp Asn Gln Gln Lys
625                 630                 635                 640

Ile Arg Glu Ser Glu Glu Ala Ala Lys Glu Ala Gln Lys Ser Gly Leu
            645                 650                 655

Ala Ala Lys Ile Phe Gly Trp Ile Ser Ala Ile Ala Ser Ile Ile Val
            660                 665                 670

Gly Ala Ile Met Val Ala Thr Gly Val Gly Ala Ala Gly Ala Leu
            675                 680                 685

Met Ile Ala Gly Gly Val Met Gly Val Val Ser Gln Ser Val Gln Gln
            690                 695                 700

Ala Ala Ala Asp Gly Leu Ile Ser Lys Glu Val Met Glu Lys Leu Gly
705                 710                 715                 720

Pro Ala Leu Met Gly Ile Glu Met Ala Val Ala Leu Leu Ala Ala Val
            725                 730                 735

Val Ser Phe Gly Gly Ser Ala Val Gly Gly Leu Ala Arg Leu Gly Ala
            740                 745                 750

Lys Ile Gly Gly Lys Ala Ala Glu Met Thr Ala Ser Leu Ala Ser Lys
            755                 760                 765

Val Ala Asp Leu Gly Gly Lys Phe Gly Ser Leu Ala Gly Gln Ser Leu
            770                 775                 780

Ser His Ser Leu Lys Leu Gly Val Gln Val Ser Asp Leu Thr Leu Asp
785                 790                 795                 800

Val Ala Asn Gly Ala Ala Gln Ala Thr His Ser Gly Phe Gln Ala Lys
            805                 810                 815

Ala Ala Asn Arg Gln Ala Asp Val Gln Glu Ser Arg Ala Asp Leu Thr
            820                 825                 830
```

Thr Leu Gln Gly Val Ile Glu Arg Leu Lys Glu Leu Ser Arg Met
            835                 840                 845

Leu Glu Ala Phe Gln Glu Ile Met Glu Arg Ile Phe Ala Met Leu Gln
    850                 855                 860

Ala Lys Gly Glu Thr Leu His Asn Leu Ser Ser Arg Pro Ala Ala Ile
865                 870                 875                 880

<210> SEQ ID NO 39
<211> LENGTH: 555
<212> TYPE: DNA
<213> ORGANISM: Artificial Sequence
<220> FEATURE:
<223> OTHER INFORMATION: synthetic construct

<400> SEQUENCE: 39
atgggcagca gccatcacca tcatcaccac agccaggatc cgatgcaaca agagacgaca      60
gacactcaag aataccagct ggcaatggaa tccttcctaa aaggagggg aactatcgcc     120 atgctcaacg aaatttcaag tgacacttta gagcaactct actctcttgc gtttaaccaa     180
taccagtcag gaaaatacga ggatgctcac aaggtctttc aagctctctg tgtgctagac     240
cactatgatt cacgtttctt tttagggcta ggcgcttgtc gtcaagccat ggggcaatac     300
gacttagcga ttcatagcta cagctatggc gccataatgg atataaaaga acctcgtttt     360
ccgtttcatg ctgccgaatg tttactgcaa aaggagagc ttgctgaagc agaaagtggc     420
ttgttcttgg ctcaagagct tatcgcagac aaacctgagt ttaaggagct tccacccga     480 gttagctcaa tgttagaagc aattaaattg aaaaaggaga tggaacatga gtgcgttgat     540
aacccatgaa agctt                                                    555

<210> SEQ ID NO 40
<211> LENGTH: 188
<212> TYPE: PRT
<213> ORGANISM: Artificial Sequence
<220> FEATURE:
<223> OTHER INFORMATION: synthetic construct

<400> SEQUENCE: 40

Met Gly Ser Ser His His His His His His Ser Gly Leu Val Pro
1               5                   10                  15

Arg Gly Ser His Met Gln Gln Glu Thr Thr Asp Thr Gln Glu Tyr Gln
            20                  25                  30

Leu Ala Met Glu Ser Phe Leu Lys Gly Gly Gly Thr Ile Ala Met Leu
        35                  40                  45

Asn Glu Ile Ser Ser Asp Thr Leu Glu Gln Leu Tyr Ser Leu Ala Phe
    50                  55                  60

Asn Gln Tyr Gln Ser Gly Lys Tyr Glu Asp Ala His Lys Val Phe Gln
65                  70                  75                  80

Ala Leu Cys Val Leu Asp His Tyr Asp Ser Arg Phe Phe Leu Gly Leu
                85                  90                  95

Gly Ala Cys Arg Gln Ala Met Gly Gln Tyr Asp Leu Ala Ile His Ser
            100                 105                 110

Tyr Ser Tyr Gly Ala Ile Met Asp Ile Lys Glu Pro Arg Phe Pro Phe
        115                 120                 125

His Ala Ala Glu Cys Leu Leu Gln Lys Gly Glu Leu Ala Glu Ala Glu
    130                 135                 140

Ser Gly Leu Phe Leu Ala Gln Glu Leu Ile Ala Asp Lys Pro Glu Phe
145                 150                 155                 160

-continued

```
Lys Glu Leu Ser Thr Arg Val Ser Ser Met Leu Glu Ala Ile Lys Leu
                165                 170                 175

Lys Lys Glu Met Glu His Glu Cys Val Asp Asn Pro
            180                 185
```

<210> SEQ ID NO 41
<211> LENGTH: 981
<212> TYPE: DNA
<213> ORGANISM: Yersinia spp

<400> SEQUENCE: 41

```
catatgatta gagcctacga acaaaaccca caacatttta ttgaggatct agaaaaagtt      60
agggtggaac aacttactgg tcatggttct tcagttttag aagaattggt tcagttagtc     120
aaagataaaa atatagatat ttccattaaa tatgatccca gaaaagattc ggaggttttt     180
gccaatagag taattactga tgatatcgaa ttgctcaaga aaatcctagc ttattttcta     240
cccgaggatg ccattcttaa aggcggtcat tatgacaacc aactgcaaaa tggcatcaag     300
cgagtaaaag agttccttga atcatcgccg aatacacaat gggaattgcg ggcgttcatg     360
gcagtaatgc atttctcttt aaccgccgat cgtatcgatg atgatatttt gaaagtgatt     420
gttgattcaa tgaatcatca tggtgatgcc cgtagcaagt tgcgtgaaga attagctgag     480
cttaccgccg aattaaagat ttattcagtt attcaagccg aaattaataa gcatctgtct     540
agtagtggca ccataaatat ccatgataaa tccattaatc tcatggataa aaatttatat     600
ggttatacag atgaagagat ttttaaagcc agcgcagagt acaaaattct cgagaaaatg     660
cctcaaacca ccattcaggt ggatgggagc gagaaaaaaa tagtctcgat aaaggacttt     720
cttggaagtg agaataaaag aaccggggcg ttgggtaatc tgaaaaactc atactcttat     780
aataaagata ataatgaatt atctcacttt gccaccacct gctcggataa gtccaggccg     840
ctcaacgact tggttagcca aaaaacaact cagctgtctg atattacatc acgttttaat     900
tcagctattg aagcactgaa ccgtttcatt cagaaatatg attcagtgat gcaacgtctg     960
ctagatgaca cgtctggtaa a                                               981
```

<210> SEQ ID NO 42
<211> LENGTH: 326
<212> TYPE: PRT
<213> ORGANISM: Yersinia spp

<400> SEQUENCE: 42

```
Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125
```

```
Asp Arg Ile Asp Asp Ile Leu Lys Val Ile Val Asp Ser Met Asn
        130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
                180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
                260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 43
<211> LENGTH: 1212
<212> TYPE: DNA
<213> ORGANISM: Yersinia spp

<400> SEQUENCE: 43
atgagtgcgt tgataaccca tgatcgctca acgccagtaa ctggaagtct acttccctac      60
gtcgagacac cagcgcccgc ccccctttcag actcaacaag tcgcgggaga actgaaggat    120
aaaaatggtg gggtgagttc tcagggcgta cagctccctg caccactagc agtggttgcc    180
agccaagtca ctgaaggaca cagcaagaa atcactaaat tattggagtc ggtcacccgc      240
ggcacggcag atctcaact gatatcaaat tatgtttcag tgctaacgaa ttttacgctc      300
gcttcacctg atacatttga gattgagtta ggtaagctag tttctaattt agaagaagta    360
cgcaaagaca taaaaatcgc tgatattcag cgtcttcatg aacaaaacat gaagaaaatt    420
gaagagaatc aagagaaaat caagaaaca gaagagaatg ccaagcaagt caagaaatcc      480
ggcatggcat caaagatttt tggctggctc agcgccatag cctcagtggt tatcggtgcc    540
atcatggtgg cctcaggggt aggagccgtt gccggtgcaa tgatgattgc ctcaggcgta    600
attgggatgg cgaatatggc tgtgaaacaa gcggcggaag atggcctgat atcccaagag    660
gcaatgcaag tattagggcc gatactcact gcgattgaag tcgcattgac tgtagttcca    720
accgtaatga ccttggcgg ttcggcacta aaatgcctgg ctgatattgg cgcaaaactc      780
ggtgctaaca ccgcaagtct tgctgctaaa ggagccgagt ttcggccaa agttgcccaa    840 atttcgacag gcatatcaaa cactgtcggg aatgcagtga ctaaattagg ggcagttttt    900
ggtagtttaa caatgagcca tgtaatccgt acaggatcac aggcaacaca gtcgccgtt    960
```

```
ggtgtgggca gcggaataac tcagaccatc aataataaaa aacaagctga tttacaacat    1020
aataacgctg atttggcctt gaacaaggca gacatggcag cgttacaaag tattattgac    1080
cgactcaaag aagagttatc ccatttgtca gagtcacatc aacaagtgat ggaactgatt    1140
ttccagatga ttaatgcaaa aggtgacatg ctgcataatt tggccggcag acccccatact    1200 gtttaaggta cc                                                        1212
```

```
<210> SEQ ID NO 44
<211> LENGTH: 401
<212> TYPE: PRT
<213> ORGANISM: Yersinia spp

<400> SEQUENCE: 44
```

```
Met Ser Ala Leu Ile Thr His Asp Arg Ser Thr Pro Val Thr Gly Ser
1               5                   10                  15

Leu Leu Pro Tyr Val Glu Thr Pro Ala Pro Ala Pro Leu Gln Thr Gln
            20                  25                  30

Gln Val Ala Gly Glu Leu Lys Asp Lys Asn Gly Gly Val Ser Ser Gln
        35                  40                  45

Gly Val Gln Leu Pro Ala Pro Leu Ala Val Val Ala Ser Gln Val Thr
    50                  55                  60

Glu Gly Gln Gln Gln Glu Ile Thr Lys Leu Leu Glu Ser Val Thr Arg
65                  70                  75                  80

Gly Thr Ala Gly Ser Gln Leu Ile Ser Asn Tyr Val Ser Val Leu Thr
                85                  90                  95

Asn Phe Thr Leu Ala Ser Pro Asp Thr Phe Glu Ile Glu Leu Gly Lys
            100                 105                 110

Leu Val Ser Asn Leu Glu Glu Val Arg Lys Asp Ile Lys Ile Ala Asp
        115                 120                 125

Ile Gln Arg Leu His Glu Gln Asn Met Lys Lys Ile Glu Glu Asn Gln
    130                 135                 140

Glu Lys Ile Lys Glu Thr Glu Glu Asn Ala Lys Gln Val Lys Lys Ser
145                 150                 155                 160

Gly Met Ala Ser Lys Ile Phe Gly Trp Leu Ser Ala Ile Ala Ser Val
                165                 170                 175

Val Ile Gly Ala Ile Met Val Ala Ser Gly Val Gly Ala Val Ala Gly
            180                 185                 190

Ala Met Met Ile Ala Ser Gly Val Gly Met Ala Asn Met Ala Val
            195                 200                 205

Lys Gln Ala Ala Glu Asp Gly Leu Ile Ser Gln Glu Ala Met Gln Val
    210                 215                 220

Leu Gly Pro Ile Leu Thr Ala Ile Glu Val Ala Leu Thr Val Val Ser
225                 230                 235                 240

Thr Val Met Thr Phe Gly Gly Ser Ala Leu Lys Cys Leu Ala Asp Ile
                245                 250                 255

Gly Ala Lys Leu Gly Ala Asn Thr Ala Ser Leu Ala Ala Lys Gly Ala
            260                 265                 270

Glu Phe Ser Ala Lys Val Ala Gln Ile Ser Thr Gly Ile Ser Asn Thr
        275                 280                 285

Val Gly Asn Ala Val Thr Lys Leu Gly Gly Ser Phe Gly Ser Leu Thr
    290                 295                 300

Met Ser His Val Ile Arg Thr Gly Ser Gln Ala Thr Gln Val Ala Val
305                 310                 315                 320
```

```
Gly Val Gly Ser Gly Ile Thr Gln Thr Ile Asn Asn Lys Lys Gln Ala
            325                 330                 335

Asp Leu Gln His Asn Asn Ala Asp Leu Ala Leu Asn Lys Ala Asp Met
        340                 345                 350

Ala Ala Leu Gln Ser Ile Ile Asp Arg Leu Lys Glu Glu Leu Ser His
        355                 360                 365

Leu Ser Glu Ser His Gln Gln Val Met Glu Leu Ile Phe Gln Met Ile
370                 375                 380

Asn Ala Lys Gly Asp Met Leu His Asn Leu Ala Gly Arg Pro His Thr
385                 390                 395                 400

Val

<210> SEQ ID NO 45
<211> LENGTH: 2199
<212> TYPE: DNA
<213> ORGANISM: Artificial Sequence
<220> FEATURE:
<223> OTHER INFORMATION: synthetic construct

<400> SEQUENCE: 45
catatgatta gagcctacga acaaaaccca caacattta ttgaggatct agaaaaagtt      60
agggtggaac aacttactgg tcatggttct tcagttttag aagaattggt tcagttagtc    120
aaagataaaa atatagatat ttccattaaa atgatcccca gaaagattc ggaggttttt     180 gccaatagag taattactga tgatatcgaa ttgctcaaga aatcctagc ttattttcta     240 cccgaggatg ccattcttaa aggcggtcat tatgacaacc aactgcaaaa tggcatcaag    300
cgagtaaaag agttccttga atcatcgccg aatacacaat gggaattgcg ggcgttcatg    360
gcagtaatgc atttctcttt aaccgccgat cgtatcgatg atgatatttt gaaagtgatt    420
gttgattcaa tgaatcatca tggtgatgcc cgtagcaagt tgcgtgaaga attagctgag    480
cttaccgccg aattaaagat ttattcagtt attcaagccg aaattaataa gcatctgtct    540
agtagtggca ccataaatat tccatgataaa tccattaatc tcatggataa aaatttatat    600
ggttatacag atgaagagat ttttaaagcc agcgcagagt acaaaattct cgagaaaatg    660
cctcaaacca ccattcaggt ggatgggagc gagaaaaaaa tagtctcgat aaaggacttt    720
cttggaagtg agaataaaag aaccggggcg ttgggtaatc tgaaaaactc atactcttat    780
aataaagata ataatgaatt atctcacttt gccaccacct gctcggataa gtccaggccg    840
ctcaacgact tggttagcca aaaaacaact cagctgtctg atattacatc acgttttaat    900
tcagctattg aagcactgaa ccgtttcatt cagaaatatg attcagtgat gcaacgtctg    960
ctagatgaca cgtctggtaa aggatccatg agtgcgttga acccatga tcgctcaacg    1020 ccagtaactg gaagtctact tccctacgtc gagacaccag cgcccgcccc ccttcagact   1080
caacaagtcg cggagaact gaaggataaa aatggtgggg tgagttctca gggcgtacag    1140
ctccctgcac cactagcagt ggttgccagc caagtcactg aaggacaaca gcaagaaatc    1200
actaaattat tggagtcggt cacccgcggc acggcaggat ctcaactgat atcaaattat    1260
gtttcagtgc taacgaattt tacgctcgct tcacctgata catttgagat tgagttaggt    1320
aagctagttt ctaatttaga agaagtacgc aaagacataa aaatcgctga tattcagcgt    1380
cttcatgaac aaaacatgaa gaaattgaa gagaatcaag agaaaatcaa agaaacagaa    1440
gagaatgcca agcaagtcaa gaatccggc atggcatcaa agatttttgg ctggctcagc    1500
gccatagcct cagtggttat cggtgccatc atggtggcct cagggggtagg agccgttgcc    1560
```

```
ggtgcaatga tgattgcctc aggcgtaatt gggatggcga atatggctgt gaaacaagcg    1620
gcggaagatg gcctgatatc ccaagaggca atgcaagtat tagggccgat actcactgcg    1680
attgaagtcg cattgactgt agtttcaacc gtaatgacct ttggcggttc ggcactaaaa    1740
tgcctggctg atattggcgc aaaactcggt gctaacaccg caagtcttgc tgctaaagga    1800
gccgagtttt cggccaaagt tgcccaaatt tcgacaggca tatcaaacac tgtcgggaat    1860
gcagtgacta aattagggg cagttttggt agtttaacaa tgagccatgt aatccgtaca    1920
ggatcacagg caacacaagt cgccgttggt gtgggcagcg aataactca gaccatcaat    1980 aataaaaaac aagctgattt acaacataat aacgctgatt tggccttgaa caaggcagac    2040
atggcagcgt acaaagtat tattgaccga ctcaaagaag agttatccca tttgtcagag    2100
tcacatcaac aagtgatgga actgattttc cagatgatta atgcaaaagg tgacatgctg    2160
cataatttgg ccggcagacc ccatactgtt taaggtacc                           2199
```

<210> SEQ ID NO 46
<211> LENGTH: 729
<212> TYPE: PRT
<213> ORGANISM: Artificial Sequence
<220> FEATURE:
<223> OTHER INFORMATION: synthetic construct

<400> SEQUENCE: 46

```
Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255
```

Tyr Ser Tyr Asn Lys Asp Asn Glu Leu Ser His Phe Ala Thr Thr
            260                 265                 270

Cys Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys Gly Ser Met Ser Ala Leu Ile Thr His Asp
                325                 330                 335

Arg Ser Thr Pro Val Thr Gly Ser Leu Leu Pro Tyr Val Glu Thr Pro
            340                 345                 350

Ala Pro Ala Pro Leu Gln Thr Gln Gln Val Ala Gly Glu Leu Lys Asp
            355                 360                 365

Lys Asn Gly Gly Val Ser Ser Gln Gly Val Gln Leu Pro Ala Pro Leu
    370                 375                 380

Ala Val Val Ala Ser Gln Val Thr Glu Gly Gln Gln Gln Glu Ile Thr
385                 390                 395                 400

Lys Leu Leu Glu Ser Val Thr Arg Gly Thr Ala Gly Ser Gln Leu Ile
                405                 410                 415

Ser Asn Tyr Val Ser Val Leu Thr Asn Phe Thr Leu Ala Ser Pro Asp
            420                 425                 430

Thr Phe Glu Ile Glu Leu Gly Lys Leu Val Ser Asn Leu Glu Glu Val
            435                 440                 445

Arg Lys Asp Ile Lys Ile Ala Asp Ile Gln Arg Leu His Glu Gln Asn
    450                 455                 460

Met Lys Lys Ile Glu Glu Asn Gln Glu Lys Ile Lys Glu Thr Glu Glu
465                 470                 475                 480

Asn Ala Lys Gln Val Lys Lys Ser Gly Met Ala Ser Lys Ile Phe Gly
                485                 490                 495

Trp Leu Ser Ala Ile Ala Ser Val Val Ile Gly Ala Ile Met Val Ala
            500                 505                 510

Ser Gly Val Gly Ala Val Ala Gly Ala Met Met Ile Ala Ser Gly Val
            515                 520                 525

Ile Gly Met Ala Asn Met Ala Val Lys Gln Ala Ala Glu Asp Gly Leu
    530                 535                 540

Ile Ser Gln Glu Ala Met Gln Val Leu Gly Pro Ile Leu Thr Ala Ile
545                 550                 555                 560

Glu Val Ala Leu Thr Val Val Ser Thr Val Met Thr Phe Gly Gly Ser
                565                 570                 575

Ala Leu Lys Cys Leu Ala Asp Ile Gly Ala Lys Leu Gly Ala Asn Thr
            580                 585                 590

Ala Ser Leu Ala Ala Lys Gly Ala Glu Phe Ser Ala Lys Val Ala Gln
            595                 600                 605

Ile Ser Thr Gly Ile Ser Asn Thr Val Gly Asn Ala Val Thr Lys Leu
    610                 615                 620

Gly Gly Ser Phe Gly Ser Leu Thr Met Ser His Val Ile Arg Thr Gly
625                 630                 635                 640

Ser Gln Ala Thr Gln Val Ala Val Gly Val Gly Ser Gly Ile Thr Gln
                645                 650                 655

Thr Ile Asn Asn Lys Lys Gln Ala Asp Leu Gln His Asn Asn Ala Asp
            660                 665                 670

| | | | | | |
|---|---|---|---|---|---|
| Leu | Ala | Leu Asn Lys Ala Asp Met Ala Ala Leu Gln Ser Ile Ile Asp | | | |
| | | 675 | 680 | | 685 |

Arg Leu Lys Glu Glu Leu Ser His Leu Ser Ser His Gln Gln Val
    690                    695                    700

Met Glu Leu Ile Phe Gln Met Ile Asn Ala Lys Gly Asp Met Leu His
705                  710                    715                    720

Asn Leu Ala Gly Arg Pro His Thr Val
              725

<210> SEQ ID NO 47
<211> LENGTH: 2784
<212> TYPE: DNA
<213> ORGANISM: Artificial Sequence
<220> FEATURE:
<223> OTHER INFORMATION: synthetic construct

<400> SEQUENCE: 47

| | |
|---|---|
| catatggaca atggcgatcg tttataccgt gccgactcgc gtcccccaga tgagattaaa | 60 |
| cgtagcggtg ggttaatgcc acgtgggcac aatgagtatt ttgaccgtgg aacacagatg | 120 |
| aacattaacc tttacgatca tgcccgtggg acccagaccg gtttgtccg ttatgatgac | 180 |
| gggtatgtta gtacgagttt gtccttacgc tccgcacacc ttgcgggaca agtatttta | 240 |
| tcaggctaca gcacatatta catttatgtg atcgccactg ccccaaacat gttcaatgtg | 300 |
| aacgatgtgt tggggttta cagcccccat ccatatgaac aagaagtctc ggcccttggg | 360 |
| gggatcccat atagccagat ttatggttgg taccgcgtaa attttggtgt gattgatgaa | 420 |
| cgtttgcatc gtaaccgtga ataccgcgat cgctactacc gtaacttgaa cattgcacct | 480 |
| gccgaggacg gctatcgttt agcgggattc ccacccgatc atcaggcgtg gcgtgaggaa | 540 |
| ccgtggatcc atcacgcccc tcaggggtgc gggaacagta gtcgccatat gattagagcc | 600 |
| tacgaacaaa acccacaaca ttttattgag gatctagaaa agttagggt ggaacaactt | 660 |
| actggtcatg gttcttcagt tttagaagaa ttggttcagt tagtcaaaga taaaaatata | 720 |
| gatatttcca ttaaatatga tcccagaaaa gattcggagg ttttttgccaa tagagtaatt | 780 |
| actgatgata tcgaattgct caagaaaatc ctagcttatt ttctacccga ggatgccatt | 840 |
| cttaaaggcg gtcattatga caaccaactg caaaatggca tcaagcgagt aaaagagttc | 900 |
| cttgaatcat cgccgaatac acaatgggaa ttgcgggcgt tcatggcagt aatgcatttc | 960 |
| tctttaaccg ccgatcgtat cgatgatgat attttgaaag tgattgttga ttcaatgaat | 1020 |
| catcatggtg atgcccgtag caagttgcgt gaagaattag ctgagcttac cgccgaatta | 1080 |
| aagatttatt cagttattca agccgaaatt aataagcatc tgtctagtag tggcaccata | 1140 |
| aatatccatg ataaatccat taatctcatg gataaaaatt tatatggtta tacagatgaa | 1200 |
| gagatttta aagccagcgc agagtacaaa attctcgaga aaatgcctca aaccaccatt | 1260 |
| caggtggatg ggagcgagaa aaaaatagtc tcgataaagg actttcttgg aagtgagaat | 1320 |
| aaaagaaccg gggcgttggg taatctgaaa aactcatact cttataataa agataataat | 1380 |
| gaattatctc actttgccac cacctgctcg gataagtcca ggccgctcaa cgacttggtt | 1440 |
| agccaaaaaa caactcagct gtctgatatt acatcacgtt ttaattcagc tattgaagca | 1500 |
| ctgaaccgtt tcattcagaa atatgattca gtgatgcaac gtctgctaga tgacacgtct | 1560 |
| ggtaaaggat ccatgagtgc gttgataacc catgatcgct caacgccagt aactggaagt | 1620 |
| ctacttccct acgtcgagac accagcgccc gccccctcc agactcaaca agtcgcggga | 1680 |
| gaactgaagg ataaaaatgg tggggtgagt tctcagggcg tacagctccc tgcaccacta | 1740 |

-continued

```
gcagtggttg ccagccaagt cactgaagga caacagcaag aaatcactaa attattggag    1800
tcggtcaccc gcggcacggc aggatctcaa ctgatatcaa attatgtttc agtgctaacg    1860
aattttacgc tcgcttcacc tgatacattt gagattgagt taggtaagct agtttctaat    1920
ttagaagaag tacgcaaaga cataaaaatc gctgatattc agcgtcttca tgaacaaaac    1980
atgaagaaaa ttgaagagaa tcaagagaaa tcaagagaaa cagaagagaa tgccaagcaa    2040
gtcaagaaat ccggcatggc atcaaagatt tttggctggc tcagcgccat agcctcagtg    2100
gttatcggtg ccatcatggt ggcctcaggg gtaggagccg ttgccggtgc aatgatgatt    2160
gcctcaggcg taattgggat ggcgaatatg gctgtgaaac aagcggcgga agatggcctg    2220
atatcccaag aggcaatgca agtattaggg ccgatactca ctgcgattga agtcgcattg    2280
actgtagttt caaccgtaat gacctttggc ggttcggcac taaaatgcct ggctgatatt    2340
ggcgcaaaac tcggtgctaa caccgcaagt cttgctgcta aggagccga gttttcggcc    2400 aaagttgccc aaatttcgac aggcatatca aacactgtcg ggaatgcagt gactaaatta    2460
gggggcagtt ttggtagttt aacaatgagc catgtaatcc gtacaggatc acaggcaaca    2520
caagtcgccg ttggtgtggg cagcggaata actcagacca tcaataataa aaaacaagct    2580
gatttacaac ataataacgc tgatttggcc ttgaacaagg cagacatggc agcgttacaa    2640
agtattattg accgactcaa agaagagtta tcccatttgt cagagtcaca tcaacaagtg    2700
atggaactga ttttccagat gattaatgca aaaggtgaca tgctgcataa tttggccggc    2760
agaccccata ctgtttaagg tacc                                          2784
```

<210> SEQ ID NO 48
<211> LENGTH: 923
<212> TYPE: PRT
<213> ORGANISM: Artificial Sequence
<220> FEATURE:
<223> OTHER INFORMATION: synthetic construct

<400> SEQUENCE: 48

```
Met Asp Asn Gly Asp Arg Leu Tyr Arg Ala Asp Ser Arg Pro Pro Asp
1               5                   10                  15

Glu Ile Lys Arg Ser Gly Gly Leu Met Pro Arg Gly His Asn Glu Tyr
                20                  25                  30

Phe Asp Arg Gly Thr Gln Met Asn Ile Asn Leu Tyr Asp His Ala Arg
            35                  40                  45

Gly Thr Gln Thr Gly Phe Val Arg Tyr Asp Asp Gly Tyr Val Ser Thr
        50                  55                  60

Ser Leu Ser Leu Arg Ser Ala His Leu Ala Gly Gln Ser Ile Leu Ser
65                  70                  75                  80

Gly Tyr Ser Thr Tyr Tyr Ile Tyr Val Ile Ala Thr Ala Pro Asn Met
                85                  90                  95

Phe Asn Val Asn Asp Val Leu Gly Val Tyr Ser Pro His Pro Tyr Glu
            100                 105                 110

Gln Glu Val Ser Ala Leu Gly Gly Ile Pro Tyr Ser Gln Ile Tyr Gly
        115                 120                 125

Trp Tyr Arg Val Asn Phe Gly Val Ile Asp Glu Arg Leu His Arg Asn
130                 135                 140

Arg Glu Tyr Arg Asp Arg Tyr Tyr Arg Asn Leu Asn Ile Ala Pro Ala
145                 150                 155                 160

Glu Asp Gly Tyr Arg Leu Ala Gly Phe Pro Pro Asp His Gln Ala Trp
                165                 170                 175
```

```
Arg Glu Glu Pro Trp Ile His His Ala Pro Gln Gly Cys Gly Asn Ser
            180                 185                 190

Ser Arg Met Ile Arg Ala Tyr Glu Gln Asn Pro Gln His Phe Ile Glu
        195                 200                 205

Asp Leu Glu Lys Val Arg Val Glu Gln Leu Thr Gly His Gly Ser Ser
    210                 215                 220

Val Leu Glu Glu Leu Val Gln Leu Val Lys Asp Lys Asn Ile Asp Ile
225                 230                 235                 240

Ser Ile Lys Tyr Asp Pro Arg Lys Asp Ser Glu Val Phe Ala Asn Arg
                245                 250                 255

Val Ile Thr Asp Asp Ile Glu Leu Leu Lys Lys Ile Leu Ala Tyr Phe
            260                 265                 270

Leu Pro Glu Asp Ala Ile Leu Lys Gly Gly His Tyr Asp Asn Gln Leu
        275                 280                 285

Gln Asn Gly Ile Lys Arg Val Lys Glu Phe Leu Glu Ser Ser Pro Asn
    290                 295                 300

Thr Gln Trp Glu Leu Arg Ala Phe Met Ala Val Met His Phe Ser Leu
305                 310                 315                 320

Thr Ala Asp Arg Ile Asp Asp Ile Leu Lys Val Ile Val Asp Ser
                325                 330                 335

Met Asn His His Gly Asp Ala Arg Ser Lys Leu Arg Glu Glu Leu Ala
            340                 345                 350

Glu Leu Thr Ala Glu Leu Lys Ile Tyr Ser Val Ile Gln Ala Glu Ile
        355                 360                 365

Asn Lys His Leu Ser Ser Ser Gly Thr Ile Asn Ile His Asp Lys Ser
    370                 375                 380

Ile Asn Leu Met Asp Lys Asn Leu Tyr Gly Tyr Thr Asp Glu Ile
385                 390                 395                 400

Phe Lys Ala Ser Ala Glu Tyr Lys Ile Leu Glu Lys Met Pro Gln Thr
                405                 410                 415

Thr Ile Gln Val Asp Gly Ser Glu Lys Lys Ile Val Ser Ile Lys Asp
            420                 425                 430

Phe Leu Gly Ser Glu Asn Lys Arg Thr Gly Ala Leu Gly Asn Leu Lys
        435                 440                 445

Asn Ser Tyr Ser Tyr Asn Lys Asp Asn Asn Glu Leu Ser His Phe Ala
    450                 455                 460

Thr Thr Cys Ser Asp Lys Ser Arg Pro Leu Asn Asp Leu Val Ser Gln
465                 470                 475                 480

Lys Thr Thr Gln Leu Ser Asp Ile Thr Ser Arg Phe Asn Ser Ala Ile
                485                 490                 495

Glu Ala Leu Asn Arg Phe Ile Gln Lys Tyr Asp Ser Val Met Gln Arg
            500                 505                 510

Leu Leu Asp Asp Thr Ser Gly Lys Gly Ser Met Ser Ala Leu Ile Thr
        515                 520                 525

His Asp Arg Ser Thr Pro Val Thr Gly Ser Leu Leu Pro Tyr Val Glu
    530                 535                 540

Thr Pro Ala Pro Ala Pro Leu Gln Thr Gln Val Ala Gly Glu Leu
545                 550                 555                 560

Lys Asp Lys Asn Gly Gly Val Ser Ser Gln Gly Val Gln Leu Pro Ala
                565                 570                 575

Pro Leu Ala Val Val Ala Ser Gln Val Thr Glu Gly Gln Gln Gln Glu
            580                 585                 590
```

```
Ile Thr Lys Leu Leu Glu Ser Val Thr Arg Gly Thr Ala Gly Ser Gln
            595                 600                 605

Leu Ile Ser Asn Tyr Val Ser Val Leu Thr Asn Phe Thr Leu Ala Ser
    610                 615                 620

Pro Asp Thr Phe Glu Ile Glu Leu Gly Lys Leu Val Ser Asn Leu Glu
625                 630                 635                 640

Glu Val Arg Lys Asp Ile Lys Ile Ala Asp Ile Gln Arg Leu His Glu
                645                 650                 655

Gln Asn Met Lys Lys Ile Glu Glu Asn Gln Lys Ile Lys Glu Thr
            660                 665                 670

Glu Glu Asn Ala Lys Gln Val Lys Lys Ser Gly Met Ala Ser Lys Ile
            675                 680                 685

Phe Gly Trp Leu Ser Ala Ile Ala Ser Val Val Ile Gly Ala Ile Met
690                 695                 700

Val Ala Ser Gly Val Gly Ala Val Ala Gly Ala Met Met Ile Ala Ser
705                 710                 715                 720

Gly Val Ile Gly Met Ala Asn Met Ala Val Lys Gln Ala Ala Glu Asp
                725                 730                 735

Gly Leu Ile Ser Gln Glu Ala Met Gln Val Leu Gly Pro Ile Leu Thr
            740                 745                 750

Ala Ile Glu Val Ala Leu Thr Val Val Ser Thr Val Met Thr Phe Gly
            755                 760                 765

Gly Ser Ala Leu Lys Cys Leu Ala Asp Ile Gly Ala Lys Leu Gly Ala
            770                 775                 780

Asn Thr Ala Ser Leu Ala Ala Lys Gly Ala Glu Phe Ser Ala Lys Val
785                 790                 795                 800

Ala Gln Ile Ser Thr Gly Ile Ser Asn Thr Val Gly Asn Ala Val Thr
                805                 810                 815

Lys Leu Gly Gly Ser Phe Gly Ser Leu Thr Met Ser His Val Ile Arg
            820                 825                 830

Thr Gly Ser Gln Ala Thr Gln Val Ala Val Gly Val Gly Ser Gly Ile
            835                 840                 845

Thr Gln Thr Ile Asn Asn Lys Lys Gln Ala Asp Leu Gln His Asn Asn
850                 855                 860

Ala Asp Leu Ala Leu Asn Lys Ala Asp Met Ala Ala Leu Gln Ser Ile
865                 870                 875                 880

Ile Asp Arg Leu Lys Glu Leu Ser His Leu Ser Glu Ser His Gln
                885                 890                 895

Gln Val Met Glu Leu Ile Phe Gln Met Ile Asn Ala Lys Gly Asp Met
            900                 905                 910

Leu His Asn Leu Ala Gly Arg Pro His Thr Val
            915                 920

<210> SEQ ID NO 49
<211> LENGTH: 546
<212> TYPE: DNA
<213> ORGANISM: Artificial Sequence
<220> FEATURE:
<223> OTHER INFORMATION: synthetic construct

<400> SEQUENCE: 49
atgggcagca gccatcacca tcatcaccac agccaggatc cgatggacta ccagaacaac      60
gtcagcgaag aacgtgttgc ggaaatgatt tgggatgccg ttagtgaagg cgccacgcta     120
aaagacgttc atggaatccc tcaagatatg atggacggtt tatatgctca tgcttatgag     180
```

```
ttttataacc agggacgact ggatgaagct gagacgttct ttcgtttctt atgcatttat    240
gatttttaca atcccgatta caccatggga ctggcggcag tatgccaact gaaaaaacaa    300
tttcagaaag catgtgacct ttatgcagta gcgtttacgt tacttaaaaa tgattatcgc    360
ccgttttttt ttaccgggca gtgtcaatta ttaatgcgta aggcagcaaa agccagacag    420
tgttttgaac ttgtcaatga acgtactgaa gatgagtctc tgcgggcaaa agcgttggtc    480
tatctggagg cgctaaaaac ggcggagaca gagcagcaca gcgagcagga aaggagtaa     540 aagctt                                                               546
```

<210> SEQ ID NO 50
<211> LENGTH: 179
<212> TYPE: PRT
<213> ORGANISM: Artificial Sequence
<220> FEATURE:
<223> OTHER INFORMATION: synthetic construct

<400> SEQUENCE: 50

```
Met Gly Ser Ser His His His His His Ser Gln Asp Pro Met Asp
1               5                   10                  15

Tyr Gln Asn Asn Val Ser Glu Glu Arg Val Ala Glu Met Ile Trp Asp
            20                  25                  30

Ala Val Ser Glu Gly Ala Thr Leu Lys Asp Val His Gly Ile Pro Gln
        35                  40                  45

Asp Met Met Asp Gly Leu Tyr Ala His Ala Tyr Glu Phe Tyr Asn Gln
    50                  55                  60

Gly Arg Leu Asp Glu Ala Glu Thr Phe Phe Arg Phe Leu Cys Ile Tyr
65                  70                  75                  80

Asp Phe Tyr Asn Pro Asp Tyr Thr Met Gly Leu Ala Ala Val Cys Gln
                85                  90                  95

Leu Lys Lys Gln Phe Gln Lys Ala Cys Asp Leu Tyr Ala Val Ala Phe
            100                 105                 110

Thr Leu Leu Lys Asn Asp Tyr Arg Pro Val Phe Phe Thr Gly Gln Cys
        115                 120                 125

Gln Leu Leu Met Arg Lys Ala Ala Lys Ala Arg Gln Cys Phe Glu Leu
    130                 135                 140

Val Asn Glu Arg Thr Glu Asp Glu Ser Leu Arg Ala Lys Ala Leu Val
145                 150                 155                 160

Tyr Leu Glu Ala Leu Lys Thr Ala Glu Thr Glu Gln His Ser Glu Gln
                165                 170                 175

Glu Lys Glu
```

<210> SEQ ID NO 51
<211> LENGTH: 1029
<212> TYPE: DNA
<213> ORGANISM: Salmonella spp

<400> SEQUENCE: 51

```
atgcttaata ttcaaaatta ttccgcttct cctcatccgg ggatcgttgc cgaacggccg     60
cagactccct cggcgagcga gcacgtcgag actgccgtgg taccgtctac cacagaacat    120
cgcggtacag atatcatttc attatcgcag gcggctacta aaatccacca ggcacagcag    180
acgctgcagt caacgccacc gatctctgaa gagaataatg acgagcgcac gctggcgcgc    240
cagcagttga ccagcagcct gaatgcgctg gcgaagtccg gcgtgtcatt atccgcagaa    300
caaaatgaga acctgcggag cgcgttttct gcgccgacgt cggccttatt tagcgcttcg    360
```

-continued

```
cctatggcgc agccgagaac aaccatttct gatgctgaga tttggatat ggtttcccaa      420 aatatatcgg cgataggtga cagctatctg ggcgtttatg aaaacgttgt cgcagtctat      480
accgattttt atcaggcctt cagtgatatt ctttccaaaa tgggaggctg ttattacca       540 ggtaaggacg gtaataccgt taagctagat gttacctcac tcaaaaatga tttaaacagt      600
ttagtcaata aatataatca aataaacagt aataccgttt tatttccagc gcagtcaggc      660
agcggcgtta aagtagccac tgaagcggaa gcgagacagt ggctcagtga attgaattta      720
ccgaatagct gcctgaaatc ttatggatcc ggttatgtcg tcaccgttga tctgacgcca      780
ttacaaaaaa tggttcagga tattgatggt ttaggcgcgc cgggaaaaga ctcaaaactc      840
gaaatggata acgccaaata tcaagcctgg cagtcgggtt ttaaagcgca ggaagaaaat      900
atgaaaacca cattacagac gctgacgcaa aaatatagca atgccaattc attgtacgac      960
aacctggtaa aagtgctgag cagtacgata agtagcagcc tggaaaccgc caaaagcttc     1020
ctgcaagga                                                             1029
```

<210> SEQ ID NO 52
<211> LENGTH: 343
<212> TYPE: PRT
<213> ORGANISM: Salmonella spp

<400> SEQUENCE: 52

```
Met Leu Asn Ile Gln Asn Tyr Ser Ala Ser Pro His Pro Gly Ile Val
1               5                   10                  15

Ala Glu Arg Pro Gln Thr Pro Ser Ala Ser Glu His Val Glu Thr Ala
            20                  25                  30

Val Val Pro Ser Thr Thr Glu His Arg Gly Thr Asp Ile Ile Ser Leu
        35                  40                  45

Ser Gln Ala Ala Thr Lys Ile His Gln Ala Gln Thr Leu Gln Ser
    50                  55                  60

Thr Pro Pro Ile Ser Glu Glu Asn Asn Asp Glu Arg Thr Leu Ala Arg
65                  70                  75                  80

Gln Gln Leu Thr Ser Ser Leu Asn Ala Leu Ala Lys Ser Gly Val Ser
                85                  90                  95

Leu Ser Ala Glu Gln Asn Glu Asn Leu Arg Ser Ala Phe Ser Ala Pro
            100                 105                 110

Thr Ser Ala Leu Phe Ser Ala Ser Pro Met Ala Gln Pro Arg Thr Thr
        115                 120                 125

Ile Ser Asp Ala Glu Ile Trp Asp Met Val Ser Gln Asn Ile Ser Ala
    130                 135                 140

Ile Gly Asp Ser Tyr Leu Gly Val Tyr Glu Asn Val Val Ala Val Tyr
145                 150                 155                 160

Thr Asp Phe Tyr Gln Ala Phe Ser Asp Ile Leu Ser Lys Met Gly Gly
                165                 170                 175

Trp Leu Leu Pro Gly Lys Asp Gly Asn Thr Val Lys Leu Asp Val Thr
            180                 185                 190

Ser Leu Lys Asn Asp Leu Asn Ser Leu Val Asn Lys Tyr Asn Gln Ile
        195                 200                 205

Asn Ser Asn Thr Val Leu Phe Pro Ala Gln Ser Gly Ser Gly Val Lys
    210                 215                 220

Val Ala Thr Glu Ala Glu Ala Arg Gln Trp Leu Ser Glu Leu Asn Leu
225                 230                 235                 240

Pro Asn Ser Cys Leu Lys Ser Tyr Gly Ser Gly Tyr Val Val Thr Val
                245                 250                 255
```

```
Asp Leu Thr Pro Leu Gln Lys Met Val Gln Asp Ile Asp Gly Leu Gly
            260                 265                 270

Ala Pro Gly Lys Asp Ser Lys Leu Glu Met Asp Asn Ala Lys Tyr Gln
        275                 280                 285

Ala Trp Gln Ser Gly Phe Lys Ala Gln Glu Asn Met Lys Thr Thr
    290                 295                 300

Leu Gln Thr Leu Thr Gln Lys Tyr Ser Asn Ala Asn Ser Leu Tyr Asp
305                 310                 315                 320

Asn Leu Val Lys Val Leu Ser Ser Thr Ile Ser Ser Leu Glu Thr
                325                 330                 335

Ala Lys Ser Phe Leu Gln Gly
            340

<210> SEQ ID NO 53
<211> LENGTH: 1782
<212> TYPE: DNA
<213> ORGANISM: Salmonella spp

<400> SEQUENCE: 53
```

| | | | | | |
|---|---|---|---|---|---|
| atggtaaatg | acgcaagtag | cattagccgt | agcggatata | cccaaaatcc | gcgcctcgct | 60 |
| gaggcggctt | ttgaaggcgt | tcgtaagaac | acggactttt | taaaagcggc | ggataaagct | 120 |
| tttaaagatg | tggtggcaac | gaaagcgggc | gaccttaaag | ccggaacaaa | gtccggcgag | 180 |
| agcgctatta | atacggtggg | tctaaagccg | cctacggacg | ccgcccggga | aaaactctcc | 240 |
| agcgaagggc | aattgacatt | actgcttggc | aagttaatga | ccctactggg | cgatgtttcg | 300 |
| ctgtctcaac | tggagtctcg | tctggcggta | tggcaggcga | tgattgagtc | acaaaaagag | 360 |
| atggggattc | aggtatcgaa | agaattccag | acgctctggg | agagggctca | ggaggcgacg | 420 |
| gatctctatg | aagccagtat | caaaaagacg | gataccgcca | agagtgttta | tgacgctgcg | 480 |
| accaaaaaac | tgacgcaggc | gcaaaataaa | ttgcaatcgc | tggacccggc | tgaccccggc | 540 |
| tatgcacaag | ctgaagccgc | ggtagaacag | gccggaaaag | aagcgacaga | ggcgaaagag | 600 |
| gccttagata | aggccacgga | tgcgacggtt | aaagcaggca | cagacgccaa | agcgaaagcc | 660 |
| gagaaagcgg | ataacattct | gaccaaattc | cagggaacgg | ctaatgccgc | ctctcagaat | 720 |
| caggtttccc | agggtgagca | ggataatctg | tcaaatgtcg | cccgcctcac | tatgctcatg | 780 |
| gccatgttta | ttgagattgt | gggcaaaaat | acggaagaaa | gcctgcaaaa | cgatcttgcg | 840 |
| cttttcaacg | ccttgcagga | agggcgtcag | gcggagatgg | aaaagaaatc | ggctgaattc | 900 |
| caggaagaga | cgcgcaaagc | cgaggaaacg | aaccgcatta | tgggatgtat | cgggaaagtc | 960 |
| ctcggcgcgc | tgctaaccat | tgtcagcgtt | gtggccgctg | tttttaccgg | tggggcgagt | 1020 |
| ctggcgctgg | ctgcggtggg | acttgcggta | atggtggccg | atgaaattgt | gaaggcggcg | 1080 |
| acgggagtgt | cgtttattca | gcaggcgcta | aacccgatta | tggagcatgt | gctgaagccg | 1140 |
| ttaatggagc | tgattggcaa | ggcgattacc | aaagcgctgg | aaggattagg | cgtcgataag | 1200 |
| aaaacggcag | agatggccgg | cagcattgtt | ggtgcgattg | tcgccgctat | tgccatggtg | 1260 |
| gcggtcattg | tggtggtcgc | agttgtcggg | aaaggcgcgg | cggcgaaact | gggtaacgcg | 1320 |
| ctgagcaaaa | tgatgggcga | aacgattaag | aagttggtgc | taacgtgct | gaaacagttg | 1380 |
| gcgcaaaacg | gcagcaaact | ctttacccag | gggatgcaac | gtattactag | cggtctgggt | 1440 |
| aatgtgggta | gcaagatggg | cctgcaaacg | aatgccttaa | gtaaagagct | ggtaggtaat | 1500 |
| accctaaata | aagtggcgtt | gggcatggaa | gtcacgaata | ccgcagccca | gtcagccggt | 1560 |

```
ggtgttgccg agggcgtatt tattaaaaat gccagcgagg cgcttgctga ttttatgctc    1620
gcccgttttg ccatggatca gattcagcag tggcttaaac aatccgtaga aatatttggt    1680
gaaaaccaga aggtaacggc ggaactgcaa aaagccatgt cttctgcggt acagcaaaat    1740
gcggatgctt cgcgttttat tctgcgccag agtcgcgcat aa                       1782
```

<210> SEQ ID NO 54
<211> LENGTH: 593
<212> TYPE: PRT
<213> ORGANISM: Salmonella spp

<400> SEQUENCE: 54

```
Met Val Asn Asp Ala Ser Ser Ile Ser Arg Ser Gly Tyr Thr Gln Asn
1               5                   10                  15

Pro Arg Leu Ala Glu Ala Ala Phe Glu Gly Val Arg Lys Asn Thr Asp
            20                  25                  30

Phe Leu Lys Ala Ala Asp Lys Ala Phe Lys Asp Val Val Ala Thr Lys
        35                  40                  45

Ala Gly Asp Leu Lys Ala Gly Thr Lys Ser Gly Glu Ser Ala Ile Asn
    50                  55                  60

Thr Val Gly Leu Lys Pro Pro Thr Asp Ala Ala Arg Glu Lys Leu Ser
65                  70                  75                  80

Ser Glu Gly Gln Leu Thr Leu Leu Gly Lys Leu Met Thr Leu Leu
                85                  90                  95

Gly Asp Val Ser Leu Ser Gln Leu Glu Ser Arg Leu Ala Val Trp Gln
            100                 105                 110

Ala Met Ile Glu Ser Gln Lys Glu Met Gly Ile Gln Val Ser Lys Glu
        115                 120                 125

Phe Gln Thr Ala Leu Gly Glu Ala Gln Glu Ala Thr Asp Leu Tyr Glu
    130                 135                 140

Ala Ser Ile Lys Lys Thr Asp Thr Ala Lys Ser Val Tyr Asp Ala Ala
145                 150                 155                 160

Thr Lys Lys Leu Thr Gln Ala Gln Asn Lys Leu Gln Ser Leu Asp Pro
                165                 170                 175

Ala Asp Pro Gly Tyr Ala Gln Ala Glu Ala Ala Val Glu Gln Ala Gly
            180                 185                 190

Lys Glu Ala Thr Glu Ala Lys Glu Ala Leu Asp Lys Ala Thr Asp Ala
        195                 200                 205

Thr Val Lys Ala Gly Thr Asp Ala Lys Ala Lys Ala Glu Lys Ala Asp
    210                 215                 220

Asn Ile Leu Thr Lys Phe Gln Gly Thr Ala Asn Ala Ala Ser Gln Asn
225                 230                 235                 240

Gln Val Ser Gln Gly Glu Gln Asp Asn Leu Ser Asn Val Ala Arg Leu
                245                 250                 255

Thr Met Leu Met Ala Met Phe Ile Glu Ile Val Gly Lys Asn Thr Glu
            260                 265                 270

Glu Ser Leu Gln Asn Asp Leu Ala Leu Phe Asn Ala Leu Gln Glu Gly
        275                 280                 285

Arg Gln Ala Glu Met Glu Lys Lys Ser Ala Glu Phe Gln Glu Glu Thr
    290                 295                 300

Arg Lys Ala Glu Glu Thr Asn Arg Ile Met Gly Cys Ile Gly Lys Val
305                 310                 315                 320

Leu Gly Ala Leu Leu Thr Ile Val Ser Val Ala Ala Val Phe Thr
                325                 330                 335
```

Gly Gly Ala Ser Leu Ala Leu Ala Ala Val Gly Leu Ala Val Met Val
            340                 345                 350

Ala Asp Glu Ile Val Lys Ala Ala Thr Gly Val Ser Phe Ile Gln Gln
    355                 360                 365

Ala Leu Asn Pro Ile Met Glu His Val Leu Lys Pro Leu Met Glu Leu
    370                 375                 380

Ile Gly Lys Ala Ile Thr Lys Ala Leu Glu Gly Leu Gly Val Asp Lys
385                 390                 395                 400

Lys Thr Ala Glu Met Ala Gly Ser Ile Val Gly Ala Ile Val Ala Ala
                405                 410                 415

Ile Ala Met Val Ala Val Ile Val Val Ala Val Gly Lys Gly
                420                 425                 430

Ala Ala Ala Lys Leu Gly Asn Ala Leu Ser Lys Met Met Gly Glu Thr
        435                 440                 445

Ile Lys Lys Leu Val Pro Asn Val Leu Lys Gln Leu Ala Gln Asn Gly
        450                 455                 460

Ser Lys Leu Phe Thr Gln Gly Met Gln Arg Ile Thr Ser Gly Leu Gly
465                 470                 475                 480

Asn Val Gly Ser Lys Met Gly Leu Gln Thr Asn Ala Leu Ser Lys Glu
                485                 490                 495

Leu Val Gly Asn Thr Leu Asn Lys Val Ala Leu Gly Met Glu Val Thr
                500                 505                 510

Asn Thr Ala Ala Gln Ser Ala Gly Gly Val Ala Glu Gly Val Phe Ile
            515                 520                 525

Lys Asn Ala Ser Glu Ala Leu Ala Asp Phe Met Leu Ala Arg Phe Ala
530                 535                 540

Met Asp Gln Ile Gln Gln Trp Leu Lys Gln Ser Val Glu Ile Phe Gly
545                 550                 555                 560

Glu Asn Gln Lys Val Thr Ala Glu Leu Gln Lys Ala Met Ser Ser Ala
                565                 570                 575

Val Gln Gln Asn Ala Asp Ala Ser Arg Phe Ile Leu Arg Gln Ser Arg
            580                 585                 590

Ala

<210> SEQ ID NO 55
<211> LENGTH: 2817
<212> TYPE: DNA
<213> ORGANISM: Artificial Sequence
<220> FEATURE:
<223> OTHER INFORMATION: synthetic construct

<400> SEQUENCE: 55
atgcttaata ttcaaaatta ttccgcttct cctcatccgg ggatcgttgc cgaacggccg      60
cagactccct cggcgagcga gcacgtcgag actgccgtgg taccgtctac cacagaacat     120
cgcggtacag atatcatttc attatcgcag gcggctacta aaatccacca ggcacagcag     180
acgctgcagt caacgccacc gatctctgaa gagaataatg acgagcgcac gctggcgcgc     240
cagcagttga ccagcagcct gaatgcgctg gcgaagtccg gcgtgtcatt atccgcagaa     300
caaaatgaga acctgcggag cgcgtttttct gcgccgacgt cggccttatt tagcgcttcg     360
cctatggcgc agccgagaac aaccatttct gatgctgaga tttgggatat ggtttcccaa     420
aatatatcgg cgataggtga cagctatctg ggcgtttatg aaaacgttgt cgcagtctat     480
accgattttt tcaggccctt cagtgatatt ctttccaaaa tgggaggctg ttattacca     540 ggtaaggacg gtaataccgt taagctagat gttacctcac tcaaaaatga tttaaacagt     600

```
ttagtcaata aatataatca aataaacagt aataccgttt tatttccagc gcagtcaggc    660
agcggcgtta aagtagccac tgaagcggaa gcgagacagt ggctcagtga attgaattta    720
ccgaatagct gcctgaaatc ttatggatcc ggttatgtcg tcaccgttga tctgacgcca    780
ttacaaaaaa tggttcagga tattgatggt ttaggcgcgc cgggaaaaga ctcaaaactc    840
gaaatggata acgccaaata tcaagcctgg cagtcgggtt ttaaagcgca ggaagaaaat    900
atgaaaacca cattacagac gctgacgcaa aaatatagca atgccaattc attgtacgac    960
aacctggtaa aagtgctgag cagtacgata agtagcagcc tggaaaccgc caaaagcttc   1020
ctgcaaggag tcgacatggt aaatgacgca agtagcatta gccgtagcgg atatacccaa   1080
aatccgcgcc tcgctgaggc ggcttttgaa ggcgttcgta agaacacgga ctttttaaaa   1140
gcggcggata aagcttttaa agatgtggtg gcaacgaaag cgggcgacct taaagccgga   1200
acaaagtccg gcgagagcgc tattaatacg gtgggtctaa agccgcctac ggacgccgcc   1260
cgggaaaaac tctccagcga agggcaattg acattactgc ttggcaagtt aatgacccta   1320
ctgggcgatg tttcgctgtc tcaactggag tctcgtctgg cggtatggca ggcgatgatt   1380
gagtcacaaa aagagatggg gattcaggta tcgaaagaat ccagacggc tctgggagag     1440 gctcaggagg cgacggatct ctatgaagcc agtatcaaaa agacggatac cgccaagagt   1500
gtttatgacg ctgcgaccaa aaaactgacg caggcgcaaa ataaattgca atcgctggac   1560
ccggctgacc ccggctatgc acaagctgaa gccgcggtag aacaggccgg aaaagaagcg   1620
acagaggcga aagaggcctt agataaggcc acggatgcga cggttaaagc aggcacagac   1680
gccaaagcga aagccgagaa agcggataac attctgacca aattccaggg aacggctaat   1740
gccgcctctc agaatcaggt ttcccagggt gagcaggata tctgtcaaa tgtcgcccgc    1800 ctcactatgc tcatggccat gtttattgag attgtgggca aaaatacgga agaaagcctg   1860
caaaacgatc ttgcgctttt caacgccttg caggaagggc gtcaggcgga gatggaaaag   1920
aaatcggctg aattccagga agagacgcgc aaagccgagg aaacgaaccg cattatggga   1980
tgtatcggga aagtcctcgg cgcgctgcta accattgtca gcgttgtggc cgctgttttt   2040
accggtgggg cgagtctggc gctggctgcg gtgggacttg cggtaatggt ggccgatgaa   2100
attgtgaagg cggcgacggg agtgtcgttt attcagcagg cgctaaaccc gattatggag   2160
catgtgctga agccgttaat ggagctgatt ggcaaggcga ttaccaaagc gctggaagga   2220
ttaggcgtcg ataagaaaac ggcagagatg gccggcagca ttgttggtgc gattgtcgcc   2280
gctattgcca tggtggcggt cattgtggtg gtcgcagttg tcgggaaagg cgcggcggcg   2340
aaactgggta acgcgctgag caaaatgatg ggcgaaacga ttaagaagtt ggtgcctaac   2400
gtgctgaaac agttggcgca aaacggcagc aaactcttta cccagggat gcaacgtatt     2460 actagcggtc tgggtaatgt gggtagcaag atgggcctgc aaacgaatgc cttaagtaaa   2520
gagctggtag gtaatacccct aaataaagtg gcgttgggca tggaagtcac gaataccgca    2580
gcccagtcag ccggtggtgt tgccgagggc gtatttatta aaaatgccag cgaggcgctt   2640
gctgatttta tgctcgcccg ttttgccatg gatcagattc agcagtggct taaacaatcc   2700
gtagaaatat ttggtgaaaa ccagaaggta acggcggaac tgcaaaaagc catgtcttct   2760
gcggtacagc aaaatgcgga tgcttcgcgt tttattctgc gccagagtcg cgcataa      2817
```

<210> SEQ ID NO 56
<211> LENGTH: 938
<212> TYPE: PRT

<213> ORGANISM: Artificial Sequence
<220> FEATURE:
<223> OTHER INFORMATION: synthetic construct

<400> SEQUENCE: 56

```
Met Leu Asn Ile Gln Asn Tyr Ser Ala Ser Pro His Pro Gly Ile Val
1               5                   10                  15

Ala Glu Arg Pro Gln Thr Pro Ser Ala Ser Glu His Val Glu Thr Ala
            20                  25                  30

Val Val Pro Ser Thr Thr Glu His Arg Gly Thr Asp Ile Ile Ser Leu
        35                  40                  45

Ser Gln Ala Ala Thr Lys Ile His Gln Ala Gln Thr Leu Gln Ser
    50                  55                  60

Thr Pro Pro Ile Ser Glu Glu Asn Asn Asp Glu Arg Thr Leu Ala Arg
65                  70                  75                  80

Gln Gln Leu Thr Ser Ser Leu Asn Ala Leu Ala Lys Ser Gly Val Ser
                85                  90                  95

Leu Ser Ala Glu Gln Asn Glu Asn Leu Arg Ser Ala Phe Ser Ala Pro
            100                 105                 110

Thr Ser Ala Leu Phe Ser Ala Ser Pro Met Ala Gln Pro Arg Thr Thr
        115                 120                 125

Ile Ser Asp Ala Glu Ile Trp Asp Met Val Ser Gln Asn Ile Ser Ala
130                 135                 140

Ile Gly Asp Ser Tyr Leu Gly Val Tyr Glu Asn Val Val Ala Val Tyr
145                 150                 155                 160

Thr Asp Phe Tyr Gln Ala Phe Ser Asp Ile Leu Ser Lys Met Gly Gly
                165                 170                 175

Trp Leu Leu Pro Gly Lys Asp Gly Asn Thr Val Lys Leu Asp Val Thr
            180                 185                 190

Ser Leu Lys Asn Asp Leu Asn Ser Leu Val Asn Lys Tyr Asn Gln Ile
        195                 200                 205

Asn Ser Asn Thr Val Leu Phe Pro Ala Gln Ser Gly Ser Gly Val Lys
    210                 215                 220

Val Ala Thr Glu Ala Glu Ala Arg Gln Trp Leu Ser Glu Leu Asn Leu
225                 230                 235                 240

Pro Asn Ser Cys Leu Lys Ser Tyr Gly Ser Gly Tyr Val Val Thr Val
                245                 250                 255

Asp Leu Thr Pro Leu Gln Lys Met Val Gln Asp Ile Asp Gly Leu Gly
            260                 265                 270

Ala Pro Gly Lys Asp Ser Lys Leu Glu Met Asp Asn Ala Lys Tyr Gln
        275                 280                 285

Ala Trp Gln Ser Gly Phe Lys Ala Gln Glu Glu Asn Met Lys Thr Thr
    290                 295                 300

Leu Gln Thr Leu Thr Gln Lys Tyr Ser Asn Ala Asn Ser Leu Tyr Asp
305                 310                 315                 320

Asn Leu Val Lys Val Leu Ser Ser Thr Ile Ser Ser Ser Leu Glu Thr
                325                 330                 335

Ala Lys Ser Phe Leu Gln Gly Val Asp Met Val Asn Asp Ala Ser Ser
            340                 345                 350

Ile Ser Arg Ser Gly Tyr Thr Gln Asn Pro Arg Leu Ala Glu Ala Ala
        355                 360                 365

Phe Glu Gly Val Arg Lys Asn Thr Asp Phe Leu Lys Ala Ala Asp Lys
    370                 375                 380

Ala Phe Lys Asp Val Val Ala Thr Lys Ala Gly Asp Leu Lys Ala Gly
```

-continued

```
            385                 390                 395                 400
Thr Lys Ser Gly Glu Ser Ala Ile Asn Thr Val Gly Leu Lys Pro Pro
                    405                 410                 415

Thr Asp Ala Ala Arg Glu Lys Leu Ser Ser Glu Gly Gln Leu Thr Leu
                420                 425                 430

Leu Leu Gly Lys Leu Met Thr Leu Gly Asp Val Ser Leu Ser Gln
            435                 440                 445

Leu Glu Ser Arg Leu Ala Val Trp Gln Ala Met Ile Glu Ser Gln Lys
        450                 455                 460

Glu Met Gly Ile Gln Val Ser Lys Glu Phe Gln Thr Ala Leu Gly Glu
465                 470                 475                 480

Ala Gln Glu Ala Thr Asp Leu Tyr Glu Ala Ser Ile Lys Lys Thr Asp
                485                 490                 495

Thr Ala Lys Ser Val Tyr Asp Ala Ala Thr Lys Lys Leu Thr Gln Ala
                500                 505                 510

Gln Asn Lys Leu Gln Ser Leu Asp Pro Ala Asp Pro Gly Tyr Ala Gln
            515                 520                 525

Ala Glu Ala Ala Val Glu Gln Ala Gly Lys Glu Ala Thr Glu Ala Lys
        530                 535                 540

Glu Ala Leu Asp Lys Ala Thr Asp Ala Thr Val Lys Ala Gly Thr Asp
545                 550                 555                 560

Ala Lys Ala Lys Ala Glu Lys Ala Asp Asn Ile Leu Thr Lys Phe Gln
                565                 570                 575

Gly Thr Ala Asn Ala Ala Ser Gln Asn Gln Val Ser Gln Gly Glu Gln
            580                 585                 590

Asp Asn Leu Ser Asn Val Ala Arg Leu Thr Met Leu Met Ala Met Phe
        595                 600                 605

Ile Glu Ile Val Gly Lys Asn Thr Glu Ser Leu Gln Asn Asp Leu
        610                 615                 620

Ala Leu Phe Asn Ala Leu Gln Glu Gly Arg Gln Ala Glu Met Glu Lys
625                 630                 635                 640

Lys Ser Ala Glu Phe Gln Glu Glu Thr Arg Lys Ala Glu Glu Thr Asn
                645                 650                 655

Arg Ile Met Gly Cys Ile Gly Lys Val Leu Gly Ala Leu Leu Thr Ile
                660                 665                 670

Val Ser Val Val Ala Ala Val Phe Thr Gly Gly Ala Ser Leu Ala Leu
            675                 680                 685

Ala Ala Val Gly Leu Ala Val Met Val Ala Asp Glu Ile Val Lys Ala
        690                 695                 700

Ala Thr Gly Val Ser Phe Ile Gln Gln Ala Leu Asn Pro Ile Met Glu
705                 710                 715                 720

His Val Leu Lys Pro Leu Met Glu Leu Ile Gly Lys Ala Ile Thr Lys
                725                 730                 735

Ala Leu Glu Gly Leu Gly Val Asp Lys Lys Thr Ala Glu Met Ala Gly
            740                 745                 750

Ser Ile Val Gly Ala Ile Val Ala Ile Ala Met Val Ala Val Ile
        755                 760                 765

Val Val Val Ala Val Val Gly Lys Gly Ala Ala Lys Leu Gly Asn
770                 775                 780

Ala Leu Ser Lys Met Met Gly Glu Thr Ile Lys Lys Leu Val Pro Asn
                785                 790                 795                 800

Val Leu Lys Gln Leu Ala Gln Asn Gly Ser Lys Leu Phe Thr Gln Gly
            805                 810                 815
```

```
Met Gln Arg Ile Thr Ser Gly Leu Gly Asn Val Gly Ser Lys Met Gly
                820                 825                 830

Leu Gln Thr Asn Ala Leu Ser Lys Glu Leu Val Gly Asn Thr Leu Asn
            835                 840                 845

Lys Val Ala Leu Gly Met Glu Val Thr Asn Thr Ala Ala Gln Ser Ala
850                 855                 860

Gly Gly Val Ala Glu Gly Val Phe Ile Lys Asn Ala Ser Glu Ala Leu
865                 870                 875                 880

Ala Asp Phe Met Leu Ala Arg Phe Ala Met Asp Gln Ile Gln Trp
                885                 890                 895

Leu Lys Gln Ser Val Glu Ile Phe Gly Glu Asn Gln Lys Val Thr Ala
            900                 905                 910

Glu Leu Gln Lys Ala Met Ser Ser Ala Val Gln Gln Asn Ala Asp Ala
        915                 920                 925

Ser Arg Phe Ile Leu Arg Gln Ser Arg Ala
    930                 935
```

<210> SEQ ID NO 57
<211> LENGTH: 3423
<212> TYPE: DNA
<213> ORGANISM: Artificial Sequence
<220> FEATURE:
<223> OTHER INFORMATION: synthetic construct

<400> SEQUENCE: 57

```
catatggaca atggcgatcg tttataccgt gccgactcgc gtcccccaga tgagattaaa    60
cgtagcggtg ggttaatgcc acgtgggcac aatgagtatt ttgaccgtgg aacacagatg   120
aacattaacc tttacgatca tgcccgtggg acccagaccg ggtttgtccg ttatgatgac   180
gggtatgtta gtacgagttt gtccttacgc tccgcacacc ttgcgggaca agtatttta   240
tcaggctaca gcacatatta catttatgtg atcgccactg ccccaaacat gttcaatgtg   300
aacgatgtgt tggggggttta cagcccccat ccatatgaac aagaagtctc ggcccttggg   360
gggatcccat atagccagat ttatggttgg taccgcgtaa attttggtgt gattgatgaa   420
cgtttgcatc gtaaccgtga ataccgcgat cgctactacc gtaacttgaa cattgcacct   480
gccgaggacg gctatcgttt agcgggattc ccacccgatc atcaggcgtg gcgtgaggaa   540
ccgtggatcc atcacgcccc tcaggggtgc gggaacagta gtcgcgggtc cgcggcatcc   600
atgcttaata ttcaaaatta ttccgcttct cctcatccgg ggatcgttgc cgaacggccg   660
cagactccct cggcgagcga gcacgtcgag actgccgtgg taccgtctac cacagaacat   720
cgcggtacag atatcatttc attatcgcag gcggctacta aaatccacca ggcacagcag   780
acgctgcagt caacgccacc gatctctgaa gagaataatg acgagcgcac gctggcgcgc   840
cagcagttga ccagcagcct gaatgcgctg gcgaagtccg gcgtgtcatt atccgcagaa   900
caaaatgaga acctgcggag cgcgtttttct gcgccgacgt cggccttatt tagcgcttcg   960
cctatggcgc agccgagaac aaccatttct gatgctgaga tttgggatat ggtttcccaa  1020
aatatatcgg cgataggtga cagctatctg ggcgtttatg aaaacgttgt cgcagtctat  1080
accgattttt atcaggcctt cagtgatatt ctttccaaaa tggaggctg gttattacca  1140
ggtaaggacg gtaataccgt taagctagat gttacctcac tcaaaatga tttaaacagt  1200
ttagtcaata aatataatca aataaacagt aataccgttt tatttccagc gcagtcaggc  1260
agcggcgtta agtagccac tgaagcggaa gcgagacagt ggctcagtga attgaattta  1320
```

```
ccgaatagct gcctgaaatc ttatggatcc ggttatgtcg tcaccgttga tctgacgcca    1380
ttacaaaaaa tggttcagga tattgatggt ttaggcgcgc cgggaaaaga ctcaaaactc    1440
gaaatggata acgccaaata tcaagcctgg cagtcgggtt ttaaagcgca ggaagaaaat    1500
atgaaaacca cattacagac gctgacgcaa aaatatagca atgccaattc attgtacgac    1560
aacctggtaa aagtgctgag cagtacgata agtagcagcc tggaaaccgc caaaagcttc    1620
ctgcaaggag tcgacatggt aaatgacgca agtagcatta gccgtagcgg atatacccaa    1680
aatccgcgcc tcgctgaggc ggcttttgaa ggcgttcgta agaacacgga cttttttaaaa   1740 gcggcggata aagcttttaa agatgtggtg gcaacgaaag cgggcgacct taaagccgga    1800
acaaagtccg gcgagagcgc tattaatacg gtgggtctaa agccgcctac ggacgccgcc    1860
cgggaaaaac tctccagcga agggcaattg acattactgc ttggcaagtt aatgacccta    1920
ctgggcgatg tttcgctgtc tcaactggag tctcgtctgg cggtatggca ggcgatgatt    1980
gagtcacaaa aagagatggg gattcaggta tcgaaagaat tccagacggc tctgggagag    2040
gctcaggagg cgacggatct ctatgaagcc agtatcaaaa agacggatac cgccaagagt    2100
gtttatgacg ctgcgaccaa aaaactgacg caggcgcaaa ataaattgca atcgctggac    2160
ccggctgacc ccggctatgc acaagctgaa gccgcgtag aacaggccgg aaaagaagcg     2220
acagaggcga agaggccttt agataaggcc acggatgcga cggttaaagc aggcacagac    2280
gccaaagcga agccgagaa agcggataac attctgacca aattccaggg aacggctaat     2340
gccgcctctc agaatcaggt ttcccagggt gagcaggata atctgtcaaa tgtcgcccgc    2400
ctcactatgc tcatggccat gtttattgag attgtgggca aaaatacgga agaaagcctg    2460
caaaacgatc ttgcgctttt caacgccttg caggaagggc gtcaggcgga gatggaaaag    2520
aaatcggctg aattccagga agagacgcgc aaagccgagg aaacgaaccg cattatggga    2580
tgtatcggga aagtcctcgg cgcgctgcta accattgtca gcgttgtggc cgctgttttt    2640
accggtgggg cgagtctggc gctggctgcg gtgggacttg cggtaatggt ggccgatgaa    2700
attgtgaagg cggcgacggg agtgtcgttt attcagcagg cgctaaaccc gattatggag    2760
catgtgctga agccgttaat ggagctgatt ggcaaggcga ttaccaaagc gctggaagga    2820
ttaggcgtcg ataagaaaac ggcagagatg gccggcagca ttgttggtgc gattgtcgcc    2880
gctattgcca tggtggcggt cattgtggtg gtcgcagttg tcgggaaagg cgcggcggcg    2940
aaactgggta acgcgctgag caaaatgatg ggcgaaacga ttaagaagtt ggtgcctaac    3000
gtgctgaaac agttggcgca aaacggcagc aaactctttta cccagggggat gcaacgtatt   3060 actagcggtc tgggtaatgt gggtagcaag atgggcctgc aaacgaatgc cttaagtaaa    3120
gagctggtag gtaatacccct aaataaagtg gcgttgggca tggaagtcac gaataccgca    3180
gcccagtcag ccggtggtgt tgccgagggc gtatttatta aaaatgccag cgaggcgctt    3240
gctgatttta tgctcgcccg ttttgccatg gatcagattc agcagtggct taaacaatcc    3300
gtagaaatat ttggtgaaaa ccagaaggta acggcggaac tgcaaaaagc catgtcttct    3360
gcggtacagc aaaatgcgga tgcttcgcgt tttattctgc gccagagtcg cgcataactc    3420
gag                                                                 3423
```

<210> SEQ ID NO 58
<211> LENGTH: 1137
<212> TYPE: PRT
<213> ORGANISM: Artificial Sequence
<220> FEATURE:
<223> OTHER INFORMATION: synthetic construct

<400> SEQUENCE: 58

Met Asp Asn Gly Asp Arg Leu Tyr Arg Ala Asp Ser Arg Pro Pro Asp
1               5                   10                  15

Glu Ile Lys Arg Ser Gly Gly Leu Met Pro Arg Gly His Asn Glu Tyr
            20                  25                  30

Phe Asp Arg Gly Thr Gln Met Asn Ile Asn Leu Tyr Asp His Ala Arg
                35                  40                  45

Gly Thr Gln Thr Gly Phe Val Arg Tyr Asp Asp Gly Tyr Val Ser Thr
    50                  55                  60

Ser Leu Ser Leu Arg Ser Ala His Leu Ala Gly Gln Ser Ile Leu Ser
65              70                  75                  80

Gly Tyr Ser Thr Tyr Tyr Ile Tyr Val Ile Ala Thr Ala Pro Asn Met
                85                  90                  95

Phe Asn Val Asn Asp Val Leu Gly Val Tyr Ser Pro His Pro Tyr Glu
                100                 105                 110

Gln Glu Val Ser Ala Leu Gly Gly Ile Pro Tyr Ser Gln Ile Tyr Gly
            115                 120                 125

Trp Tyr Arg Val Asn Phe Gly Val Ile Asp Glu Arg Leu His Arg Asn
130                 135                 140

Arg Glu Tyr Arg Asp Arg Tyr Tyr Arg Asn Leu Asn Ile Ala Pro Ala
145                 150                 155                 160

Glu Asp Gly Tyr Arg Leu Ala Gly Phe Pro Pro Asp His Gln Ala Trp
                165                 170                 175

Arg Glu Glu Pro Trp Ile His His Ala Pro Gln Gly Cys Gly Asn Ser
            180                 185                 190

Ser Arg Gly Ser Ala Ala Ser Met Leu Asn Ile Gln Asn Tyr Ser Ala
        195                 200                 205

Ser Pro His Pro Gly Ile Val Ala Glu Arg Pro Gln Thr Pro Ser Ala
    210                 215                 220

Ser Glu His Val Glu Thr Ala Val Val Pro Ser Thr Thr Glu His Arg
225                 230                 235                 240

Gly Thr Asp Ile Ile Ser Leu Ser Gln Ala Ala Thr Lys Ile His Gln
                245                 250                 255

Ala Gln Gln Thr Leu Gln Ser Thr Pro Pro Ile Ser Glu Glu Asn Asn
            260                 265                 270

Asp Glu Arg Thr Leu Ala Arg Gln Gln Leu Thr Ser Ser Leu Asn Ala
        275                 280                 285

Leu Ala Lys Ser Gly Val Ser Leu Ser Ala Glu Gln Asn Glu Asn Leu
    290                 295                 300

Arg Ser Ala Phe Ser Ala Pro Thr Ser Ala Leu Phe Ser Ala Ser Pro
305                 310                 315                 320

Met Ala Gln Pro Arg Thr Thr Ile Ser Asp Ala Glu Ile Trp Asp Met
                325                 330                 335

Val Ser Gln Asn Ile Ser Ala Ile Gly Asp Ser Tyr Leu Gly Val Tyr
                340                 345                 350

Glu Asn Val Val Ala Val Tyr Thr Asp Phe Tyr Gln Ala Phe Ser Asp
            355                 360                 365

Ile Leu Ser Lys Met Gly Gly Trp Leu Pro Gly Lys Asp Gly Asn
        370                 375                 380

Thr Val Lys Leu Asp Val Thr Ser Leu Lys Asn Asp Leu Asn Ser Leu
385                 390                 395                 400

Val Asn Lys Tyr Asn Gln Ile Asn Ser Asn Thr Val Leu Phe Pro Ala

```
            405                 410                 415
Gln Ser Gly Ser Gly Val Lys Val Ala Thr Glu Ala Glu Ala Arg Gln
            420                 425                 430

Trp Leu Ser Glu Leu Asn Leu Pro Asn Ser Cys Leu Lys Ser Tyr Gly
            435                 440                 445

Ser Gly Tyr Val Val Thr Val Asp Leu Thr Pro Leu Gln Lys Met Val
    450                 455                 460

Gln Asp Ile Asp Gly Leu Gly Ala Pro Gly Lys Asp Ser Lys Leu Glu
465                 470                 475                 480

Met Asp Asn Ala Lys Tyr Gln Ala Trp Gln Ser Gly Phe Lys Ala Gln
                485                 490                 495

Glu Glu Asn Met Lys Thr Thr Leu Gln Thr Leu Thr Gln Lys Tyr Ser
            500                 505                 510

Asn Ala Asn Ser Leu Tyr Asp Asn Leu Val Lys Val Leu Ser Ser Thr
            515                 520                 525

Ile Ser Ser Ser Leu Glu Thr Ala Lys Ser Phe Leu Gln Gly Val Asp
    530                 535                 540

Met Val Asn Asp Ala Ser Ser Ile Ser Arg Ser Gly Tyr Thr Gln Asn
545                 550                 555                 560

Pro Arg Leu Ala Glu Ala Ala Phe Glu Gly Val Arg Lys Asn Thr Asp
                565                 570                 575

Phe Leu Lys Ala Ala Asp Lys Ala Phe Lys Asp Val Val Ala Thr Lys
            580                 585                 590

Ala Gly Asp Leu Lys Ala Gly Thr Lys Ser Gly Glu Ser Ala Ile Asn
            595                 600                 605

Thr Val Gly Leu Lys Pro Pro Thr Asp Ala Ala Arg Glu Lys Leu Ser
    610                 615                 620

Ser Glu Gly Gln Leu Thr Leu Leu Leu Gly Lys Leu Met Thr Leu Leu
625                 630                 635                 640

Gly Asp Val Ser Leu Ser Gln Leu Glu Ser Arg Leu Ala Val Trp Gln
                645                 650                 655

Ala Met Ile Glu Ser Gln Lys Glu Met Gly Ile Gln Val Ser Lys Glu
            660                 665                 670

Phe Gln Thr Ala Leu Gly Glu Ala Gln Glu Ala Thr Asp Leu Tyr Glu
            675                 680                 685

Ala Ser Ile Lys Lys Thr Asp Thr Ala Lys Ser Val Tyr Asp Ala Ala
    690                 695                 700

Thr Lys Lys Leu Thr Gln Ala Gln Asn Lys Leu Gln Ser Leu Asp Pro
705                 710                 715                 720

Ala Asp Pro Gly Tyr Ala Gln Ala Glu Ala Val Glu Gln Ala Gly
                725                 730                 735

Lys Glu Ala Thr Glu Ala Lys Glu Ala Leu Asp Lys Ala Thr Asp Ala
            740                 745                 750

Thr Val Lys Ala Gly Thr Asp Ala Lys Ala Lys Ala Glu Lys Ala Asp
    755                 760                 765

Asn Ile Leu Thr Lys Phe Gln Gly Thr Ala Asn Ala Ala Ser Gln Asn
770                 775                 780

Gln Val Ser Gln Gly Glu Gln Asp Asn Leu Ser Asn Val Ala Arg Leu
785                 790                 795                 800

Thr Met Leu Met Ala Met Phe Ile Glu Ile Val Gly Lys Asn Thr Glu
                805                 810                 815

Glu Ser Leu Gln Asn Asp Leu Ala Leu Phe Asn Ala Leu Gln Glu Gly
            820                 825                 830
```

Arg Gln Ala Glu Met Glu Lys Lys Ser Ala Glu Phe Gln Glu Glu Thr
    835                 840                 845

Arg Lys Ala Glu Glu Thr Asn Arg Ile Met Gly Cys Ile Gly Lys Val
    850                 855                 860

Leu Gly Ala Leu Leu Thr Ile Val Ser Val Val Ala Ala Val Phe Thr
865                 870                 875                 880

Gly Gly Ala Ser Leu Ala Leu Ala Ala Val Gly Leu Ala Val Met Val
                885                 890                 895

Ala Asp Glu Ile Val Lys Ala Ala Thr Gly Val Ser Phe Ile Gln Gln
                900                 905                 910

Ala Leu Asn Pro Ile Met Glu His Val Leu Lys Pro Leu Met Glu Leu
                915                 920                 925

Ile Gly Lys Ala Ile Thr Lys Ala Leu Glu Gly Leu Gly Val Asp Lys
                930                 935                 940

Lys Thr Ala Glu Met Ala Gly Ser Ile Val Gly Ala Ile Val Ala Ala
945                 950                 955                 960

Ile Ala Met Val Ala Val Ile Val Val Val Ala Val Val Gly Lys Gly
                965                 970                 975

Ala Ala Ala Lys Leu Gly Asn Ala Leu Ser Lys Met Met Gly Glu Thr
                980                 985                 990

Ile Lys Lys Leu Val Pro Asn Val  Leu Lys Gln Leu Ala  Gln Asn Gly
                995                  1000                1005

Ser Lys  Leu Phe Thr Gln Gly  Met Gln Arg Ile Thr  Ser Gly Leu
    1010                1015                 1020

Gly Asn  Val Gly Ser Lys Met  Gly Leu Gln Thr Asn  Ala Leu Ser
    1025                1030                 1035

Lys Glu  Leu Val Gly Asn Thr  Leu Asn Lys Val Ala  Leu Gly Met
    1040                1045                 1050

Glu Val  Thr Asn Thr Ala Ala  Gln Ser Ala Gly Gly  Val Ala Glu
    1055                1060                 1065

Gly Val  Phe Ile Lys Asn Ala  Ser Glu Ala Leu Ala  Asp Phe Met
    1070                1075                 1080

Leu Ala  Arg Phe Ala Met Asp  Gln Ile Gln Gln Trp  Leu Lys Gln
    1085                1090                 1095

Ser Val  Glu Ile Phe Gly Glu  Asn Gln Lys Val Thr  Ala Glu Leu
    1100                1105                 1110

Gln Lys  Ala Met Ser Ser Ala  Val Gln Gln Asn Ala  Asp Ala Ser
    1115                1120                 1125

Arg Phe  Ile Leu Arg Gln Ser  Arg Ala
    1130                1135

<210> SEQ ID NO 59
<211> LENGTH: 522
<212> TYPE: DNA
<213> ORGANISM: Artificial Sequence
<220> FEATURE:
<223> OTHER INFORMATION: synthetic construct

<400> SEQUENCE: 59
atgggcagca gccatcacca tcatcaccac agccaggatc cgatgaaaaa agacccgacc      60
ctacaacagg cacatgacac gatgcggttt tccggcgtg gcggctcgct gcgtatgttg     120
ttggatgacg atgttacaca gccgcttaat actctgtatc gctatgccac gcagcttatg     180
gaggtaaaag aattcgccgg cgcagcgcga cttttcaat tgctgacgat atatgatgcc     240

```
tggtcatttg actactggtt tcggttaggg aatgctgcc aggctcaaaa acattgggg    300 gaagcgatat acgcttatgg acgcgcggca caattaaga ttgatgcgcc gcaggcgcca    360
tgggccgcag cggaatgcta tctcgcgtgt gataacgtct gttatgcaat caaagcgtta    420
aaggccgtgg tgcgtatttg cggcgaggtc agtgaacatc aaattctccg acagcgtgca    480
gaaaagatgt tacagcaact ttctgacagg agctaaaagc tt                      522
```

<210> SEQ ID NO 60
<211> LENGTH: 171
<212> TYPE: PRT
<213> ORGANISM: Artificial Sequence
<220> FEATURE:
<223> OTHER INFORMATION: synthetic construct

<400> SEQUENCE: 60

```
Met Gly Ser Ser His His His His His Ser Gln Asp Pro Met Lys
1               5                   10                  15

Lys Asp Pro Thr Leu Gln Gln Ala His Asp Thr Met Arg Phe Phe Arg
            20                  25                  30

Arg Gly Gly Ser Leu Arg Met Leu Asp Asp Val Thr Gln Pro
        35                  40                  45

Leu Asn Thr Leu Tyr Arg Tyr Ala Thr Gln Leu Met Glu Val Lys Glu
    50                  55                  60

Phe Ala Gly Ala Ala Arg Leu Phe Gln Leu Leu Thr Ile Tyr Asp Ala
65                  70                  75                  80

Trp Ser Phe Asp Tyr Trp Phe Arg Leu Gly Glu Cys Cys Gln Ala Gln
                85                  90                  95

Lys His Trp Gly Glu Ala Ile Tyr Ala Tyr Gly Arg Ala Ala Gln Ile
            100                 105                 110

Lys Ile Asp Ala Pro Gln Ala Pro Trp Ala Ala Glu Cys Tyr Leu
            115                 120                 125

Ala Cys Asp Asn Val Cys Tyr Ala Ile Lys Ala Leu Lys Ala Val Val
        130                 135                 140

Arg Ile Cys Gly Glu Val Ser Glu His Gln Ile Leu Arg Gln Arg Ala
145                 150                 155                 160

Glu Lys Met Leu Gln Gln Leu Ser Asp Arg Ser
            165                 170
```

<210> SEQ ID NO 61
<211> LENGTH: 588
<212> TYPE: DNA
<213> ORGANISM: Salmonella spp

<400> SEQUENCE: 61

```
atgtcttcag gaaacatctt atggggaagt caaaaccta ttgtgtttaa aaatagcttc      60
ggcgtcagca acgctgatac cgggagccag atgacttat cccagcaaaa tccgtttgcc    120
gaagggtatg gtgttttgct tattctcctt atggttattc aggctatcgc aaataataaa    180
tttattgaag tccagaagaa cgctgaacgt gccagaaata cccaggaaaa gtcaaatgag    240
atggatgagg tgattgctaa agcagccaaa ggggatgcta aaaccaaaga ggaggtgcct    300
gaggatgtaa ttaaatacat gcgtgataat ggtattctca tcgatggtat gaccattgat    360
gattatatgg ctaaatatgg cgatcatggg aagctggata aggtggcct acaggcgatc    420 aaagcggctt tggataatga cgccaaccgg aataccgatc ttatgagtca ggggcagata    480
acaattcaaa aaatgtctca ggagcttaac gctgtcctta cccaactgac agggcttatc    540
```
agtaagtggg gggaaatttc cagtatgata gcgcagaaaa cgtactca 588

<210> SEQ ID NO 62
<211> LENGTH: 196
<212> TYPE: PRT
<213> ORGANISM: Salmonella spp

<400> SEQUENCE: 62

Met Ser Ser Gly Asn Ile Leu Trp Gly Ser Gln Asn Pro Ile Val Phe
1               5                   10                  15

Lys Asn Ser Phe Gly Val Ser Asn Ala Asp Thr Gly Ser Gln Asp Asp
            20                  25                  30

Leu Ser Gln Gln Asn Pro Phe Ala Glu Gly Tyr Gly Val Leu Leu Ile
        35                  40                  45

Leu Leu Met Val Ile Gln Ala Ile Ala Asn Asn Lys Phe Ile Glu Val
    50                  55                  60

Gln Lys Asn Ala Glu Arg Ala Arg Asn Thr Gln Glu Lys Ser Asn Glu
65                  70                  75                  80

Met Asp Glu Val Ile Ala Lys Ala Ala Lys Gly Asp Ala Lys Thr Lys
                85                  90                  95

Glu Glu Val Pro Glu Asp Val Ile Lys Tyr Met Arg Asn Gly Ile
            100                 105                 110

Leu Ile Asp Gly Met Thr Ile Asp Asp Tyr Met Ala Lys Tyr Gly Asp
        115                 120                 125

His Gly Lys Leu Asp Lys Gly Gly Leu Gln Ala Ile Lys Ala Ala Leu
    130                 135                 140

Asp Asn Asp Ala Asn Arg Asn Thr Asp Leu Met Ser Gln Gly Gln Ile
145                 150                 155                 160

Thr Ile Gln Lys Met Ser Gln Glu Leu Asn Ala Val Leu Thr Gln Leu
                165                 170                 175

Thr Gly Leu Ile Ser Lys Trp Gly Glu Ile Ser Ser Met Ile Ala Gln
            180                 185                 190

Lys Thr Tyr Ser
        195

<210> SEQ ID NO 63
<211> LENGTH: 1455
<212> TYPE: DNA
<213> ORGANISM: Salmonella spp

<400> SEQUENCE: 63
atgaatcgaa ttcacagtaa tagcgacagc gccgcaggag taaccgcctt aacacatcat      60
cacttaagca atgtcagttg cgtttcctcg ggttcgctgg gaaagcgcca gcatcgtgtg     120
aattctactt ttggcgatgg caacgccgcg tgtctgctat ccgggaaaat tagtcttcag     180
gaggcaagca atgcgttgaa gcaactgctt gatgccgtac ccggaaatca taagcgtcca     240
tcattgcctg acttttgca gaccaatccc gcggttttat caatgatgat gacgtcatta     300
atactcaacg tctttggtaa taacgctcaa tcgttatgcc aacagcttga gcgggcaact     360
gaggtgcaaa atgcattacg taataagcag gtaaaggagt atcaggagca gatccagaaa     420
gcgatagagc aggaggataa agcgcgtaaa gcgggtattt ttggcgctat ttttgactgg     480
attaccggca tatttgaaac cgtgattggc gccttaaaag ttgtggaagg ttttctgtcc     540
ggaaatcccg cagaaatggc tagcggcgta gcttatatgg ccgcaggttg tgcaggaatg     600
gttaaagccg gagccgaaac ggcaatgatg tgcggtgctg accacgatac ctgtcaggca     660

-continued

```
attattgacg tgacaagtaa gattcaattt ggttgtgaag ccgtcgcgct ggcactggat    720
gttttccaga ttggccgtgc ttttatggcg acgagaggtt tatctggcgc agctgcaaaa    780
gtgcttgact ccggttttgg cgaggaagtg gttgagcgta tggtaggtgc aggggaagca    840
gaaatagagg agttggctga aaagtttggc gaagaagtga gcgaaagttt ttccaaacaa    900
tttgagccgc ttgaacgtga atggctatg gcgaatgaga tggcagagga ggctgccgag    960
ttttctcgta acgtagaaaa taatatgacg cgaagcgcgg gaaaaagctt tacgaaagag   1020
ggggtgaaag caatggcaaa agaagcggca aaagaagccc tggaaaaatg tgtgcaagaa   1080 ggtgaaagt tcctgttaaa aaaattccgt aataaagttc tcttcaatat gttcaaaaaa   1140
atcctgtatg ccttactgag ggattgttca tttaaaggct tacaggctat cagatgtgca   1200
accgagggcg ccagtcagat gaatactggc atggttaaca cagaaaaagc gaagatcgaa   1260
aagaaaatag agcaattaat aactcagcaa cggtttctgg atttcataat gcaacaaaca   1320
gaaaaccaga aaagataga acaaaaacgc ttagaggagc tttataaggg gagcggtgcc   1380
gcgcttagag atgtattaga taccattgat cactatagta gcgttcaggc gagaatagct   1440
ggctatcgcg cttaa                                                    1455
```

<210> SEQ ID NO 64
<211> LENGTH: 484
<212> TYPE: PRT
<213> ORGANISM: Salmonella spp

<400> SEQUENCE: 64

```
Met Asn Arg Ile His Ser Asn Ser Asp Ser Ala Ala Gly Val Thr Ala
1               5                   10                  15

Leu Thr His His His Leu Ser Asn Val Ser Cys Val Ser Ser Gly Ser
            20                  25                  30

Leu Gly Lys Arg Gln His Arg Val Asn Ser Thr Phe Gly Asp Gly Asn
        35                  40                  45

Ala Ala Cys Leu Leu Ser Gly Lys Ile Ser Leu Gln Glu Ala Ser Asn
    50                  55                  60

Ala Leu Lys Gln Leu Leu Asp Ala Val Pro Gly Asn His Lys Arg Pro
65                  70                  75                  80

Ser Leu Pro Asp Phe Leu Gln Thr Asn Pro Ala Val Leu Ser Met Met
                85                  90                  95

Met Thr Ser Leu Ile Leu Asn Val Phe Gly Asn Asn Ala Gln Ser Leu
            100                 105                 110

Cys Gln Gln Leu Glu Arg Ala Thr Glu Val Gln Asn Ala Leu Arg Asn
        115                 120                 125

Lys Gln Val Lys Glu Tyr Gln Glu Gln Ile Gln Lys Ala Ile Glu Gln
    130                 135                 140

Glu Asp Lys Ala Arg Lys Ala Gly Ile Phe Gly Ala Ile Phe Asp Trp
145                 150                 155                 160

Ile Thr Gly Ile Phe Glu Thr Val Ile Gly Ala Leu Lys Val Val Glu
                165                 170                 175

Gly Phe Leu Ser Gly Asn Pro Ala Glu Met Ala Ser Gly Val Ala Tyr
            180                 185                 190

Met Ala Ala Gly Cys Ala Gly Met Val Lys Ala Gly Glu Thr Ala
        195                 200                 205

Met Met Cys Gly Ala Asp His Asp Thr Cys Gln Ala Ile Ile Asp Val
    210                 215                 220

Thr Ser Lys Ile Gln Phe Gly Cys Glu Ala Val Ala Leu Ala Leu Asp
```

Val Phe Gln Ile Gly Arg Ala Phe Met Ala Thr Arg Gly Leu Ser Gly
225                 230                 235                 240

Ala Ala Ala Lys Val Leu Asp Ser Gly Phe Gly Glu Val Val Glu
            245                 250                 255

Arg Met Val Gly Ala Gly Glu Ala Ile Glu Leu Ala Glu Lys
            260                 265                 270

Phe Gly Glu Glu Val Ser Glu Ser Phe Ser Lys Gln Phe Glu Pro Leu
            275                 280                 285

Glu Arg Glu Met Ala Met Ala Asn Glu Met Ala Glu Ala Ala Glu
290                 295                 300

Phe Ser Arg Asn Val Glu Asn Asn Met Thr Arg Ser Ala Gly Lys Ser
305                 310                 315                 320

Phe Thr Lys Glu Gly Val Lys Ala Met Ala Lys Glu Ala Ala Lys Glu
                325                 330                 335

Ala Leu Glu Lys Cys Val Gln Glu Gly Gly Lys Phe Leu Leu Lys Lys
            340                 345                 350

Phe Arg Asn Lys Val Leu Phe Asn Met Phe Lys Lys Ile Leu Tyr Ala
    355                 360                 365

Leu Leu Arg Asp Cys Ser Phe Lys Gly Leu Gln Ala Ile Arg Cys Ala
370                 375                 380

Thr Glu Gly Ala Ser Gln Met Asn Thr Gly Met Val Asn Thr Glu Lys
385                 390                 395                 400

Ala Lys Ile Glu Lys Lys Ile Glu Gln Leu Ile Thr Gln Gln Arg Phe
                405                 410                 415

Leu Asp Phe Ile Met Gln Gln Thr Glu Asn Gln Lys Lys Ile Glu Gln
            420                 425                 430

Lys Arg Leu Glu Glu Leu Tyr Lys Gly Ser Gly Ala Ala Leu Arg Asp
        435                 440                 445

Val Leu Asp Thr Ile Asp His Tyr Ser Ser Val Gln Ala Arg Ile Ala
    450                 455                 460

Gly Tyr Arg Ala
465                 470                 475                 480

<210> SEQ ID NO 65
<211> LENGTH: 2049
<212> TYPE: DNA
<213> ORGANISM: Artificial Sequence
<220> FEATURE:
<223> OTHER INFORMATION: synthetic construct

<400> SEQUENCE: 65
atgtcttcag gaaacatctt atggggaagt caaaacccta ttgtgtttaa aaatagcttc      60
ggcgtcagca acgctgatac cgggagccag gatgacttat cccagcaaaa tccgtttgcc     120
gaagggtatg gtgttttgct tattctcctt atggttattc aggctatcgc aaataataaa     180
tttattgaag tccagaagaa cgctgaacgt gccagaaata cccagaaaaa gtcaaatgag     240
atggatgagg tgattgctaa agcagccaaa ggggatgcta aaaccaaaga ggaggtgcct     300
gaggatgtaa ttaaatacat gcgtgataat ggtattctca tcgatggtat gaccattgat     360
gattatatgc taaatatgg cgatcatggg aagctggata aggtggcct acaggcgatc     420 aaagcggctt tggataatga cgccaaccgg aataccgatc ttatgagtca ggggcagata     480
acaattcaaa aaatgtctca ggagcttaac gctgtcctta cccaactgac agggcttatc     540
agtaagtggg gggaaatttc cagtatgata gcgcagaaaa cgtactcaga gctcatgaat     600

```
cgaattcaca gtaatagcga cagcgccgca ggagtaaccg ccttaacaca tcatcactta    660
agcaatgtca gttgcgtttc ctcgggttcg ctgggaaagc gccagcatcg tgtgaattct    720
acttttggcg atggcaacgc cgcgtgtctg ctatccggga aaattagtct tcaggaggca    780
agcaatgcgt tgaagcaact gcttgatgcc gtacccggaa atcataagcg tccatcattg    840
cctgactttt tgcagaccaa tcccgcggtt ttatcaatga tgatgacgtc attaatactc    900
aacgtctttg gtaataacgc tcaatcgtta tgccaacagc ttgagcgggc aactgaggtg    960
caaaatgcat tacgtaataa gcaggtaaag gagtatcagg agcagatcca gaaagcgata   1020
gagcaggagg ataaagcgcg taaagcgggt attttttggcg ctattttttga ctggattacc   1080 ggcatatttg aaaccgtgat tggcgcctta aaagttgtgg aaggttttct gtccggaaat   1140
cccgcagaaa tggctagcgg cgtagcttat atggccgcag gttgtgcagg aatggttaaa   1200
gccggagccg aaacggcaat gatgtgcggt gctgaccacg atacctgtca ggcaattatt   1260
gacgtgacaa gtaagattca atttggttgt gaagccgtcg cgctggcact ggatgttttc   1320
cagattggcc gtgcttttat ggcgacgaga ggtttatctg cgcagctgc aaaagtgctt    1380 gactccggtt ttggcgagga gtggttgag cgtatggtag gtgcagggga agcagaaata   1440
gaggagttgg ctgaaaagtt tggcgaagaa gtgagcgaaa gtttttccaa acaatttgag   1500
ccgcttgaac gtgaaatggc tatggcgaat gagatggcag aggaggctgc cgagttttct   1560
cgtaacgtag aaaataatat gacgcgaagc gcgggaaaaa gctttacgaa agaggggggtg   1620 aaagcaatgg caaagaagc ggcaaaagaa gccctggaaa atgtgtgca agaaggtgga    1680 aagttcctgt taaaaaatt ccgtaataaa gttctcttca atatgttcaa aaaaatcctg    1740
tatgccttac tgagggattg ttcatttaaa ggcttacagg ctatcagatg tgcaaccgag   1800
ggcgccagtc agatgaatac tggcatggtt aacacagaaa aagcgaagat cgaaaagaaa   1860
atagagcaat taataactca gcaacggttt ctggatttca taatgcaaca aacagaaaac    1920
cagaaaaaga tagaacaaaa acgcttagag gagctttata agggagcgg tgccgcgctt    1980 agagatgtat tagataccat tgatcactat agtagcgttc aggcgagaat agctggctat    2040
cgcgcttaa                                                             2049
```

<210> SEQ ID NO 66
<211> LENGTH: 682
<212> TYPE: PRT
<213> ORGANISM: Artificial Sequence
<220> FEATURE:
<223> OTHER INFORMATION: synthetic construct

<400> SEQUENCE: 66

```
Met Ser Ser Gly Asn Ile Leu Trp Gly Ser Gln Asn Pro Ile Val Phe
1               5                   10                  15

Lys Asn Ser Phe Gly Val Ser Asn Ala Asp Thr Gly Ser Gln Asp Asp
            20                  25                  30

Leu Ser Gln Gln Asn Pro Phe Ala Glu Gly Tyr Gly Val Leu Leu Ile
        35                  40                  45

Leu Leu Met Val Ile Gln Ala Ile Ala Asn Asn Lys Phe Ile Glu Val
    50                  55                  60

Gln Lys Asn Ala Glu Arg Ala Arg Asn Thr Gln Glu Lys Ser Asn Glu
65                  70                  75                  80

Met Asp Glu Val Ile Ala Lys Ala Ala Lys Gly Asp Ala Lys Thr Lys
                85                  90                  95

Glu Glu Val Pro Glu Asp Val Ile Lys Tyr Met Arg Asp Asn Gly Ile
```

-continued

```
                100                 105                 110
Leu Ile Asp Gly Met Thr Ile Asp Asp Tyr Met Ala Lys Tyr Gly Asp
            115                 120                 125
His Gly Lys Leu Asp Lys Gly Leu Gln Ala Ile Lys Ala Ala Leu
    130                 135                 140
Asp Asn Asp Ala Asn Arg Asn Thr Asp Leu Met Ser Gln Gly Gln Ile
145                 150                 155                 160
Thr Ile Gln Lys Met Ser Gln Glu Leu Asn Ala Val Leu Thr Gln Leu
                165                 170                 175
Thr Gly Leu Ile Ser Lys Trp Gly Glu Ile Ser Ser Met Ile Ala Gln
            180                 185                 190
Lys Thr Tyr Ser Glu Leu Met Asn Arg Ile His Ser Asn Ser Asp Ser
        195                 200                 205
Ala Ala Gly Val Thr Ala Leu Thr His His Leu Ser Asn Val Ser
    210                 215                 220
Cys Val Ser Ser Gly Leu Gly Lys Arg Gln His Arg Val Asn Ser
225                 230                 235                 240
Thr Phe Gly Asp Gly Asn Ala Ala Cys Leu Leu Ser Gly Lys Ile Ser
                245                 250                 255
Leu Gln Glu Ala Ser Asn Ala Leu Lys Gln Leu Leu Asp Ala Val Pro
            260                 265                 270
Gly Asn His Lys Arg Pro Ser Leu Pro Asp Phe Leu Gln Thr Asn Pro
        275                 280                 285
Ala Val Leu Ser Met Met Met Thr Ser Leu Ile Leu Asn Val Phe Gly
    290                 295                 300
Asn Asn Ala Gln Ser Leu Cys Gln Gln Leu Glu Arg Ala Thr Glu Val
305                 310                 315                 320
Gln Asn Ala Leu Arg Asn Lys Gln Val Lys Glu Tyr Gln Glu Gln Ile
                325                 330                 335
Gln Lys Ala Ile Glu Gln Glu Asp Lys Ala Arg Lys Ala Gly Ile Phe
            340                 345                 350
Gly Ala Ile Phe Asp Trp Ile Thr Gly Ile Phe Glu Thr Val Ile Gly
        355                 360                 365
Ala Leu Lys Val Val Glu Gly Phe Leu Ser Gly Asn Pro Ala Glu Met
    370                 375                 380
Ala Ser Gly Val Ala Tyr Met Ala Ala Gly Cys Ala Gly Met Val Lys
385                 390                 395                 400
Ala Gly Ala Glu Thr Ala Met Met Cys Gly Ala Asp His Asp Thr Cys
                405                 410                 415
Gln Ala Ile Ile Asp Val Thr Ser Lys Ile Gln Phe Gly Cys Glu Ala
            420                 425                 430
Val Ala Leu Ala Leu Asp Val Phe Gln Ile Gly Arg Ala Phe Met Ala
        435                 440                 445
Thr Arg Gly Leu Ser Gly Ala Ala Lys Val Leu Asp Ser Gly Phe
    450                 455                 460
Gly Glu Glu Val Val Glu Arg Met Val Gly Ala Gly Glu Ala Glu Ile
465                 470                 475                 480
Glu Glu Leu Ala Glu Lys Phe Gly Glu Val Ser Ser Phe Ser
                485                 490                 495
Lys Gln Phe Glu Pro Leu Glu Arg Glu Met Ala Met Ala Asn Glu Met
            500                 505                 510
Ala Glu Glu Ala Ala Glu Phe Ser Arg Asn Val Glu Asn Asn Met Thr
        515                 520                 525
```

```
Arg Ser Ala Gly Lys Ser Phe Thr Lys Glu Gly Val Lys Ala Met Ala
            530                 535                 540
Lys Glu Ala Ala Lys Glu Ala Leu Glu Lys Cys Val Gln Glu Gly Gly
545                 550                 555                 560
Lys Phe Leu Leu Lys Lys Phe Arg Asn Lys Val Leu Phe Asn Met Phe
                565                 570                 575
Lys Lys Ile Leu Tyr Ala Leu Leu Arg Asp Cys Ser Phe Lys Gly Leu
            580                 585                 590
Gln Ala Ile Arg Cys Ala Thr Glu Gly Ala Ser Gln Met Asn Thr Gly
            595                 600                 605
Met Val Asn Thr Glu Lys Ala Lys Ile Glu Lys Lys Ile Glu Gln Leu
            610                 615                 620
Ile Thr Gln Gln Arg Phe Leu Asp Phe Ile Met Gln Thr Glu Asn
625                 630                 635                 640
Gln Lys Lys Ile Glu Gln Lys Arg Leu Glu Glu Leu Tyr Lys Gly Ser
                645                 650                 655
Gly Ala Ala Leu Arg Asp Val Leu Asp Thr Ile Asp His Tyr Ser Ser
            660                 665                 670
Val Gln Ala Arg Ile Ala Gly Tyr Arg Ala
            675                 680

<210> SEQ ID NO 67
<211> LENGTH: 2655
<212> TYPE: DNA
<213> ORGANISM: Artificial Sequence
<220> FEATURE:
<223> OTHER INFORMATION: synthetic construct

<400> SEQUENCE: 67
catatggaca atggcgatcg tttataccgt gccgactcgc gtcccccaga tgagattaaa      60
cgtagcggtg ggttaatgcc acgtgggcac aatgagtatt ttgaccgtgg aacacagatg     120
aacattaacc tttacgatca tgcccgtggg acccagaccg ggtttgtccg ttatgatgac     180
gggtatgtta gtacgagttt gtccttacgc tccgcacacc ttgcgggaca agtatttta      240 tcaggctaca gcacatatta catttatgtg atcgccactg ccccaaacat gttcaatgtg     300
aacgatgtgt tgggggttta cagcccccat ccatatgaac aagaagtctc ggcccttggg     360
gggatcccat atagccagat ttatggttgg taccgcgtaa attttggtgt gattgatgaa     420
cgtttgcatc gtaaccgtga ataccgcgat cgctactacc gtaacttgaa cattgcacct     480
gccgaggacg gctatcgttt agcgggattc ccacccgatc atcaggcgtg gcgtgaggaa     540
ccgtggatcc atcacgcccc tcaggggtgc gggaacagta gtcgcgggtc cgcggcatcc     600
atgtcttcag gaaacatctt atggggaagt caaaaccccta ttgtgtttaa aaatagcttc     660
ggcgtcagca acgctgatac cgggagccag gatgacttat cccagcaaaa tccgtttgcc     720
gaagggtatg tgttttgct tattctcctt atggttattc aggctatcgc aaataataaa     780
tttattgaag tccagaagaa cgctgaacgt gccagaaata cccaggaaaa gtcaaatgag     840
atggatgagg tgattgctaa agcagccaaa ggggatgcta aaaccaaaga ggaggtgcct     900
gaggatgtaa ttaaatacat gcgtgataat ggtattctca tcgatggtat gaccattgat     960
gattatatgg ctaaatatgg cgatcatggg aagctggata aggtggcct acaggcgatc    1020 aaagcggctt tggataatga cgccaaccgg aataccgatc ttatgagtca ggggcagata    1080
acaattcaaa aaatgtctca ggagcttaac gctgtcctta cccaactgac agggcttatc    1140
```

```
agtaagtggg gggaaatttc cagtatgata gcgcagaaaa cgtactcaga gctcatgaat   1200
cgaattcaca gtaatagcga cagcgccgca ggagtaaccg ccttaacaca tcatcactta   1260
agcaatgtca gttgcgtttc ctcgggttcg ctgggaaagc gccagcatcg tgtgaattct   1320
acttttggcg atggcaacgc cgcgtgtctg ctatccggga aaattagtct tcaggaggca   1380
agcaatgcgt tgaagcaact gcttgatgcc gtacccggaa atcataagcg tccatcattg   1440
cctgactttt tgcagaccaa tcccgcggtt ttatcaatga tgatgacgtc attaatactc   1500
aacgtctttg gtaataacgc tcaatcgtta tgccaacagc ttgagcgggc aactgaggtg   1560
caaaatgcat tacgtaataa gcaggtaaag gagtatcagg agcagatcca gaaagcgata   1620
gagcaggagg ataaagcgcg taaagcgggt attttggcg ctattttga ctggattacc   1680 ggcatatttg aaaccgtgat tggcgcctta aaagttgtgg aaggttttct gtccggaaat   1740
cccgcagaaa tggctagcgg cgtagcttat atggccgcag gttgtgcagg aatggttaaa   1800
gccggagccg aaacggcaat gatgtgcggt gctgaccacg atacctgtca ggcaattatt   1860
gacgtgacaa gtaagattca atttggttgt gaagccgtcg cgctggcact ggatgttttc   1920
cagattggcc gtgcttttat ggcgacgaga ggtttatctg gcgcagctgc aaaagtgctt   1980
gactccggtt ttggcgagga gtggttgag cgtatggtag gtgcagggga agcagaaata   2040
gaggagttgg ctgaaaagtt tggcgaagaa gtgagcgaaa gttttccaa acaatttgag   2100 ccgcttgaac gtgaaatggc tatggcgaat gagatggcag aggaggctgc cgagttttct   2160
cgtaacgtag aaaataatat gacgcgaagc gcgggaaaaa gctttacgaa agaggggtg   2220 aaagcaatgg caaagaagc ggcaaaagaa gccctgaaaa atgtgtgca agaaggtgga   2280 aagttcctgt taaaaaaatt ccgtaataaa gttctcttca atatgttcaa aaaaatcctg   2340
tatgccttac tgagggattg ttcatttaaa ggcttacagg ctatcagatg tgcaaccgag   2400
ggcgccagtc agatgaatac tggcatggtt aacacagaaa aagcgaagat cgaaaagaaa   2460
atagagcaat taataactca gcaacggttt ctggatttca taatgcaaca aacagaaaac   2520
cagaaaaaga tagaacaaaa acgcttagag gagctttata aggggagcgg tgccgcgctt   2580
agagatgtat tagataccat tgatcactat agtagcgttc aggcgagaat agctggctat   2640
cgcgcttaac tcgag                                                   2655
```

<210> SEQ ID NO 68
<211> LENGTH: 881
<212> TYPE: PRT
<213> ORGANISM: Artificial Sequence
<220> FEATURE:
<223> OTHER INFORMATION: synthetic construct

<400> SEQUENCE: 68

```
Met Asp Asn Gly Asp Arg Leu Tyr Arg Ala Asp Ser Arg Pro Pro Asp
1               5                  10                  15

Glu Ile Lys Arg Ser Gly Gly Leu Met Pro Arg Gly His Asn Glu Tyr
            20                  25                  30

Phe Asp Arg Gly Thr Gln Met Asn Ile Asn Leu Tyr Asp His Ala Arg
        35                  40                  45

Gly Thr Gln Thr Gly Phe Val Arg Tyr Asp Asp Gly Tyr Val Ser Thr
    50                  55                  60

Ser Leu Ser Leu Arg Ser Ala His Leu Ala Gly Gln Ser Ile Leu Ser
65                  70                  75                  80

Gly Tyr Ser Thr Tyr Tyr Ile Tyr Val Ile Ala Thr Ala Pro Asn Met
                85                  90                  95
```

```
Phe Asn Val Asn Asp Val Leu Gly Val Tyr Ser Pro His Pro Tyr Glu
                100                 105                 110

Gln Glu Val Ser Ala Leu Gly Gly Ile Pro Tyr Ser Gln Ile Tyr Gly
            115                 120                 125

Trp Tyr Arg Val Asn Phe Gly Val Ile Asp Glu Arg Leu His Arg Asn
130                 135                 140

Arg Glu Tyr Arg Asp Arg Tyr Tyr Arg Asn Leu Asn Ile Ala Pro Ala
145                 150                 155                 160

Glu Asp Gly Tyr Arg Leu Ala Gly Phe Pro Asp His Gln Ala Trp
                165                 170                 175

Arg Glu Glu Pro Trp Ile His His Ala Pro Gln Gly Cys Gly Asn Ser
            180                 185                 190

Ser Arg Gly Ser Ala Ala Ser Met Ser Ser Gly Asn Ile Leu Trp Gly
            195                 200                 205

Ser Gln Asn Pro Ile Val Phe Lys Asn Ser Phe Gly Val Ser Asn Ala
            210                 215                 220

Asp Thr Gly Ser Gln Asp Asp Leu Ser Gln Gln Asn Pro Phe Ala Glu
225                 230                 235                 240

Gly Tyr Gly Val Leu Leu Ile Leu Leu Met Val Ile Gln Ala Ile Ala
                245                 250                 255

Asn Asn Lys Phe Ile Glu Val Gln Lys Asn Ala Glu Arg Ala Arg Asn
            260                 265                 270

Thr Gln Glu Lys Ser Asn Glu Met Asp Glu Val Ile Ala Lys Ala Ala
            275                 280                 285

Lys Gly Asp Ala Lys Thr Lys Glu Glu Val Pro Glu Asp Val Ile Lys
            290                 295                 300

Tyr Met Arg Asp Asn Gly Ile Leu Ile Asp Gly Met Thr Ile Asp Asp
305                 310                 315                 320

Tyr Met Ala Lys Tyr Gly Asp His Gly Lys Leu Asp Lys Gly Gly Leu
                325                 330                 335

Gln Ala Ile Lys Ala Ala Leu Asp Asn Asp Ala Asn Arg Asn Thr Asp
            340                 345                 350

Leu Met Ser Gln Gly Gln Ile Thr Ile Gln Lys Met Ser Gln Glu Leu
            355                 360                 365

Asn Ala Val Leu Thr Gln Leu Thr Gly Leu Ile Ser Lys Trp Gly Glu
            370                 375                 380

Ile Ser Ser Met Ile Ala Gln Lys Thr Tyr Ser Glu Leu Met Asn Arg
385                 390                 395                 400

Ile His Ser Asn Ser Asp Ser Ala Ala Gly Val Thr Ala Leu Thr His
                405                 410                 415

His His Leu Ser Asn Val Ser Cys Val Ser Ser Gly Ser Leu Gly Lys
            420                 425                 430

Arg Gln His Arg Val Asn Ser Thr Phe Gly Asp Gly Asn Ala Ala Cys
            435                 440                 445

Leu Leu Ser Gly Lys Ile Ser Leu Gln Glu Ala Ser Asn Ala Leu Lys
450                 455                 460

Gln Leu Leu Asp Ala Val Pro Gly Asn His Lys Arg Pro Ser Leu Pro
465                 470                 475                 480

Asp Phe Leu Gln Thr Asn Pro Ala Val Leu Ser Met Met Thr Ser
                485                 490                 495

Leu Ile Leu Asn Val Phe Gly Asn Asn Ala Gln Ser Leu Cys Gln Gln
            500                 505                 510
```

```
Leu Glu Arg Ala Thr Glu Val Gln Asn Ala Leu Arg Asn Lys Gln Val
            515                 520                 525

Lys Glu Tyr Gln Glu Gln Ile Gln Lys Ala Ile Glu Gln Glu Asp Lys
530                 535                 540

Ala Arg Lys Ala Gly Ile Phe Gly Ala Ile Phe Asp Trp Ile Thr Gly
545                 550                 555                 560

Ile Phe Glu Thr Val Ile Gly Ala Leu Lys Val Glu Gly Phe Leu
                565                 570                 575

Ser Gly Asn Pro Ala Glu Met Ala Ser Gly Val Ala Tyr Met Ala Ala
            580                 585                 590

Gly Cys Ala Gly Met Val Lys Ala Gly Ala Glu Thr Ala Met Met Cys
            595                 600                 605

Gly Ala Asp His Asp Thr Cys Gln Ala Ile Ile Asp Val Thr Ser Lys
            610                 615                 620

Ile Gln Phe Gly Cys Glu Ala Val Ala Leu Ala Leu Asp Val Phe Gln
625                 630                 635                 640

Ile Gly Arg Ala Phe Met Ala Thr Arg Gly Leu Ser Gly Ala Ala Ala
                645                 650                 655

Lys Val Leu Asp Ser Gly Phe Gly Glu Val Val Glu Arg Met Val
                660                 665                 670

Gly Ala Gly Glu Ala Glu Ile Glu Glu Leu Ala Glu Lys Phe Gly Glu
            675                 680                 685

Glu Val Ser Glu Ser Phe Ser Lys Gln Phe Glu Pro Leu Glu Arg Glu
            690                 695                 700

Met Ala Met Ala Asn Glu Met Ala Glu Ala Ala Glu Phe Ser Arg
705                 710                 715                 720

Asn Val Glu Asn Asn Met Thr Arg Ser Ala Gly Lys Ser Phe Thr Lys
                725                 730                 735

Glu Gly Val Lys Ala Met Ala Lys Glu Ala Lys Glu Ala Leu Glu
                740                 745                 750

Lys Cys Val Gln Glu Gly Gly Lys Phe Leu Leu Lys Lys Phe Arg Asn
            755                 760                 765

Lys Val Leu Phe Asn Met Phe Lys Lys Ile Leu Tyr Ala Leu Leu Arg
770                 775                 780

Asp Cys Ser Phe Lys Gly Leu Gln Ala Ile Arg Cys Ala Thr Glu Gly
785                 790                 795                 800

Ala Ser Gln Met Asn Thr Gly Met Val Asn Thr Glu Lys Ala Lys Ile
                805                 810                 815

Glu Lys Lys Ile Glu Gln Leu Ile Thr Gln Gln Arg Phe Leu Asp Phe
            820                 825                 830

Ile Met Gln Gln Thr Glu Asn Gln Lys Lys Ile Glu Gln Lys Arg Leu
                835                 840                 845

Glu Glu Leu Tyr Lys Gly Ser Gly Ala Ala Leu Arg Asp Val Leu Asp
850                 855                 860

Thr Ile Asp His Tyr Ser Ser Val Gln Ala Arg Ile Ala Gly Tyr Arg
865                 870                 875                 880

Ala
```

<210> SEQ ID NO 69
<211> LENGTH: 1254
<212> TYPE: DNA
<213> ORGANISM: Artificial Sequence
<220> FEATURE:
<223> OTHER INFORMATION: synthetic construct

<400> SEQUENCE: 69

```
atgggcagca gccatcatca tcatcatcac agcagcggcc tggtgccgcg cggcagccat    60
atggacaatg gcgatcgttt ataccgtgcc gactcgcgtc ccccagatga gattaaacgt   120
agcggtgggt taatgccacg tgggcacaat gagtattttg accgtggaac acagatgaac   180
attaaccttt acgatcatgc ccgtgggacc cagaccgggt tgtccgtta tgatgacggg    240
tatgttagta cgagtttgtc cttacgctcc gcacaccttg cgggacaaag tattttatca   300
ggctacagca catattacat ttatgtgatc gccactgccc caaacatgtt caatgtgaac   360
gatgtgttgg gggtttacag ccccccatcca tatgaacaag aagtctcggc ccttgggggg  420
atcccatata gccagattta tggttggtac cgcgtaaatt ttggtgtgat tgatgaacgt   480
ttgcatcgta accgtgaata ccgcgatcgc tactaccgta acttgaacat tgcacctgcc   540
gaggacggct atcgtttagc gggattccca cccgatcatc aggcgtggcg tgaggaaccg   600
tggatccatc acgcccctca ggggtgcggg aacagtagtc gcgggtccgc ggcatccatg   660
tcttcaggaa acatcttatg gggaagtcaa aaccctattg tgtttaaaaa tagcttcggc   720
gtcagcaacg ctgataccgg gagccaggat gacttatccc agcaaaatcc gtttgccgaa   780
gggtatggtg ttttgcttat tctccttatg gttattcagg ctatcgcaaa taataaattt   840
attgaagtcc agaagaacgc tgaacgtgcc agaaatactcc aggaaaagtc aaatgagatg   900
gatgaggtga ttgctaaagc agccaaaggg gatgctaaaa ccaaagagga ggtgcctgag   960
gatgtaatta aatacatgcg tgataatggt attctcatcg atggtatgac cattgatgat  1020
tatatggcta aatatggcga tcatgggaag ctggataaag gtggcctaca ggcgatcaaa  1080
gcggctttgg ataatgacgc caaccggaat accgatctta tgagtcaggg gcagataaca  1140
attcaaaaaa tgtctcagga gcttaacgct gtccttaccc aactgacagg gcttatcagt  1200
aagtgggggg aaatttccag tatgatagcg cagaaaacgt actcataagg atcc        1254
```

<210> SEQ ID NO 70
<211> LENGTH: 415
<212> TYPE: PRT
<213> ORGANISM: Artificial Sequence
<220> FEATURE:
<223> OTHER INFORMATION: synthetic construct

<400> SEQUENCE: 70

```
Met Gly Ser Ser His His His His His Ser Ser Gly Leu Val Pro
1               5                   10                  15

Arg Gly Ser His Met Asp Asn Gly Asp Arg Leu Tyr Arg Ala Asp Ser
            20                  25                  30

Arg Pro Pro Asp Glu Ile Lys Arg Ser Gly Gly Leu Met Pro Arg Gly
        35                  40                  45

His Asn Glu Tyr Phe Asp Arg Gly Thr Gln Met Asn Ile Asn Leu Tyr
    50                  55                  60

Asp His Ala Arg Gly Thr Gln Thr Gly Phe Val Arg Tyr Asp Asp Gly
65                  70                  75                  80

Tyr Val Ser Thr Ser Leu Ser Leu Arg Ser Ala His Leu Ala Gly Gln
                85                  90                  95

Ser Ile Leu Ser Gly Tyr Ser Thr Tyr Ile Tyr Val Ile Ala Thr
                100                 105                 110

Ala Pro Asn Met Phe Asn Val Asn Asp Val Leu Gly Val Tyr Ser Pro
            115                 120                 125

His Pro Tyr Glu Gln Glu Val Ser Ala Leu Gly Gly Ile Pro Tyr Ser
```

130                 135                 140
Gln Ile Tyr Gly Trp Tyr Arg Val Asn Phe Gly Val Ile Asp Glu Arg
145                 150                 155                 160

Leu His Arg Asn Arg Glu Tyr Arg Asp Arg Tyr Tyr Arg Asn Leu Asn
                    165                 170                 175

Ile Ala Pro Ala Glu Asp Gly Tyr Arg Leu Ala Gly Phe Pro Pro Asp
                180                 185                 190

His Gln Ala Trp Arg Glu Glu Pro Trp Ile His His Ala Pro Gln Gly
                    195                 200                 205

Cys Gly Asn Ser Ser Arg Gly Ser Ala Ala Ser Met Ser Ser Gly Asn
                210                 215                 220

Ile Leu Trp Gly Ser Gln Asn Pro Ile Val Phe Lys Asn Ser Phe Gly
225                 230                 235                 240

Val Ser Asn Ala Asp Thr Gly Ser Gln Asp Asp Leu Ser Gln Gln Asn
                    245                 250                 255

Pro Phe Ala Glu Gly Tyr Gly Val Leu Leu Ile Leu Leu Met Val Ile
                260                 265                 270

Gln Ala Ile Ala Asn Asn Lys Phe Ile Glu Val Gln Lys Asn Ala Glu
                    275                 280                 285

Arg Ala Arg Asn Thr Gln Glu Lys Ser Asn Glu Met Asp Glu Val Ile
                290                 295                 300

Ala Lys Ala Ala Lys Gly Asp Ala Lys Thr Lys Glu Glu Val Pro Glu
305                 310                 315                 320

Asp Val Ile Lys Tyr Met Arg Asp Asn Gly Ile Leu Ile Asp Gly Met
                    325                 330                 335

Thr Ile Asp Asp Tyr Met Ala Lys Tyr Gly Asp His Gly Lys Leu Asp
                340                 345                 350

Lys Gly Gly Leu Gln Ala Ile Lys Ala Ala Leu Asp Asn Asp Ala Asn
                    355                 360                 365

Arg Asn Thr Asp Leu Met Ser Gln Gly Gln Ile Thr Ile Gln Lys Met
                370                 375                 380

Ser Gln Glu Leu Asn Ala Val Leu Thr Gln Leu Thr Gly Leu Ile Ser
385                 390                 395                 400

Lys Trp Gly Glu Ile Ser Ser Met Ile Ala Gln Lys Thr Tyr Ser
                    405                 410                 415

<210> SEQ ID NO 71
<211> LENGTH: 749
<212> TYPE: DNA
<213> ORGANISM: Artificial Sequence
<220> FEATURE:
<223> OTHER INFORMATION: synthetic construct

<400> SEQUENCE: 71
atgggcagca gccatcacca tcatcaccac agccaggatc cgatgagcac tccatcttct      60
aataattcta aaaaccttc ggcctctttt aataaaaaat cacgtagccg cttggccgag     120
attgctgcac aaaaaaaagc aaaagctgag gatttggaac aaaaatatcc tgttcctacg     180
gaagaggaga caaacaagt tctcatggac atcctacagg ggttaagcaa cggattaact     240
cttcagcaaa ttttaggtct ctccgacgtc tccttgaag agatctacac cgtagcatat     300
accttctact cccaagggaa atatcgggaa gctatcggtc ttttccaaat cttaacagcc     360 tccaaaccatc aatgctacaa atacatctta ggtcttagct cttgctatca ccagctaaaa     420
atgtatgatg aagccgcttt tggtttcttc ctagctttcg atgctcaacc cgaaaacccc     480

```
atccctcctt actacatcgc cgatagcttg atgaagctaa accaacccga agaatctcaa      540
gacttcctcg atattacgat cgatatgtgt aagaacaagc cggaatataa agttcttaaa      600
gatcgctgca gcattatgaa gcaatcttta gatgccgtgc tgaaaaaaga gaaatctgca      660
aaaggctctg aaacacaagc ctcctctcct aaaaacacaa agctaaaaa agctgcttct      720 aacaagaaaa aagcaaagta agcggccgc                                        749
```

<210> SEQ ID NO 72
<211> LENGTH: 246
<212> TYPE: PRT
<213> ORGANISM: Artificial Sequence
<220> FEATURE:
<223> OTHER INFORMATION: synthetic construct

<400> SEQUENCE: 72

```
Met Gly Ser Ser His His His His His His Ser Gln Asp Pro Met Ser
1               5                   10                  15

Thr Pro Ser Ser Asn Asn Ser Lys Lys Pro Ser Ala Ser Phe Asn Lys
            20                  25                  30

Lys Ser Arg Ser Arg Leu Ala Glu Ile Ala Ala Gln Lys Lys Ala Lys
        35                  40                  45

Ala Glu Asp Leu Glu Gln Lys Tyr Pro Val Pro Thr Glu Glu Glu Thr
    50                  55                  60

Lys Gln Val Leu Met Asp Ile Leu Gln Gly Leu Ser Asn Gly Leu Thr
65                  70                  75                  80

Leu Gln Gln Ile Leu Gly Leu Ser Asp Val Leu Leu Glu Glu Ile Tyr
                85                  90                  95

Thr Val Ala Tyr Thr Phe Tyr Ser Gln Gly Lys Tyr Arg Glu Ala Ile
            100                 105                 110

Gly Leu Phe Gln Ile Leu Thr Ala Ser Lys Pro Gln Cys Tyr Lys Tyr
        115                 120                 125

Ile Leu Gly Leu Ser Ser Cys Tyr His Gln Leu Lys Met Tyr Asp Glu
    130                 135                 140

Ala Ala Phe Gly Phe Phe Leu Ala Phe Asp Ala Gln Pro Glu Asn Pro
145                 150                 155                 160

Ile Pro Pro Tyr Tyr Ile Ala Asp Ser Leu Met Lys Leu Asn Gln Pro
                165                 170                 175

Glu Glu Ser Gln Asp Phe Leu Asp Ile Thr Ile Asp Met Cys Lys Asn
            180                 185                 190

Lys Pro Glu Tyr Lys Val Leu Lys Asp Arg Cys Ser Ile Met Lys Gln
        195                 200                 205

Ser Leu Asp Ala Val Leu Lys Lys Glu Lys Ser Ala Lys Gly Ser Glu
    210                 215                 220

Thr Gln Ala Ser Ser Pro Lys Asn Thr Lys Ala Lys Lys Ala Ala Ser
225                 230                 235                 240

Asn Lys Lys Lys Ala Lys
                245
```

<210> SEQ ID NO 73
<211> LENGTH: 441
<212> TYPE: DNA
<213> ORGANISM: Chlamydia spp

<400> SEQUENCE: 73

```
aaaagtgagc gtttaaaaaa attagaatca gagcttcatg atcttaccca gtggatgcaa      60
cttggccttg ttcctaaaaa agaaatcgag agacaccagg aagaaatccg tctgctagaa     120
```

| | |
|---|---|
| agcaaaatcc ttgaagagaa agaacgtcta caacttctca agaaaagcgg tgagatcaaa | 180 |
| gagtacgtaa cccctcgaag aactccagct aaaaccattt acccagatgg ccccagcgtt | 240 |
| tcagacgttg agtttgtaga atcctcggat acagaagtgg atctcgatgc cggtgacaca | 300 |
| attgagattg acctaggtga tgaggcaaga aagaaagcg gaaacgaact cgactactct | 360 |
| agtgaagacg atgaggatcc tttcagcgat cgcaatcgtt ggcgccgagg aggcatcata | 420 |
| gatcctgacg cgaatgaatg g | 441 |

<210> SEQ ID NO 74
<211> LENGTH: 148
<212> TYPE: PRT
<213> ORGANISM: Chlamydia spp

<400> SEQUENCE: 74

```
Met Lys Ser Glu Arg Leu Lys Lys Leu Glu Ser Glu Leu His Asp Leu
1               5                   10                  15
Thr Gln Trp Met Gln Leu Gly Leu Val Pro Lys Lys Glu Ile Glu Arg
            20                  25                  30
His Gln Glu Glu Ile Arg Leu Leu Glu Ser Lys Ile Leu Glu Glu Lys
        35                  40                  45
Glu Arg Leu Gln Leu Leu Lys Glu Ser Gly Glu Ile Lys Glu Tyr Val
    50                  55                  60
Thr Pro Arg Arg Thr Pro Ala Lys Thr Ile Tyr Pro Asp Gly Pro Ser
65                  70                  75                  80
Val Ser Asp Val Glu Phe Val Glu Ser Ser Asp Thr Glu Val Asp Leu
                85                  90                  95
Asp Ala Gly Asp Thr Ile Glu Ile Asp Leu Gly Asp Glu Ala Arg Glu
            100                 105                 110
Glu Ser Gly Asn Glu Leu Asp Tyr Ser Ser Glu Asp Asp Glu Asp Pro
        115                 120                 125
Phe Ser Asp Arg Asn Arg Trp Arg Arg Gly Gly Ile Ile Asp Pro Asp
    130                 135                 140
Ala Asn Glu Trp
145
```

<210> SEQ ID NO 75
<211> LENGTH: 1464
<212> TYPE: DNA
<213> ORGANISM: Chlamydia spp

<400> SEQUENCE: 75

| | |
|---|---|
| atgagcttgt catccagcag cagctcggat agttcgaatc tgaaaaatgt gttatctcag | 60 |
| gtcatcgcgt ctacaccaca gggggttcct aatgctgaca aattaaccga caatcaggta | 120 |
| aaacaagtcc agcagacccg tcaaaaccgt gatgatctgt ccatggagag cgacgtcgcg | 180 |
| gtggcgggaa cagccggaaa agatcgtgct gcgtcggcgt cccagatcga gggacaagag | 240 |
| ctgattgagc aacagggact tgcggctggg aaagagacgg cttctgctga tgctacatca | 300 |
| ttgacccagt cggcatccaa aggcgcttcc agtcagcagt gtattgagga taccagtaag | 360 |
| tccctggagc tttcttcgct ttcgagcctg tcaagcgtag atgcgacaca tttgcaggaa | 420 |
| atccaatcga tcgtgtcttc agcaatgggc gccaccaacg aattgtcatt gacgaactta | 480 |
| gagacaccgg gattaccaaa gccgagtacc actccacgcc aggaagttat ggagatcagc | 540 |
| cttgccttag cgaaggccat cactgcattg ggtgagagca ctcaggctgc cttggaaaat | 600 |

-continued

```
tttcagtcca ctcagagtca gtccgcgaac atgaataaga tgagtttgga atcccaaggc    660
ttgaaaatcg acaaggagcg tgaagaattt aagaaaatgc aggagattca gcaaagagc    720 ggcacaaatt caaccatgga tactgtgaat aaagttatga ttggcgtgac agtggcaatt    780
acagtaatct ctgttgtttc agcattgttt acctgcggtt tgggcttgat tggcacagcc    840
gctgcgggtg ccacagccgc caccgctggg gcaacggccg ccgccacgac cgctacctct    900
gtgacgacca cagtcgctac ccaggtgacg atgcaagcgg tggtccaagt cgttaagcag    960
gctattatcc aagcagtaaa acgcgccatc gtccaagcga ttaaacaggg gattaagcaa   1020
ggcattaaac aagcgatcaa acaggcagtc aaggcaagcg tgaagacact tgccaaaaat   1080
gtaggcaaga ttttcagcgc aggcaagaac gctgtgagta agtccttccc aaaattgtct   1140
aaggtgatta atacacttgg ttccaaatgg gttactcttg gcgtgggggc ccttacagcg   1200
gtgccgcagt tagtcagtgg cattacctcc cttcaattgt ctgatatgca aaagaacttt   1260
gcacaaatcc aaaaggaagt gggtgcactt acggcgcaga gtgagatgat gaaagcgttt   1320
acactgttct ggcagcaagc ttcgaaaatc gcggccaaac aaacggaatc accttcagag   1380
acgcaacaac aggcagctaa gaccggcgcc cagatcgcta aagcgttgtc cgccatttcg   1440
ggtgctttag ctgctgctgc ttag                                        1464
```

<210> SEQ ID NO 76
<211> LENGTH: 487
<212> TYPE: PRT
<213> ORGANISM: Chlamydia spp

<400> SEQUENCE: 76

```
Met Ser Leu Ser Ser Ser Ser Ser Asp Ser Ser Asn Leu Lys Asn
1               5                   10                  15

Val Leu Ser Gln Val Ile Ala Ser Thr Pro Gln Gly Val Pro Asn Ala
            20                  25                  30

Asp Lys Leu Thr Asp Asn Gln Val Lys Gln Val Gln Gln Thr Arg Gln
        35                  40                  45

Asn Arg Asp Asp Leu Ser Met Glu Ser Asp Val Ala Val Ala Gly Thr
    50                  55                  60

Ala Gly Lys Asp Arg Ala Ala Ser Ala Ser Gln Ile Glu Gly Gln Glu
65                  70                  75                  80

Leu Ile Glu Gln Gln Gly Leu Ala Ala Gly Lys Glu Thr Ala Ser Ala
                85                  90                  95

Asp Ala Thr Ser Leu Thr Gln Ser Ala Ser Lys Gly Ala Ser Ser Gln
            100                 105                 110

Gln Cys Ile Glu Asp Thr Ser Lys Ser Leu Glu Leu Ser Ser Leu Ser
        115                 120                 125

Ser Leu Ser Ser Val Asp Ala Thr His Leu Gln Glu Ile Gln Ser Ile
    130                 135                 140

Val Ser Ser Ala Met Gly Ala Thr Asn Glu Leu Ser Leu Thr Asn Leu
145                 150                 155                 160

Glu Thr Pro Gly Leu Pro Lys Pro Ser Thr Thr Pro Arg Gln Glu Val
                165                 170                 175

Met Glu Ile Ser Leu Ala Leu Ala Lys Ala Ile Thr Ala Leu Gly Glu
            180                 185                 190

Ser Thr Gln Ala Ala Leu Glu Asn Phe Gln Ser Thr Gln Ser Gln Ser
        195                 200                 205

Ala Asn Met Asn Lys Met Ser Leu Glu Ser Gln Gly Leu Lys Ile Asp
    210                 215                 220
```

| | | | | | | | | | | | |
|---|---|---|---|---|---|---|---|---|---|---|---|
|Lys|Arg|Glu|Glu|Phe|Lys|Met|Gln|Glu|Ile|Gln|Gln|Lys|Ser|
|225| | | |230| | | |235| | | |240|

Gly Thr Asn Ser Thr Met Asp Thr Val Asn Lys Val Met Ile Gly Val
            245                 250                 255

Thr Val Ala Ile Thr Val Ile Ser Val Val Ser Ala Leu Phe Thr Cys
        260                 265                 270

Gly Leu Gly Leu Ile Gly Thr Ala Ala Gly Ala Thr Ala Ala Thr
            275                 280                 285

Ala Gly Ala Thr Ala Ala Ala Thr Thr Ala Thr Ser Val Thr Thr Thr
290                 295                 300

Val Ala Thr Gln Val Thr Met Gln Ala Val Gln Val Val Lys Gln
305                 310                 315                 320

Ala Ile Ile Gln Ala Val Lys Arg Ala Ile Val Gln Ala Ile Lys Gln
                325                 330                 335

Gly Ile Lys Gln Gly Ile Lys Gln Ala Ile Lys Gln Ala Val Lys Ala
                340                 345                 350

Ser Val Lys Thr Leu Ala Lys Asn Val Gly Lys Ile Phe Ser Ala Gly
                355                 360                 365

Lys Asn Ala Val Ser Lys Ser Phe Pro Lys Leu Ser Lys Val Ile Asn
370                 375                 380

Thr Leu Gly Ser Lys Trp Val Thr Leu Gly Val Gly Ala Leu Thr Ala
385                 390                 395                 400

Val Pro Gln Leu Val Ser Gly Ile Thr Ser Leu Gln Leu Ser Asp Met
                405                 410                 415

Gln Lys Glu Leu Ala Gln Ile Gln Lys Glu Val Gly Ala Leu Thr Ala
                420                 425                 430

Gln Ser Glu Met Met Lys Ala Phe Thr Leu Phe Trp Gln Gln Ala Ser
                435                 440                 445

Lys Ile Ala Ala Lys Gln Thr Glu Ser Pro Ser Glu Thr Gln Gln Gln
450                 455                 460

Ala Ala Lys Thr Gly Ala Gln Ile Ala Lys Ala Leu Ser Ala Ile Ser
465                 470                 475                 480

Gly Ala Leu Ala Ala Ala
                485

<210> SEQ ID NO 77
<211> LENGTH: 1920
<212> TYPE: DNA
<213> ORGANISM: Artificial Sequence
<220> FEATURE:
<223> OTHER INFORMATION: synthetic construct

<400> SEQUENCE: 77
aaaagtgagc gtttaaaaaa attagaatca gagcttcatg atcttaccca gtggatgcaa      60
cttggccttg ttcctaaaaa agaaatcgag agacaccagg aagaaatccg tctgctagaa     120
agcaaaatcc ttgaagagaa agaacgtcta caacttctca aagaaagcgg tgagatcaaa     180
gagtacgtaa cccctcgaag aactccagct aaaaccattt acccagatgg ccccagcgtt     240
tcagacgttg agtttgtaga atcctcggat acagaagtgg atctcgatgc cggtgacaca     300
attgagattg acctaggtga tgaggcaaga gaagaaagcg gaaacgaact cgactactct     360
agtgaagacg atgaggatcc tttcagcgat cgcaatcgtt ggcgccgagg aggcatcata     420
gatcctgacg cgaatgaatg gggttcagct gcttcaatga gcttgtcatc cagcagcagc     480
tcggatagtt cgaatctgaa aaatgtgtta tctcaggtca tcgcgtctac accacagggg     540

```
gttcctaatg ctgacaaatt aaccgacaat caggtaaaac aagtccagca gacccgtcaa    600
aaccgtgatg atctgtccat ggagagcgac gtcgcggtgg cgggaacagc cggaaaagat    660
cgtgctgcgt cggcgtccca gatcgaggga caagagctga ttgagcaaca gggacttgcg    720
gctgggaaag agacggcttc tgctgatgct acatcattga cccagtcggc atccaaaggc    780
gcttccagtc agcagtgtat tgaggatacc agtaagtccc tggagctttc ttcgctttcg    840
agcctgtcaa gcgtagatgc gacacatttg caggaaatcc aatcgatcgt gtcttcagca    900
atgggcgcca ccaacgaatt gtcattgacg aacttagaga caccgggatt accaaagccg    960
agtaccactc cacgccagga agttatggag atcagccttg ccttagcgaa ggccatcact   1020
gcattgggtg agagcactca ggctgccttg aaaattttc agtccactca gagtcagtcc    1080
gcgaacatga ataagatgag tttggaatcc caaggcttga aaatcgacaa ggagcgtgaa   1140
gaatttaaga aaatgcagga gattcagcaa agagcggca caaattcaac catggatact    1200
gtgaataaag ttatgattgg cgtgacagtg gcaattacag taatctctgt tgtttcagca   1260
ttgtttacct gcggtttggg cttgattggc acagccgctg cgggtgccac agccgccacc   1320 gctgggcaa cggccgccgc cacgaccgct acctctgtga cgaccacagt cgctacccag    1380
gtgacgatgc aagcggtggt ccaagtcgtt aagcaggcta ttatccaagc agtaaaacgc   1440
gccatcgtcc aagcgattaa acaggggatt aagcaaggca ttaaacaagc gatcaaacag   1500
gcagtcaagg caagcgtgaa gacacttgcc aaaaatgtag gcaagatttt cagcgcaggc   1560
aagaacgctg tgagtaagtc cttcccaaaa ttgtctaagg tgattaatac acttggttcc   1620
aaatgggtta ctcttggcgt gggggcccctt acagcggtgc cgcagttagt cagtggcatt   1680
acctcccttc aattgtctga tatgcaaaaa gaacttgcac aaatccaaaa ggaagtgggt   1740
gcacttacgg cgcagagtga gatgatgaaa gcgtttacac tgttctggca gcaagcttcg   1800
aaaatcgcgg ccaaacaaac ggaatcacct tcagagacgc aacaacaggc agctaagacc   1860
ggcgcccaga tcgctaaagc gttgtccgcc atttcgggtg ctttagctgc tgctgcttag   1920
```

<210> SEQ ID NO 78
<211> LENGTH: 640
<212> TYPE: PRT
<213> ORGANISM: Artificial Sequence
<220> FEATURE:
<223> OTHER INFORMATION: synthetic construct

<400> SEQUENCE: 78

```
Met Lys Ser Glu Arg Leu Lys Lys Leu Glu Ser Glu Leu His Asp Leu
1               5                   10                  15

Thr Gln Trp Met Gln Leu Gly Leu Val Pro Lys Lys Glu Ile Glu Arg
            20                  25                  30

His Gln Glu Glu Ile Arg Leu Leu Glu Ser Lys Ile Leu Glu Glu Lys
        35                  40                  45

Glu Arg Leu Gln Leu Leu Lys Glu Ser Gly Glu Ile Lys Glu Tyr Val
    50                  55                  60

Thr Pro Arg Arg Thr Pro Ala Lys Thr Ile Tyr Pro Asp Gly Pro Ser
65                  70                  75                  80

Val Ser Asp Val Glu Phe Val Glu Ser Ser Asp Thr Glu Val Asp Leu
                85                  90                  95

Asp Ala Gly Asp Thr Ile Glu Ile Asp Leu Gly Asp Glu Ala Arg Glu
            100                 105                 110

Glu Ser Gly Asn Glu Leu Asp Tyr Ser Ser Glu Asp Asp Glu Asp Pro
```

-continued

```
            115                 120                 125
Phe Ser Asp Arg Asn Arg Trp Arg Arg Gly Ile Ile Asp Pro Asp
            130                 135                 140
Ala Asn Glu Trp Gly Ser Ala Ala Ser Met Ser Leu Ser Ser Ser
145                 150                 155                 160
Ser Ser Asp Ser Ser Asn Leu Lys Asn Val Leu Ser Gln Val Ile Ala
                165                 170                 175
Ser Thr Pro Gln Gly Val Pro Asn Ala Asp Lys Leu Thr Asp Asn Gln
            180                 185                 190
Val Lys Gln Val Gln Gln Thr Arg Gln Asn Arg Asp Asp Leu Ser Met
            195                 200                 205
Glu Ser Asp Val Ala Val Ala Gly Thr Ala Gly Lys Asp Arg Ala Ala
            210                 215                 220
Ser Ala Ser Gln Ile Glu Gly Gln Glu Leu Ile Glu Gln Gln Gly Leu
225                 230                 235                 240
Ala Ala Gly Lys Glu Thr Ala Ser Ala Asp Ala Thr Ser Leu Thr Gln
                245                 250                 255
Ser Ala Ser Lys Gly Ala Ser Ser Gln Gln Cys Ile Glu Asp Thr Ser
                260                 265                 270
Lys Ser Leu Glu Leu Ser Ser Leu Ser Ser Leu Ser Ser Val Asp Ala
            275                 280                 285
Thr His Leu Gln Glu Ile Gln Ser Ile Val Ser Ser Ala Met Gly Ala
            290                 295                 300
Thr Asn Glu Leu Ser Leu Thr Asn Leu Glu Thr Pro Gly Leu Pro Lys
305                 310                 315                 320
Pro Ser Thr Thr Pro Arg Gln Glu Val Met Glu Ile Ser Leu Ala Leu
                325                 330                 335
Ala Lys Ala Ile Thr Ala Leu Gly Glu Ser Thr Gln Ala Ala Leu Glu
                340                 345                 350
Asn Phe Gln Ser Thr Gln Ser Gln Ser Ala Asn Met Asn Lys Met Ser
            355                 360                 365
Leu Glu Ser Gln Gly Leu Lys Ile Asp Lys Glu Arg Glu Glu Phe Lys
            370                 375                 380
Lys Met Gln Glu Ile Gln Gln Lys Ser Gly Thr Asn Ser Thr Met Asp
385                 390                 395                 400
Thr Val Asn Lys Val Met Ile Gly Val Thr Val Ala Ile Thr Val Ile
                405                 410                 415
Ser Val Val Ser Ala Leu Phe Thr Cys Gly Leu Gly Leu Ile Gly Thr
                420                 425                 430
Ala Ala Ala Gly Ala Thr Ala Ala Thr Ala Gly Ala Thr Ala Ala Ala
            435                 440                 445
Thr Thr Ala Thr Ser Val Thr Thr Val Ala Thr Gln Val Thr Met
            450                 455                 460
Gln Ala Val Val Gln Val Lys Gln Ala Ile Ile Gln Ala Val Lys
465                 470                 475                 480
Arg Ala Ile Val Gln Ala Ile Lys Gln Gly Ile Lys Gln Gly Ile Lys
                485                 490                 495
Gln Ala Ile Lys Gln Ala Val Lys Ala Ser Val Lys Thr Leu Ala Lys
            500                 505                 510
Asn Val Gly Lys Ile Phe Ser Ala Gly Lys Asn Ala Val Ser Lys Ser
            515                 520                 525
Phe Pro Lys Leu Ser Lys Val Ile Asn Thr Leu Gly Ser Lys Trp Val
530                 535                 540
```

```
Thr Leu Gly Val Gly Ala Leu Thr Ala Val Pro Gln Leu Val Ser Gly
545                 550                 555                 560

Ile Thr Ser Leu Gln Leu Ser Asp Met Gln Lys Glu Leu Ala Gln Ile
                565                 570                 575

Gln Lys Glu Val Gly Ala Leu Thr Ala Gln Ser Glu Met Met Lys Ala
            580                 585                 590

Phe Thr Leu Phe Trp Gln Gln Ala Ser Lys Ile Ala Ala Lys Gln Thr
        595                 600                 605

Glu Ser Pro Ser Glu Thr Gln Gln Gln Ala Ala Lys Thr Gly Ala Gln
610                 615                 620

Ile Ala Lys Ala Leu Ser Ala Ile Ser Gly Ala Leu Ala Ala Ala Ala
625                 630                 635                 640

<210> SEQ ID NO 79
<211> LENGTH: 2517
<212> TYPE: DNA
<213> ORGANISM: Artificial Sequence
<220> FEATURE:
<223> OTHER INFORMATION: synthetic construct

<400> SEQUENCE: 79
```

| | | | | |
|---|---|---|---|---|
| catatggaca atggcgatcg tttataccgt gccgactcgc gtcccccaga tgagattaaa | 60 |
| cgtagcggtg ggttaatgcc acgtgggcac aatgagtatt ttgaccgtgg aacacagatg | 120 |
| aacattaacc tttacgatca tgcccgtggg acccagaccg ggtttgtccg ttatgatgac | 180 |
| gggtatgtta gtacgagttt gtccttacgc tccgcacacc ttgcgggaca agtatttta | 240 |
| tcaggctaca gcacatatta catttatgtg atcgccactg ccccaaacat gttcaatgtg | 300 |
| aacgatgtgt tgggggttta cagcccccat ccatatgaac aagaagtctc ggcccttggg | 360 |
| gggatcccat atagccagat ttatggttgg taccgcgtaa attttggtgt gattgatgaa | 420 |
| cgtttgcatc gtaaccgtga ataccgcgat cgctactacc gtaacttgaa cattgcacct | 480 |
| gccgaggacg gctatcgttt agcgggattc ccacccgatc atcaggcgtg gcgtgaggaa | 540 |
| ccgtggatcc atcacgcccc tcaggggtgc gggaacagta gtcgccatat gaaaagtgag | 600 |
| cgtttaaaaa aattagaatc agagcttcat gatcttaccc agtggatgca acttggcctt | 660 |
| gttcctaaaa agaaatcga gagacaccag gaagaaatcc gtctgctaga aagcaaaatc | 720 |
| cttgaagaga agaacgtct acaacttctc aaagaaagcg gtgagatcaa agagtacgta | 780 |
| accctcgaa gaactccagc taaaaccatt tacccagatg gccccagcgt ttcagacgtt | 840 |
| gagtttgtag aatcctcgga tacagaagtg gatctcgatg ccggtgacac aattgagatt | 900 |
| gacctaggtg atgaggcaag agaagaaagc ggaaacgaac tcgactactc tagtgaagac | 960 |
| gatgaggatc ctttcagcga tcgcaatcgt tggcgccgag gaggcatcat agatcctgac | 1020 |
| gcgaatgaat ggggttcagc tgcttcaatg agcttgtcat ccagcagcag ctcggatagt | 1080 |
| tcgaatctga aaatgtgtt atctcaggtc atcgcgtcta caccacaggg ggttcctaat | 1140 |
| gctgacaaat taaccgacaa tcaggtaaaa caagtccagc agacccgtca aaaccgtgat | 1200 |
| gatctgtcca tggagagcga cgtcgcggtg gcgggaacag ccggaaaaga tcgtgctgcg | 1260 |
| tcggcgtccc agatcgaggg acaagagctg attgagcaac agggacttgc ggctgggaaa | 1320 |
| gagacggctt ctgctgatgc tacatcattg acccagtcgg catccaaagg cgcttccagt | 1380 |
| cagcagtgta ttgaggatac cagtaagtcc ctggagcttt cttcgctttc gagcctgtca | 1440 |
| agcgtagatg cgacacattt gcaggaaatc caatcgatct gtcttcagc aatgggcgcc | 1500 |

```
accaacgaat tgtcattgac gaacttagag acaccgggat taccaaagcc gagtaccact   1560
ccacgccagg aagttatgga gatcagcctt gccttagcga aggccatcac tgcattgggt   1620
gagagcactc aggctgcctt ggaaaatttt cagtccactc agagtcagtc cgcgaacatg   1680
aataagatga gtttggaatc ccaaggcttg aaaatcgaca aggagcgtga agaatttaag   1740
aaaatgcagg agattcagca aaagagcggc acaaattcaa ccatggatac tgtgaataaa   1800
gttatgattg gcgtgacagt ggcaattaca gtaatctctg ttgtttcagc attgtttacc   1860
tgcggtttgg gcttgattgg cacagccgct gcgggtgcca cagccgccac cgctggggca   1920
acggccgccg ccacgaccgc tacctctgtg acgaccacag tcgctaccca ggtgacgatg   1980
caagcggtgg tccaagtcgt taagcaggct attatccaag cagtaaaacg cgccatcgtc   2040
caagcgatta aacaggggat taagcaaggc attaaacaag cgatcaaaca ggcagtcaag   2100
gcaagcgtga agacacttgc caaaaatgta ggcaagattt tcagcgcagg caagaacgct   2160
gtgagtaagt ccttcccaaa attgtctaag gtgattaata cacttggttc caaatgggtt   2220
actcttggcg tgggggccct tacagcgtg ccgcagttag tcagtggcat tacctccctt   2280
caattgtctg atatgcaaaa agaacttgca caaatccaaa aggaagtggg tgcacttacg   2340
gcgcagagtg agatgatgaa agcgtttaca ctgttctggc agcaagcttc gaaaatcgcg   2400
gccaaacaaa cggaatcacc ttcagagacg caacaacagg cagctaagac cggcgcccag   2460
atcgctaaag cgttgtccgc catttcgggt gctttagctg ctgctgctta gctcgag      2517
```

<210> SEQ ID NO 80
<211> LENGTH: 834
<212> TYPE: PRT
<213> ORGANISM: Artificial Sequence
<220> FEATURE:
<223> OTHER INFORMATION: synthetic construct

<400> SEQUENCE: 80

```
Met Asp Asn Gly Asp Arg Leu Tyr Arg Ala Asp Ser Arg Pro Pro Asp
1               5                   10                  15

Glu Ile Lys Arg Ser Gly Gly Leu Met Pro Arg Gly His Asn Glu Tyr
            20                  25                  30

Phe Asp Arg Gly Thr Gln Met Asn Ile Asn Leu Tyr Asp His Ala Arg
        35                  40                  45

Gly Thr Gln Thr Gly Phe Val Arg Tyr Asp Asp Gly Tyr Val Ser Thr
    50                  55                  60

Ser Leu Ser Leu Arg Ser Ala His Leu Ala Gly Gln Ser Ile Leu Ser
65                  70                  75                  80

Gly Tyr Ser Thr Tyr Tyr Ile Tyr Val Ile Ala Thr Ala Pro Asn Met
                85                  90                  95

Phe Asn Val Asn Asp Val Leu Gly Val Tyr Ser Pro His Pro Tyr Glu
            100                 105                 110

Gln Glu Val Ser Ala Leu Gly Gly Ile Pro Tyr Ser Gln Ile Tyr Gly
        115                 120                 125

Trp Tyr Arg Val Asn Phe Gly Val Ile Asp Glu Arg Leu His Arg Asn
    130                 135                 140

Arg Glu Tyr Arg Asp Arg Tyr Tyr Arg Asn Leu Asn Ile Ala Pro Ala
145                 150                 155                 160

Glu Asp Gly Tyr Arg Leu Ala Gly Phe Pro Pro Asp His Gln Ala Trp
                165                 170                 175

Arg Glu Glu Pro Trp Ile His His Ala Pro Gln Gly Cys Gly Asn Ser
            180                 185                 190
```

```
Ser Arg Met Lys Ser Glu Arg Leu Lys Lys Leu Glu Ser Glu Leu His
            195                 200                 205

Asp Leu Thr Gln Trp Met Gln Leu Gly Leu Val Pro Lys Lys Glu Ile
            210                 215                 220

Glu Arg His Gln Glu Glu Ile Arg Leu Leu Glu Ser Lys Ile Leu Glu
225                 230                 235                 240

Glu Lys Glu Arg Leu Gln Leu Leu Lys Glu Ser Gly Glu Ile Lys Glu
                245                 250                 255

Tyr Val Thr Pro Arg Arg Thr Pro Ala Lys Thr Ile Tyr Pro Asp Gly
            260                 265                 270

Pro Ser Val Ser Asp Val Glu Phe Val Glu Ser Ser Asp Thr Glu Val
            275                 280                 285

Asp Leu Asp Ala Gly Asp Thr Ile Glu Ile Asp Leu Gly Asp Glu Ala
            290                 295                 300

Arg Glu Glu Ser Gly Asn Glu Leu Asp Tyr Ser Ser Glu Asp Asp Glu
305                 310                 315                 320

Asp Pro Phe Ser Asp Arg Asn Arg Trp Arg Arg Gly Ile Ile Asp
                325                 330                 335

Pro Asp Ala Asn Glu Trp Gly Ser Ala Ala Ser Met Ser Leu Ser Ser
            340                 345                 350

Ser Ser Ser Ser Asp Ser Ser Asn Leu Lys Asn Val Leu Ser Gln Val
            355                 360                 365

Ile Ala Ser Thr Pro Gln Gly Val Pro Asn Ala Asp Lys Leu Thr Asp
            370                 375                 380

Asn Gln Val Lys Gln Val Gln Gln Thr Arg Gln Asn Arg Asp Asp Leu
385                 390                 395                 400

Ser Met Glu Ser Asp Val Ala Val Ala Gly Thr Ala Gly Lys Asp Arg
                405                 410                 415

Ala Ala Ser Ala Ser Gln Ile Glu Gly Gln Glu Leu Ile Glu Gln Gln
            420                 425                 430

Gly Leu Ala Ala Gly Lys Glu Thr Ala Ser Ala Asp Ala Thr Ser Leu
            435                 440                 445

Thr Gln Ser Ala Ser Lys Gly Ala Ser Ser Gln Gln Cys Ile Glu Asp
            450                 455                 460

Thr Ser Lys Ser Leu Glu Leu Ser Ser Leu Ser Ser Leu Ser Ser Val
465                 470                 475                 480

Asp Ala Thr His Leu Gln Glu Ile Gln Ser Ile Val Ser Ser Ala Met
                485                 490                 495

Gly Ala Thr Asn Glu Leu Ser Leu Thr Asn Leu Glu Thr Pro Gly Leu
            500                 505                 510

Pro Lys Pro Ser Thr Thr Pro Arg Gln Glu Val Met Glu Ile Ser Leu
            515                 520                 525

Ala Leu Ala Lys Ala Ile Thr Ala Leu Gly Glu Ser Thr Gln Ala Ala
            530                 535                 540

Leu Glu Asn Phe Gln Ser Thr Gln Ser Gln Ser Ala Asn Met Asn Lys
545                 550                 555                 560

Met Ser Leu Glu Ser Gln Gly Leu Lys Ile Asp Lys Glu Arg Glu Glu
                565                 570                 575

Phe Lys Lys Met Gln Glu Ile Gln Gln Lys Ser Gly Thr Asn Ser Thr
            580                 585                 590

Met Asp Thr Val Asn Lys Val Met Ile Gly Val Thr Ala Ile Thr
            595                 600                 605
```

```
Val Ile Ser Val Val Ser Ala Leu Phe Thr Cys Gly Leu Gly Leu Ile
610                 615                 620

Gly Thr Ala Ala Gly Ala Thr Ala Ala Thr Ala Gly Ala Thr Ala
625                 630                 635                 640

Ala Ala Thr Thr Ala Thr Ser Val Thr Thr Val Ala Thr Gln Val
            645                 650                 655

Thr Met Gln Ala Val Gln Val Val Lys Gln Ala Ile Ile Gln Ala
            660                 665                 670

Val Lys Arg Ala Ile Val Gln Ile Lys Gln Gly Ile Lys Gln Gly
            675                 680                 685

Ile Lys Gln Ala Ile Lys Gln Ala Val Lys Ala Ser Val Lys Thr Leu
690                 695                 700

Ala Lys Asn Val Gly Lys Ile Phe Ser Ala Gly Lys Asn Ala Val Ser
705                 710                 715                 720

Lys Ser Phe Pro Lys Leu Ser Lys Val Ile Asn Thr Leu Gly Ser Lys
            725                 730                 735

Trp Val Thr Leu Gly Val Gly Ala Leu Thr Ala Val Pro Gln Leu Val
            740                 745                 750

Ser Gly Ile Thr Ser Leu Gln Leu Ser Asp Met Gln Lys Glu Leu Ala
            755                 760                 765

Gln Ile Gln Lys Glu Val Gly Ala Leu Thr Ala Gln Ser Glu Met Met
770                 775                 780

Lys Ala Phe Thr Leu Phe Trp Gln Gln Ala Ser Lys Ile Ala Ala Lys
785                 790                 795                 800

Gln Thr Glu Ser Pro Ser Glu Thr Gln Gln Gln Ala Ala Lys Thr Gly
            805                 810                 815

Ala Gln Ile Ala Lys Ala Leu Ser Ala Ile Ser Gly Ala Leu Ala Ala
            820                 825                 830

Ala Ala
```

<210> SEQ ID NO 81
<211> LENGTH: 749
<212> TYPE: DNA
<213> ORGANISM: Artificial Sequence
<220> FEATURE:
<223> OTHER INFORMATION: synthetic construct

<400> SEQUENCE: 81

```
atgggcagca gccatcacca tcatcaccac agccaggatc cgatgagcac tccatcttct      60
aataattcta aaaaccttc ggcctctttt aataaaaaat cacgtagccg cttggccgag      120
attgctgcac aaaaaaaagc aaaagctgag gatttggaac aaaaatatcc tgttcctacg      180
gaagaggaga caaacaagt tctcatggac atcctacagg ggttaagcaa cggattaact      240
cttcagcaaa ttttaggtct ctccgacgtc ctccttgaag agatctacac cgtagcatat      300
accttctact cccaagggaa atatcgggaa gctatcggtc ttttccaaat cttaacagcc      360
tccaaacctc aatgctacaa atacatctta ggtcttagct cttgctatca ccagctaaaa      420
atgtatgatg aagccgcttt tggtttcttc ctagctttcg atgctcaacc cgaaaacccc      480
atccctcctt actacatcgc cgatagcttg atgaagctaa accaacccga gaatctcaa      540
gacttcctcg atattacgat cgatatgtgt aagaacaagc cggaatataa agttcttaaa      600
gatcgctgca gcattatgaa gcaatcttta gatgccgtgc tgaaaaaaga gaatctgca      660
aaaggctctg aaacacaagc ctcctctcct aaaaacacaa agctaaaaa agctgcttct      720
aacaagaaaa aagcaaagta agcggccgc                                         749
```

<210> SEQ ID NO 82
<211> LENGTH: 246
<212> TYPE: PRT
<213> ORGANISM: Artificial Sequence
<220> FEATURE:
<223> OTHER INFORMATION: synthetic construct

<400> SEQUENCE: 82

Met Gly Ser Ser His His His His His Ser Gln Asp Pro Met Ser
1               5                   10                  15

Thr Pro Ser Ser Asn Asn Ser Lys Lys Pro Ser Ala Ser Phe Asn Lys
            20                  25                  30

Lys Ser Arg Ser Arg Leu Ala Glu Ile Ala Ala Gln Lys Lys Ala Lys
        35                  40                  45

Ala Glu Asp Leu Glu Gln Lys Tyr Pro Val Pro Thr Glu Glu Thr
    50                  55                  60

Lys Gln Val Leu Met Asp Ile Leu Gln Gly Leu Ser Asn Gly Leu Thr
65                  70                  75                  80

Leu Gln Gln Ile Leu Gly Leu Ser Asp Val Leu Leu Glu Glu Ile Tyr
                85                  90                  95

Thr Val Ala Tyr Thr Phe Tyr Ser Gln Gly Lys Tyr Arg Glu Ala Ile
            100                 105                 110

Gly Leu Phe Gln Ile Leu Thr Ala Ser Lys Pro Gln Cys Tyr Lys Tyr
        115                 120                 125

Ile Leu Gly Leu Ser Ser Cys Tyr His Gln Leu Lys Met Tyr Asp Glu
    130                 135                 140

Ala Ala Phe Gly Phe Phe Leu Ala Phe Asp Ala Gln Pro Glu Asn Pro
145                 150                 155                 160

Ile Pro Pro Tyr Tyr Ile Ala Asp Ser Leu Met Lys Leu Asn Gln Pro
                165                 170                 175

Glu Glu Ser Gln Asp Phe Leu Asp Ile Thr Ile Asp Met Cys Lys Asn
            180                 185                 190

Lys Pro Glu Tyr Lys Val Leu Lys Asp Arg Cys Ser Ile Met Lys Gln
        195                 200                 205

Ser Leu Asp Ala Val Leu Lys Lys Glu Lys Ser Ala Lys Gly Ser Glu
    210                 215                 220

Thr Gln Ala Ser Ser Pro Lys Asn Thr Lys Ala Lys Lys Ala Ala Ser
225                 230                 235                 240

Asn Lys Lys Lys Ala Lys
                245

<210> SEQ ID NO 83
<211> LENGTH: 666
<212> TYPE: DNA
<213> ORGANISM: Chlamydia spp

<400> SEQUENCE: 83
atagatcctc ttaagctttt tccaaatttt gatggggata aggagagtgc t

-continued

```
gttgatttaa tcaatgggga ttttcaagcg atagctgaac atacacaaca gacggtcaag    420
cagggtaatg gtgacgaaga aaaatctgtt acacgcaaga tagtcgattg ggtctcttca    480
ggagaagaaa ttttgaatcg tgctttgttg tatttctccg atcgtaatgg agaaagagaa    540
acattagccg atttcttaaa agttcagtat gccgttcaaa gagctacaca acgcgccgag    600
ttatttgcca gtattctagg tgccacggtg agtagtgtaa aaacgattat gacaacccag    660
ttaggt                                                               666
```

<210> SEQ ID NO 84
<211> LENGTH: 222
<212> TYPE: PRT
<213> ORGANISM: Chlamydia spp

<400> SEQUENCE: 84

```
Met Ile Asp Pro Leu Lys Leu Phe Pro Asn Phe Asp Gly Asp Lys Glu
1               5                   10                  15

Ser Ala Ala Val Asn Lys Pro Ser Ala Ser Pro Met Pro Ser Glu Leu
            20                  25                  30

Ser Lys Asn Val Ala Ser Phe Ser Leu Gly Gly Gly Gly Ala Ala Leu
        35                  40                  45

Asp Ser Thr Val Ser Thr Glu Lys Leu Ser Leu Met Ala Met Met Gln
    50                  55                  60

Asp Lys Asn Ser Gln Leu Ile Asp Pro Glu Leu Glu Glu Ala Leu Asn
65                  70                  75                  80

Ser Glu Glu Leu Gln Glu Gln Ile His Leu Leu Lys Ser Arg Leu Trp
                85                  90                  95

Asp Ala Gln Thr Gln Met Gln Met Gln Asp Pro Asp Lys Leu Ala Ser
            100                 105                 110

Glu His Val Asp Ala Leu Gly Val Ile Val Asp Leu Ile Asn Gly Asp
        115                 120                 125

Phe Gln Ala Ile Ala Glu His Thr Gln Thr Val Lys Gln Gly Asn
    130                 135                 140

Gly Asp Glu Glu Lys Ser Val Thr Arg Lys Ile Val Asp Trp Val Ser
145                 150                 155                 160

Ser Gly Glu Glu Ile Leu Asn Arg Ala Leu Leu Tyr Phe Ser Asp Arg
                165                 170                 175

Asn Gly Glu Arg Glu Thr Leu Ala Asp Phe Leu Lys Val Gln Tyr Ala
            180                 185                 190

Val Gln Arg Ala Thr Gln Arg Ala Glu Leu Phe Ala Ser Ile Leu Gly
        195                 200                 205

Ala Thr Val Ser Ser Val Lys Thr Ile Met Thr Thr Gln Leu
    210                 215                 220
```

<210> SEQ ID NO 85
<211> LENGTH: 2145
<212> TYPE: DNA
<213> ORGANISM: Artificial Sequence
<220> FEATURE:
<223> OTHER INFORMATION: synthetic construct

<400> SEQUENCE: 85

```
atagatcctc ttaagctttt tccaaatttt gatggggata aggagagtgc tgcggtgaat    60
aaaccttcag catctcctat gcccagcgaa ttaagtaaaa atgttgcctc attctcttta    120
gggggtggag gtgctgcgtt ggattcgaca gtgtccacag aaaagctatc gttgatggct    180
atgatgcagg ataaaaattc gcagttgatc gatcctgagt tggaggaagc tctgaactct    240
```

```
gaagagttac aagagcagat ccatttgtta aaaagtcgtt tgtgggatgc acaaacgcag    300
atgcaaatgc aagatcccga caagttggcc tctgagcatg tagatgcttt aggagtcatt    360
gttgatttaa tcaatgggga ttttcaagcg atagctgaac atacacaaca gacggtcaag    420
cagggtaatg gtgacgaaga aaaatctgtt acacgcaaga tagtcgattg ggtctcttca    480
ggagaagaaa ttttgaatcg tgctttgttg tatttctccg atcgtaatgg agaaagagaa    540
acattagccg atttcttaaa agttcagtat gccgttcaaa gagctacaca acgcgccgag    600
ttatttgcca gtattctagg tgccacggtg agtagtgtaa aaacgattat gacaacccag    660
ttaggtggtt cagctgcttc aatgagcttg tcatccagca gcagctcgga tagttcgaat    720
ctgaaaaatg tgttatctca ggtcatcgcg tctacaccac agggggttcc taatgctgac    780
aaattaaccg acaatcaggt aaaacaagtc cagcagaccc gtcaaaaccg tgatgatctg    840
tccatggaga gcgacgtcgc ggtggcggga acagccggaa aagatcgtgc tgcgtcggcg    900
tcccagatcg agggacaaga gctgattgag caacagggac ttgcggctgg aaagagacg    960 gcttctgctg atgctacatc attgacccag tcggcatcca aaggcgcttc cagtcagcag   1020
tgtattgagg ataccagtaa gtccctggag ctttcttcgc tttcgagcct gtcaagcgta   1080
gatgcgacac atttgcagga atccaatcg atcgtgtctt cagcaatggg cgccaccaac   1140
gaattgtcat tgacgaactt agagacaccg ggattaccaa agccgagtac cactccacgc   1200
caggaagtta tggagatcag ccttgcctta gcgaaggcca tcactgcatt gggtgagagc   1260
actcaggctg ccttggaaaa ttttcagtcc actcagagtc agtccgcgaa catgaataag   1320
atgagtttgg aatcccaagg cttgaaaatc gacaaggagc gtgaagaatt taagaaaatg   1380
caggagattc agcaaaagag cggcacaaat tcaaccatgg atactgtgaa taagttatg    1440 attggcgtga cagtggcaat tacagtaatc tctgttgttt cagcattgtt tacctgcggt   1500
ttgggcttga ttggcacagc cgctgcgggt gccacagccg ccaccgctgg ggcaacggcc   1560
gccgccacga ccgctaccct tgtgacgacc acagtcgcta cccaggtgac gatgcaagcg   1620
gtggtccaag tcgttaagca ggctattatc caagcagtaa aacgcgccat cgtccaagcg   1680
attaaacagg ggattaagca aggcattaaa caagcgatca acaggcagt caaggcaagc   1740 gtgaagacac ttgccaaaaa tgtaggcaag attttcagcg caggcaagaa cgctgtgagt   1800
aagtccttcc caaaattgtc taaggtgatt aatacacttg gttccaaatg ggttactctt   1860
ggcgtggggg cccttacagc ggtgccgcag ttagtcagtg cattacctc ccttcaattg    1920 tctgatatgc aaaagaact tgcacaaatc caaaaggaag tgggtgcact acggcgcag   1980 agtgagatga tgaaagcgtt tacactgttc tggcagcaag cttcgaaaat cgcggccaaa   2040
caaacggaat caccttcaga gacgcaacaa caggcagcta agaccggcgc ccagatcgct   2100
aaagcgttgt ccgccatttc gggtgcttta gctgctgctg cttag                  2145
```

<210> SEQ ID NO 86
<211> LENGTH: 715
<212> TYPE: PRT
<213> ORGANISM: Artificial Sequence
<220> FEATURE:
<223> OTHER INFORMATION: synthetic construct

<400> SEQUENCE: 86

Met Ile Asp Pro Leu Lys Leu Phe Pro Asn Phe Asp Gly Asp Lys Glu
1               5                   10                  15

Ser Ala Ala Val Asn Lys Pro Ser Ala Ser Pro Met Pro Ser Glu Leu

```
              20                  25                  30
Ser Lys Asn Val Ala Ser Phe Ser Leu Gly Gly Gly Ala Ala Leu
            35                  40                  45

Asp Ser Thr Val Ser Thr Glu Lys Leu Ser Leu Met Ala Met Met Gln
 50                  55                  60

Asp Lys Asn Ser Gln Leu Ile Asp Pro Glu Leu Glu Ala Leu Asn
 65                  70                  75                  80

Ser Glu Glu Leu Gln Glu Gln Ile His Leu Leu Lys Ser Arg Leu Trp
                    85                  90                  95

Asp Ala Gln Thr Gln Met Gln Met Gln Asp Pro Asp Lys Leu Ala Ser
                100                 105                 110

Glu His Val Asp Ala Leu Gly Val Ile Val Asp Leu Ile Asn Gly Asp
                115                 120                 125

Phe Gln Ala Ile Ala Glu His Thr Gln Gln Thr Val Lys Gln Gly Asn
                130                 135                 140

Gly Asp Glu Glu Lys Ser Val Thr Arg Lys Ile Val Asp Trp Val Ser
145                 150                 155                 160

Ser Gly Glu Glu Ile Leu Asn Arg Ala Leu Leu Tyr Phe Ser Asp Arg
                165                 170                 175

Asn Gly Glu Arg Glu Thr Leu Ala Asp Phe Leu Lys Val Gln Tyr Ala
                180                 185                 190

Val Gln Arg Ala Thr Gln Arg Ala Glu Leu Phe Ala Ser Ile Leu Gly
                195                 200                 205

Ala Thr Val Ser Ser Val Lys Thr Ile Met Thr Thr Gln Leu Gly Gly
                210                 215                 220

Ser Ala Ala Ser Met Ser Leu Ser Ser Ser Ser Ser Asp Ser Ser
225                 230                 235                 240

Asn Leu Lys Asn Val Leu Ser Gln Val Ile Ala Ser Thr Pro Gln Gly
                245                 250                 255

Val Pro Asn Ala Asp Lys Leu Thr Asp Asn Gln Val Lys Gln Val Gln
                260                 265                 270

Gln Thr Arg Gln Asn Arg Asp Asp Leu Ser Met Glu Ser Asp Val Ala
                275                 280                 285

Val Ala Gly Thr Ala Gly Lys Asp Arg Ala Ala Ser Ala Ser Gln Ile
                290                 295                 300

Glu Gly Gln Glu Leu Ile Glu Gln Gln Gly Leu Ala Ala Gly Lys Glu
305                 310                 315                 320

Thr Ala Ser Ala Asp Ala Thr Ser Leu Thr Gln Ser Ala Ser Lys Gly
                325                 330                 335

Ala Ser Ser Gln Gln Cys Ile Glu Asp Thr Ser Lys Ser Leu Glu Leu
                340                 345                 350

Ser Ser Leu Ser Ser Leu Ser Ser Val Asp Ala Thr His Leu Gln Glu
                355                 360                 365

Ile Gln Ser Ile Val Ser Ser Ala Met Gly Ala Thr Asn Glu Leu Ser
                370                 375                 380

Leu Thr Asn Leu Glu Thr Pro Gly Leu Pro Lys Pro Ser Thr Thr Pro
385                 390                 395                 400

Arg Gln Glu Val Met Glu Ile Ser Leu Ala Leu Ala Lys Ala Ile Thr
                405                 410                 415

Ala Leu Gly Glu Ser Thr Gln Ala Ala Leu Glu Asn Phe Gln Ser Thr
                420                 425                 430

Gln Ser Gln Ser Ala Asn Met Asn Lys Met Ser Leu Glu Ser Gln Gly
                435                 440                 445
```

Leu Lys Ile Asp Lys Glu Arg Glu Glu Phe Lys Met Gln Glu Ile
            450                 455                 460

Gln Gln Lys Ser Gly Thr Asn Ser Thr Met Asp Thr Val Asn Lys Val
465                 470                 475                 480

Met Ile Gly Val Thr Val Ala Ile Thr Val Ile Ser Val Ser Val Ala
                485                 490                 495

Leu Phe Thr Cys Gly Leu Gly Leu Ile Gly Thr Ala Ala Gly Ala
            500                 505                 510

Thr Ala Ala Thr Ala Gly Ala Thr Ala Ala Thr Thr Ala Thr Ser
            515                 520                 525

Val Thr Thr Thr Val Ala Thr Gln Val Thr Met Gln Ala Val Val Gln
530                 535                 540

Val Val Lys Gln Ala Ile Ile Gln Ala Val Lys Arg Ala Ile Val Gln
545                 550                 555                 560

Ala Ile Lys Gln Gly Ile Lys Gln Gly Ile Lys Gln Ala Ile Lys Gln
            565                 570                 575

Ala Val Lys Ala Ser Val Lys Thr Leu Ala Lys Asn Val Gly Lys Ile
            580                 585                 590

Phe Ser Ala Gly Lys Asn Ala Val Ser Lys Ser Phe Pro Lys Leu Ser
            595                 600                 605

Lys Val Ile Asn Thr Leu Gly Ser Lys Trp Val Thr Leu Gly Val Gly
610                 615                 620

Ala Leu Thr Ala Val Pro Gln Leu Val Ser Gly Ile Thr Ser Leu Gln
625                 630                 635                 640

Leu Ser Asp Met Gln Lys Glu Leu Ala Gln Ile Gln Lys Glu Val Gly
                645                 650                 655

Ala Leu Thr Ala Gln Ser Glu Met Met Lys Ala Phe Thr Leu Phe Trp
            660                 665                 670

Gln Gln Ala Ser Lys Ile Ala Ala Lys Gln Thr Glu Ser Pro Ser Glu
            675                 680                 685

Thr Gln Gln Gln Ala Ala Lys Thr Gly Ala Gln Ile Ala Lys Ala Leu
690                 695                 700

Ser Ala Ile Ser Gly Ala Leu Ala Ala Ala
705                 710                 715

<210> SEQ ID NO 87
<211> LENGTH: 2742
<212> TYPE: DNA
<213> ORGANISM: Artificial Sequence
<220> FEATURE:
<223> OTHER INFORMATION: synthetic construct

<400> SEQUENCE: 87
catatggaca atggcgatcg tttataccgt gccgactcgc gtcccccaga tgagattaaa    60
cgtagcggtg ggttaatgcc acgtgggcac aatgagtatt ttgaccgtgg aacacagatg   120
aacattaacc tttacgatca tgcccgtggg acccagaccg ggtttgtccg ttatgatgac   180
gggtatgtta gtacgagttt gtccttacgc tccgcacacc ttgcgggaca agtatttta   240 tcaggctaca gcacatatta catttatgtg atcgccactg ccccaaacat gttcaatgtg   300
aacgatgtgt tggggttta cagcccccat ccatatgaac aagaagtctc ggcccttggg   360
gggatcccat atagccagat ttatggttgg taccgcgtaa attttggtgt gattgatgaa   420
cgtttgcatc gtaaccgtga ataccgcgat cgctactacc gtaacttgaa cattgcacct   480
gccgaggacg gctatcgttt agcgggattc ccacccgatc atcaggcgtg gcgtgaggaa   540

```
ccgtggatcc atcacgcccc tcagggqtgc gggaacagta gtcgccatat gatagatcct    600
cttaagcttt ttccaaattt tgatggggat aaggagagtg ctgcggtgaa taaaccttca    660
gcatctccta tgcccagcga attaagtaaa aatgttgcct cattctcttt agggggtgga    720
ggtgctgcgt tggattcgac agtgtccaca gaaaagctat cgttgatggc tatgatgcag    780
gataaaaatt cgcagttgat cgatcctgag ttggaggaag ctctgaactc tgaagagtta    840
caagagcaga tccatttgtt aaaaagtcgt ttgtgggatg cacaaacgca gatgcaaatg    900
caagatcccg acaagttggc ctctgagcat gtagatgctt taggagtcat tgttgattta    960
atcaatgggg attttcaagc gatagctgaa catacacaac agacggtcaa gcagggtaat   1020
ggtgacgaag aaaaatctgt tacacgcaag atagtcgatt gggtctcttc aggagaagaa   1080
attttgaatc gtgctttgtt gtatttctcc gatcgtaatg gagaaagaga acattagcc    1140
gatttcttaa aagttcagta tgccgttcaa agagctacac aacgcgccga gttatttgcc   1200
agtattctag gtgccacggt gagtagtgta aaaacgatta tgacaaccca gttaggtggt   1260
tcagctgctt caatgagctt gtcatccagc agcagctcgg atagttcgaa tctgaaaaat   1320
gtgttatctc aggtcatcgc gtctacacca caggggqttc ctaatgctga caaattaacc   1380
gacaatcagg taaaacaagt ccagcagacc cgtcaaaacc gtgatgatct gtccatggag   1440
agcgacgtcg cggtggcggg aacagccgga aaagatcgtg ctgcgtcggc gtcccagatc   1500
gagggacaag agctgattga gcaacaggga cttgcggctg ggaaagagac ggcttctgct   1560
gatgctacat cattgaccca gtcggcatcc aaaggcgctt ccagtcagca gtgtattgag   1620
gataccagta agtccctgga gctttcttcg ctttcgagcc tgtcaagcgt agatgcgaca   1680
catttgcagg aaatccaatc gatcgtgtct cagcaatgg gcgccaccaa cgaattgtca   1740
ttgacgaact tagagacacc gggattacca agccgagta ccactccacg ccaggaagtt   1800
atggagatca gccttgcctt agcgaaggcc atcactgcat tgggtgagag cactcaggct   1860
gccttggaaa atttteagtc cactcagagt cagtccgcga acatgaataa gatgagtttg   1920
gaatcccaag gcttgaaaat cgacaaggag cgtgaagaat ttaagaaaat gcaggagatt   1980
cagcaaaaga gcggcacaaa ttcaaccatg gatactgtga ataaagttat gattggcgtg   2040
acagtggcaa ttacagtaat ctctgttgtt tcagcattgt ttacctgcgg tttgggcttg   2100
attggcacag ccgctgcggg tgccacagcc gccaccgctg ggcaacggc cgccgccacg   2160
accgctacct ctgtgacgac cacagtcgct acccaggtga cgatgcaagc ggtggtccaa   2220
gtcgttaagc aggctattat ccaagcagta aaacgcgcca tcgtccaagc gattaaacag   2280
gggattaagc aaggcattaa acaagcgatc aaacaggcag tcaaggcaag cgtgaagaca   2340
cttgccaaaa atgtaggcaa gattttcagc gcaggcaaga acgctgtgag taagtccttc   2400
ccaaaattgt ctaaggtgat taatacactt ggttccaaat gggttactct tggcgtgggg   2460
gcccttacag cggtgccgca gttagtcagt ggcattacct cccttcaatt gtctgatatg   2520
caaaaagaac ttgcacaaat ccaaaaggaa gtgggtgcac ttacggcgca gagtgagatg   2580
atgaaagcgt ttacactgtt ctggcagcaa gcttcgaaaa tcgcggccaa acaaacggaa   2640
tcaccttcag agacgcaaca acaggcagct aagaccggcg cccagatcgc taaagcgttg   2700
tccgccattt cgggtgcttt agctgctgct gcttagctcg ag                     2742
```

<210> SEQ ID NO 88
<211> LENGTH: 909
<212> TYPE: PRT

<213> ORGANISM: Artificial Sequence
<220> FEATURE:
<223> OTHER INFORMATION: synthetic construct

<400> SEQUENCE: 88

```
Met Asp Asn Gly Asp Arg Leu Tyr Arg Ala Asp Ser Arg Pro Pro Asp
1               5                   10                  15

Glu Ile Lys Arg Ser Gly Gly Leu Met Pro Arg Gly His Asn Glu Tyr
            20                  25                  30

Phe Asp Arg Gly Thr Gln Met Asn Ile Asn Leu Tyr Asp His Ala Arg
        35                  40                  45

Gly Thr Gln Thr Gly Phe Val Arg Tyr Asp Asp Gly Tyr Val Ser Thr
    50                  55                  60

Ser Leu Ser Leu Arg Ser Ala His Leu Ala Gly Gln Ser Ile Leu Ser
65                  70                  75                  80

Gly Tyr Ser Thr Tyr Tyr Ile Tyr Val Ile Ala Thr Ala Pro Asn Met
                85                  90                  95

Phe Asn Val Asn Asp Val Leu Gly Val Tyr Ser Pro His Pro Tyr Glu
            100                 105                 110

Gln Glu Val Ser Ala Leu Gly Gly Ile Pro Tyr Ser Gln Ile Tyr Gly
        115                 120                 125

Trp Tyr Arg Val Asn Phe Gly Val Ile Asp Glu Arg Leu His Arg Asn
    130                 135                 140

Arg Glu Tyr Arg Asp Arg Tyr Tyr Arg Asn Leu Asn Ile Ala Pro Ala
145                 150                 155                 160

Glu Asp Gly Tyr Arg Leu Ala Gly Phe Pro Pro Asp His Gln Ala Trp
                165                 170                 175

Arg Glu Glu Pro Trp Ile His His Ala Pro Gln Gly Cys Gly Asn Ser
            180                 185                 190

Ser Arg Met Ile Asp Pro Leu Lys Leu Phe Pro Asn Phe Asp Gly Asp
        195                 200                 205

Lys Glu Ser Ala Ala Val Asn Lys Pro Ser Ala Ser Pro Met Pro Ser
    210                 215                 220

Glu Leu Ser Lys Asn Val Ala Ser Phe Ser Leu Gly Gly Gly Gly Ala
225                 230                 235                 240

Ala Leu Asp Ser Thr Val Ser Thr Glu Lys Leu Ser Leu Met Ala Met
                245                 250                 255

Met Gln Asp Lys Asn Ser Gln Leu Ile Asp Pro Glu Leu Glu Glu Ala
            260                 265                 270

Leu Asn Ser Glu Glu Leu Gln Glu Gln Ile His Leu Leu Lys Ser Arg
        275                 280                 285

Leu Trp Asp Ala Gln Thr Gln Met Gln Met Gln Asp Pro Asp Lys Leu
    290                 295                 300

Ala Ser Glu His Val Asp Ala Leu Gly Val Ile Val Asp Leu Ile Asn
305                 310                 315                 320

Gly Asp Phe Gln Ala Ile Ala Glu His Thr Gln Thr Val Lys Gln
                325                 330                 335

Gly Asn Gly Asp Glu Glu Lys Ser Val Thr Arg Lys Ile Val Asp Trp
            340                 345                 350

Val Ser Gly Glu Glu Ile Leu Asn Arg Ala Leu Leu Tyr Phe Ser
        355                 360                 365

Asp Arg Asn Gly Glu Arg Glu Thr Leu Ala Asp Phe Leu Lys Val Gln
    370                 375                 380

Tyr Ala Val Gln Arg Ala Thr Gln Arg Ala Glu Leu Phe Ala Ser Ile
```

```
               385                 390                 395                 400
Leu Gly Ala Thr Val Ser Ser Val Lys Thr Ile Met Thr Thr Gln Leu
                        405                 410                 415
Gly Gly Ser Ala Ala Ser Met Ser Leu Ser Ser Ser Ser Ser Ser Asp
                        420                 425                 430
Ser Ser Asn Leu Lys Asn Val Leu Ser Gln Val Ile Ala Ser Thr Pro
                        435                 440                 445
Gln Gly Val Pro Asn Ala Asp Lys Leu Thr Asp Asn Gln Val Lys Gln
            450                 455                 460
Val Gln Gln Thr Arg Gln Asn Arg Asp Asp Leu Ser Met Glu Ser Asp
465                 470                 475                 480
Val Ala Val Ala Gly Thr Ala Gly Lys Asp Arg Ala Ala Ser Ala Ser
                        485                 490                 495
Gln Ile Glu Gly Gln Glu Leu Ile Glu Gln Gln Gly Leu Ala Ala Gly
                        500                 505                 510
Lys Glu Thr Ala Ser Ala Asp Ala Thr Ser Leu Thr Gln Ser Ala Ser
                        515                 520                 525
Lys Gly Ala Ser Ser Gln Gln Cys Ile Glu Asp Thr Ser Lys Ser Leu
            530                 535                 540
Glu Leu Ser Ser Leu Ser Ser Leu Ser Ser Val Asp Ala Thr His Leu
545                 550                 555                 560
Gln Glu Ile Gln Ser Ile Val Ser Ser Ala Met Gly Ala Thr Asn Glu
                        565                 570                 575
Leu Ser Leu Thr Asn Leu Glu Thr Pro Gly Leu Pro Lys Pro Ser Thr
                        580                 585                 590
Thr Pro Arg Gln Glu Val Met Glu Ile Ser Leu Ala Leu Ala Lys Ala
                        595                 600                 605
Ile Thr Ala Leu Gly Glu Ser Thr Gln Ala Ala Leu Glu Asn Phe Gln
            610                 615                 620
Ser Thr Gln Ser Gln Ser Ala Asn Met Asn Lys Met Ser Leu Glu Ser
625                 630                 635                 640
Gln Gly Leu Lys Ile Asp Lys Glu Arg Glu Phe Lys Lys Met Gln
                        645                 650                 655
Glu Ile Gln Gln Lys Ser Gly Thr Asn Ser Thr Met Asp Thr Val Asn
                        660                 665                 670
Lys Val Met Ile Gly Val Thr Val Ala Ile Thr Val Ile Ser Val Val
                        675                 680                 685
Ser Ala Leu Phe Thr Cys Gly Leu Gly Leu Ile Gly Thr Ala Ala Ala
            690                 695                 700
Gly Ala Thr Ala Ala Thr Ala Gly Ala Thr Ala Ala Thr Thr Ala
705                 710                 715                 720
Thr Ser Val Thr Thr Val Ala Thr Gln Val Thr Met Gln Ala Val
                        725                 730                 735
Val Gln Val Val Lys Gln Ala Ile Ile Gln Ala Val Lys Arg Ala Ile
                        740                 745                 750
Val Gln Ala Ile Lys Gln Gly Ile Lys Gln Gly Ile Lys Gln Ala Ile
                        755                 760                 765
Lys Gln Ala Val Lys Ala Ser Val Lys Thr Leu Ala Lys Asn Val Gly
            770                 775                 780
Lys Ile Phe Ser Ala Gly Lys Asn Ala Val Ser Lys Ser Phe Pro Lys
785                 790                 795                 800
Leu Ser Lys Val Ile Asn Thr Leu Gly Ser Lys Trp Val Thr Leu Gly
                        805                 810                 815
```

| Val | Gly | Ala | Leu | Thr | Ala | Val | Pro | Gln | Leu | Val | Ser | Gly | Ile | Thr | Ser |
| | | | | 820 | | | | 825 | | | | 830 | | | |

| Leu | Gln | Leu | Ser | Asp | Met | Gln | Lys | Glu | Leu | Ala | Gln | Ile | Gln | Lys | Glu |
| | | | 835 | | | | | 840 | | | | | 845 | | |

| Val | Gly | Ala | Leu | Thr | Ala | Gln | Ser | Glu | Met | Met | Lys | Ala | Phe | Thr | Leu |
| | 850 | | | | | 855 | | | | | 860 | | | | |

| Phe | Trp | Gln | Gln | Ala | Ser | Lys | Ile | Ala | Ala | Lys | Gln | Thr | Glu | Ser | Pro |
| 865 | | | | | 870 | | | | | 875 | | | | | 880 |

| Ser | Glu | Thr | Gln | Gln | Gln | Ala | Ala | Lys | Thr | Gly | Ala | Gln | Ile | Ala | Lys |
| | | | | 885 | | | | | 890 | | | | | 895 | |

| Ala | Leu | Ser | Ala | Ile | Ser | Gly | Ala | Leu | Ala | Ala | Ala |
| | | | 900 | | | | | 905 | | | |

<210> SEQ ID NO 89
<211> LENGTH: 647
<212> TYPE: DNA
<213> ORGANISM: Artificial Sequence
<220> FEATURE:
<223> OTHER INFORMATION: synthetic construct

<400> SEQUENCE: 89

| atgggcagca | gccatcacca | tcatcaccac | agccaggatc | cgatgccacc | aagcaagatc | 60 |
| caatgtcttg | aaactttga | aagaacttat | ggacaccttt | atctacaaca | tgcgtcccta | 120 |
| atgcgtcatt | tagcctatct | actcgataaa | attgctcgct | cttaccctca | tatgtgtccg | 180 |
| cttcccgata | atatggaagc | gtactttgag | aattatatcc | ccaataaaga | tatccctctg | 240 |
| gacacctatc | aaaaaatttt | caaactgtcc | tcagaagatc | ttgaacaagt | ctacaaggaa | 300 |
| ggatacaacg | cctatttaca | aggagactat | gaggaaagtt | ctaccgcttt | ttactggttg | 360 |
| attttcttta | acccatttgt | gtctaaattt | tggttttcat | taggagcttc | gctccatatg | 420 |
| cgccaaaaat | atcaacaagc | tcttcatgct | tatggtgtag | ctgctttgct | aagagaaaaa | 480 |
| gacccttatc | ctcattacta | tgcctacatc | tgctacaccc | tgctcaataa | tcctgaagaa | 540 |
| gctgaaaaag | ctcttgatct | tgcttggcaa | aaagtaaaaa | caagctctgc | ctatagctct | 600 |
| ttaaaagaag | aaattttagc | gatcaaatcg | tacgcctaag | cggccgc | | 647 |

<210> SEQ ID NO 90
<211> LENGTH: 212
<212> TYPE: PRT
<213> ORGANISM: Artificial Sequence
<220> FEATURE:
<223> OTHER INFORMATION: synthetic construct

<400> SEQUENCE: 90

| Met | Gly | Ser | Ser | His | His | His | His | His | His | Ser | Gln | Asp | Pro | Met | Pro |
| 1 | | | | 5 | | | | | 10 | | | | | 15 | |

| Pro | Ser | Lys | Ile | Gln | Cys | Leu | Glu | Thr | Phe | Glu | Arg | Thr | Tyr | Gly | His |
| | | | 20 | | | | | 25 | | | | | 30 | | |

| Leu | Tyr | Leu | Gln | His | Ala | Ser | Leu | Met | Arg | His | Leu | Ala | Tyr | Leu | Leu |
| | | | | 35 | | | | | 40 | | | | | 45 | |

| Asp | Lys | Ile | Ala | Arg | Ser | Tyr | Pro | His | Met | Cys | Pro | Leu | Pro | Asp | Asn |
| | | 50 | | | | | 55 | | | | | 60 | | | |

| Met | Glu | Ala | Tyr | Phe | Glu | Asn | Tyr | Ile | Pro | Asn | Lys | Asp | Ile | Pro | Leu |
| 65 | | | | | 70 | | | | | 75 | | | | | 80 |

| Asp | Thr | Tyr | Gln | Lys | Ile | Phe | Lys | Leu | Ser | Ser | Glu | Asp | Leu | Glu | Gln |
| | | | | 85 | | | | | 90 | | | | | 95 | |

Val Tyr Lys Glu Gly Tyr Asn Ala Tyr Leu Gln Gly Asp Tyr Glu Glu
            100                 105                 110

Ser Ser Thr Ala Phe Tyr Trp Leu Ile Phe Phe Asn Pro Phe Val Ser
            115                 120                 125

Lys Phe Trp Phe Ser Leu Gly Ala Ser Leu His Met Arg Gln Lys Tyr
            130                 135                 140

Gln Gln Ala Leu His Ala Tyr Gly Val Ala Ala Leu Leu Arg Glu Lys
145                 150                 155                 160

Asp Pro Tyr Pro His Tyr Tyr Ala Tyr Ile Cys Tyr Thr Leu Leu Asn
                    165                 170                 175

Asn Pro Glu Glu Ala Glu Lys Ala Leu Asp Leu Ala Trp Gln Lys Val
            180                 185                 190

Lys Thr Ser Ser Ala Tyr Ser Ser Leu Lys Glu Glu Ile Leu Ala Ile
            195                 200                 205

Lys Ser Tyr Ala
        210

<210> SEQ ID NO 91
<211> LENGTH: 1521
<212> TYPE: DNA
<213> ORGANISM: Chlamydia spp

<400> SEQUENCE: 91

| | | | | | |
|---|---|---|---|---|---|
| atgagctctt | ggtttgcaca | ggcgacggac | gtcgctttga | gccagaccct | tgatctgcct | 60 |
| gacgcttcat | tggcggttca | aaccgaaaaa | tttccataca | gctgttcaat | ctctaaggaa | 120 |
| tccgccccat | catgtattcg | taaaatcttc | gcccatttag | catctcagaa | ggaaagtgct | 180 |
| ccgctgtctt | tttctcgttt | acaaccgact | actccgaaag | aacgcatcct | gttttcgggg | 240 |
| tcatcgcctt | cctcccaatt | gtcctcgact | gtccgcacca | caacctcttc | tccatggaat | 300 |
| cttttagca | actcccaggc | acgcaactcg | accgtaaat | tgtcggagaa | gcttcatttg | 360 |
| agctcagagt | tatccgcccg | tgactccact | aagccttcgt | cgagcgaacc | ggttaaacca | 420 |
| tcggaaaatc | ttttgcacac | ccctgagcat | cataaggaat | ccttctcaag | tttgaaaaag | 480 |
| gataacttat | ctcctatcat | ggaggagatc | gactcattct | ctgcagagac | agagtccctt | 540 |
| gaagagcgtt | tggtcaccca | gaaaaaggag | gagacggtgg | cccaggagca | aaagcaccca | 600 |
| tgctgcgta | catctactcc | gccatcaaag | gccagcgggg | aatcacaaga | ttctagcgaa | 660 |
| cacagctcaa | aggaagatcc | ttatagtcaa | caaccgagcc | ataaaatcca | acgccgtaaa | 720 |
| gagcgtgcta | agcgcgtcgt | cccaattatt | actccgccaa | cggtgggtat | ctttagtttg | 780 |
| agctaccttc | ttacaaaaca | ggggatctta | gcggatttca | gcgcctattc | ggcatacaag | 840 |
| gataatttag | aaacaactca | gcaagagctg | accatgttgc | atcaagaacg | tatcgagcaa | 900 |
| gtccaaaaga | tcgtggataa | agtaagaca | atgcgctttt | gggattcatt | agcatccatt | 960 |
| gtggccacaa | tcattccatg | gatcgaaatg | ggtgttgcag | taaccatcat | cgcactggga | 1020 |
| ggtggaatcc | tttcctggtg | ctctcttttt | gctgcgctta | tcatgattgt | aatttcatta | 1080 |
| ttggaagcat | cgacgggtg | gcgtgcaatc | gctaagcatt | taccaggtaa | cgatcttgaa | 1140 |
| aagaagatgc | gttatttagg | ttacgtaaag | ttggccttaa | ctgtgttctc | gtgcttactg | 1200 |
| agtttaagcg | ccttgtatgt | agcaaaatta | ggaatgagtc | cgcttttgga | ggggttgtg | 1260 |
| aagagtatcg | caccagcatt | aagtggtatg | ctgggtttga | ctcaaggcgt | agcactgtat | 1320 |
| ttacaatctt | catcgcaaaa | gattcgtgcc | cgctgcactc | agatcgacgc | acgcattgaa | 1380 |
| ttgattaact | gggaacgcga | tgagtatttc | ttgcgtgctg | aacaacttct | tgattcaatg | 1440 |

```
caaacgtcct tcgaacaact tactgaaaca ttacagttac aacgtgaaat tgatcagaca    1500
tttacagacg ctttgcgcta g                                              1521
```

<210> SEQ ID NO 92
<211> LENGTH: 506
<212> TYPE: PRT
<213> ORGANISM: Chlamydia spp

<400> SEQUENCE: 92

```
Met Ser Ser Trp Phe Ala Gln Ala Thr Asp Val Ala Leu Ser Gln Thr
1               5                   10                  15

Leu Asp Leu Pro Asp Ala Ser Leu Ala Val Gln Thr Glu Lys Phe Pro
            20                  25                  30

Tyr Ser Cys Ser Ile Ser Lys Glu Ser Ala Pro Ser Cys Ile Arg Lys
        35                  40                  45

Ile Phe Ala His Leu Ala Ser Gln Lys Glu Ser Ala Pro Leu Ser Phe
    50                  55                  60

Ser Arg Leu Gln Pro Thr Thr Pro Lys Glu Arg Ile Leu Phe Phe Gly
65                  70                  75                  80

Ser Ser Pro Ser Ser Gln Leu Ser Ser Thr Val Arg Thr Thr Thr Ser
                85                  90                  95

Ser Pro Trp Asn Leu Phe Ser Asn Ser Gln Ala Arg Asn Ser Thr Arg
            100                 105                 110

Lys Leu Ser Glu Lys Leu His Leu Ser Ser Glu Leu Ser Ala Arg Asp
        115                 120                 125

Ser Thr Lys Pro Ser Ser Ser Glu Pro Val Lys Pro Ser Glu Asn Leu
    130                 135                 140

Leu His Thr Pro Glu His His Lys Glu Ser Phe Ser Ser Leu Lys Lys
145                 150                 155                 160

Asp Asn Leu Ser Pro Ile Met Glu Glu Ile Asp Ser Phe Ser Ala Glu
                165                 170                 175

Thr Glu Ser Leu Glu Glu Arg Leu Val Thr Gln Lys Lys Glu Glu Thr
            180                 185                 190

Val Ala Gln Glu Gln Lys His Pro Leu Leu Arg Thr Ser Thr Pro Pro
        195                 200                 205

Ser Lys Ala Ser Gly Glu Ser Gln Asp Ser Ser Glu His Ser Ser Lys
    210                 215                 220

Glu Asp Pro Tyr Ser Gln Gln Pro Ser His Lys Ile Gln Arg Arg Lys
225                 230                 235                 240

Glu Arg Ala Lys Arg Val Val Pro Ile Ile Thr Pro Pro Thr Val Gly
                245                 250                 255

Ile Phe Ser Leu Ser Tyr Leu Leu Thr Lys Gln Gly Ile Leu Ala Asp
            260                 265                 270

Phe Ser Ala Tyr Ser Ala Tyr Lys Asp Asn Leu Glu Thr Thr Gln Gln
        275                 280                 285

Glu Leu Thr Met Leu His Gln Glu Arg Ile Glu Gln Val Gln Lys Ile
    290                 295                 300

Val Asp Lys Ser Lys Thr Met Arg Phe Trp Asp Ser Leu Ala Ser Ile
305                 310                 315                 320

Val Ala Thr Ile Ile Pro Trp Ile Glu Met Gly Val Ala Val Thr Ile
                325                 330                 335

Ile Ala Leu Gly Gly Gly Ile Leu Ser Trp Cys Ser Leu Phe Ala Ala
            340                 345                 350
```

```
Leu Ile Met Ile Val Ile Ser Leu Leu Glu Ala Phe Asp Gly Trp Arg
            355                 360                 365

Ala Ile Ala Lys His Leu Pro Gly Asn Asp Leu Glu Lys Lys Met Arg
        370                 375                 380

Tyr Leu Gly Tyr Val Lys Leu Ala Leu Thr Val Phe Ser Cys Leu Leu
385                 390                 395                 400

Ser Leu Ser Ala Leu Tyr Val Ala Lys Leu Gly Met Ser Pro Leu Leu
                405                 410                 415

Glu Gly Val Val Lys Ser Ile Ala Pro Ala Leu Ser Gly Met Leu Gly
                420                 425                 430

Leu Thr Gln Gly Val Ala Leu Tyr Leu Gln Ser Ser Ser Gln Lys Ile
            435                 440                 445

Arg Ala Arg Cys Thr Gln Ile Asp Ala Arg Ile Glu Leu Ile Asn Trp
        450                 455                 460

Glu Arg Asp Glu Tyr Phe Leu Arg Ala Glu Gln Leu Leu Asp Ser Met
465                 470                 475                 480

Gln Thr Ser Phe Glu Gln Leu Thr Glu Thr Leu Gln Leu Gln Arg Glu
                485                 490                 495

Ile Asp Gln Thr Phe Thr Asp Ala Leu Arg
                500                 505
```

<210> SEQ ID NO 93
<211> LENGTH: 1977
<212> TYPE: DNA
<213> ORGANISM: Artificial Sequence
<220> FEATURE:
<223> OTHER INFORMATION: synthetic construct

<400> SEQUENCE: 93

```
aaaagtgagc gtttaaaaaa attagaatca gagcttcatg atcttaccca gtggatgcaa      60
cttggccttg ttcctaaaaa agaaatcgag agacaccagg aagaaatccg tctgctagaa     120
agcaaaatcc ttgaagagaa agaacgtcta caacttctca aagaaagcgg tgagatcaaa     180
gagtacgtaa cccctcgaag aactccagct aaaaccattt acccagatgg ccccagcgtt     240
tcagacgttg agtttgtaga atcctcggat acagaagtgg atctcgatgc cggtgacaca     300
attgagattg acctaggtga tgaggcaaga aagaaagcg aaacgaact cgactactct       360
agtgaagacg atgaggatcc tttcagcgat cgcaatcgtt ggcgccgagg aggcatcata     420
gatcctgacg cgaatgaatg gggttcagct gcttcaatga gctcttggtt tgcacaggcg     480
acggacgtcg ctttgagcca gaccttgat ctgcctgacg cttcattggc ggttcaaacc      540
gaaaaatttc catacagctg ttcaatctct aaggaatccg ccccatcatg tattcgtaaa     600
atcttcgccc atttagcatc tcagaaggaa agtgctccgc tgtcttttt cgtttacaa      660
ccgactactc cgaaagaacg catcctgttt ttcgggtcat cgccttcctc ccaattgtcc     720
tcgactgtcc gcaccacaac ctcttctcca tggaatcttt ttagcaactc ccaggcacgc     780
aactcgaccc gtaaattgtc ggagaagctt catttgagct cagagttatc cgcccgtgac     840
tccactaagc cttcgtcgag cgaaccggtt aaaccatcgg aaaatctttt gcacacccct     900
gagcatcata aggaatcctt ctcaagtttg aaaaaggata acttatctcc tatcatggag     960
gagatcgact cattctctgc agagacagag tcccttgaag agcgtttggt cacccagaaa    1020
aaggaggaga cggtggccca ggagcaaaag cacccattgc tgcgtacatc tactccgcca    1080
tcaaaggcca gcggggaatc acaagattct agcgaacaca gctcaaagga agatccttat    1140
agtcaacaac cgagccataa aatccaacgc cgtaaagagc gtgctaagcg cgtcgtccca    1200
```

```
attattactc cgccaacggt gggtatcttt agtttgagct accttcttac aaaacagggg      1260
atcttagcgg atttcagcgc ctattcggca tacaaggata atttagaaac aactcagcaa      1320
gagctgacca tgttgcatca agaacgtatc gagcaagtcc aaaagatcgt ggataaaagt      1380
aagacaatgc gcttttggga ttcattagca tccattgtgg ccacaatcat tccatggatc      1440
gaaatgggtg ttgcagtaac catcatcgca ctgggaggtg aatcctttc ctggtgctct       1500 cttttgctg cgcttatcat gattgtaatt tcattattgg aagcattcga cgggtggcgt       1560
gcaatcgcta agcatttacc aggtaacgat cttgaaaaga agatgcgtta tttaggttac      1620
gtaaagttgg ccttaactgt gttctcgtgc ttactgagtt taagcgcctt gtatgtagca      1680
aaattaggaa tgagtccgct tttggagggg gttgtgaaga gtatcgcacc agcattaagt      1740
ggtatgctgg gtttgactca aggcgtagca ctgtatttac aatcttcatc gcaaaagatt      1800
cgtgcccgct gcactcagat cgacgcacgc attgaattga ttaactggga acgcgatgag      1860
tatttcttgc gtgctgaaca acttcttgat tcaatgcaaa cgtccttcga caacttact       1920 gaaacattac agttacaacg tgaaattgat cagacattta cagacgcttt cgcgctag       1977
```

<210> SEQ ID NO 94
<211> LENGTH: 659
<212> TYPE: PRT
<213> ORGANISM: Artificial Sequence
<220> FEATURE:
<223> OTHER INFORMATION: synthetic construct

<400> SEQUENCE: 94

```
Met Lys Ser Glu Arg Leu Lys Lys Leu Glu Ser Glu Leu His Asp Leu
1               5                   10                  15

Thr Gln Trp Met Gln Leu Gly Leu Val Pro Lys Lys Glu Ile Glu Arg
            20                  25                  30

His Gln Glu Glu Ile Arg Leu Leu Glu Ser Lys Ile Leu Glu Glu Lys
        35                  40                  45

Glu Arg Leu Gln Leu Leu Lys Glu Ser Gly Glu Ile Lys Glu Tyr Val
    50                  55                  60

Thr Pro Arg Arg Thr Pro Ala Lys Thr Ile Tyr Pro Asp Gly Pro Ser
65                  70                  75                  80

Val Ser Asp Val Glu Phe Val Glu Ser Ser Asp Thr Glu Val Asp Leu
                85                  90                  95

Asp Ala Gly Asp Thr Ile Glu Ile Asp Leu Gly Asp Glu Ala Arg Glu
            100                 105                 110

Glu Ser Gly Asn Glu Leu Asp Tyr Ser Ser Glu Asp Glu Asp Pro
        115                 120                 125

Phe Ser Asp Arg Asn Arg Trp Arg Arg Gly Gly Ile Ile Asp Pro Asp
    130                 135                 140

Ala Asn Glu Trp Gly Ser Ala Ala Ser Met Ser Ser Trp Phe Ala Gln
145                 150                 155                 160

Ala Thr Asp Val Ala Leu Ser Gln Thr Leu Asp Leu Pro Asp Ala Ser
                165                 170                 175

Leu Ala Val Gln Thr Glu Lys Phe Pro Tyr Ser Cys Ser Ile Ser Lys
            180                 185                 190

Glu Ser Ala Pro Ser Cys Ile Arg Lys Ile Phe Ala His Leu Ala Ser
        195                 200                 205

Gln Lys Glu Ser Ala Pro Leu Ser Phe Ser Arg Leu Gln Pro Thr Thr
    210                 215                 220
```

-continued

```
Pro Lys Glu Arg Ile Leu Phe Phe Gly Ser Ser Pro Ser Ser Gln Leu
225                 230                 235                 240

Ser Ser Thr Val Arg Thr Thr Ser Ser Pro Trp Asn Leu Phe Ser
            245                 250                 255

Asn Ser Gln Ala Arg Asn Ser Thr Arg Lys Leu Ser Glu Lys Leu His
        260                 265                 270

Leu Ser Ser Glu Leu Ser Ala Arg Asp Ser Thr Lys Pro Ser Ser Ser
    275                 280                 285

Glu Pro Val Lys Pro Ser Glu Asn Leu Leu His Thr Pro Glu His His
    290                 295                 300

Lys Glu Ser Phe Ser Ser Leu Lys Lys Asp Asn Leu Ser Pro Ile Met
305                 310                 315                 320

Glu Glu Ile Asp Ser Phe Ser Ala Glu Thr Glu Ser Leu Glu Glu Arg
                325                 330                 335

Leu Val Thr Gln Lys Lys Glu Glu Thr Val Ala Gln Glu Gln Lys His
            340                 345                 350

Pro Leu Leu Arg Thr Ser Thr Pro Pro Ser Lys Ala Ser Gly Glu Ser
        355                 360                 365

Gln Asp Ser Ser Glu His Ser Ser Lys Glu Asp Pro Tyr Ser Gln Gln
    370                 375                 380

Pro Ser His Lys Ile Gln Arg Arg Lys Glu Arg Ala Lys Arg Val Val
385                 390                 395                 400

Pro Ile Ile Thr Pro Pro Thr Val Gly Ile Phe Ser Leu Ser Tyr Leu
                405                 410                 415

Leu Thr Lys Gln Gly Ile Leu Ala Asp Phe Ser Ala Tyr Ser Ala Tyr
            420                 425                 430

Lys Asp Asn Leu Glu Thr Thr Gln Gln Glu Leu Thr Met Leu His Gln
        435                 440                 445

Glu Arg Ile Glu Gln Val Gln Lys Ile Val Asp Lys Ser Lys Thr Met
    450                 455                 460

Arg Phe Trp Asp Ser Leu Ala Ser Ile Val Ala Thr Ile Ile Pro Trp
465                 470                 475                 480

Ile Glu Met Gly Val Ala Val Thr Ile Ile Ala Leu Gly Gly Gly Ile
                485                 490                 495

Leu Ser Trp Cys Ser Leu Phe Ala Ala Leu Ile Met Ile Val Ile Ser
            500                 505                 510

Leu Leu Glu Ala Phe Asp Gly Trp Arg Ala Ile Ala Lys His Leu Pro
        515                 520                 525

Gly Asn Asp Leu Glu Lys Lys Met Arg Tyr Leu Gly Tyr Val Lys Leu
    530                 535                 540

Ala Leu Thr Val Phe Ser Cys Leu Leu Ser Leu Ser Ala Leu Tyr Val
545                 550                 555                 560

Ala Lys Leu Gly Met Ser Pro Leu Leu Glu Gly Val Val Lys Ser Ile
                565                 570                 575

Ala Pro Ala Leu Ser Gly Met Leu Gly Leu Thr Gln Gly Val Ala Leu
            580                 585                 590

Tyr Leu Gln Ser Ser Ser Gln Lys Ile Arg Ala Arg Cys Thr Gln Ile
        595                 600                 605

Asp Ala Arg Ile Glu Leu Ile Asn Trp Glu Arg Asp Glu Tyr Phe Leu
    610                 615                 620

Arg Ala Glu Gln Leu Leu Asp Ser Met Gln Thr Ser Phe Glu Gln Leu
625                 630                 635                 640

Thr Glu Thr Leu Gln Leu Gln Arg Glu Ile Asp Gln Thr Phe Thr Asp
```

Ala Leu Arg

<210> SEQ ID NO 95
<211> LENGTH: 2574
<212> TYPE: DNA
<213> ORGANISM: Artificial Sequence
<220> FEATURE:
<223> OTHER INFORMATION: synthetic construct

<400> SEQUENCE: 95

| | | | | | |
|---|---|---|---|---|---|
| catatggaca | atggcgatcg | tttataccgt | gccgactcgc | gtcccccaga | tgagattaaa | 60 |
| cgtagcggtg | ggttaatgcc | acgtgggcac | aatgagtatt | ttgaccgtgg | aacacagatg | 120 |
| aacattaacc | tttacgatca | tgcccgtggg | acccagaccg | ggtttgtccg | ttatgatgac | 180 |
| gggtatgtta | gtacgagttt | gtccttacgc | tccgcacacc | ttgcgggaca | agtatttta | 240 |
| tcaggctaca | gcacatatta | catttatgtg | atcgccactg | ccccaaacat | gttcaatgtg | 300 |
| aacgatgtgt | tgggggttta | cagccccat | ccatatgaac | aagaagtctc | ggcccttggg | 360 |
| gggatcccat | atagccagat | ttatggttgg | taccgcgtaa | attttggtgt | gattgatgaa | 420 |
| cgtttgcatc | gtaaccgtga | ataccgcgat | cgctactacc | gtaacttgaa | cattgcacct | 480 |
| gccgaggacg | gctatcgttt | agcgggattc | cacccgatc | atcaggcgtg | gcgtgaggaa | 540 |
| ccgtggatcc | atcacgcccc | tcaggggtgc | gggaacagta | gtcgccatat | gaaaagtgag | 600 |
| cgtttaaaaa | aattagaatc | agagcttcat | gatcttaccc | agtggatgca | acttggcctt | 660 |
| gttcctaaaa | agaaatcga | gagacaccag | gaagaaatcc | gtctgctaga | aagcaaaatc | 720 |
| cttgaagaga | agaacgtct | acaacttctc | aaagaaagcg | gtgagatcaa | agagtacgta | 780 |
| accccctcgaa | gaactccagc | taaaaccatt | tacccagatg | gccccagcgt | ttcagacgtt | 840 |
| gagtttgtag | aatcctcgga | tacagaagtg | gatctcgatg | ccggtgacac | aattgagatt | 900 |
| gacctaggtg | atgaggcaag | agaagaaagc | ggaaacgaac | tcgactactc | tagtgaagac | 960 |
| gatgaggatc | ctttcagcga | tcgcaatcgt | tggcgccgag | gaggcatcat | agatcctgac | 1020 |
| gcgaatgaat | ggggttcagc | tgcttcaatg | agctcttggt | ttgcacaggc | gacggacgtc | 1080 |
| gctttgagcc | agacccttga | tctgcctgac | gcttcattgg | cggttcaaac | cgaaaaattt | 1140 |
| ccatacagct | gttcaatctc | taaggaatcc | gccccatcat | gtattcgtaa | aatcttcgcc | 1200 |
| catttagcat | ctcagaagga | aagtgctccg | ctgtctttt | ctcgtttaca | accgactact | 1260 |
| ccgaaagaac | gcatcctgtt | tttcgggtca | tcgccttcct | cccaattgtc | ctcgactgtc | 1320 |
| cgcaccacaa | cctcttctcc | atggaatctt | tttagcaact | cccaggcacg | caactcgacc | 1380 |
| cgtaaattgt | cggagaagct | tcatttgagc | tcagagttat | ccgcccgtga | ctccactaag | 1440 |
| ccttcgtcga | gcgaaccggt | taaaccatcg | gaaaatcttt | tgcacacccc | tgagcatcat | 1500 |
| aaggaatcct | tctcaagttt | gaaaaaggat | aacttatctc | ctatcatgga | ggagatcgac | 1560 |
| tcattctctg | cagagacaga | gtcccttgaa | gagcgtttgg | tcacccagaa | aaaggaggag | 1620 |
| acggtggccc | aggagcaaaa | gcacccattg | ctgcgtacat | ctactccgcc | atcaaaggcc | 1680 |
| agcggggaat | cacaagattc | tagcgaacac | agctcaaagg | aagatcctta | tagtcaacaa | 1740 |
| ccgagccata | aaatccaacg | ccgtaaagag | cgtgctaagc | gcgtcgtccc | aattattact | 1800 |
| ccgccaacgg | tgggtatctt | tagtttgagc | taccttctta | caaaacaggg | gatcttagcg | 1860 |
| gatttcagcg | cctattcggc | atacaaggat | aatttagaaa | caactcagca | agagctgacc | 1920 |
| atgttgcatc | aagaacgtat | cgagcaagtc | caaaagatcg | tggataaaag | taagacaatg | 1980 |

```
cgcttttggg attcattagc atccattgtg gccacaatca ttccatggat cgaaatgggt    2040
gttgcagtaa ccatcatcgc actgggaggt ggaatccttt cctggtgctc tcttttgct     2100 gcgcttatca tgattgtaat ttcattattg gaagcattcg acgggtggcg tgcaatcgct    2160
aagcatttac caggtaacga tcttgaaaag aagatgcgtt atttaggtta cgtaaagttg    2220
gccttaactg tgttctcgtg cttactgagt ttaagcgcct tgtatgtagc aaaattagga    2280
atgagtccgc ttttggaggg ggttgtgaag agtatcgcac cagcattaag tggtatgctg    2340
ggtttgactc aaggcgtagc actgtattta caatcttcat cgcaaaagat cgtgcccgc     2400 tgcactcaga tcgacgcacg cattgaattg attaactggg aacgcgatga gtatttcttg    2460
cgtgctgaac aacttcttga ttcaatgcaa acgtccttcg aacaacttac tgaaacatta    2520
cagttacaac gtgaaattga tcagacattt acagacgctt tgcgctagct cgag          2574
```

<210> SEQ ID NO 96
<211> LENGTH: 853
<212> TYPE: PRT
<213> ORGANISM: Artificial Sequence
<220> FEATURE:
<223> OTHER INFORMATION: synthetic construct

<400> SEQUENCE: 96

```
Met Asp Asn Gly Asp Arg Leu Tyr Arg Ala Asp Ser Arg Pro Pro Asp
1               5                   10                  15

Glu Ile Lys Arg Ser Gly Gly Leu Met Pro Arg Gly His Asn Glu Tyr
            20                  25                  30

Phe Asp Arg Gly Thr Gln Met Asn Ile Asn Leu Tyr Asp His Ala Arg
        35                  40                  45

Gly Thr Gln Thr Gly Phe Val Arg Tyr Asp Asp Gly Tyr Val Ser Thr
    50                  55                  60

Ser Leu Ser Leu Arg Ser Ala His Leu Ala Gly Gln Ser Ile Leu Ser
65                  70                  75                  80

Gly Tyr Ser Thr Tyr Tyr Ile Tyr Val Ile Ala Thr Ala Pro Asn Met
                85                  90                  95

Phe Asn Val Asn Asp Val Leu Gly Val Tyr Ser Pro His Pro Tyr Glu
            100                 105                 110

Gln Glu Val Ser Ala Leu Gly Gly Ile Pro Tyr Ser Gln Ile Tyr Gly
        115                 120                 125

Trp Tyr Arg Val Asn Phe Gly Val Ile Asp Glu Arg Leu His Arg Asn
    130                 135                 140

Arg Glu Tyr Arg Asp Arg Tyr Tyr Arg Asn Leu Asn Ile Ala Pro Ala
145                 150                 155                 160

Glu Asp Gly Tyr Arg Leu Ala Gly Phe Pro Pro Asp His Gln Ala Trp
                165                 170                 175

Arg Glu Glu Pro Trp Ile His His Ala Pro Gln Gly Cys Gly Asn Ser
            180                 185                 190

Ser Arg Met Lys Ser Glu Arg Leu Lys Lys Leu Glu Ser Glu Leu His
        195                 200                 205

Asp Leu Thr Gln Trp Met Gln Leu Gly Leu Val Pro Lys Lys Glu Ile
    210                 215                 220

Glu Arg His Gln Glu Glu Ile Arg Leu Leu Glu Ser Lys Ile Leu Glu
225                 230                 235                 240

Glu Lys Glu Arg Leu Gln Leu Leu Lys Glu Ser Gly Glu Ile Lys Glu
                245                 250                 255
```

```
Tyr Val Thr Pro Arg Arg Thr Pro Ala Lys Thr Ile Tyr Pro Asp Gly
            260                 265                 270

Pro Ser Val Ser Asp Val Glu Phe Val Glu Ser Ser Asp Thr Glu Val
            275                 280                 285

Asp Leu Asp Ala Gly Asp Thr Ile Glu Ile Asp Leu Gly Asp Glu Ala
            290                 295                 300

Arg Glu Glu Ser Gly Asn Glu Leu Asp Tyr Ser Ser Glu Asp Asp Glu
305                 310                 315                 320

Asp Pro Phe Ser Asp Arg Asn Arg Trp Arg Arg Gly Ile Ile Asp
                325                 330                 335

Pro Asp Ala Asn Glu Trp Gly Ser Ala Ala Ser Met Ser Ser Trp Phe
            340                 345                 350

Ala Gln Ala Thr Asp Val Ala Leu Ser Gln Thr Leu Asp Leu Pro Asp
            355                 360                 365

Ala Ser Leu Ala Val Gln Thr Glu Lys Phe Pro Tyr Ser Cys Ser Ile
            370                 375                 380

Ser Lys Glu Ser Ala Pro Ser Cys Ile Arg Lys Ile Phe Ala His Leu
385                 390                 395                 400

Ala Ser Gln Lys Glu Ser Ala Pro Leu Ser Phe Ser Arg Leu Gln Pro
                405                 410                 415

Thr Thr Pro Lys Glu Arg Ile Leu Phe Phe Gly Ser Ser Pro Ser Ser
            420                 425                 430

Gln Leu Ser Ser Thr Val Arg Thr Thr Thr Ser Ser Pro Trp Asn Leu
            435                 440                 445

Phe Ser Asn Ser Gln Ala Arg Asn Ser Thr Arg Lys Leu Ser Glu Lys
450                 455                 460

Leu His Leu Ser Ser Glu Leu Ser Ala Arg Asp Ser Thr Lys Pro Ser
465                 470                 475                 480

Ser Ser Glu Pro Val Lys Pro Ser Glu Asn Leu Leu His Thr Pro Glu
                485                 490                 495

His His Lys Glu Ser Phe Ser Ser Leu Lys Lys Asp Asn Leu Ser Pro
                500                 505                 510

Ile Met Glu Glu Ile Asp Ser Phe Ser Ala Glu Thr Glu Ser Leu Glu
            515                 520                 525

Glu Arg Leu Val Thr Gln Lys Lys Glu Glu Thr Val Ala Gln Glu Gln
            530                 535                 540

Lys His Pro Leu Leu Arg Thr Ser Thr Pro Pro Ser Lys Ala Ser Gly
545                 550                 555                 560

Glu Ser Gln Asp Ser Ser Glu His Ser Ser Lys Glu Asp Pro Tyr Ser
                565                 570                 575

Gln Gln Pro Ser His Lys Ile Gln Arg Arg Lys Glu Arg Ala Lys Arg
            580                 585                 590

Val Val Pro Ile Ile Thr Pro Pro Thr Val Gly Ile Phe Ser Leu Ser
            595                 600                 605

Tyr Leu Leu Thr Lys Gln Gly Ile Leu Ala Asp Phe Ser Ala Tyr Ser
            610                 615                 620

Ala Tyr Lys Asp Asn Leu Glu Thr Thr Gln Gln Glu Leu Thr Met Leu
625                 630                 635                 640

His Gln Glu Arg Ile Glu Gln Val Gln Lys Ile Val Asp Lys Ser Lys
                645                 650                 655

Thr Met Arg Phe Trp Asp Ser Leu Ala Ser Ile Val Ala Thr Ile Ile
                660                 665                 670

Pro Trp Ile Glu Met Gly Val Ala Val Thr Ile Ile Ala Leu Gly Gly
```

```
                675                 680                 685
Gly Ile Leu Ser Trp Cys Ser Leu Phe Ala Ala Leu Ile Met Ile Val
        690                 695                 700

Ile Ser Leu Leu Glu Ala Phe Asp Gly Trp Arg Ala Ile Ala Lys His
705                 710                 715                 720

Leu Pro Gly Asn Asp Leu Glu Lys Lys Met Arg Tyr Leu Gly Tyr Val
                725                 730                 735

Lys Leu Ala Leu Thr Val Phe Ser Cys Leu Leu Ser Leu Ser Ala Leu
            740                 745                 750

Tyr Val Ala Lys Leu Gly Met Ser Pro Leu Leu Glu Gly Val Val Lys
        755                 760                 765

Ser Ile Ala Pro Ala Leu Ser Gly Met Leu Gly Leu Thr Gln Gly Val
    770                 775                 780

Ala Leu Tyr Leu Gln Ser Ser Ser Gln Lys Ile Arg Ala Arg Cys Thr
785                 790                 795                 800

Gln Ile Asp Ala Arg Ile Glu Leu Ile Asn Trp Glu Arg Asp Glu Tyr
                805                 810                 815

Phe Leu Arg Ala Glu Gln Leu Leu Asp Ser Met Gln Thr Ser Phe Glu
            820                 825                 830

Gln Leu Thr Glu Thr Leu Gln Leu Gln Arg Glu Ile Asp Gln Thr Phe
        835                 840                 845

Thr Asp Ala Leu Arg
    850

<210> SEQ ID NO 97
<211> LENGTH: 647
<212> TYPE: DNA
<213> ORGANISM: Artificial Sequence
<220> FEATURE:
<223> OTHER INFORMATION: synthetic construct

<400> SEQUENCE: 97
atgggcagca gccatcacca tcatcaccac agccaggatc cgatgccacc aagcaagatc      60
caatgtcttg aaacttttga agaacttat ggacaccttt atctacaaca tgcgtcccta     120
atgcgtcatt tagcctatct actcgataaa attgctcgct cttaccctca tatgtgtccg     180
cttcccgata tatggaagc gtactttgag aattatatcc ccaataaaga tatccctctg     240
gacacctatc aaaaaatttt caaactgtcc tcagaagatc ttgaacaagt ctacaaggaa     300
ggatacaacg cctatttaca aggagactat gaggaaagtt ctaccgcttt ttactggttg     360 attttctttta acccatttgt gtctaaattt tggttttcat taggagcttc gctccatatg     420
cgccaaaaat atcaacaagc tcttcatgct tatggtgtag ctgctttgct aagagaaaaa     480
gacccttatc ctcattacta tgcctacatc tgctacaccc tgctcaataa tcctgaagaa     540
gctgaaaaag ctcttgatct tgcttggcaa aaagtaaaaa caagctctgc ctatagctct     600
ttaaaagaag aaattttagc gatcaaatcg tacgcctaag cggccgc                   647

<210> SEQ ID NO 98
<211> LENGTH: 212
<212> TYPE: PRT
<213> ORGANISM: Artificial Sequence
<220> FEATURE:
<223> OTHER INFORMATION: synthetic construct

<400> SEQUENCE: 98

Met Gly Ser Ser His His His His His His Ser Gln Asp Pro Met Pro
1               5                  10                  15
```

```
Pro Ser Lys Ile Gln Cys Leu Glu Thr Phe Glu Arg Thr Tyr Gly His
         20                  25                  30

Leu Tyr Leu Gln His Ala Ser Leu Met Arg His Leu Ala Tyr Leu Leu
     35                  40                  45

Asp Lys Ile Ala Arg Ser Tyr Pro His Met Cys Pro Leu Pro Asp Asn
 50                  55                  60

Met Glu Ala Tyr Phe Glu Asn Tyr Ile Pro Asn Lys Asp Ile Pro Leu
 65                  70                  75                  80

Asp Thr Tyr Gln Lys Ile Phe Lys Leu Ser Ser Glu Asp Leu Glu Gln
                 85                  90                  95

Val Tyr Lys Glu Gly Tyr Asn Ala Tyr Leu Gln Gly Asp Tyr Glu Glu
                100                 105                 110

Ser Ser Thr Ala Phe Tyr Trp Leu Ile Phe Phe Asn Pro Phe Val Ser
            115                 120                 125

Lys Phe Trp Phe Ser Leu Gly Ala Ser Leu His Met Arg Gln Lys Tyr
    130                 135                 140

Gln Gln Ala Leu His Ala Tyr Gly Val Ala Ala Leu Leu Arg Glu Lys
145                 150                 155                 160

Asp Pro Tyr Pro His Tyr Tyr Ala Tyr Ile Cys Tyr Thr Leu Leu Asn
                165                 170                 175

Asn Pro Glu Glu Ala Glu Lys Ala Leu Asp Leu Ala Trp Gln Lys Val
            180                 185                 190

Lys Thr Ser Ser Ala Tyr Ser Ser Leu Lys Glu Glu Ile Leu Ala Ile
        195                 200                 205

Lys Ser Tyr Ala
    210

<210> SEQ ID NO 99
<211> LENGTH: 1977
<212> TYPE: DNA
<213> ORGANISM: Artificial Sequence
<220> FEATURE:
<223> OTHER INFORMATION: synthetic construct

<400> SEQUENCE: 99
aaaagtgagc gtttaaaaaa attagaatca gagcttcatg atcttaccca gtggatgcaa      60
cttggccttg ttcctaaaaa agaaatcgag agacaccagg aagaaatccg tctgctagaa     120
agcaaaatcc ttgaagagaa agaacgtcta caacttctca agaaagcgg tgagatcaaa      180 gagtacgtaa cccctcgaag aactccagct aaaaccattt acccagatgg ccccagcgtt     240
tcagacgttg agtttgtaga atcctcggat acagaagtgg atctcgatgc cggtgacaca     300
attgagattg acctaggtga tgaggcaaga gaagaaagcg gaaacgaact cgactactct     360
agtgaagacg atgaggatcc tttcagcgat cgcaatcgtt ggcgccgagg aggcatcata     420
gatcctgacg cgaatgaatg gggttcagct gcttcaatga gctcttggtt tgcacaggcg     480
acggacgtcg ctttgagcca gacccttgat ctgcctgacg cttcattggc ggttcaaacc     540
gaaaaatttc catacagctg ttcaatctct aaggaatccg ccccatcatg tattcgtaaa     600
atcttcgccc atttagcatc tcagaaggaa agtgctccgc tgtctttttc tcgtttacaa     660
ccgactactc cgaaagaacg catcctgttt ttcgggtcat cgccttcctc ccaattgtcc     720
tcgactgtcc gcaccacaac ctcttctcca tggaatcttt ttagcaactc ccaggcacgc     780
aactcgaccg gtaaattgtc ggagaagctt catttgagct cagagttatc cgcccgtgac     840
tccactaagc cttcgtcgag cgaaccggtt aaaccatcgg aaaatctttt gcacacccct     900
```

```
gagcatcata aggaatcctt ctcaagtttg aaaaaggata acttatctcc tatcatggag    960
gagatcgact cattctctgc agagacagag tcccttgaag agcgtttggt cacccagaaa   1020
aaggaggaga cggtggccca ggagcaaaag cacccattgc tgcgtacatc tactccgcca   1080
tcaaaggcca gcgggaatc acaagattct agcgaacaca gctcaaagga agatccttat   1140
agtcaacaac cgagccataa aatccaacgc cgtaaagagc gtgctaagcg cgtcgtccca   1200
attattactc cgccaacggt gggtatcttt agtttgagct accttcttac aaaacagggg   1260
atcttagcgg atttcagcgc ctattcggca tacaaggata atttagaaac aactcagcaa   1320
gagctgacca tgttgcatca agaacgtatc gagcaagtcc aaaagatcgt ggataaaagt   1380
aagacaatgc gcttttggga ttcattagca tccattgtgg ccacaatcat tccatggatc   1440
gaaatgggtg ttgcagtaac catcatcgca ctgggaggtg aatcctttc ctggtgctct   1500 cttttttgctg cgcttatcat gattgtaatt tcattattgg aagcattcga cgggtggcgt   1560
gcaatcgcta agcatttacc aggtaacgat cttgaaaaga agatgcgtta tttaggttac   1620
gtaaagttgg ccttaactgt gttctcgtgc ttactgagtt taagcgcctt gtatgtagca   1680
aaattaggaa tgagtccgct tttggagggg gttgtgaaga gtatcgcacc agcattaagt   1740
ggtatgctgg gtttgactca aggcgtagca ctgtatttac aatcttcatc gcaaaagatt   1800
cgtgcccgct gcactcagat cgacgcacgc attgaattga ttaactggga acgcgatgag   1860
tatttcttgc gtgctgaaca acttcttgat tcaatgcaaa cgtccttcga caacttact    1920 gaaacattac agttacaacg tgaaattgat cagacattta cagacgcttt gcgctag    1977
```

<210> SEQ ID NO 100
<211> LENGTH: 659
<212> TYPE: PRT
<213> ORGANISM: Artificial Sequence
<220> FEATURE:
<223> OTHER INFORMATION: synthetic construct

<400> SEQUENCE: 100

```
Met Lys Ser Glu Arg Leu Lys Lys Leu Glu Ser Glu Leu His Asp Leu
1               5                   10                  15

Thr Gln Trp Met Gln Leu Gly Leu Val Pro Lys Lys Glu Ile Glu Arg
            20                  25                  30

His Gln Glu Glu Ile Arg Leu Leu Glu Ser Lys Ile Leu Glu Glu Lys
        35                  40                  45

Glu Arg Leu Gln Leu Leu Lys Glu Ser Gly Glu Ile Lys Glu Tyr Val
    50                  55                  60

Thr Pro Arg Arg Thr Pro Ala Lys Thr Ile Tyr Pro Asp Gly Pro Ser
65                  70                  75                  80

Val Ser Asp Val Glu Phe Val Glu Ser Ser Asp Thr Glu Val Asp Leu
                85                  90                  95

Asp Ala Gly Asp Thr Ile Glu Ile Asp Leu Gly Asp Glu Ala Arg Glu
            100                 105                 110

Glu Ser Gly Asn Glu Leu Asp Tyr Ser Ser Glu Asp Glu Asp Pro
        115                 120                 125

Phe Ser Asp Arg Asn Arg Trp Arg Arg Gly Gly Ile Ile Asp Pro Asp
    130                 135                 140

Ala Asn Glu Trp Gly Ser Ala Ala Ser Met Ser Ser Trp Phe Ala Gln
145                 150                 155                 160

Ala Thr Asp Val Ala Leu Ser Gln Thr Leu Asp Leu Pro Asp Ala Ser
                165                 170                 175
```

```
Leu Ala Val Gln Thr Glu Lys Phe Pro Tyr Ser Cys Ser Ile Ser Lys
            180                 185                 190

Glu Ser Ala Pro Ser Cys Ile Arg Lys Ile Phe Ala His Leu Ala Ser
            195                 200                 205

Gln Lys Glu Ser Ala Pro Leu Ser Phe Ser Arg Leu Gln Pro Thr Thr
            210                 215                 220

Pro Lys Glu Arg Ile Leu Phe Phe Gly Ser Ser Pro Ser Ser Gln Leu
225                 230                 235                 240

Ser Ser Thr Val Arg Thr Thr Ser Ser Pro Trp Asn Leu Phe Ser
            245                 250                 255

Asn Ser Gln Ala Arg Asn Ser Thr Arg Lys Leu Ser Glu Lys Leu His
            260                 265                 270

Leu Ser Ser Glu Leu Ser Ala Arg Asp Ser Thr Lys Pro Ser Ser Ser
            275                 280                 285

Glu Pro Val Lys Pro Ser Glu Asn Leu Leu His Thr Pro Glu His His
            290                 295                 300

Lys Glu Ser Phe Ser Ser Leu Lys Lys Asp Asn Leu Ser Pro Ile Met
305                 310                 315                 320

Glu Glu Ile Asp Ser Phe Ser Ala Glu Thr Glu Ser Leu Glu Glu Arg
            325                 330                 335

Leu Val Thr Gln Lys Lys Glu Glu Thr Val Ala Gln Glu Gln Lys His
            340                 345                 350

Pro Leu Leu Arg Thr Ser Thr Pro Pro Ser Lys Ala Ser Gly Glu Ser
            355                 360                 365

Gln Asp Ser Ser Glu His Ser Ser Lys Glu Asp Pro Tyr Ser Gln Gln
            370                 375                 380

Pro Ser His Lys Ile Gln Arg Arg Lys Glu Arg Ala Lys Arg Val Val
385                 390                 395                 400

Pro Ile Ile Thr Pro Pro Thr Val Gly Ile Phe Ser Leu Ser Tyr Leu
            405                 410                 415

Leu Thr Lys Gln Gly Ile Leu Ala Asp Phe Ser Ala Tyr Ser Ala Tyr
            420                 425                 430

Lys Asp Asn Leu Glu Thr Thr Gln Gln Glu Leu Thr Met Leu His Gln
            435                 440                 445

Glu Arg Ile Glu Gln Val Gln Lys Ile Val Asp Lys Ser Lys Thr Met
            450                 455                 460

Arg Phe Trp Asp Ser Leu Ala Ser Ile Val Ala Thr Ile Ile Pro Trp
465                 470                 475                 480

Ile Glu Met Gly Val Ala Val Thr Ile Ile Ala Leu Gly Gly Gly Ile
            485                 490                 495

Leu Ser Trp Cys Ser Leu Phe Ala Ala Leu Ile Met Ile Val Ile Ser
            500                 505                 510

Leu Leu Glu Ala Phe Asp Gly Trp Arg Ala Ile Ala Lys His Leu Pro
            515                 520                 525

Gly Asn Asp Leu Glu Lys Lys Met Arg Tyr Leu Gly Tyr Val Lys Leu
            530                 535                 540

Ala Leu Thr Val Phe Ser Cys Leu Leu Ser Leu Ser Ala Leu Tyr Val
545                 550                 555                 560

Ala Lys Leu Gly Met Ser Pro Leu Leu Glu Gly Val Val Lys Ser Ile
            565                 570                 575

Ala Pro Ala Leu Ser Gly Met Leu Gly Leu Thr Gln Gly Val Ala Leu
            580                 585                 590
```

```
Tyr Leu Gln Ser Ser Gln Lys Ile Arg Ala Arg Cys Thr Gln Ile
        595                 600                 605

Asp Ala Arg Ile Glu Leu Ile Asn Trp Glu Arg Asp Glu Tyr Phe Leu
610                 615                 620

Arg Ala Glu Gln Leu Leu Asp Ser Met Gln Thr Ser Phe Glu Gln Leu
625                 630                 635                 640

Thr Glu Thr Leu Gln Leu Gln Arg Glu Ile Asp Gln Thr Phe Thr Asp
                645                 650                 655

Ala Leu Arg

<210> SEQ ID NO 101
<211> LENGTH: 2574
<212> TYPE: DNA
<213> ORGANISM: Artificial Sequence
<220> FEATURE:
<223> OTHER INFORMATION: synthetic construct

<400> SEQUENCE: 101
```

| | | | | | |
|---|---|---|---|---|---|
| catatggaca | atggcgatcg | tttataccgt | gccgactcgc | gtcccccaga | tgagattaaa | 60 |
| cgtagcggtg | ggttaatgcc | acgtgggcac | aatgagtatt | tgaccgtgg | aacacagatg | 120 |
| aacattaacc | tttacgatca | tgcccgtggg | acccagaccg | ggtttgtccg | ttatgatgac | 180 |
| gggtatgtta | gtacgagttt | gtccttacgc | tccgcacacc | ttgcgggaca | agtatttta | 240 |
| tcaggctaca | gcacatatta | catttatgtg | atcgccactg | ccccaaacat | gttcaatgtg | 300 |
| aacgatgtgt | gggggtttta | cagcccccat | ccatatgaac | aagaagtctc | ggcccttggg | 360 |
| gggatcccat | atagccagat | ttatggttgg | taccgcgtaa | attttggtgt | gattgatgaa | 420 |
| cgtttgcatc | gtaaccgtga | ataccgcgat | cgctactacc | gtaacttgaa | cattgcacct | 480 |
| gccgaggacg | gctatcgttt | agcgggattc | ccacccgatc | atcaggcgtg | gcgtgaggaa | 540 |
| ccgtggatcc | atcacgcccc | tcaggggtgc | gggaacagta | gtcgccatat | gaaaagtgag | 600 |
| cgtttaaaaa | aattgaatc | agagcttcat | gatcttaccc | agtggatgca | acttggcctt | 660 |
| gttcctaaaa | agaaatcga | gagacaccag | gaagaaatcc | gtctgctaga | aagcaaaatc | 720 |
| cttgaagaga | agaacgtct | acaacttctc | aaagaaagcg | gtgagatcaa | agagtacgta | 780 |
| accccctcgaa | gaactccagc | taaaaccatt | tacccagatg | gccccagcgt | tcagacgtt | 840 |
| gagtttgtag | aatcctcgga | tacagaagtg | gatctcgatg | ccggtgacac | aattgagatt | 900 |
| gacctaggtg | atgaggcaag | agaagaaagc | ggaaacgaac | tcgactactc | tagtgaagac | 960 |
| gatgaggatc | ctttcagcga | tcgcaatcgt | tggcgccgag | gaggcatcat | agatcctgac | 1020 |
| gcgaatgaat | ggggttcagc | tgcttcaatg | agctcttggt | ttgcacaggc | gacggacgtc | 1080 |
| gctttgagcc | agacccttga | tctgcctgac | gcttcattgg | cggttcaaac | cgaaaaattt | 1140 |
| ccatacagct | gttcaatctc | taaggaatcc | gccccatcat | gtattcgtaa | aatcttcgcc | 1200 |
| catttagcat | ctcagaagga | aagtgctccg | ctgtcttttt | ctcgtttaca | accgactact | 1260 |
| ccgaaagaac | gcatcctgtt | tttcgggtca | tcgccttcct | cccaattgtc | ctcgactgtc | 1320 |
| cgcaccacaa | cctcttctcc | atggaatctt | tttagcaact | cccaggcacg | caactcgacc | 1380 |
| cgtaaattgt | cggagaagct | tcatttgagc | tcagagttat | ccgccgtga | ctccactaag | 1440 |
| ccttcgtcga | gcgaaccggt | taaccatcg | gaaaatcttt | tgcacacccc | tgagcatcat | 1500 |
| aaggaatcct | tctcaagttt | gaaaaggat | aacttatctc | ctatcatgga | ggagatcgac | 1560 |
| tcattctctg | cagagacaga | gtcccttgaa | gagcgtttgg | tcacccagaa | aaaggaggag | 1620 |
| acggtggccc | aggagcaaaa | gcacccattg | ctgcgtacat | ctactccgcc | atcaaaggcc | 1680 |

-continued

```
agcggggaat cacaagattc tagcgaacac agctcaaagg aagatcctta tagtcaacaa   1740
ccgagccata aaatccaacg ccgtaaagag cgtgctaagc gcgtcgtccc aattattact   1800
ccgccaacgg tgggtatctt tagtttgagc taccttctta caaaacaggg gatcttagcg   1860
gatttcagcg cctattcggc atacaaggat aatttagaaa caactcagca agagctgacc   1920
atgttgcatc aagaacgtat cgagcaagtc caaaagatcg tggataaaag taagacaatg   1980
cgcttttggg attcattagc atccattgtg gccacaatca ttccatggat cgaaatgggt   2040
gttgcagtaa ccatcatcgc actgggaggt ggaatccttt cctggtgctc tcttttgct    2100
gcgcttatca tgattgtaat ttcattattg gaagcattcg acgggtggcg tgcaatcgct   2160
aagcatttac caggtaacga tcttgaaaag aagatgcgtt atttaggtta cgtaaagttg   2220
gccttaactg tgttctcgtg cttactgagt ttaagcgcct tgtatgtagc aaaattagga   2280
atgagtccgc ttttggaggg ggttgtgaag agtatcgcac cagcattaag tggtatgctg   2340
ggtttgactc aaggcgtagc actgtattta caatcttcat cgcaaaagat tcgtgcccgc   2400
tgcactcaga tcgacgcacg cattgaattg attaactggg aacgcgatga gtatttcttg   2460
cgtgctgaac aacttcttga ttcaatgcaa acgtccttcg aacaacttac tgaaacatta   2520
cagttacaac gtgaaattga tcagacattt acagacgctt gcgctagct cgag          2574
```

<210> SEQ ID NO 102
<211> LENGTH: 853
<212> TYPE: PRT
<213> ORGANISM: Artificial Sequence
<220> FEATURE:
<223> OTHER INFORMATION: synthetic construct

<400> SEQUENCE: 102

```
Met Asp Asn Gly Asp Arg Leu Tyr Arg Ala Asp Ser Arg Pro Pro Asp
1               5                   10                  15

Glu Ile Lys Arg Ser Gly Gly Leu Met Pro Arg Gly His Asn Glu Tyr
            20                  25                  30

Phe Asp Arg Gly Thr Gln Met Asn Ile Asn Leu Tyr Asp His Ala Arg
        35                  40                  45

Gly Thr Gln Thr Gly Phe Val Arg Tyr Asp Asp Gly Tyr Val Ser Thr
    50                  55                  60

Ser Leu Ser Leu Arg Ser Ala His Leu Ala Gly Gln Ser Ile Leu Ser
65                  70                  75                  80

Gly Tyr Ser Thr Tyr Tyr Ile Tyr Val Ile Ala Thr Ala Pro Asn Met
                85                  90                  95

Phe Asn Val Asn Asp Val Leu Gly Val Tyr Ser Pro His Pro Tyr Glu
            100                 105                 110

Gln Glu Val Ser Ala Leu Gly Gly Ile Pro Tyr Ser Gln Ile Tyr Gly
        115                 120                 125

Trp Tyr Arg Val Asn Phe Gly Val Ile Asp Glu Arg Leu His Arg Asn
    130                 135                 140

Arg Glu Tyr Arg Asp Arg Tyr Tyr Arg Asn Leu Asn Ile Ala Pro Ala
145                 150                 155                 160

Glu Asp Gly Tyr Arg Leu Ala Gly Phe Pro Pro Asp His Gln Ala Trp
                165                 170                 175

Arg Glu Glu Pro Trp Ile His His Ala Pro Gln Gly Cys Gly Asn Ser
            180                 185                 190

Ser Arg Met Lys Ser Glu Arg Leu Lys Lys Leu Glu Ser Glu Leu His
        195                 200                 205
```

```
Asp Leu Thr Gln Trp Met Gln Leu Gly Leu Val Pro Lys Lys Glu Ile
    210                 215                 220

Glu Arg His Gln Glu Glu Ile Arg Leu Leu Glu Ser Lys Ile Leu Glu
225                 230                 235                 240

Glu Lys Glu Arg Leu Gln Leu Leu Lys Glu Ser Gly Glu Ile Lys Glu
                245                 250                 255

Tyr Val Thr Pro Arg Arg Thr Pro Ala Lys Thr Ile Tyr Pro Asp Gly
            260                 265                 270

Pro Ser Val Ser Asp Val Glu Phe Val Glu Ser Ser Asp Thr Glu Val
        275                 280                 285

Asp Leu Asp Ala Gly Asp Thr Ile Glu Ile Asp Leu Gly Asp Glu Ala
    290                 295                 300

Arg Glu Glu Ser Gly Asn Glu Leu Asp Tyr Ser Ser Glu Asp Asp Glu
305                 310                 315                 320

Asp Pro Phe Ser Asp Arg Asn Arg Trp Arg Arg Gly Gly Ile Ile Asp
                325                 330                 335

Pro Asp Ala Asn Glu Trp Gly Ser Ala Ala Ser Met Ser Ser Trp Phe
            340                 345                 350

Ala Gln Ala Thr Asp Val Ala Leu Ser Gln Thr Leu Asp Leu Pro Asp
        355                 360                 365

Ala Ser Leu Ala Val Gln Thr Glu Lys Phe Pro Tyr Ser Cys Ser Ile
    370                 375                 380

Ser Lys Glu Ser Ala Pro Ser Cys Ile Arg Lys Ile Phe Ala His Leu
385                 390                 395                 400

Ala Ser Gln Lys Glu Ser Ala Pro Leu Ser Phe Ser Arg Leu Gln Pro
                405                 410                 415

Thr Thr Pro Lys Glu Arg Ile Leu Phe Phe Gly Ser Ser Pro Ser Ser
            420                 425                 430

Gln Leu Ser Ser Thr Val Arg Thr Thr Thr Ser Ser Pro Trp Asn Leu
        435                 440                 445

Phe Ser Asn Ser Gln Ala Arg Asn Ser Thr Arg Lys Leu Ser Glu Lys
    450                 455                 460

Leu His Leu Ser Ser Glu Leu Ser Ala Arg Asp Ser Thr Lys Pro Ser
465                 470                 475                 480

Ser Ser Glu Pro Val Lys Pro Ser Glu Asn Leu Leu His Thr Pro Glu
                485                 490                 495

His His Lys Glu Ser Phe Ser Ser Leu Lys Lys Asp Asn Leu Ser Pro
            500                 505                 510

Ile Met Glu Glu Ile Asp Ser Phe Ser Ala Glu Thr Glu Ser Leu Glu
        515                 520                 525

Glu Arg Leu Val Thr Gln Lys Lys Glu Glu Thr Val Ala Gln Glu Gln
    530                 535                 540

Lys His Pro Leu Leu Arg Thr Ser Thr Pro Pro Ser Lys Ala Ser Gly
545                 550                 555                 560

Glu Ser Gln Asp Ser Ser Glu His Ser Ser Lys Glu Asp Pro Tyr Ser
                565                 570                 575

Gln Gln Pro Ser His Lys Ile Gln Arg Arg Lys Glu Arg Ala Lys Arg
            580                 585                 590

Val Val Pro Ile Ile Thr Pro Pro Thr Val Gly Ile Phe Ser Leu Ser
        595                 600                 605

Tyr Leu Leu Thr Lys Gln Gly Ile Leu Ala Asp Phe Ser Ala Tyr Ser
    610                 615                 620
```

```
Ala Tyr Lys Asp Asn Leu Glu Thr Thr Gln Gln Glu Leu Thr Met Leu
625                 630                 635                 640

His Gln Glu Arg Ile Glu Gln Val Gln Lys Ile Val Asp Lys Ser Lys
                645                 650                 655

Thr Met Arg Phe Trp Asp Ser Leu Ala Ser Ile Val Ala Thr Ile Ile
            660                 665                 670

Pro Trp Ile Glu Met Gly Val Ala Val Thr Ile Ile Ala Leu Gly Gly
        675                 680                 685

Gly Ile Leu Ser Trp Cys Ser Leu Phe Ala Ala Leu Ile Met Ile Val
    690                 695                 700

Ile Ser Leu Leu Glu Ala Phe Asp Gly Trp Arg Ala Ile Ala Lys His
705                 710                 715                 720

Leu Pro Gly Asn Asp Leu Glu Lys Lys Met Arg Tyr Leu Gly Tyr Val
                725                 730                 735

Lys Leu Ala Leu Thr Val Phe Ser Cys Leu Leu Ser Leu Ser Ala Leu
            740                 745                 750

Tyr Val Ala Lys Leu Gly Met Ser Pro Leu Leu Glu Gly Val Val Lys
        755                 760                 765

Ser Ile Ala Pro Ala Leu Ser Gly Met Leu Gly Leu Thr Gln Gly Val
770                 775                 780

Ala Leu Tyr Leu Gln Ser Ser Ser Gln Lys Ile Arg Ala Arg Cys Thr
785                 790                 795                 800

Gln Ile Asp Ala Arg Ile Glu Leu Ile Asn Trp Glu Arg Asp Glu Tyr
                805                 810                 815

Phe Leu Arg Ala Glu Gln Leu Leu Asp Ser Met Gln Thr Ser Phe Glu
            820                 825                 830

Gln Leu Thr Glu Thr Leu Gln Leu Gln Arg Glu Ile Asp Gln Thr Phe
        835                 840                 845

Thr Asp Ala Leu Arg
    850

<210> SEQ ID NO 103
<211> LENGTH: 810
<212> TYPE: DNA
<213> ORGANISM: Artificial Sequence
<220> FEATURE:
<223> OTHER INFORMATION: synthetic construct

<400> SEQUENCE: 103
atgcgttgca ctcgggcaat tcgccaaacc gcaagaacag gctggctgac gtggctggcg    60
attcttgccg tcacggcgcc cgtgacttcg ccggcatggg ccgacgatcc tcccgccacc   120
gtataccgct atgactcccg cccgccggag gacgttttcc agaacggatt cacggcgtgg   180
ggaaacaacg acaatgtgct cgaccatctg accggacgtt cctgccaggt cggcagcagc   240
aacagcgctt tcgtctccac cagcagcagc cggcgctata ccgaggtcta tctcgaacat   300
cgcatgcagg aagcggtcga ggccgaacgc gccggcaggg gcaccggcca cttcatcggc   360
tacatctacg aagtccgcgc cgacaacaat ttctacggcg ccgccagctc gtacttcgaa   420
tacgtcgaca cttatggcga caatgccggc cgtatcctcg ccggcgcgct ggccacctac   480
cagagcgaat atctggcaca ccggcgcatt ccgcccgaaa acatccgcag ggtaacgcgg   540
gtctatcaca acggcatcac cggcgagacc acgaccacgg agtattccaa cgctcgctac   600
gtcagccagc agactcgcgc caatcccaac ccctacacat cgcgaaggtc cgtagcgtcg   660
atcgtcggca cattggtgcg catggcgccg gtgataggcg cttgcatggc gcggcaggcc   720
```

```
gaaagctccg aggccatggc agcctggtcc gaacgcgccg gcgaggcgat ggttctcgtg      780
tactacgaaa gcatcgcgta ttcgttctag                                       810
```

<210> SEQ ID NO 104
<211> LENGTH: 269
<212> TYPE: PRT
<213> ORGANISM: Artificial Sequence
<220> FEATURE:
<223> OTHER INFORMATION: synthetic construct

<400> SEQUENCE: 104

```
Met Arg Cys Thr Arg Ala Ile Arg Gln Thr Ala Arg Thr Gly Trp Leu
1               5                   10                  15

Thr Trp Leu Ala Ile Leu Ala Val Thr Ala Pro Val Thr Ser Pro Ala
            20                  25                  30

Trp Ala Asp Asp Pro Pro Ala Thr Val Tyr Arg Tyr Asp Ser Arg Pro
        35                  40                  45

Pro Glu Asp Val Phe Gln Asn Gly Phe Thr Ala Trp Gly Asn Asn Asp
    50                  55                  60

Asn Val Leu Asp His Leu Thr Gly Arg Ser Cys Gln Val Gly Ser Ser
65                  70                  75                  80

Asn Ser Ala Phe Val Ser Thr Ser Ser Arg Arg Tyr Thr Glu Val
                85                  90                  95

Tyr Leu Glu His Arg Met Gln Glu Ala Val Glu Ala Glu Arg Ala Gly
            100                 105                 110

Arg Gly Thr Gly His Phe Ile Gly Tyr Ile Tyr Glu Val Arg Ala Asp
        115                 120                 125

Asn Asn Phe Tyr Gly Ala Ala Ser Ser Tyr Phe Glu Tyr Val Asp Thr
    130                 135                 140

Tyr Gly Asp Asn Ala Gly Arg Ile Leu Ala Gly Ala Leu Ala Thr Tyr
145                 150                 155                 160

Gln Ser Glu Tyr Leu Ala His Arg Arg Ile Pro Pro Glu Asn Ile Arg
                165                 170                 175

Arg Val Thr Arg Val Tyr His Asn Gly Ile Thr Gly Glu Thr Thr Thr
            180                 185                 190

Thr Glu Tyr Ser Asn Ala Arg Tyr Val Ser Gln Gln Thr Arg Ala Asn
        195                 200                 205

Pro Asn Pro Tyr Thr Ser Arg Arg Ser Val Ala Ser Ile Val Gly Thr
    210                 215                 220

Leu Val Arg Met Ala Pro Val Ile Gly Ala Cys Met Ala Arg Gln Ala
225                 230                 235                 240

Glu Ser Ser Glu Ala Met Ala Ala Trp Ser Glu Arg Ala Gly Glu Ala
                245                 250                 255

Met Val Leu Val Tyr Tyr Glu Ser Ile Ala Tyr Ser Phe
            260                 265
```

<210> SEQ ID NO 105
<211> LENGTH: 681
<212> TYPE: DNA
<213> ORGANISM: Artificial Sequence
<220> FEATURE:
<223> OTHER INFORMATION: synthetic construct

<400> SEQUENCE: 105

```
atgccgatcg accgcaagac gctctgccat ctcctgtccg ttctgccgtt ggccctcctc       60
ggatctcacg tggcgcgggc ctccacgcca ggcatcgtca ttccgccgca ggaacagatt      120
```

-continued

```
acccagcatg gcagccccta tgacgctgc gcgaacaaga cccgtgccct gaccgtggcg      180
gaattgcgcg gcagcggcga tctgcaggag tacctgcgtc atgtgacgcg cggctggtca      240
atatttgcgc tctacgatgg cacctatctc ggcggcgaat atggcggcgt gatcaaggac      300
ggaacacccg cgcgcatt cgacctgaaa cgacgttct gcatcatgac cacgcgcaat         360
acgggtcaac ccgcaacgga tcactactac agcaacgtca ccgccactcg cctgctctcc      420
agcaccaaca gcaggctatg cgcggtcttc gtcagaagcg ggcaaccggt cattggcgcc      480
tgcaccagcc cgtatgacgg caagtactgg agcatgtaca gccggctgcg gaaaatgctt      540
tacctgatct acgtggccgg catctccgta cgcgtccatg tcagcaagga agaacagtat      600
tacgactatg aggacgcaac gttcgagact tacgccctta ccggcatctc catctgcaat      660
cctggatcat ccttatgctg a                                                681
```

<210> SEQ ID NO 106
<211> LENGTH: 226
<212> TYPE: PRT
<213> ORGANISM: Artificial Sequence
<220> FEATURE:
<223> OTHER INFORMATION: synthetic construct

<400> SEQUENCE: 106

```
Met Pro Ile Asp Arg Lys Thr Leu Cys His Leu Leu Ser Val Leu Pro
1               5                   10                  15

Leu Ala Leu Leu Gly Ser His Val Ala Arg Ala Ser Thr Pro Gly Ile
            20                  25                  30

Val Ile Pro Pro Gln Glu Gln Ile Thr Gln His Gly Gly Pro Tyr Gly
        35                  40                  45

Arg Cys Ala Asn Lys Thr Arg Ala Leu Thr Val Ala Glu Leu Arg Gly
    50                  55                  60

Ser Gly Asp Leu Gln Glu Tyr Leu Arg His Val Thr Arg Gly Trp Ser
65                  70                  75                  80

Ile Phe Ala Leu Tyr Asp Gly Thr Tyr Leu Gly Gly Glu Tyr Gly Gly
                85                  90                  95

Val Ile Lys Asp Gly Thr Pro Gly Gly Ala Phe Asp Leu Lys Thr Thr
            100                 105                 110

Phe Cys Ile Met Thr Thr Arg Asn Thr Gly Gln Pro Ala Thr Asp His
        115                 120                 125

Tyr Tyr Ser Asn Val Thr Ala Thr Arg Leu Leu Ser Ser Thr Asn Ser
    130                 135                 140

Arg Leu Cys Ala Val Phe Val Arg Ser Gly Gln Pro Val Ile Gly Ala
145                 150                 155                 160

Cys Thr Ser Pro Tyr Asp Gly Lys Tyr Trp Ser Met Tyr Ser Arg Leu
                165                 170                 175

Arg Lys Met Leu Tyr Leu Ile Tyr Val Ala Gly Ile Ser Val Arg Val
            180                 185                 190

His Val Ser Lys Glu Glu Gln Tyr Tyr Asp Tyr Glu Asp Ala Thr Phe
        195                 200                 205

Glu Thr Tyr Ala Leu Thr Gly Ile Ser Ile Cys Asn Pro Gly Ser Ser
    210                 215                 220

Leu Cys
225
```

<210> SEQ ID NO 107
<211> LENGTH: 684
<212> TYPE: DNA

<213> ORGANISM: Artificial Sequence
<220> FEATURE:
<223> OTHER INFORMATION: synthetic construct

<400> SEQUENCE: 107

```
atgctgatca acaacaagaa gctgcttcat cacattctgc ccatcctggt gctcgccctg      60
ctgggcatgc gcacggccca ggccgttgcg ccaggcatcg tcatcccgcc gaaggcactg     120
ttcacccaac agggcggcgc ctatggacgc tgcccgaacg gaacccgcgc cttgaccgtg     180
gccgaactgc gcggcaacgc cgaattgcag acgtatttgc gccagataac gcccggctgg     240
tccatatacg gtctctatga cggtacgtac ctgggccagg cgtacggcgg catcatcaag     300
gacgcgccgc caggcgcggg gttcatttat cgcgaaactt tctgcatcac gaccatatac     360
aagaccgggc aaccggctgc ggatcactac tacagcaagg tcacggccac gcgcctgctc     420
gccagcacca acagcaggct gtgcgcggta ttcgtcaggg acgggcaatc ggtcatcgga     480
gcctgcgcca gcccgtatga aggcaggtac agagacatgt acgacgcgct gcggcgcctg     540
ctgtacatga tctatatgtc cggccttgcc gtacgcgtcc acgtcagcaa ggaagagcag     600
tattacgact acgaggacgc cacattccag acctatgccc tcaccggcat tccctctgc      660
aacccggcag cgtcgatatg ctga                                            684
```

<210> SEQ ID NO 108
<211> LENGTH: 227
<212> TYPE: PRT
<213> ORGANISM: Artificial Sequence
<220> FEATURE:
<223> OTHER INFORMATION: synthetic construct

<400> SEQUENCE: 108

```
Met Leu Ile Asn Asn Lys Lys Leu Leu His His Ile Leu Pro Ile Leu
1               5                   10                  15

Val Leu Ala Leu Leu Gly Met Arg Thr Ala Gln Ala Val Ala Pro Gly
            20                  25                  30

Ile Val Ile Pro Pro Lys Ala Leu Phe Thr Gln Gln Gly Gly Ala Tyr
        35                  40                  45

Gly Arg Cys Pro Asn Gly Thr Arg Ala Leu Thr Val Ala Glu Leu Arg
    50                  55                  60

Gly Asn Ala Glu Leu Gln Thr Tyr Leu Arg Gln Ile Thr Pro Gly Trp
65                  70                  75                  80

Ser Ile Tyr Gly Leu Tyr Asp Gly Thr Tyr Leu Gly Gln Ala Tyr Gly
                85                  90                  95

Gly Ile Ile Lys Asp Ala Pro Pro Gly Ala Gly Phe Ile Tyr Arg Glu
            100                 105                 110

Thr Phe Cys Ile Thr Thr Ile Tyr Lys Thr Gly Gln Pro Ala Ala Asp
        115                 120                 125

His Tyr Tyr Ser Lys Val Thr Ala Thr Arg Leu Leu Ala Ser Thr Asn
    130                 135                 140

Ser Arg Leu Cys Ala Val Phe Val Arg Asp Gly Gln Ser Val Ile Gly
145                 150                 155                 160

Ala Cys Ala Ser Pro Tyr Glu Gly Arg Tyr Arg Asp Met Tyr Asp Ala
                165                 170                 175

Leu Arg Arg Leu Leu Tyr Met Ile Tyr Met Ser Gly Leu Ala Val Arg
            180                 185                 190

Val His Val Ser Lys Glu Glu Gln Tyr Tyr Asp Tyr Glu Asp Ala Thr
        195                 200                 205
```

Phe Gln Thr Tyr Ala Leu Thr Gly Ile Ser Leu Cys Asn Pro Ala Ala
    210                 215                 220

Ser Ile Cys
225

<210> SEQ ID NO 109
<211> LENGTH: 459
<212> TYPE: DNA
<213> ORGANISM: Artificial Sequence
<220> FEATURE:
<223> OTHER INFORMATION: synthetic construct

<400> SEQUENCE: 109

```
atgctgagac gcttccccac tcgaaccacc gccccgggac agggcggcgc cggcggtcg      60 cgcgtgcgcg ccctggcgtg gttgctggca tccggcgcga tgacgcatct tcccccgcc     120 ctggccgacg ttccttatgt gctggtgaag accaatatgg tggtcaccag cgtagccatg    180
aagccgtatg aagtcacccc gacgcgcatg ctggtctgcg gcatcgccgc caaactgggc    240
gccgcggcca gcagcccgga cgcgcacgtg ccgttctgct tcggcaagga tctcaagcgt    300
cccggcagca gtcccatgga agtcatgttg cgcgccgtct tcatgcaaca acggccgctg    360
cgcatgtttc tgggtcccaa gcaactcact ttcgaaggca agcccgcgct cgaactgatc    420
cggatggtcg aatgcagcgg caagcaggat tgcccctga                            459
```

<210> SEQ ID NO 110
<211> LENGTH: 152
<212> TYPE: PRT
<213> ORGANISM: Artificial Sequence
<220> FEATURE:
<223> OTHER INFORMATION: synthetic construct

<400> SEQUENCE: 110

Met Leu Arg Arg Phe Pro Thr Arg Thr Thr Ala Pro Gly Gln Gly Gly
1               5                   10                  15

Ala Arg Arg Ser Arg Val Arg Ala Leu Ala Trp Leu Leu Ala Ser Gly
            20                  25                  30

Ala Met Thr His Leu Ser Pro Ala Leu Ala Asp Val Pro Tyr Val Leu
        35                  40                  45

Val Lys Thr Asn Met Val Val Thr Ser Val Ala Met Lys Pro Tyr Glu
    50                  55                  60

Val Thr Pro Thr Arg Met Leu Val Cys Gly Ile Ala Ala Lys Leu Gly
65                  70                  75                  80

Ala Ala Ala Ser Ser Pro Asp Ala His Val Pro Phe Cys Phe Gly Lys
                85                  90                  95

Asp Leu Lys Arg Pro Gly Ser Ser Pro Met Glu Val Met Leu Arg Ala
            100                 105                 110

Val Phe Met Gln Gln Arg Pro Leu Arg Met Phe Leu Gly Pro Lys Gln
        115                 120                 125

Leu Thr Phe Glu Gly Lys Pro Ala Leu Glu Leu Ile Arg Met Val Glu
    130                 135                 140

Cys Ser Gly Lys Gln Asp Cys Pro
145                 150

<210> SEQ ID NO 111
<211> LENGTH: 402
<212> TYPE: DNA
<213> ORGANISM: Artificial Sequence
<220> FEATURE:
<223> OTHER INFORMATION: synthetic construct

<400> SEQUENCE: 111

```
atgcagcggc aagcaggatt gccctgaag gcgaacccca tgcataccat cgcatccatc      60
ctgttgtccg tgctcggcat atacagcccg gctgacgtcg ccggcttgcc gacccatctg    120
tacaagaact tcactgtcca ggagctggcc ttgaaactga agggcaagaa tcaggagttc    180
tgcctgaccg ccttcatgtc gggcagaagc ctggtccggg cgtgcctgtc cgacgcggga    240
cacgagcacg acacgtggtt cgacaccatg cttggctttg ccatatccgc gtatgcgctc    300
aagagccgga tcgcgctgac ggtggaagac tcgccgtatc cgggcactcc cggcgatctg    360
ctcgaactgc agatctgccc gctcaacgga tattgcgaat ga                       402
```

<210> SEQ ID NO 112
<211> LENGTH: 133
<212> TYPE: PRT
<213> ORGANISM: Artificial Sequence
<220> FEATURE:
<223> OTHER INFORMATION: synthetic construct

<400> SEQUENCE: 112

```
Met Gln Arg Gln Ala Gly Leu Pro Leu Lys Ala Asn Pro Met His Thr
1               5                   10                  15

Ile Ala Ser Ile Leu Leu Ser Val Leu Gly Ile Tyr Ser Pro Ala Asp
            20                  25                  30

Val Ala Gly Leu Pro Thr His Leu Tyr Lys Asn Phe Thr Val Gln Glu
        35                  40                  45

Leu Ala Leu Lys Leu Lys Gly Lys Asn Gln Glu Phe Cys Leu Thr Ala
    50                  55                  60

Phe Met Ser Gly Arg Ser Leu Val Arg Ala Cys Leu Ser Asp Ala Gly
65                  70                  75                  80

His Glu His Asp Thr Trp Phe Asp Thr Met Leu Gly Phe Ala Ile Ser
                85                  90                  95

Ala Tyr Ala Leu Lys Ser Arg Ile Ala Leu Thr Val Glu Asp Ser Pro
            100                 105                 110

Tyr Pro Gly Thr Pro Gly Asp Leu Leu Glu Leu Gln Ile Cys Pro Leu
        115                 120                 125

Asn Gly Tyr Cys Glu
    130
```

<210> SEQ ID NO 113
<211> LENGTH: 868
<212> TYPE: DNA
<213> ORGANISM: Artificial Sequence
<220> FEATURE:
<223> OTHER INFORMATION: synthetic construct

<400> SEQUENCE: 113

```
atgattgaca tcatgttgca tataggttag ataaaacaag tggttatctt tccggattgt      60
cttcttgtat gatatataag ttttcctcga tgaaaaatat aactttcatt tttttttattt   120
tattagcatc gccattatat gcaaatggcg acagattata ccgtgctgac tctagacccc    180
cagatgaaat aaaacgtttc cggagtctta tgcccagagg taatgagtac ttcgatagag    240
gaactcaaat gaatattaat ctttatgatc acgcgagagg aacacaaacc ggctttgtca    300
gatatgatga cggatatgtt tccacttctc ttagtttgag aagtgctcac ttagcaggac    360
agtatatatt atcaggatat tcacttacta tatatcgt tatagcaaat atgtttaatg     420
ttaatgatgt aattagcgta tacagccctc acccatatga acaggaggtt tctgcgttag    480
```

```
gtggaatacc atattctcag atatatggat ggtatcgtgt taattttggt gtgattgatg      540
aacgattaca tcgtaacagg gaatatagag accggtatta cagaaatctg aatatagctc      600
cggcagagga tggttacaga ttagcaggtt tcccaccgga tcaccaagct ggagagaag       660 aaccctggat tcatcatgca ccacaaggtt gtggagattc atcaggaaca atcacaggtg      720
atacttgtaa tgaggagacc cagaatctga gcacaatata tgccagggaa tatcaatcaa      780
aagttaagag gcagatattt tcagactatc agtcagaggt tgacatatat aacagaattc      840
gggatgaatt atgaataaag taaaatgt                                         868
```

<210> SEQ ID NO 114
<211> LENGTH: 604
<212> TYPE: DNA
<213> ORGANISM: Artificial Sequence
<220> FEATURE:
<223> OTHER INFORMATION: synthetic construct

<400> SEQUENCE: 114

```
gttgacatat ataacagaat tcgggatgaa ttatgaataa agtaaaatgt tatgtttttat      60 ttacggcgtt actatcctct ctatatgcac acggagctcc ccagactatt acagaactat      120
gttcggaata tcgcaacaca caaatatata cgataaatga caagatacta tcatatacgg      180
aatcgatggc aggcaaaaga gaatggtta tcattacatt taagagcggc gaaacatttc       240
aggtcgaagt cccgggcagt caacatatag actcccagaa aaaagccatt gaaggatga      300 aggacacatt aagaatcaca tatctgaccg agaccaaaat tgataaatta tgtgtatgga      360
ataataaaac ccccaattca attgcggcaa tcagtatgaa aaactagttt gctttaaaag      420
catgtctaat gctaggaacc tatataacaa ctactgtact tatactaatg agccttatgc      480
tgcatttgaa aaggcggtag aggaggcaat accgatcctt aaactgtaac actataacag      540
cttccactac agggagctgt tatagcacac agaaaaaact aagctaggct ggaggggcaa      600
gctt                                                                  604
```

<210> SEQ ID NO 115
<211> LENGTH: 777
<212> TYPE: DNA
<213> ORGANISM: Vibrio cholerae

<400> SEQUENCE: 115

```
atggtaaaga taatatttgt gttttttatt ttcttatcat cattttcata tgcaaatgat       60
gataagttat atcgggcaga ttctagacct cctgatgaaa taaagcagtc aggtggtctt      120
atgccaagag gacagagtga gtactttgac cgaggtactc aaatgaatat caacctttat      180
gatcatgcaa gaggaactca gacgggattt gttaggcacg atgatggata tgtttccacc      240
tcaattagtt tgagaagtgc ccacttagtg ggtcaaacta tattgtctgg tcattctact      300
tattatatat atgttatagc cactgcaccc aacatgttta cgttaatga tgtattaggg       360 gcatacagtc ctcatccaga tgaacaagaa gtttctgctt taggtgggat tccatactcc      420
caaatatatg gatggtatcg agttcatttt ggggtgcttg atgaacaatt acatcgtaat      480
aggggctaca gagatagata ttacagtaac ttagatattg ctccagcagc agatggttat      540
ggattggcag gtttccctcc ggagcataga gcttggaggg aagagccgtg gattcatcat      600
gcaccgccgg gttgtgggaa tgctccaaga tcatcgatca gtaatacttg cgatgaaaaa      660
acccaaagtc taggtgtaaa attccttgac gaataccaat ctaaagttaa aagcaaaata      720
ttttcaggct atcaatctga tattgataca cataatagaa ttaaggatga attatga        777
```

<210> SEQ ID NO 116
<211> LENGTH: 70
<212> TYPE: PRT
<213> ORGANISM: Vibrio cholerae

<400> SEQUENCE: 116

His Arg Ala Trp Arg Glu Glu Pro Trp Ile His His Ala Pro Pro Gly
1               5                   10                  15

Cys Gly Asn Ala Pro Arg Ser Ser Met Ser Asn Thr Cys Asp Glu Lys
            20                  25                  30

Thr Gln Ser Leu Gly Val Lys Phe Leu Asp Glu Tyr Gln Ser Lys Val
        35                  40                  45

Lys Arg Gln Ile Phe Ser Gly Tyr Gln Ser Asp Ile Asp Thr His Asn
    50                  55                  60

Arg Ile Lys Asp Glu Leu
65                  70

<210> SEQ ID NO 117
<211> LENGTH: 375
<212> TYPE: DNA
<213> ORGANISM: Vibrio cholerae

<400> SEQUENCE: 117
atgattaaat taaaatttgg tgttttttttt acagttttac tatcttcagc atatgcacat      60
ggaacacctc aaaatattac tgatttgtgt gcagaatacc acaacacaca aatatatacg     120
ctaaatgata agatattttc gtatacagaa tctctagctg gaaaaagaga gatggctatc     180
attactttta agaatggtgc aattttttcaa gtagaagtac caggtagtca acatatagat     240
tcacaaaaaa aagcgattga aaggatgaag gataccctga ggattgcata tcttactgaa     300
gctaaagtcg aaaagttatg tgtatggaat aataaaacgc ctcatgcgat tgccgcaatt     360
agtatggcaa attaa                                                       375

<210> SEQ ID NO 118
<211> LENGTH: 124
<212> TYPE: PRT
<213> ORGANISM: Vibrio cholerae

<400> SEQUENCE: 118

Met Ile Lys Leu Lys Phe Gly Val Phe Phe Thr Val Leu Leu Ser Ser
1               5                   10                  15

Ala Tyr Ala His Gly Thr Pro Gln Asn Ile Thr Asp Leu Cys Ala Glu
            20                  25                  30

Tyr His Asn Thr Gln Ile Tyr Thr Leu Asn Asp Lys Ile Phe Ser Tyr
        35                  40                  45

Thr Glu Ser Leu Ala Gly Lys Arg Glu Met Ala Ile Ile Thr Phe Lys
    50                  55                  60

Asn Gly Ala Ile Phe Gln Val Glu Val Pro Gly Ser Gln His Ile Asp
65                  70                  75                  80

Ser Gln Lys Lys Ala Ile Glu Arg Met Lys Asp Thr Leu Arg Ile Ala
                85                  90                  95

Tyr Leu Thr Glu Ala Lys Val Glu Lys Leu Cys Val Trp Asn Asn Lys
            100                 105                 110

Thr Pro His Ala Ile Ala Ala Ile Ser Met Ala Asn
        115                 120